United States Patent
Borriello et al.

(10) Patent No.: US 11,993,644 B2
(45) Date of Patent: May 28, 2024

(54) ANTIGEN BINDING MOLECULES TARGETING SARS-COV-2

(71) Applicant: Generate Biomedicines, Inc., Somerville, MA (US)

(72) Inventors: Francesco Borriello, Cambridge, MA (US); Alexis Hiram Ramos, Wilbraham, MA (US)

(73) Assignee: Generate Biomedicines, Inc., Somerville, MA (US)

( * ) Notice: Subject to any disclaimer, the term of this patent is extended or adjusted under 35 U.S.C. 154(b) by 0 days.

(21) Appl. No.: 18/313,306

(22) Filed: May 5, 2023

(65) Prior Publication Data

US 2023/0357366 A1 Nov. 9, 2023

Related U.S. Application Data

(60) Provisional application No. 63/492,206, filed on Mar. 24, 2023, provisional application No. 63/480,903, filed on Jan. 20, 2023, provisional application No. 63/478,650, filed on Jan. 5, 2023, provisional application No. 63/385,957, filed on Dec. 2, 2022, provisional application No. 63/383,695, filed on Nov. 14, 2022, provisional application No. 63/424,945, filed on Nov. 13, 2022, provisional application No. 63/381,131, filed on Oct. 26, 2022, provisional application No. 63/381,132, filed on Oct. 26, 2022, provisional application No. 63/364,328, filed on May 6, 2022, provisional application No. 63/364,331, filed on May 6, 2022.

(51) Int. Cl.
| | |
|---|---|
| *C07K 16/10* | (2006.01) |
| *A61K 31/13* | (2006.01) |
| *A61K 31/215* | (2006.01) |
| *A61K 31/45* | (2006.01) |
| *A61K 31/4706* | (2006.01) |
| *A61K 31/4965* | (2006.01) |
| *A61K 31/675* | (2006.01) |
| *A61K 31/7052* | (2006.01) |
| *A61K 31/7068* | (2006.01) |
| *A61K 31/7088* | (2006.01) |
| *A61K 39/215* | (2006.01) |
| *A61K 39/42* | (2006.01) |
| *A61K 45/06* | (2006.01) |
| *A61P 31/14* | (2006.01) |
| *A61K 39/00* | (2006.01) |

(52) U.S. Cl.
CPC .......... *C07K 16/1003* (2023.08); *A61K 31/13* (2013.01); *A61K 31/215* (2013.01); *A61K 31/45* (2013.01); *A61K 31/4706* (2013.01); *A61K 31/4965* (2013.01); *A61K 31/675* (2013.01); *A61K 31/7052* (2013.01); *A61K 31/7068* (2013.01); *A61K 31/7088* (2013.01); *A61K 39/215* (2013.01); *A61K 39/42* (2013.01); *A61K 45/06* (2013.01); *A61P 31/14* (2018.01); *A61K 2039/505* (2013.01); *A61K 2039/507* (2013.01); *C07K 2317/24* (2013.01); *C07K 2317/34* (2013.01); *C07K 2317/55* (2013.01); *C07K 2317/567* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 8,088,376 | B2 | 1/2012 | Chamberlain et al. |
| 8,394,925 | B2 | 3/2013 | Chamberlain et al. |
| 8,546,543 | B2 | 10/2013 | Lazar |
| 9,803,023 | B2 | 10/2017 | Chamberlain et al. |
| 10,336,818 | B2 | 7/2019 | Chamberlain et al. |
| 10,787,501 | B1 | 9/2020 | Babb et al. |
| 11,028,167 | B1 | 6/2021 | Glanville et al. |
| 11,168,128 | B2 | 11/2021 | Corti et al. |
| 11,192,940 | B2 | 12/2021 | Walker et al. |
| 2015/0152183 | A1 | 6/2015 | Chamberlain et al. |
| 2016/0046720 | A1 | 2/2016 | Sato et al. |
| 2021/0214431 | A1 | 7/2021 | Rommelaere et al. |
| 2021/0261650 | A1 | 8/2021 | Corti et al. |

(Continued)

FOREIGN PATENT DOCUMENTS

| | | |
|---|---|---|
| EP | 2235059 B1 | 2/2015 |
| EP | 2444423 B1 | 3/2015 |

(Continued)

OTHER PUBLICATIONS

Almagro et al., Front. Immunol., 8:1751, doi: 10.3389/fimmu.2017.01751 (Year: 2018).*

(Continued)

*Primary Examiner* — Jessica H Roark
(74) *Attorney, Agent, or Firm* — Hamilton, Brook, Smith & Reynolds, P.C.

(57) ABSTRACT

The disclosure provides, in various embodiments, polypeptides (e.g., antibodies and antigen binding fragments thereof) that specifically bind to S2 domains of betacoronavirus Spike glycoproteins, such as severe acute respiratory syndrome coronavirus 2 (SARS-CoV-2) Spike glycoproteins. The disclosure also provides, in various embodiments, fusion proteins comprising one or more of polypeptides, polynucleotides encoding polypeptides, vectors and host cells suitable for expressing polypeptides, and methods for treating viral infections (e.g., COVID-19).

30 Claims, 58 Drawing Sheets
Specification includes a Sequence Listing.

(56) References Cited

U.S. PATENT DOCUMENTS

| | | |
|---|---|---|
| 2021/0277095 A1 | 9/2021 | Chamberlain et al. |
| 2022/0112307 A1 | 4/2022 | Chamberlain et al. |
| 2022/0403009 A1 | 12/2022 | Hinton et al. |
| 2023/0279081 A1 | 9/2023 | Grigoryan et al. |
| 2023/0287089 A1 | 9/2023 | Grigoryan et al. |
| 2023/0295275 A1 | 9/2023 | Grigoryan et al. |
| 2023/0357367 A1 | 11/2023 | Borriello et al. |

FOREIGN PATENT DOCUMENTS

| | | |
|---|---|---|
| EP | 3031913 A1 | 6/2016 |
| EP | 2808343 B1 | 5/2019 |
| EP | 3872091 A1 | 9/2021 |
| EP | 3138853 B1 | 11/2021 |
| EP | 4147716 A1 | 3/2023 |
| WO | 2005/012360 A2 | 2/2005 |
| WO | 2005/054469 A1 | 6/2005 |
| WO | 2006/051091 A1 | 5/2006 |
| WO | 2006/053301 A2 | 5/2006 |
| WO | 2009/058492 A2 | 5/2009 |
| WO | 2009/086320 A1 | 7/2009 |
| WO | 2021/156490 A2 | 8/2021 |
| WO | 2021/158521 A1 | 8/2021 |
| WO | 2021/173753 A1 | 9/2021 |
| WO | 2021/186190 A1 | 9/2021 |
| WO | 2021/203053 A1 | 10/2021 |
| WO | 2021/207152 A1 | 10/2021 |
| WO | 2021/211775 A1 | 10/2021 |
| WO | 2021/226560 A1 | 11/2021 |
| WO | 2022/010912 A1 | 1/2022 |
| WO | 2022/010921 A1 | 1/2022 |
| WO | 2022/015573 A2 | 1/2022 |
| WO | 2022/047033 A1 | 3/2022 |
| WO | 2022/140845 A1 | 7/2022 |
| WO | WO-2022140845 A1 * | 7/2022 |
| WO | 2023/037119 A1 | 3/2023 |
| WO | 2023/215910 A1 | 11/2023 |

OTHER PUBLICATIONS

De Genst et al., Dev Comp Immunol; 30:187-98 (Year: 2006).*
Yoshinaga et al., J. Biochem; 143:593-601 (Year: 2008).*
Baud et al. "Real estimates of mortality following COVID-19 infection", Lancet Infect Dis. 20(7):773 (2020).
Baden et al. "Covid-19—The Search for Effective Therapy", N Engl J Med. 382(19):1851-52 (2020).
Song et al. "Cytokine storm induced by SARS-COV-2", Clin Chim Acta. 509:280-7 (2020).
Jennewein et al. "Isolation and characterization of cross-neutralizing coronavirus antibodies from COVID-19+ subjects", Cell Rep. 36(2):109353 (2021).
Pinto et al. "Cross-neutralization of SARS-COV-2 by a human monoclonal SARS-COV antibody", Nature 583: 290-95 (2020).
Tortorici et al. "Broad sarbecovirus neutralization by a human monoclonal antibody", Nature. Sep. 2021;597 (7874):103-108. doi: 10.1038/s41586-021-03817-4. Epub Jul. 19, 2021 PMID: 34280951.
Li et al. "Structural Basis and Mode of Action for Two Broadly Neutralizing Antibodies Against SARS-COV-2 Emerging Variants of Concern", Cell Reports 38(2):110210 (2021).
Ingraham et al. "Generative models for graph-based protein design", 33rd Conference on Neural Information Processing Systems (NeurIPS 2019), Vancouver, Canada.
Zhou et al. "A general-purpose protein design framework based on mining sequence-structure relationships in known protein structures", Proc Natl Acad Sci U S A. 117(2):1059-68 (2020).
Chen et al. "CoV-Spectrum: analysis of globally shared SARS-COV-2 data to identify and characterize new variants", Bioinformatics 38(6):1735-37 (2022).
Corti et al. "Tackling COVID-19 with neutralizing monoclonal antibodies", Cell 184(12):3086-3108 (2021).
Hurlburt et al. "Structural definition of a pan-sarbecovirus neutralizing epitope on the spike S2 subunit", Commun Biol. 5(1):342 (2022).
Rambaut et al. "A dynamic nomenclature proposal for SARS-COV-2 lineages to assist genomic epidemiology", Nat Microbiol. 5(11):1403-07 (2020).
Ullah et al. "Live imaging of SARS-COV-2 infection in mice reveals that neutralizing antibodies require Fc function for optimal efficacy", Immunity. 54(9):2143-58 (2021).
Database, RCSB PDB [Online], "7NAB Crystal structure of human neutralizing mAb CV3-25 binding to SARS-CoV-2 S MPER peptide 1140-1165", 5 pages, PDB DOI: https://doi.org/10.2210/pdb7NAB/pdb (2021).
Non Final Office Action for U.S. Appl. No. 18/314,091 date dated Aug. 30, 2023.
Almagro et al., "Progress and Challenges in the Design and Clinical Development of Antibodies for Cancer Therapy" Front. Immunol., 8:1751, doi: 10.3389/fimmu.2017.01751 (2018).
De Genst et al., "Antibody repertoire development in camelids" Dev Comp Immunol; 30:187-98 (2006).
Yoshinaga et al., "Ig L-chain Shuffling for Affinity Maturation of Phage Library-derived Human Anti-human MCP-1 Antibody Blocking its Chemotactic Activity" J. Biochem; 143:593-601 (2008).
International Search Report and Written Opinion for International Application No. PCT/US2023/066714, dated Sep. 18, 2023.
Pinto et al. "CORONAVIRUS Broad betacoronavirus neutralization by a stem helix-specific human antibody", Sep. 3, 2021 (Sep. 3, 2021) Retrieved from the Internet: URL:https://pubmed.ncbi.nlm.nih.gov/34344823/XP055896554 [retrieved on Mar. 1, 2022].
Ladner et al. "Epitope-resolved profiling of the SARS-COV-2 antibody response identifies cross-reactivity with endemic human coronaviruses", Jan. 1, 2021 ( an. 1, 2021), vol. 2, No. 1, p. 100189, Retrieved from the Internet: URL:https://www.cell.com/cell-reports-medicine/pdfExtended/S2666-3791(20)30244-5XP055847640, DOI: 10.1016/j.xcrm.2020.100189, ISSN:2666-3791.
Sauer et al. "Structural basis for broad coronavirus neutralization", May 12, 2021 (2021-05-12), vol. 28, No. 6, p. 478-486, XP037479244, Doi: 10.1038/S41594-021-00596-4, Issn: 1545-9993 [retrieved on 2021-05-12].
Wrapp et al. "Cryo-EM structure of the 2019-nCOV spike in the prefusion conformation", Science, vol. 367, No. 6483, Mar. 13, 2020 (Mar. 13, 2020), p. 1260-1263, XP093045004, DOI: 10.1126/science.abb2507, ISSN:0036-8075.
Zhou et al. "A human antibody reveals a conserved site on beta-coronavirus spike proteins and confers protection against SARS-COV-2 infection", Science Translational Medicine, vol. 14, No. 637, Mar. 23, 2022 (Mar. 23, 2022), XP093039808, DOI: 10.1126/scitranslmed.abi9215.
Rudikoff et al. "Single amino acid substitution altering antigen-binding specificity", Proceedings of the National Academy of Sciences, National Academy of Sciences, vol. 79, Mar. 1, 1982 (Mar. 1, 1982), p. 1979-1983, XP007901436, DOI: 10.1073/PNAS.79.6.1979, ISSN:0027-8424.
Haraya, K. et al., "Translational Approach for Predicting Human Pharmacokinetics of Engineered Therapeutic Monoclonal Antibodies with Increased FcRn-Binding Mutations," BioDrugs, vol. 37; No. 1; 99-108 (2023).
Harpaz R. et al., "Prevalence of Immunosuppression Among US Adults, 2013," JAMA, vol. 316; No. 23; 2547-2548 (2016).
Hastie, K.M. et al., "Defining variant-resistant epitopes targeted by SARS-CoV-2 antibodies: A global consortium study," Science, 10.1126/science.abh2315; 13 pages (2021).
Hastie, K.M. et al., "Defining variant-resistant epitopes targeted by SARS-CoV-2 antibodies: A global consortium study," Science, 10.1126/science.abh2315; 13 pages; Supplemental Information (2021).
Hie, B.L. et al., "Efficient evolution of human antibodies from general protein language models," Nature Biotechnology, https://doi.org/10.1038/s41587-023-01763-2; 26 pages (2023).
Highlights of Emergency Use Authorization, Bebtelovimab, 21 pages (2022).
Highlights of Emergency Use Authorization, Evusheld, 27 pages (2021).

(56) References Cited

OTHER PUBLICATIONS

Highlights of Emergency Use Authorization, Evusheld; 30 pages; Revised Jan. 2023.
Hirsch C. et al., "SARS-CoV-2-neutralising monoclonal antibodies to prevent COVID-19," Cochrane Database Syst Rev., Issue 6; Art No. CD014945; 106 pages (2022).
Hirsch C. et al., "SARS-CoV-2-neutralising monoclonal antibodies to prevent COVID-19," Cochrane Database Syst Rev., vol. 6; Issue 6; Art No. CD014945; 89 pages (2022).
Holland et al., ACTIV-3-Therapeutics for Inpatients with COVID-19 (TICO) Study Group. Tixagevimab-cilgavimab for treatment of patients hospitalised with COVID-19: a randomised, double-blind, phase 3 trial. Lancet Respir Med. Oct. 2022; 10(10):972-984. doi: 10.1016/S2213-2600(22)00215-6. Epub Jul. 8, 2022. Erratum in: Lancet Respir Med. Nov. 7, 2022;: PMID: 35817072; PMCID: PMC9270059.
Hu, D. and Irving, A.T., "Massively-multiplexed epitope mapping techniques for viral antigen discovery," Front. Immunol., vol. 14; 1192385; 13 pages (2023).
Hua L et al., MEDI4893* Promotes Survival and Extends the Antibiotic Treatment Window in a Staphylococcus aureus Immunocompromised Pneumonia Model. Antimicrob Agents Chemother. Aug. 2015;59(8):4526-32. doi: 10.1128/AAC.00510-15. Epub May 18, 2015. PMID: 25987629; PMCID: PMC4505239.
Huang, Y. et al., "Identification of a conserved neutralizing epitope present on spike proteins from all highly pathogenic coronaviruses," bioRxiv, 27 (2021).
Huang, Y. et al., "Identification of a conserved neutralizing epitope present on spike proteins from all highly pathogenic coronaviruses," bioRxiv, 27; Supplemental Information (2021).
Huo, J. et al., "Neutralizing nanobodies bind SARS-CoV-2 spike RBD and block interaction with ACE2," Nature Structural and Molecular Biology, vol. 27; 846-854 (2020).
Irvin SC et al., REGEN-COV® antibody cocktail bioanalytical strategy: comparison of LC-MRM-MS and immunoassay methods for drug quantification. Bioanalysis. Dec. 2021;13(24):1827-1836. doi: 10.4155/bio-2021-0190. Epub Nov. 8, 2021. PMID: 34743612; PMCID: PMC8579949.
Isa F et al., Repeat subcutaneous administration of casirivimab and imdevimab in adults is well-tolerated and prevents the occurrence of COVID-19. Int J Infect Dis. Sep. 2022;122:585-592. doi: 10.1016/j.ijid.2022.06.045. Epub Jul. 2, 2022. PMID: 35788416; PMCID: PMC9249725.
Ishino, T. et al., "Engineering a Monomeric Fc Domain Modality by N-Glycosylation for the Half-life Extension of Biotherapeutics," Journal of Biological Chemistry, vol. 288; No. 23; 16529-16537 (2013).
Janeway et al., The Recognition of Antigen, Immunobiology, 3rd edition, Garland Publishing Inc., 1997, pp. 3:1-3:11.
Jette, C.A. et al., "Broad cross-reactivity across sarbecoviruses exhibited by a subset of COVID-19 donor-derived neutralizing antibodies," Cell Reports, vol. 36; 109760; 23 pages (2021).
Jiang, N. et al., "Bivalent mRNA vaccine improves antibody-mediated neutralization of many SARS-CoV-2 Omicron lineage variants," bioRxiv; 21 pages (2023).
Jiang, W. et al., "Characterization of MW06, a human monoclonal antibody with cross-neutralization activity against both SARS-CoV-2 and SARS-Cov," MABS, vol. 13; No. 1; e1953683; 12 pages (2021).
Jones, B.E. et al., "The neutralizing antibody, LY-CoV555, protects against SARS-CoV-2 infection in nonhuman primates," Sci. Transl. Med., vol. 13; eabf1906; 17 pages (2021).
JP Morgan Healthcare Conference, Regeneron; Retrieved from Internet URL: https://investor.regeneron.com/events/event-details/41st-annual-jp-morgan-healthcare-conference; 37 pages; Retrieved on Jan. 29, 2024.
Ju, B. et al., "Potent human neutralizing antibodies elicited by SARS-CoV-2 infection," retrieved from Internet URL: http://www.biorxiv.org/content/10.1101/2020.03.21.990770V2.full.pdf; 42 Pages; Retrieved on Oct. 6, 2020.

Kaku Y et al., Virological characteristics of the SARS-CoV-2 JN.1 variant. Lancet Infect Dis. Feb. 2024;24(2):e82. doi: 10.1016/S1473-3099(23)00813-7. Epub Jan. 3, 2024. PMID: 38184005.
Kc, B.B. et al., "A machine learning platform to estimate anti-SARS-CoV-2 activities," Nature Machine Intelligence, https://doi.org/10.1038/s42256-021-00335-w; 9 pages (2021).
Khoury DS et al., Neutralizing antibody levels are highly predictive of immune protection from symptomatic SARS-CoV-2 infection. Nat Med. Jul. 2021;27(7):1205-1211. doi: 10.1038/s41591-021-01377-8. Epub May 17, 2021. PMID: 34002089.
Killingley, B. et al., "Safety, tolerability and viral kinetics during SARS-CoV-2 human challenge in young adults," Nature Medicine, vol. 28, 1031-1041 (2022).
Knierman, M.D. et al., "The Human Leukocyte Antigen Class II Immunopeptidome of the SARS-CoV-2 Spike Glycoprotein," Cell Reports, vol. 33; 1 08454; 15 pages (2020).
Kreuzberger N. et al., "SARS-CoV-2-neutralising monoclonal antibodies for treatment of COVID-19," Cochrane Database Syst Rev, vol. 9; No. 9 229 pages (2021).
Kunik, V. et al., "Paratome: an online tool for systematic identification of antigen-binding regions in antibodies based on sequence or structure," Nucleic Acids Research, vol. 40; W521-W524 (2012).
Kupferschmidt, K., "Evolving threat," Science, vol. 373; No. 6557; 844-849 (2021).
Kurasaki, H. et al., "Safety and Pharmacokinetics of PA-001, a New Potential COVID-19 Drug That Targets the S2 Subunit of SARS-CoV-2 Spike Protein, in Healthy Subjects," Poster Abstracts; Abstract citation ID: ofad500.2142 (2023).
Kurhade C et al., Low neutralization of SARS-CoV-2 Omicron BA.2.75.2, BQ.1.1 and XBB.1 by parental mRNA vaccine or a BA.5 bivalent booster. Nat Med. Feb. 2023;29(2):344-347. Safety and efficacy of inhaled IBIO123 for severe covid (preprint).
Ladde, S.M. et al., "Safety and efficacy of inhaled IBIO123 for severe COVID-19: a randomised, double-blind, dose-ascending, placebo-controlled, phase 1/2 trial," The Lancet, 35 pages (2023).
Ladner, J. T., et al., "Epitope-resolved profiling of the SARS-CoV-2 antibody response identifies cross-reactivity with endemic human coronaviruses", Cell Reports Medicine, vol. 2 No. 1, Jan. 1, 2021, 18 pages.
Laracy JC et al., Long and persistent COVID-19 in patients with hematologic malignancies: from bench to bedside. Curr Opin Infect Dis. Aug. 1, 2022;35(4):271-279. doi: 10.1097/QCO.0000000000000841. Epub Jul. 5, 2022. PMID: 35849516; PMCID: PMC9922441.
Leach, M.W. et al., "Use of tissue cross-reactivity studies in the development of antibody-based biopharmaceuticals: history, experience, methodology, and future directions," Toxicol Pathol, vol. 38; No. 7; 1138-1166 (2010).
Levin EG et al., Waning Immune Humoral Response to BNT162b2 Covid-19 Vaccine over 6 Months. N Engl J Med. Dec. 9, 2021;385(24):e84. doi: 10.1056/NEJMoa2114583. Epub Oct. 6, 2021. PMID: 34614326; PMCID: PMC8522797.
Levin M.J. et al., "Intramuscular AZD7442 (Tixagevimab-Cilgavimab) for Prevention of Covid-19," N. Engl. J. Med., vol. 386; No. 23; 2188-2200 (2022).
Levin M.J. et al., "Intramuscular AZD7442 (Tixagevimab-Cilgavimab) for Prevention of Covid-19," N. Engl. J. Med., vol. 386; No. 23; 2188-2200; The Protocol; 424 pages (2022).
Levin, M.J. et al., "AZD7442 (Tixagevimab/Cilgavimab) for Post-Exposure Prophylaxis of Symptomatic Coronavirus Disease 2019," Clinical Infectious Diseases, vol. 76; No. 7; 1247-1256 (2023).
Li, T. et al., "A synthetic nanobody targeting RBD protects hamsters from SARS-CoV-2 infection," Nature Communication, vol. 12; 4635; 13 pages (2021).
Liu Z et al., Identification of SARS-CoV-2 spike mutations that attenuate monoclonal and serum antibody neutralization. Cell Host Microbe. Mar. 1, 20210;29(3):477-488.e4. doi: 10.1016/j.chom.2021.01.014. Epub Jan. 27, 2021. PMID: 33535027; PMCID: PMC7839837.
Liu, H. and Wilson, I.A., "Protective neutralizing epitopes in SARS-CoV-2," Immunol Rev, vol. 310; No. 1; 76-92 (2022).

(56) References Cited

OTHER PUBLICATIONS

Liu, H. et al., "A combination of cross-neutralizing antibodies synergizes to prevent SARS-CoV-2 and SARS-CoV pseudovirus infection," Cell Host & Microbe, vol. 29; 806-818 (2021).

Liu, L. et al., "Anti-spike IgG causes severe acute lung injury by skewing macrophage responses during acute SARS-CoV infection," JCI Insight, vol. 4; No. 4; e123158; 20 pages (2019).

Liu, L. et al., "Antibodies targeting a quaternary site on SARS-CoV-2 spike glycoprotein prevent viral receptor engagement by conformational locking," Immunity, vol. 56(10); 2442-2455 (2023).

Weinreich DM et al., REGN-COV2, a Neutralizing Antibody Cocktail, in Outpatients with Covid-19, N Engl J Med. 384(3):238-251 (2021).

Westendorf, K. et al., "LY-CoV1404 (bebtelovimab) potently neutralizes SARS-CoV-2 variants," Cell Rep., vol. 39; No. 7; 110812; 72 Pages (2022).

WHO website. WHO Coronavirus (COVID-19) Dashboard With Vaccination Data. Updated Feb. 17, 2023. Accessed Feb. 19, 2023. https://covid19.who.int/.

Worzner, K. et al., "Adjuvanted SARS-CoV-2 spike protein elicits neutralizing antibodies and CD4 T cell responses after a single immunization in mice," EBioMedicine, vol. 63; 103197; 9 pages (2021).

Wrapp, D. et al., "Crystal structure of the SARS-CoV-1 RBD bound by the cross-reactive single-domain antibody SARS VHH-72," Protein Data Bank (PDB) Accession No. 6WAQ, retrieved from Internet URL: https://www.rcsb.org/structure/6waq; Retrieved on Sep. 15, 2023; 5 pages.

Wrapp, D. et al., "Structural Basis for Potent Neutralization of Betacoronaviruses by Single-Doman Camelid Antibodies," Cell, vol. 181; 1004-1015 (2020).

Wrapp, D., et al., "Cryo-EM structure of the 2019-nCoV spike in the prefusion conformation", Science, vol. 367, No. 6483, Feb. 19, 2020, pp. 1260-1263.

Wu H et al., Development of motavizumab, an ultra-potent antibody for the prevention of respiratory syncytial virus infection in the upper and lower respiratory tract. J Mol Biol. May 4, 2007;368(3):652-65. doi: 10.1016/j.jmb.2007.02.024. Epub Feb. 20, 2007. PMID: 17362988.

Wu, Y. et al., "A noncompeting pair of human neutralizing antibodies block COVID-19 virus binding to its receptor ACE2," Science, vol. 368; 1274-1278 (2020).

Wu, Y. et al., "Identification of Human Single-Domain Antibodies against SARS-CoV-2," Cell Host & Microbe, vol. 27; 891-898 (2020).

Xiang, Y. et al., 'Versatile, Multivalent Nanobody Cocktails Efficiently Neutralize SARS-CoV-2, bioRxiv, Retrieved from Internet URL: https://www.biorxiv.org/content/10.1101.2020.08.24.264333v3.full.pdf; 34 Pages (2020).

Xu, J. et al., "Nanobodies from camelid mice and llamas neutralize SARS-CoV-2 variants," Nature, vol. 595; 278-282 (2021).

Yamin R et al., Fc-engineered antibody therapeutics with improved anti-SARS-CoV-2 efficacy. Nature. Nov. 2021;599(7885):465-470. doi: 10.1038/s41586-021-04017-w. Epub Sep. 2, 20211. PMID: 34547765; PMCID: PMC9038156.

Yang, D. et al., "Comparison of biosensor platforms in the evaluation of high affinity antibody-antigen binding kinetics," Analytical Biochemistry, vol. 508; 78-96 (2016).

Yonesi, M. and Rezazadeh, A., "Plants as a prospective source of natural anti-viral compounds and oral vaccines against COVID-19 coronavirus," preprint, https://doi.org/10.20944/preprints202004.0321.v1; 31 pages (2020).

Young, S. and Linville-Engler, G., "Invivyd Submits Request for Emergency Use Authorization (EUA) To U.S. FDA for VYD222FOR the Pre-Exposure Prevention of COVID-19 in Immunocompromised Adults Andadolescents," Retrieved from Internet URL: https://investors.adagiotx.com/news-releases/news-release-details/invivyd . . . ; 3 pages; Retrieved on Jan. 3, 2024.

Yuan M et al., A broad and potent neutralization epitope in SARS-related coronaviruses. Proc Natl Acad Sci U S A. Jul. 19, 2022;119(29):e2205784119. doi: 10.1073/pnas.2205784119. Epub Jun. 29, 2022. PMID: 35767670; PMCID: PMC9304036.

Yuan, M. et al., "A higly conserved cryptic epitope in the receptor binding domains of SARS-CoV-2 and SARS-CoV," Science, vol. 368; 4 pages (2020).

Zalevsky, J. et al., "Enhanced antibody half-life improves in vivo activity," Nat. Biotechnol., vol. 28; No. 2; 157-159 (2010).

Zhang A et al., Beyond neutralization: Fc-dependent antibody effector functions in SARS-CoV-2 infection. Nat Rev Immunol. Jun. 2023;23(6):381-396. doi: 10.1038/s41577-022-00813-1. Epub Dec. 19, 2022. PMID: 36536068; PMCID: PMC9761659.

Zhang, F. et al., "Human anti-ACE2 monoclonal antibodies as pan-sarbecovirus prophylactic agents," bioRxiv; https://doi.org/10.1101/2022.08.24.505169; 47 pages (2022).

Zhang, H. et al., "Algorithm for Optimized mRNA Design Improves Stability and Immunogenicity," Nature, https://doi.org/10.1038/s41586-023-06127-z, 52 pages (2023).

Zhao, E. et al., "The Secretogranin II-Derived Peptide Secretoneurin Stimulates Luteinizing Hormone Secretion from Gonadotrophs," Endocrinology, vol. 150; No. 5; 2273-2282 (2009).

Zhao, F. et al., "Broadening a SARS-CoV-1 neutralizing antibody for potent SARS-CoV-2 neutralization through directed evolution," Retrieved from Internet URL: http://biorxiv.org/content/10.1101.2021.05.29.443900v1.full. pdf; 46 ages; Retrieved on Oct. 5, 2021.

Zhou, D. et al., "Evidence of escape of SARS-CoV-2 variant B.1.351 from natural and vaccine-induced sera," Cell, vol. 184(9); 2348-2361 (2021).

Zhou, P., et al., "A human antibody reveals a conserved site on beta-coronavirus spike proteins and confers protection against SARS-CoV-2 infection", Science Translational Medicine, vol. 14, No. 637, Mar. 23, 2022, 2 pages.

Zhou, Q., "Considerations Regarding Assessment of A Modified Monoclonal Antibody (mAb) Product Related to A Prototype mAb Product in Addressing Emerging SARS-CoV-2 Variants—A CMC Perspective," Presentation; EMA-FDA Workshop; Dec. 15, 2022.

Ziegler, C.G.K. et al., "SARS-CoV-2 Receptor ACE2 Is an Interferon-Stimulated Gene in Human Airway Epithelial Cells and Is Detected in Specific Cell Subsets Across Tissues," Cell, vol. 181; 1016-1035 (2020).

Zost SJ et al., Potently neutralizing and protective human antibodies against SARS-CoV-2. Nature. Aug. 2020; 584(7821): 443-449. doi: 10.1038/s41586-020-2548-6. Epub Jul. 15, 2020. PMID: 32668443; PMCID: PMC7584396.

Zupancic, J.M. et al., "Engineered Multivalent Nanobodies Potently and Broadly Neutralize SARS-CoV-2," Advanced Therapeutics, vol. 4; 2100099; 9 Pages (2021).

Liu, L. et al., "Potent neutralizing antibodies against multiple epitopes on SARS-CoV-2 spike," Nature, vol. 584; 450-456 (2020).

Loo, Y.M. et al., "The SARS-CoV-2 monoclonal antibody combination, AZD7442, is protective in nonhuman primates and has an extended half-life in humans," Sci. Transl. Med., vol. 14; No. 635; eabl8124; 15 Pages (2022).

Low, J.S. et al., "ACE2 engagement exposes the fusion peptide to pan-coronavirus neutralizing antibodies," bioRxiv, 56 pages (2022).

Magar, R. et al., "Potential Neutralizing Antibodies Discovered for Novel Corona Virus Using Machine Learning," Cornell University Library, New York, 35 pages (2020).

Mahoney, K. et al., "1363. Preliminary Safety Results from a Phase 1 First in Human Study of VYD222: an Extended Half-Life Monoclonal Antibody (mAb) in Development for COVID-19 Prevention," Open Forum Infect Dis. Nov. 27, 2023;10(Suppl 2):ofad500.1200. doi: 10.1093/ofid/ofad500.1200. PMCID: PMC10678193.

Markovic, I. and Savvides, S., "Modulation of Signaling Mediated by TSLP and IL-7 in Inflammation, Autoimmune Diseases, and Cancer," Frontiers in Immunology, vol. 11; Art. 1557; 19 pages (2020).

Martinez, D.R. et al., "A broadly cross-reactive antibody neutralizes and protects against sarbecovirus challenge in mice," Sci. Transl. Med., 10.1126/scitranslmed. abj7125; Jan. 26, 2022; 14(629): eabj7125; 18 pages.

McCallum, M. et al., "Structural basis of SARS-CoV-2 Omicron immune evasion and receptor engagement," bioRxiv, 27 pages (2021).

(56) References Cited

OTHER PUBLICATIONS

McMahan, K. et al., "Correlates of protection against SARS-CoV-2 in rhesus macaques," Nature, vol. 590(7847); 630-634; Supp'l Data included (2021).

McNeilly AS et al., The differential secretion of FSH and LH: regulation through genes, feedback and packaging. Reprod Suppl. 2003;61:463-76. PMID: 14635955.

Melanie, P. et al., "Modeling brings additional insights into the kinetics of SARS-CoV-2 neutralizing antibody," MedRxiv; https://doi.org/10.1101/2021.10.13.21264693; 4 pages (2021).

Menzies-Gow, A. et al., "Tezepelumab in Adults and Adolescents with Severe, Uncontrolled Asthma," N Eng J Med, vol. 384; 1800-1809 (2021).

Menzies-Gow, A. et al., "Unmet need in severe, uncontrolled asthma: can anti-TSLP therapy with tezepelumab provide a valuable new treatment option?," Respiratory Research, vol. 21(1); 268; 7 pages (2020).

Meyer, M.C. et al., "Development Approach for Anti-Spike Monoclonal Antibodies to Keep Pace with SARS-CoV-2 Variants," EMA-FDA Workshop: Efficacy of monoclonal antibodies in the context of rapidly evolving SARS-CoV-2 variants, Presentation; 10 pages (2022).

Miller, J. et al., "Substantial Neutralization Escape by the SARS-CoV-2 Omicron Variant BQ. 1.1," bioRxiv, https://doi.org/10.1101/2022.11.01.514722; 17 pages (2022).

Montgomery, H. et al., "Efficacy and safety of intramuscular administration of tixagevimab—cilgavimab for early outpatient treatment of COVID-19 (Tackle): a phase 3, randomised, double-blind, placebo-controlled trial," Lancet Respir Med, https://doi.org/10.1016/S2213-2600(22)00180-1; 206 pages; The Protocol (2022).

Montgomery, H. et al., "Efficacy and safety of intramuscular administration of tixagevimab-cilgavimab for early outpatient treatment of COVID-19 (TACKLE): a phase 3, randomised, double-blind, placebo-controlled trial," Lancet Respir Med, vol. 10(10); 985-996; doi: 10.1016/S2213-2600(22)00180-1; Epub Jun. 7, 2022. PMID: 35688164; PMCID: PMC9173721; 12 pages (2022).

Moulana A et al., Compensatory epistasis maintains ACE2 affinity in SARS-CoV-2 Omicron BA.1. Nat Commun. Nov. 16, 2022; 13(1):7011. doi: 10.1038/s41467-022-34506-z. PMID: 36384919; PMCID: PMC9668218.

Muñoz-Fontela C et al., Advances and gaps in SARS-CoV-2 infection models. PLoS Pathog. Jan. 13, 2022;18(1):e1010161. doi: 10.1371/journal.ppat. 1010161. PMID: 35025969; PMCID: PMC8757994.

Nader A et al., Pharmacokinetics, Safety, and Tolerability of Anti-SARS-CoV-2 Monoclonal Antibody, Sotrovimab, Delivered Intravenously or Intramuscularly in Japanese and Caucasian Healthy Volunteers. Clin Pharmacokinet. Jan. 2024;63(1): 57-68. doi: 10.1007/s40262-023-01319-2. Epub Nov. 13, 2023. PMID: 37955825; PMCID: PMC10786731.

Naldini L et al., Efficient transfer, integration, and sustained long-term expression of the transgene in adult rat brains injected with a lentiviral vector. Proc Natl Acad Sci U S A. Oct. 15, 1996;93(21): 11382-8. doi: 10.1073/pnas.93.21.11382. PMID: 8876144; PMCID: PMC38066.

Narkhede, Y.B. et al., "Targeting Viral Surface Proteins through Structure-Based Design," Viruses, vol. 13; 1320; 18 pages (2021).

Needleman, S.B. and Wunsch, C.D., "A General Method Applicable to the Search of Similarities in the Amino Acid Sequence of Two Proteins," J. Mol. Biol., vol. 48; 443-453 (1970).

Nicol L et al., Differential secretion of gonadotrophins: investigation of the role of secretogranin II and chromogranin A in the release of LH and FSH in LbetaT2 cells. J Mol Endocrinol. Apr. 2004;32(2):467-80. doi: 10.1677/jme.0.0320467. PMID: 15072552.

O'Brien, M.P et al., "Subcutaneous REGEN-COV Antibody Combination to Prevent Covid-19," The New England Journal of Medicine, vol. 385(13); 1184-1195 (2021).

Ozawa, H. et al., "The Granin Family-Its Role in Sorting and Secretory Granule Formation," Cell Structure and Function, vol. 20; 415-420 (1995).

Pantaleo, G. et al., "Antibodies to combat viral infections: development strategies and progress," Nat Rev Drug Discov., Sep. 2022;21(9):676-696. doi: 10.1038/s41573-022-00495-3. Epub Jun. 20, 2022. PMID: 35725925; PMCID: PMC9207876.

Park, T. et al., "Spike protein binding prediction with neutralizing antibodies of SARS-CoV-2" retrieved from Internet URL: http://www.biorxiv.org/content/10.1101/2020.02.22.951178v1.full.pdf; 22 Pages; Retrieved on Jun. 9, 2021.

Park, Y. et al., "Antibody-mediated broad sarbecovirus neutralization through ACE2 molecular mimicry," Science, 10.1126/science.abm8143; 14 pages (2022).

Park, Y. et al., "Imprinted antibody responses against SARS-CoV-2 Omicron sublineages," bioRxiv, 68 pages (2022).

Pearson, W.R. and Lipman, D.J., "Improved tools for biological sequence comparison," Proc. Natl. Acad. Sci., vol. 85; 2444-2448 (1988).

Perez, J.L., "Use of neutralizing antibody or PK/IC50 threshold to expedite clinical development for prophylactic monoclonal antibodies," EMA/FDA workshop on monoclonal antibodies against SARS-CoV-2, AstraZeneca, Vaccines & Immune Therapies Unit; Presentation; 6 pages (2022).

Perez-Vargas J et al., Discovery of lead natural products for developing pan-SARS-CoV-2 therapeutics. Antiviral Res. Jan. 2023;209:105484. doi: 10.1016/j.antiviral.2022.105484. Epub Dec. 8, 2022. Erratum in: Antiviral Res. May 2023;213: 105577. PMID: 36503013; PMCID: PMC9729583.

Petkova SB et al., Enhanced half-life of genetically engineered human IgG1 antibodies in a humanized FcRn mouse model: potential application in humorally mediated autoimmune disease. Int Immunol. Dec. 2006; 18(12): 1759-69. doi: 10.1093/intimm/dxl110. Epub Oct. 31, 2006. PMID: 17077181.

Pinto, D. et al., "Broad betacoronavirus neutralization by a stem helix—specific human antibody," Science, Supplemental Materials, 37 pages (2021).

Pinto, D. et al., "Structural and functional analysis of a potent sarbecovirus neutralizing antibody," Retrieved from Internet URL: http://www.biorxiv.org/content/10.1101.2020.04.07.023903v3.full.pdf; 28 pages; Retrieved on Apr. 10, 2020.

Pinto, D., et al., "Broad betacoronavirus neutralization by a stem helix—specific human antibody", Coronavirus, vol. 373, No. 6559, Sep. 3, 2021, pp. 1109-1116.

Planas, D. et al., "Reduced sensitivity of SARA-CoV-2 variant Delta to antibody neutralization," Nature, 22 pages (2021).

Polack, F.P. et al., "Safety and Efficacy of the BNT162b2 mRNA Covid-19 Vaccine," N. Engl. J. Med, vol. 383; No. 27; 2603-2615 (2020).

Portal-Celhay, C. et al., "Phase 2 dose-ranging study of the virologic efficacy and safety of the combination COVID-19 antibodies casirivimab and imdevimab in the outpatient setting," medRxiv; https://doi.org/10.1101/2021.11.09.21265912; 35 pages (2021).

Pradhan, A. et al., "Affinity maturation of cross-reactive CR3022 antibody against the receptor binding domain of SARS-CoV-2 via in silico site-directed mutagenesis," Retrieved from Internet URL: http://assets.researchsquare.com/files/rs-92745/v1/60243c22-34a9-439c-89cb-d45b2b46b396.pdf?c=1631858249; 10 pages; Retrieved on Oct. 5, 2021.

Prévost J et al., Cross-Sectional Evaluation of Humoral Responses against SARS-CoV-2 Spike. Cell Rep Med. Oct. 20, 2020;1(7):100126. doi: 10.1016/j.xcrm.2020.100126. Epub Sep. 30, 2020. PMID: 33015650; PMCID: PMC7524645.

Pymm, P. et al., "Nanobody cocktails potently neutralize SARS-CoV-2 D614G N501Y variant and protect mice," PNAS, vol. 118; No. 19; e2101918118, 12 pages (2021).

Quanterix, The Science of Precision Health, "Simoa® SARS CoV-2 N Protein Advantage Kit: HD-X Data Sheet," Quanterix Corporation, DOC Template-0061 03; DS-0528 01DS-0528; 2 pages (2020).

Quanterix, The Science of Precision Health, "Simoa® SARS-CoV-2 Spike IgG Advantage Kit: HD-X Data Sheet," Quanterix Corporation, DOC Template-0061 03; DS-0521 01DS-0521; 3 pages (2020).

Rappazzo CG et al., Broad and potent activity against SARS-like viruses by an engineered human monoclonal antibody. Science. Feb. 19, 2021;371(6531):823-829. doi: 10.1126/science.abf4830. Epub Jan. 25, 2021. PMID: 33495307; PMCID: PMC7963221.

(56) References Cited

OTHER PUBLICATIONS

Rockett, R. et al., "Resistance Mutations in SARS-CoV-2 Delta Variant after Sotrovimab Use," N Engl J Med, vol. 386; No. 15; 4 pages (2022).

Rudikoff, S., et al., "Single amino acid substitution altering antigen-binding specificity.", Proceedings Of The National Academy Of Sciences, National Academy Of Sciences, vol. 79, Mar. 1, 1982, pp. 1979-1983.

Rujas, E. et al., "Multivalency transforms SARS-CoV-2 antibodies into ultrapotent neutralizers," Nature Communications, vol. 12(1); 3661; 12 pages (2021).

Saunders, K.O., "Conceptual Approaches to Modulating Antibody Effector Functions and Circulation Half-Life," Front Immunol., vol. 10; 1296 (2019).

Crawford JL & McNeilly AS. Co-localisation of gonadotrophins and granins in gonadotrophs at different stages of the oestrous cycle in sheep. J Endocrinol. Aug. 2002; 174(2): 179-94. doi: 10.1677/joe.0.1740179. PMID: 12176657.

Crawford KHD et al., Protocol and Reagents for Pseudotyping Lentiviral Particles with SARS-CoV-2 Spike Protein for Neutralization Assays. Viruses. May 6, 2020; 12(5):513. doi: 10.3390/v12050513. PMID: 32384820; PMCID: PMC7291041.

Credle, J.J. et al., "Unbiased discovery of autoantibodies associated with severe COVID-19 via genome-scale self-assembled DNA-barcoded protein libraries," Nature Biomedical Engineering, vol. 6(8); 992-1003 (2022).

Cromer D et al., Neutralising antibody titres as predictors of protection against SARS-CoV-2 variants and the impact of boosting: a meta-analysis. Lancet Microbe. Jan. 2022;3(1): e52-e61. doi: 10.1016/S2666-5247(21)00267-6. Epub Nov. 1, 20215. PMID: 34806056; PMCID: PMC8592563.

Cuccarese, M.F. et al., "Functional immune mapping with deep-learning enabled phenomics applied to immunomodulatory and COVID-19 drug discovery," bioRxiv, 24 pages (2020).

Davenport, M., "Correlates of protection using a neutralisation approach," Kirby Institute, 25 pages (2022).

Davis-Gardner, M.E. et al., "mRNA bivalent booster enhances neutralization against BA.2.75.2 and BQ.1.1," bioRxiv; https://doi.org/10.1101/2022.10.31.514636; 7 pages (2022).

de Gasparo, R.D. et al., "Bispecific IgG neutralizes SARS-CoV-2 variants and prevents escape in mice," Nature, vol. 593(7859); 424-428 (2020).

Dejnirattisai, W. et al., "The antigenic anatomy of SARS-CoV-2 receptor binding domain," Cell, vol. 184; 2183-2200 (2021).

Dings C et al., Pharmacometric Modeling of the Impact of Azelastine Nasal Spray on SARS-CoV-2 Viral Load and Related Symptoms in COVID-19 Patients. Pharmaceutics. Sep. 27, 2022; 14(10):2059. doi: 10.3390/pharmaceutics 14102059. PMID: 36297492; PMCID: PMC9609097.

Divine, R. et al., "Designed proteins assemble antibodies into modular nanocages," Science, vol. 372(6537); No. 47; 17 pages (2021).

Dougan, M. et al., "A randomized, placebo-controlled clinical trial of bamlanivimab and etesevimab together in high-risk ambulatory patients with COVID-19 and validation of the prognostic value of persistently high viral load," Oxford University Press for the Infectious Diseases Society of America; 29 pages (2021).

Dougan, M. et al., "Bebtelovimab, alone or together with bamlanivimab and etesevimab, as a broadly neutralizing monoclonal antibody treatment for mild to moderate, ambulatory COVID-19," medRxiv, 33 pages (2022).

Dube, S. et al., "Fully vaccinated individuals with immunocompromised conditions are still at increased risk of severe COVID-19 outcomes from the Omicron variant: initial results from Inform, a retrospective health database observational study in England," Presented at IDWeek (Abstract 1096); Oct. 11-15, 2023; Boston, Massachusetts, USA; 20 pages.

Durán-Pastén ML & Fiordelisio T. GnRH-Induced Ca(2+) Signaling Patterns and Gonadotropin Secretion in Pituitary Gonadotrophs. Functional Adaptations to Both Ordinary and Extraordinary Physiological Demands. Front Endocrinol (Lausanne). Sep. 30, 2013;4:127. doi: 10.3389/fendo.2013.00127. PMID: 24137156; PMCID: PMC3786263.

Edara VV et al., Neutralizing Antibodies Against SARS-CoV-2 Variants After Infection and Vaccination. JAMA. May 11, 2021;325(18): 1896-1898. doi: 10.1001/jama.2021.4388. PMID: 33739374; PMCID: PMC7980146.

EMA website. CHMP Assessment Report for Sotrovimab, Dec. 2021. Updated Jan. 12, 2023. Accessed May 22, 2023. https://www.ema.europa.eu/en/documents/assessmentreport/xevudy-epar-public-assessment-report_en.pdf.

Esparza, T.J. and Brody, D.L., "High Affinity Nanobodies Block SARS-CoV-2 Spike Receptor Binding Domain Interaction with Human Angiotensin Converting Enzyme," bioRxiv, Retrieved from Internet URL: https://www.biorxiv.org/content/10.1101/2020.07.24.219857v1.full.pdf; 15 Pages (2020).

European Cancer Patient Coalition (ECPC). Joint statement on the protection of immunocompromised patients during the COVID-19 pandemic. Updated Jul. 7, 2022. Accessed Feb. 17, 2023. https://ecpc.org/joint-statement-on-the-protection-ofimmunocompromised-patients/.

European Medicines Agency, Assessment Report, Evusheld, 155 pages (2022).

European Medicines Agency, CHMP Assessment Report for Xevudy; 120 pages (2021).

Eyal, N. et al., "Human Challenge Studies to Accelerate Coronavirus Vaccine Licensure," The Journal of Infectious Diseases, vol. 221; 1752-1756 (2020).

Fact Sheet for Health Care Providers, Bamlanivimab and Etesevimab, Eli Lilly and Company, 45 pages (2021).

Fact Sheet for Health Care Providers, casirivimab and imdevimab, Regeneron Pharmaceuticals, Inc, 54 pages (2021).

Fact Sheet for Health Care Providers, Sotrovimab, GlaxoSmithKline LLC, 37 pages (2022).

FDA Briefing Document, "Bezlotoxumab Injection, Meeting of the Antimicrobial Drugs Advisory Committee (AMDAC)" 29 pages (2016).

FDA Briefing Document, "Vaccines and Related Biological Products Advisory Committee Meeting," EUA amendment request for use of the Moderna COVID-19 Vaccine in children 6 months through 17 years of age, 190 pages (2022).

Fedry, J. et al., "Structural insights into the cross-neutralization of SARS-CoV and SARS-CoV-2 by the human monoclonal antibody 47D11," Sci. Adv., vol. 7(23); eabf5632, 11 pages (2021).

Fenwick, C. et al., "A highly potent antibody effective against SARS-CoV-2 variants of concern," Cell Reports, vol. 37(2); 109814; 19 pages (2021).

Fenwick, C. et al., "Patient-derived monoclonal antibody neutralizes SARS-CoV-2 Omicron variants and confers full protection in monkeys," Nature Microbiology, 33 pages (2022).

Follmann D et al., Examining protective effects of SARS-CoV-2 neutralizing antibodies after vaccination or monoclonal antibody administration. Nat Commun. Jun. 17, 2023; 14(1): 23 pages; Supplemental Materials.

Follmann D et al., Examining protective effects of SARS-CoV-2 neutralizing antibodies after vaccination or monoclonal antibody administration. Nat Commun. Jun. 17, 2023;14(1):3605. doi: 10.1038/s41467-023-39292-w. PMID: 37330602; PMCID: PMC10276829.

Francica, J.R. et al., "The SARS-CoV-2 monoclonal antibody AZD3152 potently neutralises historical and currently circulating variants," Presented at the European Congress of Clinical Microbiology and Infectious Diseases (ECCMID), Poster P2636; Copenhagen, Denmark, Apr. 15-18, 2023.

Francica, J.R. et al., "The SARS-CoV-2 Monoclonal Antibody AZD3152 Potently Neutralizes Historical and Emerging Variants and is Being Developed for the Prevention and Treatment of COVID-19 in High-Risk Individuals," IDWeek 2023, Oct. 11-15, 2023, Boston, MA, USA; Poster.

Gau, B.C. et al., "Oligonucleotide mapping via mass spectrometry to enable comprehensive primary structure characterization of an mRNA vaccine against SARS-CoV-2," Scientific Reports, vol. 13; 9038; 16 pages (2023).

(56) References Cited

OTHER PUBLICATIONS

Gauvreau, G.M. et al., "Effects of an Anti-TSLP Antibody on Allergen-Induced Asthmatic Responses," N. Eng J Med, vol. 370; 2102-2110 (2014).

GenBank, "Lama glama immunoglobulin heavy chain variable region mRNA, partial eds," Database accession No. MT350284; 2 Pages (2020).

Gilbert PB et al., Immune correlates analysis of the mRNA-1273 COVID-19 vaccine efficacy clinical trial. Science. Jan. 7, 2022;375(6576): 75 pages; Supplemental Material.

Gilbert PB et al., Immune correlates analysis of the mRNA-1273 COVID-19 vaccine efficacy clinical trial. Science. Jan. 7, 2022;375(6576):43-50. doi: 10.1126/science.abm3425. Epub Nov. 23, 2021. PMID: 34812653; PMCID: PMC9017870.

Gilbert, P.B. et al., "A Covid-19 Milestone Attained—A Correlate of Protection for Vaccines," N Engl J Med, vol. 387; No. 24; 2203-2206 (2022).

Gobeil, S. et al., "Structural diversity of the SARS-CoV-2 Omicron spike," bioRxiv; 35 pages (2022).

Gov.UK, "Winter Coronavirus (COVID-19) Infection Study: estimates of epidemiological characteristics, Dec. 21, 2023," Retrieved from Internet URL: https://www.gov.uk/government/statistics/winter-coronavirus-covid-19-infection . . . ; 14 pages; Retrieved on Dec. 21, 2023.

Greaney AJ et al., Complete Mapping of Mutations to the SARS-CoV-2 Spike Receptor-Binding Domain that Escape Antibody Recognition. Cell Host Microbe. Jan. 13, 2021;29(1):44-57.e9. doi: 10.1016/j.chom.2020.11.007. Epub Nov. 19, 2020. PMID: 33259788; PMCID: PMC7676316.

Greaney, A.J. et al., "Comprehensive mapping of mutations to the SARS-CoV-2 receptor-binding domain that affect recognition by polyclonal human serum antibodies," bioRxiv, 35 pages (2021).

Gruell, H. et al., "Antibody-mediated neutralization of SARS-CoV-2," Immunity, vol. 55(6); 925-944 (2022).

Gupta, A. et al., "Early Treatment for Covid-19 with SARS-CoV-2 Neutralizing Antibody Sotrovimab," N Eng J Med, vol. 385(21); 1941-1950 (2021).

Gupta, A. et al., "Early Treatment for Covid-19 with SARS-CoV-2 Neutralizing Antibody Sotrovimab," N Eng J Med, vol. 385(21); The Protocol; 269 pages (2021).

Gutgsell, A.R. et al., "Biosensor-Enabled Deconvolution of the Avidity-Induced Affinity Enhancement for the SARS-CoV-2 Spike Protein and ACE2 Interaction," Anal Chem, vol. 94; 1187-1194 (2022).

Haagmans, B.L. et al., "SARS-CoV-2 Neutralizing Human Antibodies Protect Against Lower Respiratory Tract Disease in a Hamster Model," Journal of Infectious Diseases, vol. 223(12):2020-2028 (2021).

Hansen, J. et al., "Studies in humanized mice and convalescent humans yield a SARS-CoV-2 antibody cocktail," Science, vol. 369(6506); 1010-1014 (2020).

Saunders, K.O., "Developing a Neutralizing Antibody Vaccine for Pandemic and Pre-Emergent Coronaviruses," Duke University School of Medicine, IDWeek, 31 pages (2023).

Schepens, B. et al., "An affinity-enhanced, broadly neutralizing heavy chain-only antibody protects against SARS-CoV-2 infection in animal models," Sci Transl Med., vol. 13; eabi7826; 18 pages (2021).

Schoof, M. et al., "An ultra-potent synthetic nanobody neutralizes SARS-CoV-2 by locking Spike into an inactive conformation," bioRxiv, Retrieved from Internet URL: https://www.biorxiv.org/content/10.1101/2020.08.08.238469v2.full.pdf; 24 pages (2020).

Service, R.F., "New antibodies that the coronavirus can't elude," Science, vol. 380; Issue 6647; 779-780 (2023).

Seydoux E. et al., Analysis of a SARS-CoV-2-Infected Individual Reveals Development of Potent Neutralizing Antibodies with Limited Somatic Mutation. Immunity. Jul. 1, 20204;53(1):98-105.e5. doi: 10.1016/j.immuni.2020.06.001. Epub Jun. 8, 2020. PMID: 32561270; PMCID: PMC7276322.

Sheridan, D. et al., "Design and preclinical characterization of ALXN1210: A novel anti-C5 antibody with extneded duration of action," PLoS One, vol. 13; No. 4; e0195909; 15 pages (2018).

Sherman, A.C. et al., "The Future of Flu: A Review of the Human Challenge Model and Systems Biology fort Advancement of Influenza Vaccinology," Frontiers in Cellular and Infection Microbiology, vol. 9; Article 107; 9 pages (2019).

Sheward, D.J. et al., "Structural basis of Omicron neutralization by affinity-matured public antibodies," bioRxiv, 24 pages (2022).

Shi, R. et al., "A human neutralizing antibody targets the receptor-binding site of SARS-CoV-2," Nature, vol. 584; No. 7819; 120-124 (2020).

Sia SF, Yan LM, Chin AWH, et al. Pathogenesis and transmission of SARS-CoV-2 in golden hamsters. Nature. 2020;583(7818):834-838.

Sia, S.F. et al., "Pathogenesis and transmission of SARS-CoV-2 in golden hamsters," Nature, vol. 583; 834-837; Supp'l Data included (2020).

Smith, T.F. and Waterman, M.S., "Comparison of Biosequences," Advances in Applied Mathematics, vol. 2; 482-489 (1981).

Snijder J et al., An Antibody Targeting the Fusion Machinery Neutralizes Dual-Tropic Infection and Defines a Site of Vulnerability on Epstein-Barr Virus. Immunity. Apr. 17, 2018;48(4):799-811.e9. doi: 10.1016/j.immuni.2018.03.026. PMID: 29669253; PMCID: PMC5909843.

Song, Y. et al., "Effects of Secretoneurin and Gonadotropin-Releasing Hormone Agonist on the Spawning of Captive Greater Amberjack (Seriola dumerili)," Life, vol. 12; 1457; 14 pages (2022).

Stadler, E. et al., "Determinants of passive antibody effectiveness in SARS-CoV-2 infection," medRxiv; https://doi.org/10.1101/2022.03.21.22272672; 28 pages (2022).

Stadler, E. et al., "Monoclonal antibody levels and protection from COVID-19," medRxiv; https://doi.org/10.1101/2022.11.22.22282199; 26 pages (2022).

Stamatatos L et al., mRNA vaccination boosts cross-variant neutralizing antibodies elicited by SARS-CoV-2 infection. Science. Mar. 25, 2021;372(6549):1413-8. doi: 10.1126/science.abg9175. Epub ahead of print. PMID: 33766944; PMCID: PMC8139425.

Starr, T.N. et al., "SARS-CoV-2 Rbd antibodies that maximize breadth and resistance to escape," Nature, https://doi.org/10.1038/s41586-021-03807-6; 36 pages (2021).

Stryer, L., Biochemistry, 4th edition, W. H. Freeman and Company, 1995, pp. 18-23.

Sun, B., "Neutralization mechanism of a human antibody with pan-coronavirus reactivity including SARS-CoV-2," Nature Portfolio, Nature Microbiology, Reviewer comments & Editors Decisions, 55 pages, No Date Given.

Sun, D. et al., "Potent neutralizing nanobodies resist convergent circulating variants of SARS-CoV-2 by targeting diverse and conserved epitopes," Nature Communications, vol. 12; 4676; 14 pages (2021).

Sun, X. et al., "Neutralization mechanism of a human antibody with pan-coronavirus reactivity including SARS-CoV-2," Nature Microbiology, vol. 7; 1063-1074 (2022).

Sun, X. et al., "Neutralization mechanism of a human antibody with pan-coronavirus reactivity including SARS-CoV-2," Nature Microbiology, vol. 7; 1063-1074; Supplemental Data (2022).

Tabynov, K. et al., "An adjuvanted subunit SARS-CoV-2 spike protein vaccine provides protection against Covid-19 infection and transmission," npj Vaccines, vol. 7; No. 24; 10 pages (2022).

Tao, K. et al., "The biological and clinical significance of emerging Sars- CoV-2 variants," Nature Reviews Genet., vol. 22; 757-773 (2021).

ter Meulen J et al., Human monoclonal antibody as prophylaxis for SARS coronavirus infection in ferrets. Lancet. Jun. 26, 2004;363(9427):2139-41. doi: 10.1016/S0140-6736(04)16506-9. PMID: 15220038; PMCID: PMC7112500.

ter Meulen, J. et al., "Human Monoclonal Antibody Combination against SARA Coronavirus: Synergy and Coverage of Escape Mutants," PloS; vol. 3; Issue 7; e237; 9 pages (2006).

(56) References Cited

OTHER PUBLICATIONS

Tian, X. et al., "Potent binding of 2019 novel coronavirus spike protein by a SARA coronavirus-specific human monoclonal antibody," Emerging Microbes & Infections, vol. 9; 4 pages (2020).
Tortorici et al. "Broad sarbecovirus neutralization by a human monoclonal antibody", Nature. Sep. 2021;597(7874):103-108. doi: 10.1038/s41586-021-03817-4. Epub Jul. 19, 2021 PMID: 34280951; Suppl. info.
Tortorici, M.A. et al., "Ultrapotent human antibodies protect against SARS-CoV-2 challenge via multiple mechanisms," Science, vol. 370; 950-957 (2020).
Trudeau VL et al., Is secretoneurin a new hormone? Gen Comp Endocrinol. Jan. 1, 2012;175(1):10-8. doi: 10.1016/j.ygcen.2011. 10.008. Epub Oct. 20, 2011. PMID: 22036841.
Turelli, P. et al., "P2G3 human monoclonal antibody neutralizes SARS-CoV-2 Omicron subvariants including BA.4 and BA.5 and Bebtelovimab escape mutants," bioRxiv, 15 pages (2022).
U.S. Department of Health and Human Services, "COVID-19: Developing Drugs and Biological Products for Treatment or Prevention Guidance for Industry," Center for Drug Evaluation and Research (CDER); Center for Biologics Evaluation and Research (CBER); 22 pages (2023).
U.S. Department of Health and Human Services, "Development of Monoclonal Antibody Products Targeting SARS-COV-2 for Emergency Use Authorization Guidance for Industry," Center for Drug Evaluation and Research (CDER); 14 pages (2023).
Ullah, I. et al., "Live imaging of SARS-CoV-2 infection in mice reveals that neutralizing antibodies require Fc function for optimal efficacy," Immunity, vol. 54; 2143-2158; Supplemental Information (2021).
Vajdos et al. (J Mol Biol. Jul. 5, 2002; 320(2):415-28). (Year: 2002).
Van Egerens, D. et al., "Risk of evolutionary escape from neutralizing antibodies targeting SARS-CoV-2 spike protein," medRxiv, https://doi.org/10.1101/2020.11.17.20233726; 28 pages (2020).
Veesler, D. et al., "SARS-CoV-2 S glycoprotein in complex with S2X259 Fab," Worldwide Protein Data Bank, Full wwPDB EM Validation Report; EMBD ID: EMD-24347, PDB ID: 7RA8; 76 pages (2022).
Verstraete, K. et al., "Structure and antagonism of the receptor complex mediated by human TSLP in allergy and asthma," Nature Communications, vol. 8; 14937; 17 pages (2017).
Vir Biotechnology, "Vir Biotechnology Announces Topline Data from Phase 2 Peninsula Trial Evaluating VIR-2482 for thePrevention of Seasonal Infl uenza A Illness," Retrieved from Internet URLhttps://investors.vir.bio/news/news-details/2023/Vir-Biotechnology-Announces-Topline-Data . . . ; 3 pages; Retrieved on Dec. 5, 2023.
Walker KW et al., Pharmacokinetic comparison of a diverse panel of non-targeting human antibodies as matched IgG1 and IgG2 isotypes in rodents and non-human primates. PLoS One. May 23, 2019;14(5):e0217061. doi: 10.1371/journal.pone.0217061. PMID: 31120944; PMCID: PMC6533040.
Walker, L.M. and Burton, D.R., "Passive immunotherapy of viral infections: 'super-antibodies' enter the fray," Nature Reviews, vol. 18; 297-308 (2018).
Walser, M. et al., Highly potent anti-SARS-CoV-2 multi-DARPin therapeutic candidates, bioRxiv, 39 pages (2020).
Wang, C. et al., "A human monoclonal antibody blocking SARS-CoV-2 infection," bioRxiv, 24 pages (2020).
Wang, C. et al., "A human monoclonal antibody blocking SARS-CoV-2 infection," Nature Communications, vol. 11; 2251; 6 pages (2020).
Wang, E.Y. et al., "Diverse functional autoantibodies in patients with COVID-19," Nature, Jul. 2021;595(7866):283-288. doi: 10.1038/s41586-021-03631-y. Epub May 19, 2021. PMID: 34010947.
Wang, N. et al., "Subunit Vaccines Against Emerging Pathogenic Human Coronaviruses," Frontiers in Microbiology, vol. 11; Article 298, 19 pages (2020).
Wang, Q. et al., Alarming antibody evasion properties of rising SARS-CoV-2 BQ and XBB subvariants Cell, vol. 186; 279-286 (2023).
Wang, Z. et al., "Analysis of memory B cells identifies conserved neutralizing epitopes on the N-terminal domain of variant SARS-Cov-2 spike proteins," Immunity, vol. 55; 1-15, 24 pages (2022).
Wang, Z. et al., "Analysis of memory B cells identifies conserved neutralizing epitopes on the N-terminal domain of variant SARS-Cov-2 spike proteins," Immunity, vol. 55; 1-15, 24 pages; Supplemental Information (2022).
Abbasi J., "Researchers Tie Severe Immunosuppression to Chronic COVID-19 and Virus Variants," JAMA, vol. 325; No. 20; 2033-2035 (2021).
Agrawal U et al., Severe COVID-19 outcomes after full vaccination of primary schedule and initial boosters: pooled analysis of national prospective cohort studies of 30 million individuals in England, Northern Ireland, Scotland, and Wales. Lancet. Oct. 15, 2022;400(10360):1305-1320. doi: 10.1016/S0140-6736(22)01656-7. PMID: 36244382; PMCID: PMC9560746.
Al-Lazikani, B. et al., "Standard Conformations for the Canonical Structures of Immunoglobulins," J. Mol. Biol., vol. 273; 927-948 (1997).
Almagro, J.C., "Identification of differences in the specificity-determining residues of antibodies that recognize antigens of different size: implications for the rational design of antibody repertoires," Journal of Molecular Recognition, vol. 17; 132-143 (2004).
Andreano, E. et al., "mRNA vaccines and hybrid immunity use different B cell germlines to neutralize Omicron BA.4 and BA.5," bioRxiv, https://doi.org/10.1101/2022.08.04.502828; 31 pages (2022).
Aschner, C.B. et al., "A multi-specific, multi-affinity antibody platform neutralizes sarbecoviruses and confers protection against SARS-CoV-2 in vivo," Sci. Transl. Med., vol. 15(697); eadf4549, 13 pages (2023).
Australian Government, "Australian Public Assessment Report for Sotrovimab," Proprietary Product Name: Xevudy, Sponsor: GlaxoSmithKline Australia Pty Ltd; 58 pages (2021).
Baden, L.R. and Rubin, E.J., "Covid-19—The Search for Effective Therapy," N Engl J Med, vol. 389; No. 19; 1851-1852 (2020).
Baden, L.R. and Rubin, E.J., "Covid-19—The Search for Effective Therapy," The New England Journal of Medicine, vol. 382; No. 19; 1851-1852 (2020).
Barnes CO et al., SARS-CoV-2 neutralizing antibody structures inform therapeutic strategies. Nature. Dec. 2020;588(7839):682-687. doi: 10.1038/s41586-020-2852-1. Epub Oct. 12, 2020. PMID: 33045718; PMCID: PMC8092461.
Bartsch, Y.C. et al., "Antibody effector functions are associated with protection from respiratory syncytial virus," Cell, vol. 185; 4873-4886 (2022).
Bassetti M et al., Co-localization of secretogranins/chromogranins with thyrotropin and luteinizing hormone in secretory granules of cow anterior pituitary. J Histochem Cytochem. Sep. 1990;38(9):1353-63. doi: 10.1177/38.9.2387987. PMID: 2387987.
Baum A. et al., "REGN-COV2 antibodies prevent and treat SARSCoV-2 infection in rhesus macaques and hamsters," Science, vol. 370; No. 6520; 1110-1115 (2020).
Baum, A. et al., "Antibody cocktail to SARS-CoV-2 spike protein prevents rapid mutational escape seen with individual antibodies," Science, vol. 369; 1014-1018 (2020).
Bedouelle et al. (FEBS J. Jan. 2006; 273(1):34-46). (Year: 2006).
Bender Ignacio RA et al., Comparative Pharmacokinetics of Tixagevimab/Cilgavimab (AZD7442) Administered Intravenously Versus Intramuscularly in Symptomatic SARS-CoV-2 Infection. Clin Pharmacol Ther. Dec. 2022;112(6):1207-1213. doi: 10.1002/cpt.2706. Epub Jul. 26, 2022. PMID: 35797235; PMCID: PMC9349574.
Boggiano, C. et al., "Update on and Future Directions for Use of Anti-SARS-CoV-2 Antibodies: National Institutes of Health Summit on Treatment and Prevention of COVID-19," Ann Intern Med, 9 pages (2021).
Böttcher E et al. Proteolytic activation of influenza viruses by serine proteases TMPRSS2 and HAT from human airway epithelium. J Virol. Oct. 2006;80(19):9896-8. doi: 10.1128/JVI.01118-06. PMID: 16973594; PMCID: PMC1617224.
Bournazos S et al., Broadly neutralizing anti-HIV-1 antibodies require Fc effector functions for in vivo activity. Cell. Sep. 11, 2014;158(6):1243-1253. doi: 10.1016/j.cell.2014.08.023. PMID: 25215485; PMCID: PMC4167398.

(56) References Cited

OTHER PUBLICATIONS

Brown et al. (J Immunol. May 1, 1996; 156(9):3285-91). (Year: 1996).
Bruel, T., "Evidence in support of the use of serum neutralisation data to justify a dose increase of monoclonal antibodies to tackle new variants," EMA/FDA joint meeting, Institut Pasteur, Virus and Immunity Unit, Olivier Schwartz's Lab, 15 pages (2022).
Bulun, S.E., "Reproductive Physiology," Physiology and Pathology of the Female Reproductive Axis, Chapter 17; pp. 590-663; Williams Textbook of Endocrinology, Fourteenth Edition (2020).
Burnett, D.L. et al., "Immunizations with diverse sarbecovirus receptor-binding domains elicit SARS-CoV-2 neutralizing antibodies against a conserved site of vulnerability," Immunity, vol. 54(12); 2908-2921 (2021).
Cao Z et al., VV116 versus Nirmatrelvir-Ritonavir for Oral Treatment of Covid-19. N Engl J Med. Feb. 2, 2023;388(5):406-417. doi: 10.1056/NEJMoa2208822. Epub Dec. 28, 2022. PMID: 36577095; PMCID: PMC9812289.
Cao Z et al., VV116 versus Nirmatrelvir-Ritonavir for Oral Treatment of Covid-19. N Engl J Med. Feb. 2, 2023;388(5):406-417. doi: 10.1056/NEJMoa2208822. Epub Dec. 28, 2022. PMID: 36577095; PMCID: PMC9812289; Supplemental Information.
Cao Z et al., VV116 versus Nirmatrelvir-Ritonavir for Oral Treatment of Covid-19. N Engl J Med. Feb. 2, 2023;388(5):406-417. doi: 10.1056/NEJMoa2208822. Epub Dec. 28, 2022. PMID: 36577095; PMCID: PMC9812289; The Protocol.
Cao, Y. et al., "B.1.1.529 escapes the majority of SARS-CoV-2 neutralizing antibodies of diverse epitopes," bioRxiv, 30 pages (2021).
Cao, Y. et al., "BA.2.12.1, BA.4 and BA.5 escape antibodies elicited by Omicron infection," Nature, vol. 608(7923); 593-602 (2022).
Cao, Y. et al., "Imprinted SARS-CoV-2 humoral immunity induces convergent Omicron RBD evolution," bioRxiv, 38 pages (2022).
Cao, Y. et al., "Omicron BA.2 specifically evades broad sarbecovirus neutralizing antibodies," bioRxiv, 39 pages (2022).
Case JB et al., Neutralizing Antibody and Soluble ACE2 Inhibition of a Replication-Competent VSV-SARS-CoV-2 and a Clinical Isolate of SARS-CoV-2. Cell Host Microbe. Sep. 9, 2020;28(3):475-485.e5. doi: 10.1016/j.chom.2020.06.021. Epub Jul. 3, 2020. PMID: 32735849; PMCID: PMC7332453.
Case JB et al., Resilience of S309 and AZD7442 monoclonal antibody treatments against infection by SARS-CoV-2 Omicron lineage strains. Nat Commun. Jul. 2, 2022;13(1):3824. doi: 10.1038/s41467-022-31615-7. PMID: 35780162; PMCID: PMC9250508.
Case, B., "Development of a Pan-Sarbecovirus Mucosal Vaccine," Instructor in Medicine Washington University School of Medicine IDWeek: Next Generation COVID-19 Vaccines, Boston, MA, 16 pages (2023).
Cathcart A.L. et al., "The dual function monoclonal antibodies VIR-7831 and VIR-7832 demonstrate potent in vitro and in vivo activity against SARS-CoV-2," BioRxiv, https://doi.org/10.1101/2021.03.09.434607 (2022).
Centers for Disease Control and Prevention website. COVID-19 vaccines for people who are moderately or severely immunocompromised. Updated Jan. 31, 2023. Accessed Feb. 17, 2023. https://www.cdc.gov/coronavirus/2019-ncov/vaccines/recommendations/immuno.html.
Cerutti, G. et al., "Structural basis for accommodation of emerging B.1.351 and B.1.1.7 variants by two potent SARSCoV-2 neutralizing antibodies," Structure, vol. 29(7); 655-663 (2021).
Chan, J.F. et al., "Simulation of the Clinical and Pathological Manifestations of Coronavirus Disease 2019 (COVID-19) in a Golden Syrian Hamster Model: Implications for Disease Pathogenesis and Transmissibility," Clin Infect Dis., vol. 71; No. 9; 2428-2446 (2020).
Chan, K.K. et al., "Engineering human ACE2 to optimize binding to the spike protein of SARS coronavirus 2," Science. Sep. 4, 2020;369(6508):1261-1265. doi: 10.1126/science.abc0870. Epub Aug. 4, 2020. PMID: 32753553; PMCID: PMC7574912.
Chen, J. et al., "Review of COVID-19 Antibody Therapies," Cornell University Library, New York, 30 pages (2020).
Chen, P. et al., "First-in-Human Study of Bamlanivimab in a Randomized Trial of Hospitalized Patients With COVID-19," Clinical Pharmacology & Therapeutics, vol. 110; No. 6; 1467-1477 (2021).
Chigutsa, E. et al., "A Quantitative Modeling and Simulation Framework to Support Candidate and Dose Selection of Anti-SARS-CoV-2 Monoclonal Antibodies to Advance Bamlanivimab Into a First-in-Human Clinical Trial," Clinical Pharmacology & Therapeutics, vol. 111; No. 3; 595-604 (2022).
Chigutsa, E. et al., "Population Pharmacokinetics and Pharmacodynamics of the Neutralizing Antibodies Bamlanivimab and Etesevimab in Patients With Mild to Moderate COVID-19 Infection," Clinical Pharmacology & Therapeutics, vol. 110; No. 5; 1302-1310 (2021).
Chothia, C. and Lesk, A.M., "Canonical Structures for the Hypervariable Regions of Immunoglobulins," J. Mol. Biol., vol. 196; 901-917 (1987).
Chothia, C. et al., "Conformations of immunoglobulin hypervariable regions," Nature, vol. 342; 877-883 (1989).
Choy, R.K.M. et al., "Controlled Human Infection Models To Accelerate Vaccine Development," Clinical Microbiology Reviews, vol. 35; Issue 3; 163 pages (2022).
Colman (Research in Immunology, 145:33-36, 1994). (Year: 1994).
Copin, R. et al., "The monoclonal antibody combination REGEN-COV protects against SARS-CoV-2 mutational escape in preclinical and human studies," Cell, vol. 184(15); 3949-3961 (2021).
Corbett, K.S. et al., "Immune Correlates of Protection by mRNA-1273 Vaccine against SARS-CoV-2 in Nonhuman Primates," Science, vol. 373; No. 6561; eabj0299; 23 pages (2021).
Correa Giron, C. et al., "On the interactions of the receptor-binding domain of SARS-CoV-1 and SARS-CoV-2 spike proteins with monoclonal antibodies and the receptor ACE2," Virus Research, vol. 285; 198021; 13 pages (2020).

\* cited by examiner

MFVFLVLLPLVSSQCVNLTTRTQLPPAYTNSFTRGVYYPDKVFRSSVLHSTQDLFLPFFSNVTWFHAIHVSGTNGTKR
FDNPVLPFNDGVYFASTEKSNIIRGWIFGTTLDSKTQSLLIVNNATNVVIKVCEFQFCNDPFLGVYYHKNNKSWMESE
FRVYSSANNCTFEYVSQPFLMDLEGKQGNFKNLREFVFKNIDGYFKIYSKHTPINLVRDLPQGFSALEPLVDLPIGIN
ITRFQTLLALHRSYLTPGDSSSGWTAGAAAYYVGYLQPRTFLLKYNENGTITDAVDCALDPLSETKCTLKSFTVEKGI
YQTSNFRVQPTESIVRFPNITNLCPFGEVFNATRFASVYAWNRKRISNCVADYSVLYNSASFSTFKCYGVSPTKLNDL
CFTNVYADSFVIRGDEVRQIAPGQTGKIADYNYKLPDDFTGCVIAWNSNNLDSKVGGNYNYLYRLFRKSNLKPFERDI
STEIYQAGSTPCNGVEGFNCYFPLQSYGFQPTNGVGYQPYRVVVLSFELLHAPATVCGPKKSTNLVKNKCVNFNFNGL
TGTGVLTESNKKFLPFQQFGRDIADTTDAVRDPQTLEILDITPCSFGGVSVITPGTNTSNQVAVLYQDVNCTEVPVAI
HADQLTPTWRVYSTGSNVFQTRAGCLIGAEHVNNSYECDIPIGAGICASYQTQTNSPRRARSVASQSIIAYTMSLGAE
NSVAYSNNSIAIPTNFTISVTTEILPVSMTKTSVDCTMYICGDSTECSNLLLQYGSFCTQLNRALTGIAVEQDKNTQE
VFAQVKQIYKTPPIKDFGGFNFSQILPDPSKPSKRSFIEDLLFNKVTLADAGFIKQYGDCLGDIAARDLICAQKFNGL
TVLPPLLTDEMIAQYTSALLAGTITSGWTFGAGAALQIPFAMQMAYRFNGIGVTQNVLYENQKLIANQFNSAIGKIQD
SLSSTASALGKLQDVVNQNAQALNTLVKQLSSNFGAISSVLNDILSRLDKVEAEVQIDRLITGRLQSLQTYVTQQLIR
AAEIRASANLAATKMSECVLGQSKRVDFCGKGYHLMSFPQSAPHGVVFLHVTYVPAQEKNFTTAPAICHDGKAHFPRE
GVFVSNGTHWFVTQRNFYEPQIITTDNTFVSGNCDVVIGIVNNTVYDPLQPELDSFKEELDKYFKNHTSPDVDLGDIS
GINASVVNIQKEIDRLNEVAKNLNESLIDLQELGKYEQYIKWPWYIWLGFIAGLIAIVMVTIMLCCMTSCCSCLKGCC
SCGSCCKFDEDDSEPVLKGVKLHYT (SEQ ID NO:1)

FIG. 1

```
                    HCDR1                                              HCDR2
            *****                                       *  *  *
Reference EVQLVESGAEVKKPGESLKISCKGSGYTFTRYWIGWVRQMPGKGLEWMGIIYPGDSDTRYSPSFQGHV
AB-1      EVQLVESGAEVKKPGESLKISCKGSGYTFTRYWIGWVRQMPGKGLEWMGIIYPGDSDVRYSPSFQGHV
                                                              NEV
                                                              A
                                                              R
                                                              L
                                                              F HCDR3
             *                      *****           * *
Reference TISADKSISTAYLQWNSLKASDTAMYYCARLPQYCSNGVCQRWFDPWGQGTLVTVSS (SEQ ID NO:3)
AB-1      TISADKSISTAYLQWNSLKASDTAMYYCARLPQYCSKGVCYRWFDPWGQGTLVTVSS (SEQ ID NO:4)
          V                         QKNI Y
                                    RALS K
                                    KS K F
                                    YR   H
                                    DE
                                    E
```

FIG. 2

```
              LCDR1                                    LCDR2
Reference  EIVLTQSPSSVSASVGDRVTITCRASQGISSWLAWYQQKPGKAPKLLIYAASSLQSGVPSRFSGSGSG
AB-1       EIVLTQSPSSVSASVGDRVTITCRASQGISSWLAWYQQKPGKAPKLLIYAASSLQSGVPSRFSGSGSG
                                          KS  RN
                                          I   V
```

```
              LCDR3
Reference  TDFTLTISSLQPEDFATYYCQQGNSFPYTFGQGTNLEIK (SEQ ID NO:50)
AB-1       TDFTLTISSLQPEDFATYYCQQGHSFPYTFGQGTNLEIK (SEQ ID NO:51)
                                 HQY L
                                 D   L
                                 Y   V
                                 S   T
                                     D
```

VS-330 Top Hits - Metrics Table - Binding & Potency

| rank | protein | sample_type_2 | distance_from_reference | composite_neutralization_score | composite_binding_score | neut_delta_lenti_luminescence_3 | neut_omicron_ba-2_lenti_luminescence_3 |
|---|---|---|---|---|---|---|---|
| 1 | AB-13 | design | 5 | 0.98 | 0.19 | 97.61 | 98.40 |
| 2 | AB-18 | design | 7 | 0.95 | 0.17 | 96.59 | 97.29 |
| 3 | AB-14 | design | 1 | 0.90 | 0.25 | 90.04 | 98.67 |
| 4 | AB-12 | design | 3 | 0.90 | 0.16 | 94.73 | 93.31 |
| 5 | AB-19 | design | 5 | 0.90 | 0.21 | 93.20 | 94.78 |
| 6 | AB-5 | design | 5 | 0.90 | | 91.15 | 96.69 |
| 7 | AB-3 | design | 9 | 0.88 | 0.14 | 94.21 | 91.83 |
| 8 | AB-20 | design | 5 | 0.88 | 0.22 | 90.74 | 95.16 |
| 9 | AB-8 | design | 10 | 0.86 | 0.22 | 87.07 | 97.47 |
| 10 | AB-1 | cmc_lead | 4 | 0.86 | 0.21 | 92.71 | 91.28 |
| 11 | AB-17 | cmc_lead | 8 | 0.86 | 0.15 | 90.46 | 93.55 |
| 12 | AB-6 | design | 10 | 0.86 | 0.17 | 92.13 | 91.84 |
| 13 | AB-2 | design | 8 | 0.85 | 0.15 | 85.65 | 98.23 |
| 14 | AB-15 | cmc_lead | 5 | 0.83 | 0.23 | 96.37 | 85.07 |
| 15 | AB-11 | design | 4 | 0.83 | 0.14 | 89.31 | 91.49 |
| 16 | AB-4 | design | 5 | 0.82 | 0.17 | 91.62 | 88.51 |
| 17 | AB-10 | design | 4 | 0.82 | 0.21 | 83.55 | 96.48 |
| 18 | AB-7 | design | 2 | 0.81 | 0.25 | 82.35 | 97.22 |
| 19 | AB-9 | design | 8 | 0.80 | 0.20 | 92.29 | 85.03 |
| 20 | AB-16 | design | 7 | 0.80 | 0.18 | 93.06 | 84.32 |
| 128 | Clinical-stage Control | | | 0.35 | 0.25 | 98.52 | 34.89 |
| 143 | Reference | | | 0.27 | 0.17 | 64.84 | 41.62 |

FIG. 6A

VS-330 Top Hits - Metrics Table - Developability

| rank | protein | sample_type_2 | distance_from_reference | acsins | sec | psr_dna | pI | lm_score | lm_score_t1_0 | lm_score_t1_1 | n_paratope_mutations | exp_flag |
|---|---|---|---|---|---|---|---|---|---|---|---|---|
| 1 | AB-13 | design | 5 | 20.21 | 89.40 | 3.88 | 8.54 | 2 | 0 | 0 | 0 | ok |
| 2 | AB-18 | design | 7 | 22.56 | 99.08 | 3.54 | 8.54 | 4 | 0 | 0 | 0 | ok |
| 3 | AB-14 | design | 1 | 23.76 | 99.80 | 2.43 | 8.46 | 3 | 1 | 0 | 0 | ok |
| 4 | AB-12 | design | 3 | 21.27 | | 1.32 | 8.54 | 2 | 0 | 0 | 0 | ok |
| 5 | AB-19 | design | 5 | 21.20 | | 2.19 | 8.53 | 2 | 0 | 1 | 1 | ok |
| 6 | AB-5 | design | 5 | 21.62 | 100.00 | 12.78 | 8.46 | 2 | 1 | 0 | 0 | ok |
| 7 | AB-3 | design | 9 | 21.38 | 92.06 | 4.34 | 8.53 | 2 | 0 | 0 | 0 | ok |
| 8 | AB-20 | design | 5 | 19.24 | 97.84 | 1.73 | 8.54 | 2 | 1 | 0 | 1 | ok |
| 9 | AB-8 | design | 10 | 23.83 | 99.26 | 2.80 | 8.46 | 2 | 0 | 0 | 0 | ok |
| 10 | AB-1 | cmc_lead | 4 | 23.69 | 99.11 | 1.12 | 8.46 | 2 | 1 | 0 | 0 | ok |
| 11 | AB-17 | cmc_lead | 8 | 24.42 | 98.87 | 12.21 | 8.60 | 2 | 0 | 0 | 0 | ok |
| 12 | AB-6 | design | 10 | 18.31 | | 10.47 | 8.60 | 2 | 1 | 0 | 0 | ok |
| 13 | AB-2 | design | 8 | 22.79 | 99.16 | 3.51 | 8.46 | 3 | 0 | 0 | 0 | ok |
| 14 | AB-15 | cmc_lead | 5 | 22.85 | 99.43 | 1.93 | 8.46 | 2 | 0 | 0 | 0 | ok |
| 15 | AB-11 | design | 4 | 18.31 | 98.79 | 1.71 | 8.54 | 3 | 1 | 0 | 0 | ok |
| 16 | AB-4 | design | 5 | 19.88 | 82.42 | 1.39 | 8.53 | 3 | 0 | 0 | 0 | ok |
| 17 | AB-10 | design | 4 | 20.71 | 99.48 | 3.35 | 8.37 | 2 | 1 | 0 | 0 | ok |
| 18 | AB-7 | design | 2 | 22.83 | 97.31 | 4.54 | 8.46 | 3 | 0 | 0 | 0 | ok |
| 19 | AB-9 | design | 8 | 21.33 | 98.35 | 3.29 | 8.46 | 2 | 1 | 0 | 0 | ok |
| 20 | AB-16 | design | 7 | 20.49 | 97.48 | 4.33 | 8.54 | 3 | 0 | 0 | | ok |
| 128 | Clinical-stage Control | | | | | | | | | | | |
| 143 | Reference | | 0 | 16.32 | 99.57 | 0.85 | 8.37 | 3 | 1 | 0 | 0 | ok |

FIG. 6B

| Variant PRO-ID | Molecular or Bioanalytical Property ||||| Response to Stress |||||
|---|---|---|---|---|---|---|---|---|---|---|
| | Tm1 (°C)[1] | PSR-DNA (DELFIA Value)[2] | PSR-Insulin (DELFIA Value)[3] | ACSINS (λ shift, nm)[4] | CHOCell Extract Binding (ZScore)[5] | F/T (5 cycles) || Low pH (pH 3.5 up to 2 hrs) |||
| | | | | | | Δ% SEC Mono[6] | Δ% HIC Main[7] | Δ% SEC Mono[8] | Δ% HIC[a] Main[9] | Δ% CIEF Main[10] |
| AB-17 | 66.8 ± 0.2 | 1,300 ± 100 | 1,580 ± 99 | 15.9 ± 0.8 | +2.2 | 0 | +1.9 | 0 ± 0 | -2.7 | -2.2 |
| AB-15 | 66.7 ± 0.07 | 160 ± 50 | 290 ± 60 | 19 ± 1 | -0.60 | 0 | -4 ± 2 | 0 ± 0 | +0 ± 2 | +3 ± 3 |
| AB-1 | 66.8 ± 0.07 | 80 ± 50 | 55 ± 20 | 13.6 ± 0.5 | -0.49 | 0 ± 0 | -1.1 ± 0.7 | 0 ± 0 | +1.1 | +4 ± 2 |

Benchmark comparison Ranges (in order from left to right: acceptable, may be acceptable, outside acceptable range)
1. Tm1: >60 °C; 50-60 °C; <50°C
2. DNA score: <score of 350; -350~550; >550
3. Insulin score: <score of 210; 210~260; >260
4. λshift <10 nm; 10~15 nm; >15 nm
5. Z-score is relative to sample set tested; color designation based on Z score distance from clinical benchmark
6-10. Δ% >-5%; -5~-10%; <-10%
Ranges, based on TSLP developability studies where appropriate, are arbitrary and separated at least by averaged std errors or SDs a. Method optimization ongoing
Error bars are standard deviations for at least duplicates where available

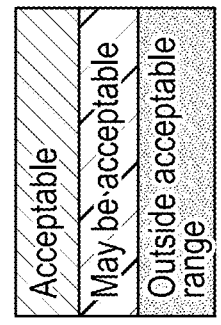

Acceptable
May be acceptable
Outside acceptable range

FIG. 12

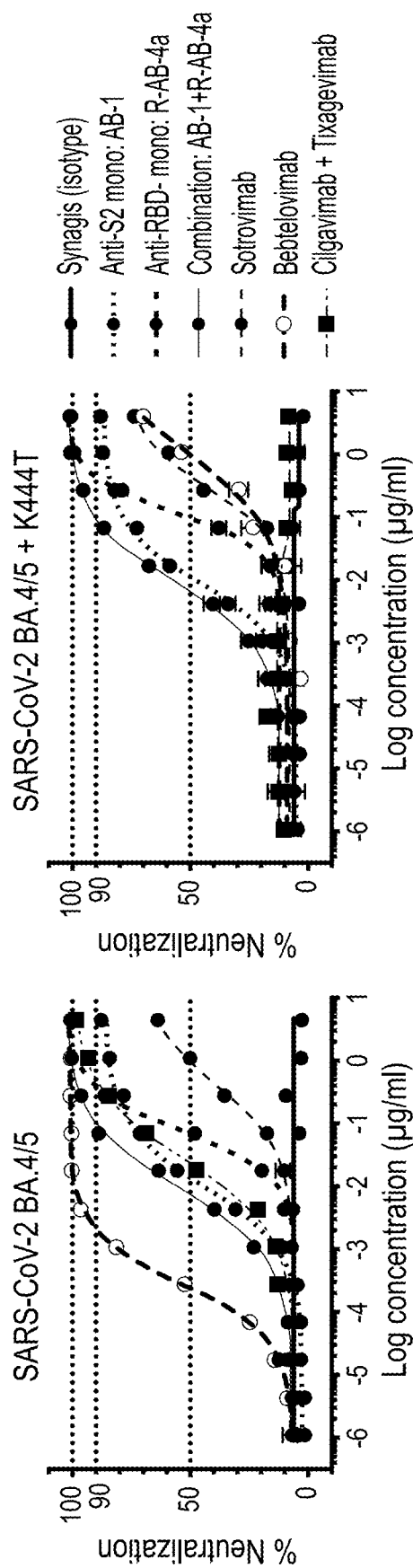

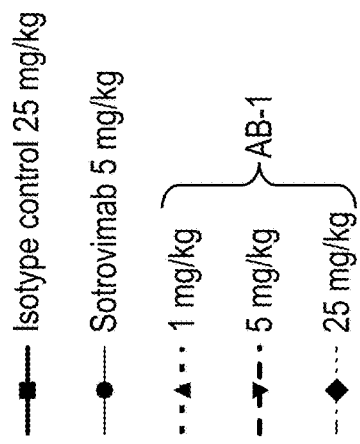
FIG. 15A
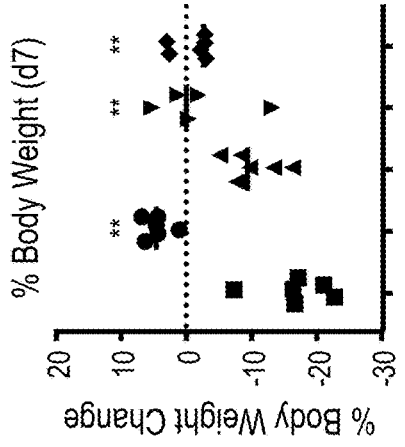
FIG. 15B
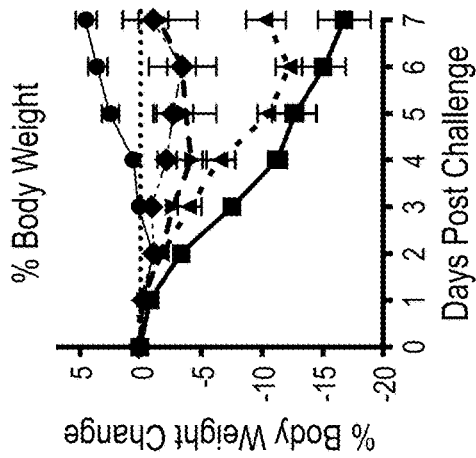
FIG. 15C
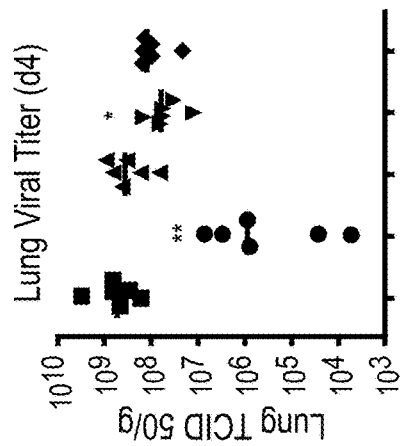
FIG. 15D
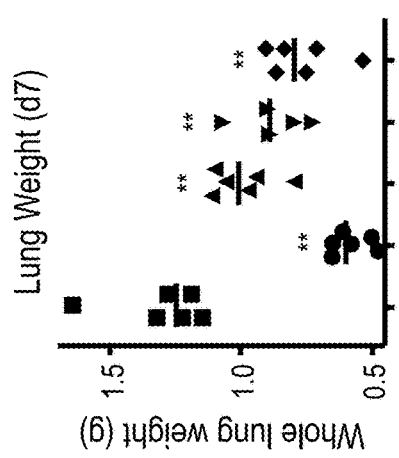

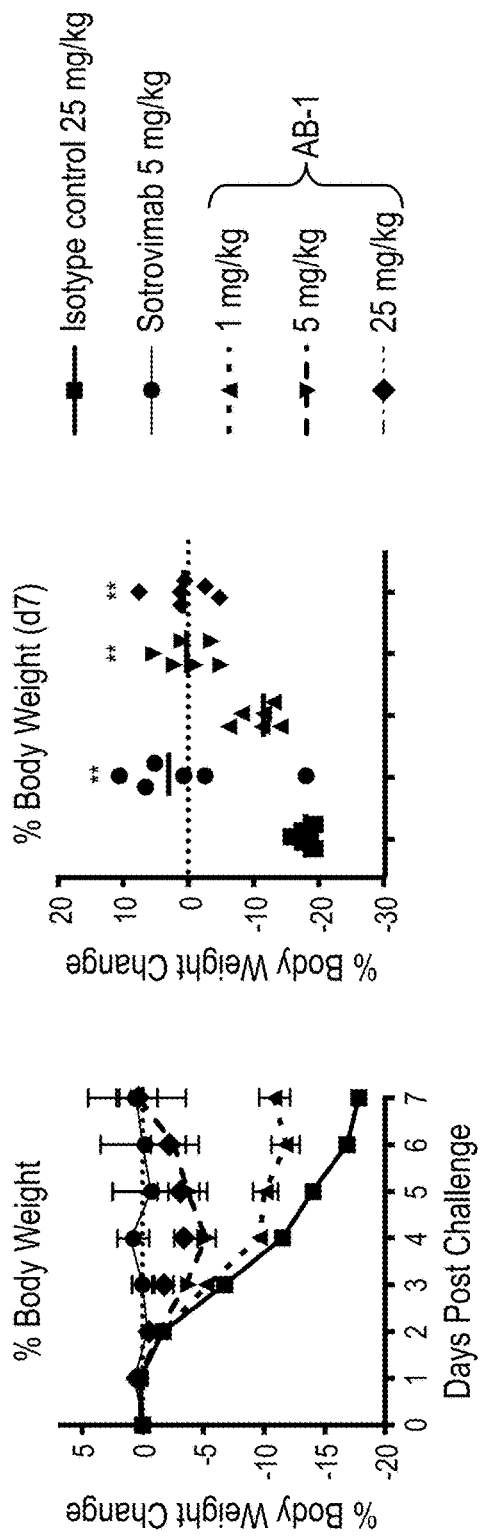
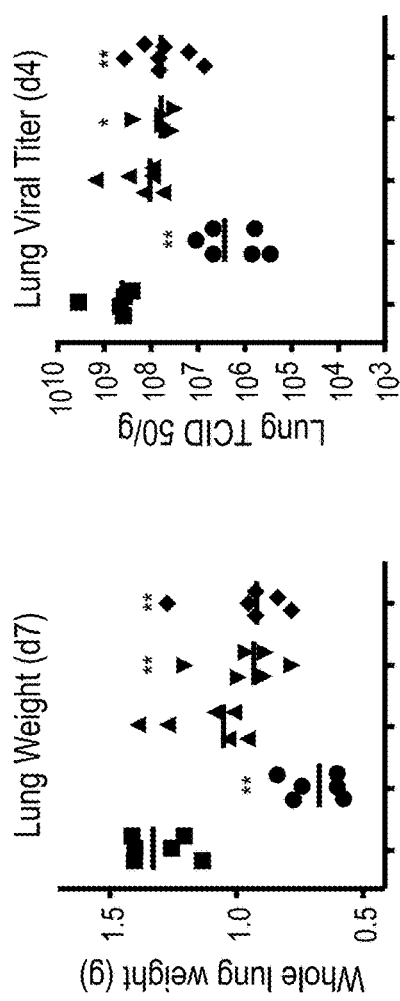
FIG. 15E
FIG. 15F
FIG. 15G
FIG. 15H

FIG. 17A

| [ng/ml] | AB-1 | R-AB-3a | AB-1 + R-AB-3a | EC50 (95% CI) AB-1 + Sotrovimab | AB-1 + Bebtelovimab | AB-1 + P2G3 | AB-1 + AZD1061 |
|---|---|---|---|---|---|---|---|
| BQ.1.1 | 25.8 (18.1, 37.6) | 400.5 (332.9, 488.7) | 11.0 (7.8, 15.5) | 13.1 (8.8, 19.5) | 6.5 (4.2, 9.8) | 12.0 (8.6, 16.8) | 16.2 (11.0, 24.0) |

≤ 200 ng/ml  200 - 1000 ng/ml  ≥ 1000 ng/ml

| [ng/ml] | AB-1 | R-AB-3a | AB-1 + R-AB-3a | % Median neutralization at 18 µg/ml (95% CI) AB-1 + Sotrovimab | AB-1 + Bebtelovimab | AB-1 + P2G3 | AB-1 + AZD1061 |
|---|---|---|---|---|---|---|---|
| BQ.1.1 | 92.6 (88.5, 95.1) | 100.0 (99.9, 100.1) | 99.9 (99.7, 99.9) | 96.4 (92.4, 99.3) | 96.0 (90.8, 97.4) | 93.1 (88.7, 97.7) | 92.1 (87.7, 94.8) |

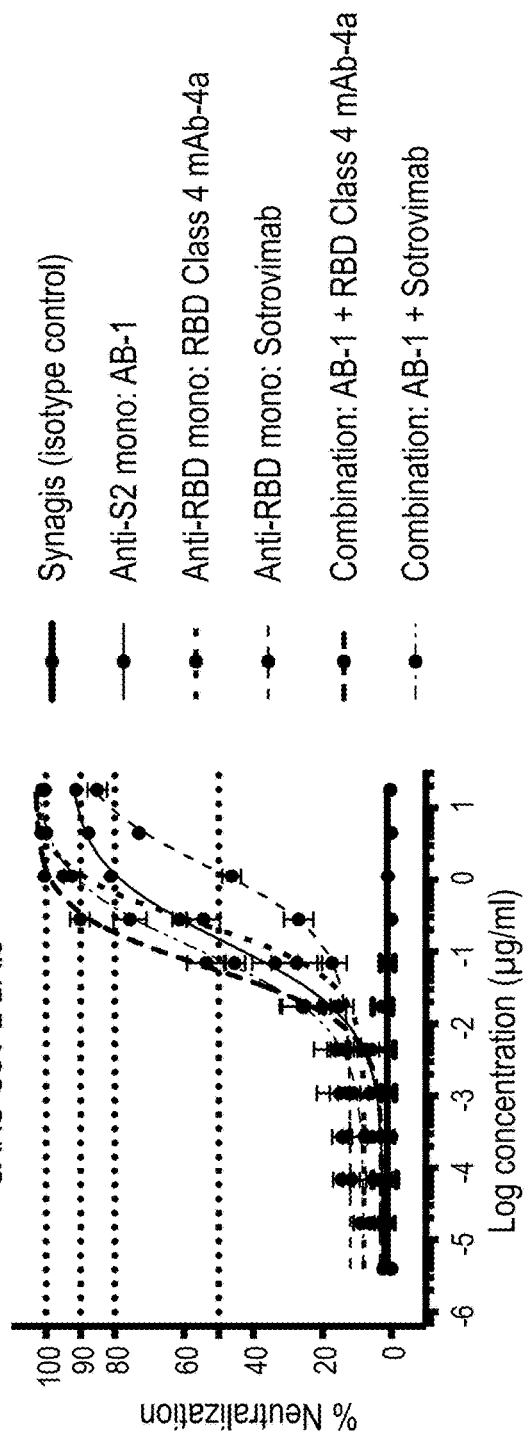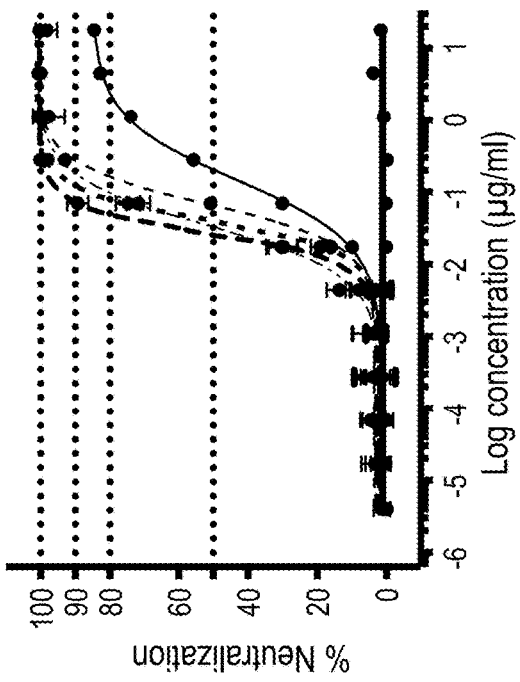
FIG. 18A
FIG. 18B

| [ng/ml] | AB-1 | R-AB-4a | Sotrovimab | AB-1 + R-AB-4a | AB-1 + Sotrovimab |
|---|---|---|---|---|---|
| Delta | 148.1 (127.9, 172.2) | 40.6 (37.7, 43.8) | 69.3 (63.4, 75.7) | 27.0 (24.8, 29.5) | 34.5 (30.8, 38.6) |
| BA.5 | 135.5 (107.8, 172.8) | 251.8 (195.2, 324.1) | 1554 (1023, 3551) | 61.0 (51.8, 71.7) | 105.7 (82.6, 137.0) |

EC50 (95% CI)

| [ng/ml] | AB-1 | R-AB-4a | Sotrovimab | AB-1 + R-AB-4 | AB-1 + Sotrovimab |
|---|---|---|---|---|---|
| Delta | 84.4 (83.8, 85.8) | 100.5 (100.3, 100.6) | 100.5 (100.2, 100.7) | 100.2 (100.0, 100.2) | 99.9 (94.7, 100.4) |
| BA.5 | 91.2 (89.9, 93.1) | 100.6 (100.1, 100.6) | 85.3 (82.2, 87.9) | 101.3 (100.9, 101.6) | 100.8 (100.3, 101.0) |

% Median neutralization at 18 μg/ml (95% CI)

FIG. 18C

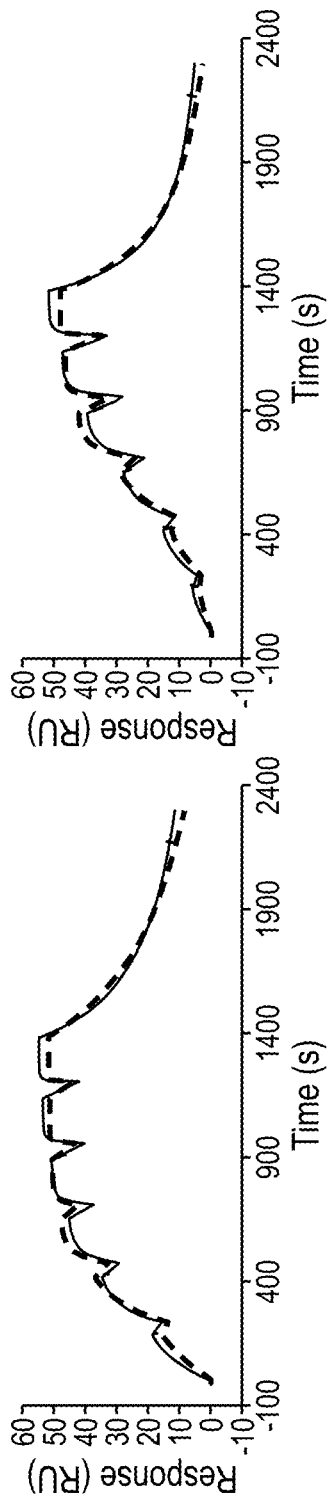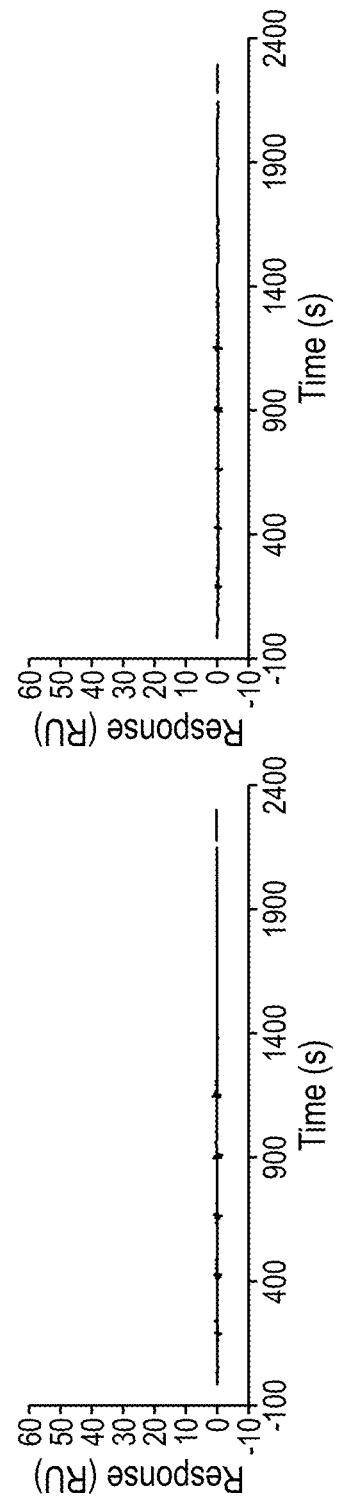
FIG. 23A  FIG. 23B  FIG. 23C  FIG. 23D

SEQUENCE LISTING

```
Sequence total quantity: 214
SEQ ID NO: 1            moltype = AA  length = 1273
FEATURE                 Location/Qualifiers
REGION                  1..1273
                        note = SARS-CoV-2
source                  1..1273
                        mol_type = protein
                        organism = synthetic construct
SEQUENCE: 1
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
```

```
SVTTEILPVS MTKTSVDCTM YICGDSTECS NLLLQYGSFC TQLNRALTGI AVEQDKNTQE    780
VFAQVKQIYK TPPIKDFGGF NFSQILPDPS KPSKRSFIED LLFNKVTLAD AGFIKQYGDC    840
LGDIAARDLI CAQKFNGLTV LPPLLTDEMI AQYTSALLAG TITSGWTFGA GAALQIPFAM    900
QMAYRFNGIG VTQNVLYENQ KLIANQFNSA IGKIQDSLSS TASALGKLQD VVNQNAQALN    960
TLVKQLSSNF GAISSVLNDI LSRLDKVEAE VQIDRLITGR LQSLQTYVTQ QLIRAAEIRA   1020
SANLAATKMS ECVLGQSKRV DFCGKGYHLM SFPQSAPHGV VFLHVTYVPA QEKNFTTAPA   1080
ICHDGKAHFP REGVFVSNGT HWFVTQRNFY EPQIITTDNT FVSGNCDVVI GIVNNTVYDP   1140
LQPELDSFKE ELDKYFKNHT SPDVDLGDIS GINASVVNIQ KEIDRLNEVA KNLNESLIDL   1200
QELGKYEQYI KWPWYIWLGF IAGLIAIVMV TIMLCCMTSC CSCLKGCCSC GSCCKFDEDD   1260
SEPVLKGVKL HYT                                                     1273

SEQ ID NO: 2           moltype = AA  length = 125
FEATURE                Location/Qualifiers
REGION                 1..125
                       note = asdf
REGION                 56..58
                       note = misc_feature - Xaa can be any naturally occurring
                        amino acid
SITE                   99
                       note = misc_feature - Xaa can be any naturally occurring
                        amino acid
REGION                 104..107
                       note = misc_feature - Xaa can be any naturally occurring
                        amino acid
SITE                   109
                       note = misc_feature - Xaa can be any naturally occurring
                        amino acid
source                 1..125
                       mol_type = protein
                       organism = synthetic construct
SEQUENCE: 2
EVQLVESGAE VKKPGESLKI SCKGSGYTFT RYWIGWVRQM PGKGLEWMGI IYPGDXXXRY     60
SPSFQGHVTI SADKSISTAY LQWNSLKASD TAMYYCARXP QYCXXXXCXR WFDPWGQGTL    120
VTVSS                                                                125

SEQ ID NO: 3           moltype = AA  length = 125
FEATURE                Location/Qualifiers
REGION                 1..125
                       note = antibody heavy chain variable region
source                 1..125
                       mol_type = protein
                       organism = synthetic construct
SEQUENCE: 3
EVQLVESGAE VKKPGESLKI SCKGSGYTFT RYWIGWVRQM PGKGLEWMGI IYPGDSDTRY     60
SPSFQGHVTI SADKSISTAY LQWNSLKASD TAMYYCARLP QYCSNGVCQR WFDPWGQGTL    120
VTVSS                                                                125

SEQ ID NO: 4           moltype = AA  length = 125
FEATURE                Location/Qualifiers
REGION                 1..125
                       note = antibody heavy chain variable region
source                 1..125
                       mol_type = protein
                       organism = synthetic construct
SEQUENCE: 4
EVQLVESGAE VKKPGESLKI SCKGSGYTFT RYWIGWVRQM PGKGLEWMGI IYPGDSDVRY     60
SPSFQGHVTI SADKSISTAY LQWNSLKASD TAMYYCARLP QYCSKGVCYR WFDPWGQGTL    120
VTVSS                                                                125

SEQ ID NO: 5           moltype = AA  length = 125
FEATURE                Location/Qualifiers
REGION                 1..125
                       note = antibody heavy chain variable region
source                 1..125
                       mol_type = protein
                       organism = synthetic construct
SEQUENCE: 5
EVQLVESGAE VKKPGESLKI SCKGSGYTFT RYWIGWVRQM PGKGLEWMGI IYPGDSDTRY     60
SPSFQGHVTI SADKSISTAY LQWNSLKASD TAMYYCARLP QYCQNGICKR WFDPWGQGTL    120
VTVSS                                                                125

SEQ ID NO: 6           moltype = AA  length = 125
FEATURE                Location/Qualifiers
REGION                 1..125
                       note = antibody heavy chain variable region
source                 1..125
                       mol_type = protein
                       organism = synthetic construct
SEQUENCE: 6
```

```
EVQLVESGAE VKKPGESLKI SCKGSGYTFT RYWIGWVRQM PGKGLEWMGI IYPGDNDVRY    60
SPSFQGHVTI SADKSISTAY LQWNSLKASD TAMYYCARLP QYCRKGICKR WFDPWGQGTL   120
VTVSS                                                              125

SEQ ID NO: 7            moltype = AA   length = 125
FEATURE                 Location/Qualifiers
REGION                  1..125
                        note = antibody heavy chain variable region
source                  1..125
                        mol_type = protein
                        organism = synthetic construct
SEQUENCE: 7
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCRNGVCYR WFDPWGQGTL   120
VTVSS                                                              125

SEQ ID NO: 8            moltype = AA   length = 125
FEATURE                 Location/Qualifiers
REGION                  1..125
                        note = antibody heavy chain variable region
source                  1..125
                        mol_type = protein
                        organism = synthetic construct
SEQUENCE: 8
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCRANVCFR WFDPWGQGTL   120
VTVSS                                                              125

SEQ ID NO: 9            moltype = AA   length = 125
FEATURE                 Location/Qualifiers
REGION                  1..125
                        note = antibody heavy chain variable region
source                  1..125
                        mol_type = protein
                        organism = synthetic construct
SEQUENCE: 9
EVQLVESGAE VKKPGESLKI SCKGSGYTFT RYWIGWVRQM PGKGLEWMGI IYPGDSDVRY    60
SPSFQGHVTI SADKSISTAY LQWNSLKASD TAMYYCARLP QYCKKLICKR WFDPWGQGTL   120
VTVSS                                                              125

SEQ ID NO: 10           moltype = AA   length = 125
FEATURE                 Location/Qualifiers
REGION                  1..125
                        note = antibody heavy chain variable region
source                  1..125
                        mol_type = protein
                        organism = synthetic construct
SEQUENCE: 10
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCRNGVCQR WFDPWGQGTL   120
VTVSS                                                              125

SEQ ID NO: 11           moltype = AA   length = 125
FEATURE                 Location/Qualifiers
REGION                  1..125
                        note = antibody heavy chain variable region
source                  1..125
                        mol_type = protein
                        organism = synthetic construct
SEQUENCE: 11
EVQLVESGAE VKKPGESLKI SCKGSGYTFT RYWIGWVRQM PGKGLEWMGI IYPGDNDVRY    60
SPSFQGHVTI SADKSISTAY LQWNSLKASD TAMYYCARLP QYCSAGSCFR WFDPWGQGTL   120
VTVSS                                                              125

SEQ ID NO: 12           moltype = AA   length = 125
FEATURE                 Location/Qualifiers
REGION                  1..125
                        note = antibody heavy chain variable region
source                  1..125
                        mol_type = protein
                        organism = synthetic construct
SEQUENCE: 12
EVQLVESGAE VKKPGESLKI SCKGSGYTFT RYWIGWVRQM PGKGLEWMGI IYPGDNDVRY    60
SPSFQGHVTI SADKSISTAY LQWNSLKASD TAMYYCARLP QYCRSGICKR WFDPWGQGTL   120
VTVSS                                                              125

SEQ ID NO: 13           moltype = AA   length = 125
FEATURE                 Location/Qualifiers
REGION                  1..125
```

```
                         note = antibody heavy chain variable region
source                   1..125
                         mol_type = protein
                         organism = synthetic construct
SEQUENCE: 13
EVQLVESGAE VKKPGESLKI SCKGSGYTFT RYWIGWVRQM PGKGLEWMGI IYPGDSDVRY   60
SPSFQGHVTI SADKSISTAY LQWNSLKASD TAMYYCARLP QYCSAGVCFR WFDPWGQGTL  120
VTVSS                                                              125

SEQ ID NO: 14            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 14
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCRNGVCHR WFDPWGQGTL  120
VTVSS                                                              125

SEQ ID NO: 15            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 15
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCSRGVCKR WFDPWGQGTL  120
VTVSS                                                              125

SEQ ID NO: 16            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 16
EVQLVESGAE VKKPGESLKI SCKGSGYTFT RYWIGWVRQM PGKGLEWMGI IYPGDSDVRY   60
SPSFQGHVTI SADKSISTAY LQWNSLKASD TAMYYCARLP QYCRKGVCHR WFDPWGQGTL  120
VTVSS                                                              125

SEQ ID NO: 17            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 17
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCYAGVCHR WFDPWGQGTL  120
VTVSS                                                              125

SEQ ID NO: 18            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 18
EVQLVESGAE VKKPGESLKI SCKGSGYTFT RYWIGWVRQM PGKGLEWMGI IYPGDSDVRY   60
SPSFQGHVTI SADKSISTAY LQWNSLKASD TAMYYCARLP QYCRSGSCHR WFDPWGQGTL  120
VTVSS                                                              125

SEQ ID NO: 19            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 19
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCRNGSCKR WFDPWGQGTL  120
```

```
-continued

VTVSS                                                              125

SEQ ID NO: 20           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 20
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCRAGVCHR WFDPWGQGTL  120
VTVSS                                                              125

SEQ ID NO: 21           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 21
EVQLVESGAE VKKPGESLKI SCKGSGYTFT RYWIGWVRQM PGKGLEWMGI IYPGDADVRY   60
SPSFQGHVTI SADKSISTAY LQWNSLKASD TAMYYCARLP QYCRKGVCYR WFDPWGQGTL  120
VTVSS                                                              125

SEQ ID NO: 22           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 22
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCRSGVCQR WFDPWGQGTL  120
VTVSS                                                              125

SEQ ID NO: 23           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 23
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCRSGSCYR WFDPWGQGTL  120
VTVSS                                                              125

SEQ ID NO: 24           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 24
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARLP QYCYAGVCKR WFDPWGQGTL  120
VTVSS                                                              125

SEQ ID NO: 25           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 25
EVQLVESGAE VKKPGESLKI SCKGSGYTFT RYWIGWVRQM PGKGLEWMGI IYPGDSDTRY   60
SPSFQGHVTI SADKSISTAY LQWNSLKASD TAMYYCARVP QYCRSGVCFR WFDPWGQGTL  120
VTVSS                                                              125

SEQ ID NO: 26           moltype = AA  length = 125
FEATURE                 Location/Qualifiers
REGION                  1..125
                        note = antibody heavy chain variable region
source                  1..125
```

```
                        mol_type = protein
                        organism = synthetic construct
SEQUENCE: 26
EVQLVESGAE VKKPGESLKI SCKGSGYTFT RYWIGWVRQM PGKGLEWMGI IYPGDSETRY    60
SPSFQGHVTI SADKSISTAY LQWNSLKASD TAMYYCARVP QYCSRGVCYR WFDPWGQGTL   120
VTVSS                                                               125

SEQ ID NO: 27           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 27
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCYRGVCKR WFDPWGQGTL   120
VTVSS                                                               125

SEQ ID NO: 28           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 28
EVQLVESGAE VKKPGESLKI SCKGSGYTFT RYWIGWVRQM PGKGLEWMGI IYPGDRDTRY    60
SPSFQGHVTI SADKSISTAY LQWNSLKASD TAMYYCARLP QYCSRGVCFR WFDPWGQGTL   120
VTVSS                                                               125

SEQ ID NO: 29           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 29
EVQLVESGAE VKKPGESLKI SCKGSGYTFT RYWIGWVRQM PGKGLEWMGI IYPGDLDTRY    60
SPSFQGHVTI SADKSISTAY LQWNSLKASD TAMYYCARLP QYCYKGVCKR WFDPWGQGTL   120
VTVSS                                                               125

SEQ ID NO: 30           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 30
EVQLVESGAE VKKPGESLKI SCKGSGYTFT RYWIGWVRQM PGKGLEWMGI IYPGDSETRY    60
SPSFQGHVTI SADKSISTAY LQWNSLKASD TAMYYCARLP QYCRRGVCKR WFDPWGQGTL   120
VTVSS                                                               125

SEQ ID NO: 31           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 31
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCRAGKCKR WFDPWGQGTL   120
VTVSS                                                               125

SEQ ID NO: 32           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 32
EVQLVESGAE VKKPGESLKI SCKGSGYTFT RYWIGWVRQM PGKGLEWMGI IYPGDADVRY    60
SPSFQGHVTI SADKSISTAY LQWNSLKASD TAMYYCARLP QYCRKGVCKR WFDPWGQGTL   120
VTVSS                                                               125
```

```
SEQ ID NO: 33            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 33
EVQLVESGAE VKKPGESLKI SCKGSGYTFT RYWIGWVRQM PGKGLEWMGI IYPGDADTRY    60
SPSFQGHVTI SADKSISTAY LQWNSLKASD TAMYYCARLP QYCSRGVCQR WFDPWGQGTL   120
VTVSS                                                               125

SEQ ID NO: 34            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 34
EVQLVESGAE VKKPGESLKI SCKGSGYTFT RYWIGWVRQM PGKGLEWMGI IYPGDADTRY    60
SPSFQGHVTI SADKSISTAY LQWNSLKASD TAMYYCARLP QYCSKGVCYR WFDPWGQGTL   120
VTVSS                                                               125

SEQ ID NO: 35            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 35
EVQLVESGAE VKKPGESLKI SCKGSGYTFT RYWIGWVRQM PGKGLEWMGI IYPGDFDTRY    60
SPSFQGHVTI SADKSISTAY LQWNSLKASD TAMYYCARLP QYCRRGICFR WFDPWGQGTL   120
VTVSS                                                               125

SEQ ID NO: 36            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 36
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCQRGVCQR WFDPWGQGTL   120
VTVSS                                                               125

SEQ ID NO: 37            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 37
EVQLVESGAE VKKPGESLKI SCKGSGYTFT RYWIGWVRQM PGKGLEWMGI IYPGDADVRY    60
SPSFQGHVTI SADKSISTAY LQWNSLKASD TAMYYCARLP QYCRKGKCKR WFDPWGQGTL   120
VTVSS                                                               125

SEQ ID NO: 38            moltype = AA  length = 125
FEATURE                  Location/Qualifiers
REGION                   1..125
                         note = antibody heavy chain variable region
source                   1..125
                         mol_type = protein
                         organism = synthetic construct
SEQUENCE: 38
EVQLVESGAE VKKPGESLKI SCKGSGYTFT RYWIGWVRQM PGKGLEWMGI IYPGDSETRY    60
SPSFQGHVTI SADKSISTAY LQWNSLKASD TAMYYCARLP QYCRSGVCQR WFDPWGQGTL   120
VTVSS                                                               125

SEQ ID NO: 39            moltype = AA  length = 125
FEATURE                  Location/Qualifiers
REGION                   1..125
                         note = antibody heavy chain variable region
source                   1..125
                         mol_type = protein
                         organism = synthetic construct
```

```
SEQUENCE: 39
EVQLVESGAE VKKPGESLKI SCKGSGYTFT RYWIGWVRQM PGKGLEWMGI IYPGDNDVRY    60
SPSFQGHVTI SADKSISTAY LQWNSLKASD TAMYYCARLP QYCSAGVCFR WFDPWGQGTL   120
VTVSS                                                              125

SEQ ID NO: 40           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 40
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCQSGVCKR WFDPWGQGTL   120
VTVSS                                                              125

SEQ ID NO: 41           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 41
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCSAGVCFR WFDPWGQGTL   120
VTVSS                                                              125

SEQ ID NO: 42           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 42
EVQLVESGAE VKKPGESLKI SCKGSGYTFT RYWIGWVRQM PGKGLEWMGI IYPGDLDVRY    60
SPSFQGHVTI SADKSISTAY LQWNSLKASD TAMYYCARLP QYCREGKCHR WFDPWGQGTL   120
VTVSS                                                              125

SEQ ID NO: 43           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 43
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCSSGVCQR WFDPWGQGTL   120
VTVSS                                                              125

SEQ ID NO: 44           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 44
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCSSGVCHR WFDPWGQGTL   120
VTVSS                                                              125

SEQ ID NO: 45           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 45
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCQNGVCHR WFDPWGQGTL   120
VTVSS                                                              125

SEQ ID NO: 46           moltype = AA  length = 125
FEATURE                 Location/Qualifiers
```

```
REGION                  1..125
                        note = antibody heavy chain variable region
source                  1..125
                        mol_type = protein
                        organism = synthetic construct
SEQUENCE: 46
EVQLVESGAE VKKPGESLKI SCKGSGYTFT RYWIGWVRQM PGKGLEWMGI IYPGDNDVRY    60
SPSFQGHVTI SADKSISTAY LQWNSLKASD TAMYYCARLP QYCDKGICKR WFDPWGQGTL   120
VTVSS                                                               125

SEQ ID NO: 47           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 47
EVQLVESGAE VKKPGESLKI SCKGSGYTFT RYWIGWVRQM PGKGLEWMGI IYPGDSDTRY    60
SPSFQGHVTI SADKSISTAY LQWNSLKASD TAMYYCARLP QYCENGICKR WFDPWGQGTL   120
VTVSS                                                               125

SEQ ID NO: 48           moltype = AA  length = 125
FEATURE                 Location/Qualifiers
REGION                  1..125
                        note = antibody heavy chain variable region
source                  1..125
                        mol_type = protein
                        organism = synthetic construct
SEQUENCE: 48
EVQLVESGAE VKKPGESLKI SCKGSGYTFT RYWIGWVRQM PGKGLEWMGI IYPGDADVRY    60
SPSFQGHVTI SADKSISTAY LQWNSLKASD TAMYYCARLP QYCSSGSCFR WFDPWGQGTL   120
VTVSS                                                               125

SEQ ID NO: 49           moltype = AA  length = 107
FEATURE                 Location/Qualifiers
REGION                  1..107
                        note = antibody light chain variable region
REGION                  27..28
                        note = misc_feature - Xaa can be any naturally occurring
                         amino acid
REGION                  30..31
                        note = misc_feature - Xaa can be any naturally occurring
                         amino acid
REGION                  92..94
                        note = misc_feature - Xaa can be any naturally occurring
                         amino acid
SITE                    96
                        note = misc_feature - Xaa can be any naturally occurring
                         amino acid
source                  1..107
                        mol_type = protein
                        organism = synthetic construct
SEQUENCE: 49
EIVLTQSPSS VSASVGDRVT ITCRASXXIX XWLAWYQQKP GKAPKLLIYA ASSLQSGVPS    60
RFSGSGSGTD FTLTISSLQP EDFATYYCQQ GXXXPXTFGQ GTNLEIK                 107

SEQ ID NO: 50           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 50
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GNSFPYTFGQ GTNLEIK                 107

SEQ ID NO: 51           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 51
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GHSFPYTFGQ GTNLEIK                 107
```

```
SEQ ID NO: 52            moltype = AA  length = 107
FEATURE                  Location/Qualifiers
REGION                   1..107
                         note = antibody light chain variable region
source                   1..107
                         mol_type = protein
                         organism = synthetic construct
SEQUENCE: 52
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GDQYPLTFGQ GTNLEIK                 107

SEQ ID NO: 53            moltype = AA  length = 107
FEATURE                  Location/Qualifiers
REGION                   1..107
                         note = antibody light chain variable region
source                   1..107
                         mol_type = protein
                         organism = synthetic construct
SEQUENCE: 53
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GDQLPYTFGQ GTNLEIK                 107

SEQ ID NO: 54            moltype = AA  length = 107
FEATURE                  Location/Qualifiers
REGION                   1..107
                         note = antibody light chain variable region
source                   1..107
                         mol_type = protein
                         organism = synthetic construct
SEQUENCE: 54
EIVLTQSPSS VSASVGDRVT ITCRASKGIS SWLAWYQQKP GKAPKLLIYA ASSLQSGVPS    60
RFSGSGSGTD FTLTISSLQP EDFATYYCQQ GNQVPYTFGQ GTNLEIK                 107

SEQ ID NO: 55            moltype = AA  length = 107
FEATURE                  Location/Qualifiers
REGION                   1..107
                         note = antibody light chain variable region
source                   1..107
                         mol_type = protein
                         organism = synthetic construct
SEQUENCE: 55
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GDQLPYTFGQ GTNLEIK                 107

SEQ ID NO: 56            moltype = AA  length = 107
FEATURE                  Location/Qualifiers
REGION                   1..107
                         note = antibody light chain variable region
source                   1..107
                         mol_type = protein
                         organism = synthetic construct
SEQUENCE: 56
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GNQFPYTFGQ GTNLEIK                 107

SEQ ID NO: 57            moltype = AA  length = 107
FEATURE                  Location/Qualifiers
REGION                   1..107
                         note = antibody light chain variable region
source                   1..107
                         mol_type = protein
                         organism = synthetic construct
SEQUENCE: 57
EIVLTQSPSS VSASVGDRVT ITCRASIGIR NWLAWYQQKP GKAPKLLIYA ASSLQSGVPS    60
RFSGSGSGTD FTLTISSLQP EDFATYYCQQ GYSYPYTFGQ GTNLEIK                 107

SEQ ID NO: 58            moltype = AA  length = 107
FEATURE                  Location/Qualifiers
REGION                   1..107
                         note = antibody light chain variable region
source                   1..107
                         mol_type = protein
                         organism = synthetic construct
SEQUENCE: 58
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GDQFPYTFGQ GTNLEIK                 107

SEQ ID NO: 59            moltype = AA  length = 107
FEATURE                  Location/Qualifiers
```

```
REGION                      1..107
                            note = antibody light chain variable region
source                      1..107
                            mol_type = protein
                            organism = synthetic construct
SEQUENCE: 59
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GNSYPYTFGQ GTNLEIK                 107

SEQ ID NO: 60               moltype = AA  length = 107
FEATURE                     Location/Qualifiers
REGION                      1..107
                            note = antibody light chain variable region
source                      1..107
                            mol_type = protein
                            organism = synthetic construct
SEQUENCE: 60
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GNQFPYTFGQ GTNLEIK                 107

SEQ ID NO: 61               moltype = AA  length = 107
FEATURE                     Location/Qualifiers
REGION                      1..107
                            note = antibody light chain variable region
source                      1..107
                            mol_type = protein
                            organism = synthetic construct
SEQUENCE: 61
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GHSFPYTFGQ GTNLEIK                 107

SEQ ID NO: 62               moltype = AA  length = 107
FEATURE                     Location/Qualifiers
REGION                      1..107
                            note = antibody light chain variable region
source                      1..107
                            mol_type = protein
                            organism = synthetic construct
SEQUENCE: 62
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GYSFPYTFGQ GTNLEIK                 107

SEQ ID NO: 63               moltype = AA  length = 107
FEATURE                     Location/Qualifiers
REGION                      1..107
                            note = antibody light chain variable region
source                      1..107
                            mol_type = protein
                            organism = synthetic construct
SEQUENCE: 63
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GHQFPYTFGQ GTNLEIK                 107

SEQ ID NO: 64               moltype = AA  length = 107
FEATURE                     Location/Qualifiers
REGION                      1..107
                            note = antibody light chain variable region
source                      1..107
                            mol_type = protein
                            organism = synthetic construct
SEQUENCE: 64
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GDQFPLTFGQ GTNLEIK                 107

SEQ ID NO: 65               moltype = AA  length = 107
FEATURE                     Location/Qualifiers
REGION                      1..107
                            note = antibody light chain variable region
source                      1..107
                            mol_type = protein
                            organism = synthetic construct
SEQUENCE: 65
EIVLTQSPSS VSASVGDRVT ITCRASQGIV SWLAWYQQKP GKAPKLLIYA ASSLQSGVPS    60
RFSGSGSGTD FTLTISSLQP EDFATYYCQQ GHSFPYTFGQ GTNLEIK                 107

SEQ ID NO: 66               moltype = AA  length = 107
FEATURE                     Location/Qualifiers
REGION                      1..107
                            note = antibody light chain variable region
```

```
source                  1..107
                        mol_type = protein
                        organism = synthetic construct
SEQUENCE: 66
EIVLTQSPSS VSASVGDRVT ITCRASQSIS SWLAWYQQKP GKAPKLLIYA ASSLQSGVPS    60
RFSGSGSGTD FTLTISSLQP EDFATYYCQQ GSQTPYTFGQ GTNLEIK                 107

SEQ ID NO: 67           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 67
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GHSTPYTFGQ GTNLEIK                 107

SEQ ID NO: 68           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 68
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GYSVPYTFGQ GTNLEIK                 107

SEQ ID NO: 69           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 69
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GNQVPYTFGQ GTNLEIK                 107

SEQ ID NO: 70           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 70
EIVLTQSPSS VSASVGDRVT ITCRASQGIR SWLAWYQQKP GKAPKLLIYA ASSLQSGVPS    60
RFSGSGSGTD FTLTISSLQP EDFATYYCQQ GHSVPYTFGQ GTNLEIK                 107

SEQ ID NO: 71           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 71
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GNQLPYTFGQ GTNLEIK                 107

SEQ ID NO: 72           moltype = AA  length = 107
FEATURE                 Location/Qualifiers
REGION                  1..107
                        note = antibody light chain variable region
source                  1..107
                        mol_type = protein
                        organism = synthetic construct
SEQUENCE: 72
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GNQYPYTFGQ GTNLEIK                 107

SEQ ID NO: 73           moltype = AA  length = 107
FEATURE                 Location/Qualifiers
REGION                  1..107
                        note = antibody light chain variable region
source                  1..107
                        mol_type = protein
```

```
                         organism = synthetic construct
SEQUENCE: 73
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GHSTPYTFGQ GTNLEIK                107

SEQ ID NO: 74            moltype = AA   length = 107
FEATURE                  Location/Qualifiers
REGION                   1..107
                         note = antibody light chain variable region
source                   1..107
                         mol_type = protein
                         organism = synthetic construct
SEQUENCE: 74
EIVLTQSPSS VSASVGDRVT ITCRASQGIS NWLAWYQQKP GKAPKLLIYA ASSLQSGVPS    60
RFSGSGSGTD FTLTISSLQP EDFATYYCQQ GYSYPYTFGQ GTNLEIK                107

SEQ ID NO: 75            moltype = AA   length = 107
FEATURE                  Location/Qualifiers
REGION                   1..107
                         note = antibody light chain variable region
source                   1..107
                         mol_type = protein
                         organism = synthetic construct
SEQUENCE: 75
EIVLTQSPSS VSASVGDRVT ITCRASQGIR NWLAWYQQKP GKAPKLLIYA ASSLQSGVPS    60
RFSGSGSGTD FTLTISSLQP EDFATYYCQQ GDQDPLTFGQ GTNLEIK                107

SEQ ID NO: 76            moltype = AA   length = 107
FEATURE                  Location/Qualifiers
REGION                   1..107
                         note = antibody light chain variable region
source                   1..107
                         mol_type = protein
                         organism = synthetic construct
SEQUENCE: 76
EIVLTQSPSS VSASVGDRVT ITCRASQGIS SWLAWYQQKP GKAPKLLIYA ASSLQSGVPS    60
RFSGSGSGTD FTLTISSLQP EDFATYYCQQ GYSTPYTFGQ GTNLEIK                107

SEQ ID NO: 77            moltype = AA   length = 8
FEATURE                  Location/Qualifiers
REGION                   1..8
                         note = antibody heavy chain complementarity-determining
                          region 1
source                   1..8
                         mol_type = protein
                         organism = synthetic construct
SEQUENCE: 77
GYTFTRYW                                                             8

SEQ ID NO: 78            moltype = AA   length = 8
FEATURE                  Location/Qualifiers
REGION                   1..8
                         note = antibody heavy chain complementarity-determining
                          region 2
REGION                   6..8
                         note = misc_feature - Xaa can be any naturally occurring
                          amino acid
source                   1..8
                         mol_type = protein
                         organism = synthetic construct
SEQUENCE: 78
IYPGDXXX                                                             8

SEQ ID NO: 79            moltype = AA   length = 8
FEATURE                  Location/Qualifiers
REGION                   1..8
                         note = antibody heavy chain complementarity-determining
                          region 2
source                   1..8
                         mol_type = protein
                         organism = synthetic construct
SEQUENCE: 79
IYPGDSDT                                                             8

SEQ ID NO: 80            moltype = AA   length = 8
FEATURE                  Location/Qualifiers
REGION                   1..8
                         note = antibody heavy chain complementarity-determining
                          region 2
```

```
source                  1..8
                        mol_type = protein
                        organism = synthetic construct
SEQUENCE: 80
IYPGDSDV                                                                    8

SEQ ID NO: 81           moltype = AA  length = 8
FEATURE                 Location/Qualifiers
REGION                  1..8
                        note = antibody heavy chain complementarity-determining
                         region 2
source                  1..8
                        mol_type = protein
                        organism = synthetic construct
SEQUENCE: 81
IYPGDNDV                                                                    8

SEQ ID NO: 82           moltype = AA  length = 8
FEATURE                 Location/Qualifiers
REGION                  1..8
                        note = antibody heavy chain complementarity-determining
                         region 2
source                  1..8
                        mol_type = protein
                        organism = synthetic construct
SEQUENCE: 82
IYPGDADV                                                                    8

SEQ ID NO: 83           moltype = AA  length = 8
FEATURE                 Location/Qualifiers
REGION                  1..8
                        note = antibody heavy chain complementarity-determining
                         region 2
source                  1..8
                        mol_type = protein
                        organism = synthetic construct
SEQUENCE: 83
IYPGDSET                                                                    8

SEQ ID NO: 84           moltype = AA  length = 8
FEATURE                 Location/Qualifiers
REGION                  1..8
                        note = antibody heavy chain complementarity-determining
                         region 2
source                  1..8
                        mol_type = protein
                        organism = synthetic construct
SEQUENCE: 84
IYPGDRDT                                                                    8

SEQ ID NO: 85           moltype = AA  length = 8
FEATURE                 Location/Qualifiers
REGION                  1..8
                        note = antibody heavy chain complementarity-determining
                         region 2
source                  1..8
                        mol_type = protein
                        organism = synthetic construct
SEQUENCE: 85
IYPGDLDT                                                                    8

SEQ ID NO: 86           moltype = AA  length = 8
FEATURE                 Location/Qualifiers
REGION                  1..8
                        note = antibody heavy chain complementarity-determining
                         region 2
source                  1..8
                        mol_type = protein
                        organism = synthetic construct
SEQUENCE: 86
IYPGDADT                                                                    8

SEQ ID NO: 87           moltype = AA  length = 8
FEATURE                 Location/Qualifiers
REGION                  1..8
                        note = antibody heavy chain complementarity-determining
                         region 2
source                  1..8
                        mol_type = protein
```

```
                        organism = synthetic construct
SEQUENCE: 87
IYPGDFDT                                                                        8

SEQ ID NO: 88           moltype = AA   length = 8
FEATURE                 Location/Qualifiers
REGION                  1..8
                        note = antibody heavy chain complementarity-determining
                         region 2
source                  1..8
                        mol_type = protein
                        organism = synthetic construct
SEQUENCE: 88
IYPGDLDV                                                                        8

SEQ ID NO: 89           moltype = AA   length = 18
FEATURE                 Location/Qualifiers
REGION                  1..18
                        note = antibody heavy chain complementarity-determining
                         region 3
SITE                    3
                        note = misc_feature - Xaa can be any naturally occurring
                         amino acid
REGION                  8..11
                        note = misc_feature - Xaa can be any naturally occurring
                         amino acid
SITE                    13
                        note = misc_feature - Xaa can be any naturally occurring
                         amino acid
source                  1..18
                        mol_type = protein
                        organism = synthetic construct
SEQUENCE: 89
ARXPQYCXXX XCXRWFDP                                                            18

SEQ ID NO: 90           moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 90
ARLPQYCSNG VCQRWFDP                                                            18

SEQ ID NO: 91           moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 91
ARLPQYCSKG VCYRWFDP                                                            18

SEQ ID NO: 92           moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 92
ARLPQYCQNG ICKRWFDP                                                            18

SEQ ID NO: 93           moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 93
ARLPQYCRKG ICKRWFDP                                                            18
```

| | |
|---|---|
| SEQ ID NO: 94 | moltype = AA  length = 18 |
| FEATURE | Location/Qualifiers |
| REGION | 1..18 |
| | note = antibody heavy chain complementarity-determining region 3 |
| source | 1..18 |
| | mol_type = protein |
| | organism = synthetic construct |

SEQUENCE: 94
ARLPQYCRNG VCYRWFDP                                                18

| | |
|---|---|
| SEQ ID NO: 95 | moltype = AA  length = 18 |
| FEATURE | Location/Qualifiers |
| REGION | 1..18 |
| | note = antibody heavy chain complementarity-determining region 3 |
| source | 1..18 |
| | mol_type = protein |
| | organism = synthetic construct |

SEQUENCE: 95
ARLPQYCRAN VCFRWFDP                                                18

| | |
|---|---|
| SEQ ID NO: 96 | moltype = AA  length = 18 |
| FEATURE | Location/Qualifiers |
| REGION | 1..18 |
| | note = antibody heavy chain complementarity-determining region 3 |
| source | 1..18 |
| | mol_type = protein |
| | organism = synthetic construct |

SEQUENCE: 96
ARLPQYCKKL ICKRWFDP                                                18

| | |
|---|---|
| SEQ ID NO: 97 | moltype = AA  length = 18 |
| FEATURE | Location/Qualifiers |
| REGION | 1..18 |
| | note = antibody heavy chain complementarity-determining region 3 |
| source | 1..18 |
| | mol_type = protein |
| | organism = synthetic construct |

SEQUENCE: 97
ARLPQYCRNG VCQRWFDP                                                18

| | |
|---|---|
| SEQ ID NO: 98 | moltype = AA  length = 18 |
| FEATURE | Location/Qualifiers |
| REGION | 1..18 |
| | note = antibody heavy chain complementarity-determining region 3 |
| source | 1..18 |
| | mol_type = protein |
| | organism = synthetic construct |

SEQUENCE: 98
ARLPQYCSAG SCFRWFDP                                                18

| | |
|---|---|
| SEQ ID NO: 99 | moltype = AA  length = 18 |
| FEATURE | Location/Qualifiers |
| REGION | 1..18 |
| | note = antibody heavy chain complementarity-determining region 3 |
| source | 1..18 |
| | mol_type = protein |
| | organism = synthetic construct |

SEQUENCE: 99
ARLPQYCRSG ICKRWFDP                                                18

| | |
|---|---|
| SEQ ID NO: 100 | moltype = AA  length = 18 |
| FEATURE | Location/Qualifiers |
| REGION | 1..18 |
| | note = antibody heavy chain complementarity-determining region 3 |
| source | 1..18 |
| | mol_type = protein |
| | organism = synthetic construct |

SEQUENCE: 100
ARLPQYCSAG VCFRWFDP                                                18

| | |
|---|---|
| SEQ ID NO: 101 | moltype = AA  length = 18 |
| FEATURE | Location/Qualifiers |

```
REGION                  1..18
                        note = antibody heavy chain complementarity-determining
                         region 3
source                  1..18
                        mol_type = protein
                        organism = synthetic construct
SEQUENCE: 101
ARLPQYCRNG VCHRWFDP                                                           18

SEQ ID NO: 102          moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 102
ARLPQYCSRG VCKRWFDP                                                           18

SEQ ID NO: 103          moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 103
ARLPQYCRKG VCHRWFDP                                                           18

SEQ ID NO: 104          moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 104
ARLPQYCYAG VCHRWFDP                                                           18

SEQ ID NO: 105          moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 105
ARLPQYCRSG SCHRWFDP                                                           18

SEQ ID NO: 106          moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 106
ARLPQYCRNG SCKRWFDP                                                           18

SEQ ID NO: 107          moltype = AA   length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 107
ARLPQYCRAG VCHRWFDP                                                           18

SEQ ID NO: 108          moltype = AA   length = 18
FEATURE                 Location/Qualifiers
REGION                  1..18
                        note = antibody heavy chain complementarity-determining
```

```
                        region 3
source                  1..18
                        mol_type = protein
                        organism = synthetic construct
SEQUENCE: 108
ARLPQYCRKG VCYRWFDP                                                        18

SEQ ID NO: 109          moltype = AA  length = 18
FEATURE                 Location/Qualifiers
REGION                  1..18
                        note = antibody heavy chain complementarity-determining
                        region 3
source                  1..18
                        mol_type = protein
                        organism = synthetic construct
SEQUENCE: 109
ARLPQYCRSG VCQRWFDP                                                        18

SEQ ID NO: 110          moltype = AA  length = 18
FEATURE                 Location/Qualifiers
REGION                  1..18
                        note = antibody heavy chain complementarity-determining
                        region 3
source                  1..18
                        mol_type = protein
                        organism = synthetic construct
SEQUENCE: 110
ARLPQYCRSG SCYRWFDP                                                        18

SEQ ID NO: 111          moltype = AA  length = 18
FEATURE                 Location/Qualifiers
REGION                  1..18
                        note = antibody heavy chain complementarity-determining
                        region 3
source                  1..18
                        mol_type = protein
                        organism = synthetic construct
SEQUENCE: 111
ARLPQYCYAG VCKRWFDP                                                        18

SEQ ID NO: 112          moltype = AA  length = 18
FEATURE                 Location/Qualifiers
REGION                  1..18
                        note = antibody heavy chain complementarity-determining
                        region 3
source                  1..18
                        mol_type = protein
                        organism = synthetic construct
SEQUENCE: 112
ARVPQYCRSG VCFRWFDP                                                        18

SEQ ID NO: 113          moltype = AA  length = 18
FEATURE                 Location/Qualifiers
REGION                  1..18
                        note = antibody heavy chain complementarity-determining
                        region 3
source                  1..18
                        mol_type = protein
                        organism = synthetic construct
SEQUENCE: 113
ARVPQYCSRG VCYRWFDP                                                        18

SEQ ID NO: 114          moltype = AA  length = 18
FEATURE                 Location/Qualifiers
REGION                  1..18
                        note = antibody heavy chain complementarity-determining
                        region 3
source                  1..18
                        mol_type = protein
                        organism = synthetic construct
SEQUENCE: 114
ARLPQYCYRG VCKRWFDP                                                        18

SEQ ID NO: 115          moltype = AA  length = 18
FEATURE                 Location/Qualifiers
REGION                  1..18
                        note = antibody heavy chain complementarity-determining
                        region 3
source                  1..18
```

```
                              mol_type = protein
                              organism = synthetic construct
SEQUENCE: 115
ARLPQYCSRG VCFRWFDP                                                 18

SEQ ID NO: 116           moltype = AA   length = 18
FEATURE                  Location/Qualifiers
REGION                   1..18
                         note = antibody heavy chain complementarity-determining
                           region 3
source                   1..18
                         mol_type = protein
                         organism = synthetic construct
SEQUENCE: 116
ARLPQYCYKG VCKRWFDP                                                 18

SEQ ID NO: 117           moltype = AA   length = 18
FEATURE                  Location/Qualifiers
REGION                   1..18
                         note = antibody heavy chain complementarity-determining
                           region 3
source                   1..18
                         mol_type = protein
                         organism = synthetic construct
SEQUENCE: 117
ARLPQYCRRG VCKRWFDP                                                 18

SEQ ID NO: 118           moltype = AA   length = 18
FEATURE                  Location/Qualifiers
REGION                   1..18
                         note = antibody heavy chain complementarity-determining
                           region 3
source                   1..18
                         mol_type = protein
                         organism = synthetic construct
SEQUENCE: 118
ARLPQYCRAG KCKRWFDP                                                 18

SEQ ID NO: 119           moltype = AA   length = 18
FEATURE                  Location/Qualifiers
REGION                   1..18
                         note = antibody heavy chain complementarity-determining
                           region 3
source                   1..18
                         mol_type = protein
                         organism = synthetic construct
SEQUENCE: 119
ARLPQYCRKG VCKRWFDP                                                 18

SEQ ID NO: 120           moltype = AA   length = 18
FEATURE                  Location/Qualifiers
REGION                   1..18
                         note = antibody heavy chain complementarity-determining
                           region 3
source                   1..18
                         mol_type = protein
                         organism = synthetic construct
SEQUENCE: 120
ARLPQYCSRG VCQRWFDP                                                 18

SEQ ID NO: 121           moltype = AA   length = 18
FEATURE                  Location/Qualifiers
REGION                   1..18
                         note = antibody heavy chain complementarity-determining
                           region 3
source                   1..18
                         mol_type = protein
                         organism = synthetic construct
SEQUENCE: 121
ARLPQYCRRG ICFRWFDP                                                 18

SEQ ID NO: 122           moltype = AA   length = 18
FEATURE                  Location/Qualifiers
REGION                   1..18
                         note = antibody heavy chain complementarity-determining
                           region 3
source                   1..18
                         mol_type = protein
                         organism = synthetic construct
```

```
SEQUENCE: 122
ARLPQYCQRG VCQRWFDP                                               18

SEQ ID NO: 123          moltype = AA  length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 123
ARLPQYCRKG KCKRWFDP                                               18

SEQ ID NO: 124          moltype = AA  length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 124
ARLPQYCQSG VCKRWFDP                                               18

SEQ ID NO: 125          moltype = AA  length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 125
ARLPQYCREG KCHRWFDP                                               18

SEQ ID NO: 126          moltype = AA  length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 126
ARLPQYCSSG VCQRWFDP                                               18

SEQ ID NO: 127          moltype = AA  length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 127
ARLPQYCSSG VCHRWFDP                                               18

SEQ ID NO: 128          moltype = AA  length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 128
ARLPQYCQNG VCHRWFDP                                               18

SEQ ID NO: 129          moltype = AA  length = 18
FEATURE                 Location/Qualifiers
REGION                  1..18
                        note = antibody heavy chain complementarity-determining
                         region 3
source                  1..18
                        mol_type = protein
                        organism = synthetic construct
SEQUENCE: 129
ARLPQYCDKG ICKRWFDP                                               18
```

```
SEQ ID NO: 130          moltype = AA  length = 18
FEATURE                 Location/Qualifiers
REGION                  1..18
                        note = antibody heavy chain complementarity-determining
                          region 3
source                  1..18
                        mol_type = protein
                        organism = synthetic construct
SEQUENCE: 130
ARLPQYCENG ICKRWFDP                                                       18

SEQ ID NO: 131          moltype = AA  length = 18
FEATURE                 Location/Qualifiers
REGION                  1..18
                        note = antibody heavy chain complementarity-determining
                          region 3
source                  1..18
                        mol_type = protein
                        organism = synthetic construct
SEQUENCE: 131
ARLPQYCSSG SCFRWFDP                                                       18

SEQ ID NO: 132          moltype =     length =
SEQUENCE: 132
000

SEQ ID NO: 133          moltype = AA  length = 6
FEATURE                 Location/Qualifiers
REGION                  1..6
                        note = antibody light chain complementarity-determining
                          region 1
source                  1..6
                        mol_type = protein
                        organism = synthetic construct
SEQUENCE: 133
QGISSW                                                                     6

SEQ ID NO: 134          moltype = AA  length = 6
FEATURE                 Location/Qualifiers
REGION                  1..6
                        note = antibody light chain complementarity-determining
                          region 1
source                  1..6
                        mol_type = protein
                        organism = synthetic construct
SEQUENCE: 134
QGIRSW                                                                     6

SEQ ID NO: 135          moltype = AA  length = 6
FEATURE                 Location/Qualifiers
REGION                  1..6
                        note = antibody light chain complementarity-determining
                          region 1
source                  1..6
                        mol_type = protein
                        organism = synthetic construct
SEQUENCE: 135
KGISSW                                                                     6

SEQ ID NO: 136          moltype = AA  length = 6
FEATURE                 Location/Qualifiers
REGION                  1..6
                        note = antibody light chain complementarity-determining
                          region 1
source                  1..6
                        mol_type = protein
                        organism = synthetic construct
SEQUENCE: 136
IGIRNW                                                                     6

SEQ ID NO: 137          moltype = AA  length = 6
FEATURE                 Location/Qualifiers
REGION                  1..6
                        note = antibody light chain complementarity-determining
                          region 1
source                  1..6
                        mol_type = protein
                        organism = synthetic construct
```

```
SEQUENCE: 137
QGIVSW                                                                        6

SEQ ID NO: 138         moltype = AA  length = 6
FEATURE                Location/Qualifiers
REGION                 1..6
                       note = antibody light chain complementarity-determining
                        region 1
source                 1..6
                       mol_type = protein
                       organism = synthetic construct
SEQUENCE: 138
QSISSW                                                                        6

SEQ ID NO: 139         moltype = AA  length = 6
FEATURE                Location/Qualifiers
REGION                 1..6
                       note = antibody light chain complementarity-determining
                        region 1
source                 1..6
                       mol_type = protein
                       organism = synthetic construct
SEQUENCE: 139
QGISNW                                                                        6

SEQ ID NO: 140         moltype = AA  length = 6
FEATURE                Location/Qualifiers
REGION                 1..6
                       note = antibody light chain complementarity-determining
                        region 1
source                 1..6
                       mol_type = protein
                       organism = synthetic construct
SEQUENCE: 140
QGIRNW                                                                        6

SEQ ID NO: 141         moltype =     length =
SEQUENCE: 141
000

SEQ ID NO: 142         moltype = AA  length = 9
FEATURE                Location/Qualifiers
REGION                 1..9
                       note = antibody light chain complementarity-determining
                        region 3
REGION                 4..6
                       note = misc_feature - Xaa can be any naturally occurring
                        amino acid
SITE                   8
                       note = misc_feature - Xaa can be any naturally occurring
                        amino acid
source                 1..9
                       mol_type = protein
                       organism = synthetic construct
SEQUENCE: 142
QQGXXXPXT                                                                     9

SEQ ID NO: 143         moltype = AA  length = 9
FEATURE                Location/Qualifiers
REGION                 1..9
                       note = antibody light chain complementarity-determining
                        region 3
source                 1..9
                       mol_type = protein
                       organism = synthetic construct
SEQUENCE: 143
QQGNSFPYT                                                                     9

SEQ ID NO: 144         moltype = AA  length = 9
FEATURE                Location/Qualifiers
REGION                 1..9
                       note = antibody light chain complementarity-determining
                        region 3
source                 1..9
                       mol_type = protein
                       organism = synthetic construct
SEQUENCE: 144
QQGHSFPYT                                                                     9
```

```
SEQ ID NO: 145           moltype = AA   length = 9
FEATURE                  Location/Qualifiers
REGION                   1..9
                         note = antibody light chain complementarity-determining
                          region 3
source                   1..9
                         mol_type = protein
                         organism = synthetic construct
SEQUENCE: 145
QQGDQYPLT                                                                  9

SEQ ID NO: 146           moltype = AA   length = 9
FEATURE                  Location/Qualifiers
REGION                   1..9
                         note = antibody light chain complementarity-determining
                          region 3
source                   1..9
                         mol_type = protein
                         organism = synthetic construct
SEQUENCE: 146
QQGDQLPYT                                                                  9

SEQ ID NO: 147           moltype = AA   length = 9
FEATURE                  Location/Qualifiers
REGION                   1..9
                         note = antibody light chain complementarity-determining
                          region 3
source                   1..9
                         mol_type = protein
                         organism = synthetic construct
SEQUENCE: 147
QQGNQVPYT                                                                  9

SEQ ID NO: 148           moltype = AA   length = 9
FEATURE                  Location/Qualifiers
REGION                   1..9
                         note = antibody light chain complementarity-determining
                          region 3
source                   1..9
                         mol_type = protein
                         organism = synthetic construct
SEQUENCE: 148
QQGNQFPYT                                                                  9

SEQ ID NO: 149           moltype = AA   length = 9
FEATURE                  Location/Qualifiers
REGION                   1..9
                         note = antibody light chain complementarity-determining
                          region 3
source                   1..9
                         mol_type = protein
                         organism = synthetic construct
SEQUENCE: 149
QQGYSYPYT                                                                  9

SEQ ID NO: 150           moltype = AA   length = 9
FEATURE                  Location/Qualifiers
REGION                   1..9
                         note = antibody light chain complementarity-determining
                          region 3
source                   1..9
                         mol_type = protein
                         organism = synthetic construct
SEQUENCE: 150
QQGDQFPYT                                                                  9

SEQ ID NO: 151           moltype = AA   length = 9
FEATURE                  Location/Qualifiers
REGION                   1..9
                         note = antibody light chain complementarity-determining
                          region 3
source                   1..9
                         mol_type = protein
                         organism = synthetic construct
SEQUENCE: 151
QQGNSYPYT                                                                  9

SEQ ID NO: 152           moltype = AA   length = 9
FEATURE                  Location/Qualifiers
```

```
REGION                  1..9
                        note = antibody light chain complementarity-determining
                         region 3
source                  1..9
                        mol_type = protein
                        organism = synthetic construct
SEQUENCE: 152
QQGYSFPYT                                                                 9

SEQ ID NO: 153          moltype = AA   length = 9
FEATURE                 Location/Qualifiers
REGION                  1..9
                        note = antibody light chain complementarity-determining
                         region 3
source                  1..9
                        mol_type = protein
                        organism = synthetic construct
SEQUENCE: 153
QQGHQFPYT                                                                 9

SEQ ID NO: 154          moltype = AA   length = 9
FEATURE                 Location/Qualifiers
REGION                  1..9
                        note = antibody light chain complementarity-determining
                         region 3
source                  1..9
                        mol_type = protein
                        organism = synthetic construct
SEQUENCE: 154
QQGDQFPLT                                                                 9

SEQ ID NO: 155          moltype = AA   length = 9
FEATURE                 Location/Qualifiers
REGION                  1..9
                        note = antibody light chain complementarity-determining
                         region 3
source                  1..9
                        mol_type = protein
                        organism = synthetic construct
SEQUENCE: 155
QQGSQTPYT                                                                 9

SEQ ID NO: 156          moltype = AA   length = 9
FEATURE                 Location/Qualifiers
REGION                  1..9
                        note = antibody light chain complementarity-determining
                         region 3
source                  1..9
                        mol_type = protein
                        organism = synthetic construct
SEQUENCE: 156
QQGHSTPYT                                                                 9

SEQ ID NO: 157          moltype = AA   length = 9
FEATURE                 Location/Qualifiers
REGION                  1..9
                        note = antibody light chain complementarity-determining
                         region 3
source                  1..9
                        mol_type = protein
                        organism = synthetic construct
SEQUENCE: 157
QQGYSVPYT                                                                 9

SEQ ID NO: 158          moltype = AA   length = 9
FEATURE                 Location/Qualifiers
REGION                  1..9
                        note = antibody light chain complementarity-determining
                         region 3
source                  1..9
                        mol_type = protein
                        organism = synthetic construct
SEQUENCE: 158
QQGHSVPYT                                                                 9

SEQ ID NO: 159          moltype = AA   length = 9
FEATURE                 Location/Qualifiers
REGION                  1..9
                        note = antibody light chain complementarity-determining
```

```
                            region 3
source                      1..9
                            mol_type = protein
                            organism = synthetic construct
SEQUENCE: 159
QQGNQLPYT                                                                   9

SEQ ID NO: 160              moltype = AA  length = 9
FEATURE                     Location/Qualifiers
REGION                      1..9
                            note = antibody light chain complementarity-determining
                             region 3
source                      1..9
                            mol_type = protein
                            organism = synthetic construct
SEQUENCE: 160
QQGNQYPYT                                                                   9

SEQ ID NO: 161              moltype = AA  length = 9
FEATURE                     Location/Qualifiers
REGION                      1..9
                            note = antibody light chain complementarity-determining
                             region 3
source                      1..9
                            mol_type = protein
                            organism = synthetic construct
SEQUENCE: 161
QQGDQDPLT                                                                   9

SEQ ID NO: 162              moltype = AA  length = 9
FEATURE                     Location/Qualifiers
REGION                      1..9
                            note = antibody light chain complementarity-determining
                             region 3
source                      1..9
                            mol_type = protein
                            organism = synthetic construct
SEQUENCE: 162
QQGYSTPYT                                                                   9

SEQ ID NO: 163              moltype = AA  length = 125
FEATURE                     Location/Qualifiers
REGION                      1..125
                            note = antibody heavy chain variable region
SITE                        56
                            note = misc_feature - Xaa can be any naturally occurring
                             amino acid
SITE                        58
                            note = misc_feature - Xaa can be any naturally occurring
                             amino acid
REGION                      104..107
                            note = misc_feature - Xaa can be any naturally occurring
                             amino acid
SITE                        109
                            note = misc_feature - Xaa can be any naturally occurring
                             amino acid
source                      1..125
                            mol_type = protein
                            organism = synthetic construct
SEQUENCE: 163
EVQLVESGAE VKKPGESLKI SCKGSGYTFT RYWIGWVRQM PGKGLEWMGI IYPGDXDXRY         60
SPSFQGHVTI SADKSISTAY LQWNSLKASD TAMYYCARLP QYCXXXXCXR WFDPWGQGTL        120
VTVSS                                                                   125

SEQ ID NO: 164              moltype = AA  length = 125
FEATURE                     Location/Qualifiers
REGION                      1..125
                            note = antibody heavy chain variable region
SITE                        56
                            note = misc_feature - Xaa can be any naturally occurring
                             amino acid
SITE                        58
                            note = misc_feature - Xaa can be any naturally occurring
                             amino acid
REGION                      104..105
                            note = misc_feature - Xaa can be any naturally occurring
                             amino acid
SITE                        107
                            note = misc_feature - Xaa can be any naturally occurring
```

```
                        amino acid
SITE                    109
                        note = misc_feature - Xaa can be any naturally occurring
                          amino acid
source                  1..125
                        mol_type = protein
                        organism = synthetic construct
SEQUENCE: 164
EVQLVESGAE VKKPGESLKI SCKGSGYTFT RYWIGWVRQM PGKGLEWMGI IYPGDXDXRY    60
SPSFQGHVTI SADKSISTAY LQWNSLKASD TAMYYCARLP QYCXXGXCXR WFDPWGQGTL   120
VTVSS                                                               125

SEQ ID NO: 165          moltype = AA  length = 107
FEATURE                 Location/Qualifiers
REGION                  1..107
                        note = antibody light chain variable region
SITE                    27
                        note = misc_feature - Xaa can be any naturally occurring
                          amino acid
REGION                  30..31
                        note = misc_feature - Xaa can be any naturally occurring
                          amino acid
REGION                  92..94
                        note = misc_feature - Xaa can be any naturally occurring
                          amino acid
SITE                    96
                        note = misc_feature - Xaa can be any naturally occurring
                          amino acid
source                  1..107
                        mol_type = protein
                        organism = synthetic construct
SEQUENCE: 165
EIVLTQSPSS VSASVGDRVT ITCRASXGIX XWLAWYQQKP GKAPKLLIYA ASSLQSGVPS    60
RFSGSGSGTD FTLTISSLQP EDFATYYCQQ GXXXPXTFGQ GTNLEIK                 107

SEQ ID NO: 166          moltype = AA  length = 107
FEATURE                 Location/Qualifiers
REGION                  1..107
                        note = antibody light chain variable region
REGION                  30..31
                        note = misc_feature - Xaa can be any naturally occurring
                          amino acid
REGION                  92..94
                        note = misc_feature - Xaa can be any naturally occurring
                          amino acid
SITE                    96
                        note = misc_feature - Xaa can be any naturally occurring
                          amino acid
source                  1..107
                        mol_type = protein
                        organism = synthetic construct
SEQUENCE: 166
EIVLTQSPSS VSASVGDRVT ITCRASQGIX XWLAWYQQKP GKAPKLLIYA ASSLQSGVPS    60
RFSGSGSGTD FTLTISSLQP EDFATYYCQQ GXXXPXTFGQ GTNLEIK                 107

SEQ ID NO: 167          moltype = AA  length = 8
FEATURE                 Location/Qualifiers
REGION                  1..8
                        note = antibody heavy chain complementarity-determining
                          region 2
SITE                    6
                        note = misc_feature - Xaa can be any naturally occurring
                          amino acid
SITE                    8
                        note = misc_feature - Xaa can be any naturally occurring
                          amino acid
source                  1..8
                        mol_type = protein
                        organism = synthetic construct
SEQUENCE: 167
IYPGDXDX                                                              8

SEQ ID NO: 168          moltype = AA  length = 18
FEATURE                 Location/Qualifiers
REGION                  1..18
                        note = antibody heavy chain complementarity-determining
                          region 3
REGION                  8..11
                        note = misc_feature - Xaa can be any naturally occurring
```

```
                       amino acid
SITE                   13
                       note = misc_feature - Xaa can be any naturally occurring
                         amino acid
source                 1..18
                       mol_type = protein
                       organism = synthetic construct
SEQUENCE: 168
ARLPQYCXXX XCXRWFDP                                                     18

SEQ ID NO: 169         moltype = AA  length = 18
FEATURE                Location/Qualifiers
REGION                 1..18
                       note = antibody heavy chain complementarity-determining
                         region 3
REGION                 8..9
                       note = misc_feature - Xaa can be any naturally occurring
                         amino acid
SITE                   11
                       note = misc_feature - Xaa can be any naturally occurring
                         amino acid
SITE                   13
                       note = misc_feature - Xaa can be any naturally occurring
                         amino acid
source                 1..18
                       mol_type = protein
                       organism = synthetic construct
SEQUENCE: 169
ARLPQYCXXG XCXRWFDP                                                     18

SEQ ID NO: 170         moltype =   length =
SEQUENCE: 170
000

SEQ ID NO: 171         moltype = AA  length = 6
FEATURE                Location/Qualifiers
REGION                 1..6
                       note = antibody light chain complementarity-determining
                         region 1
REGION                 4..5
                       note = misc_feature - Xaa can be any naturally occurring
                         amino acid
source                 1..6
                       mol_type = protein
                       organism = synthetic construct
SEQUENCE: 171
QGIXXW                                                                   6

SEQ ID NO: 172         moltype = AA  length = 9
FEATURE                Location/Qualifiers
REGION                 1..9
                       note = antibody light chain complementarity-determining
                         region 3
REGION                 4..6
                       note = misc_feature - Xaa can be any naturally occurring
                         amino acid
SITE                   8
                       note = misc_feature - Xaa can be any naturally occurring
                         amino acid
source                 1..9
                       mol_type = protein
                       organism = synthetic construct
SEQUENCE: 172
QQGXXXPXT                                                                9

SEQ ID NO: 173         moltype = AA  length = 9
FEATURE                Location/Qualifiers
REGION                 1..9
                       note = antibody light chain complementarity-determining
                         region 3
REGION                 4..6
                       note = misc_feature - Xaa can be any naturally occurring
                         amino acid
SITE                   8
                       note = misc_feature - Xaa can be any naturally occurring
                         amino acid
source                 1..9
                       mol_type = protein
                       organism = synthetic construct
```

```
SEQUENCE: 173
QQGXXXPXT                                                                    9

SEQ ID NO: 174            moltype = AA  length = 126
FEATURE                   Location/Qualifiers
REGION                    1..126
                          note = antibody heavy chain variable region
source                    1..126
                          mol_type = protein
                          organism = synthetic construct
SEQUENCE: 174
QVQLVQSGAE VKKPGSSVKV SCKASGGYDN TYTISWVRQA PGQGLEWMGR IILLFGAANY   60
AQKIQGRVTI TADKSTSTAY MELTSLRSDD TAVYYCARGF HPDYYGWGDD DAFDFWGQGT  120
LVTVYS                                                            126

SEQ ID NO: 175            moltype = AA  length = 126
FEATURE                   Location/Qualifiers
REGION                    1..126
                          note = antibody heavy chain variable region
source                    1..126
                          mol_type = protein
                          organism = synthetic construct
SEQUENCE: 175
QVQLVQSGAE VKKPGSSVKV SCKASGDTSD TYTISWVRQA PGQGLEWMGR IILLSGYANY   60
AQKIQGRVTI TADKSTSTAY MELTSLRSDD TAVYYCARGF NGDYYGWGDD DAFDFWGQGT  120
LVTVYS                                                            126

SEQ ID NO: 176            moltype = AA  length = 126
FEATURE                   Location/Qualifiers
REGION                    1..126
                          note = antibody heavy chain variable region
source                    1..126
                          mol_type = protein
                          organism = synthetic construct
SEQUENCE: 176
QVQLVQSGAE VKKPGSSVKV SCKASGDTSD TYTISWVRQA PGQGLEWMGR IILMSGYANY   60
AQKIQGRVTI TADKSTSTAY MELTSLRSDD TAVYYCARGF NGDYYGWGDD DAFDFWGQGT  120
LVTVYS                                                            126

SEQ ID NO: 177            moltype = AA  length = 126
FEATURE                   Location/Qualifiers
REGION                    1..126
                          note = antibody heavy chain variable region
source                    1..126
                          mol_type = protein
                          organism = synthetic construct
SEQUENCE: 177
QVQLVQSGAE VKKPGSSVKV SCKASGGYDN TYTISWVRQA PGQGLEWMGR IILLFGAANY   60
AQKIQGRVTI TADKSTSTAY MELTSLRSDD TAVYYCARGF NGDYYGWGDD DAFDFWGQGT  120
LVTVYS                                                            126

SEQ ID NO: 178            moltype = AA  length = 113
FEATURE                   Location/Qualifiers
REGION                    1..113
                          note = antibody light chain variable region
source                    1..113
                          mol_type = protein
                          organism = synthetic construct
SEQUENCE: 178
QTVLTQPPSV SGAPGQRVTI SCTGSSSNIG AGYDVHWYQQ LPGTAPKLLI CGRDNRPSGV   60
PDRFSGSKSG TSASLAITGL QAEDEADYYC QSYDSSSSGP HWVFGGGTKL TVL         113

SEQ ID NO: 179            moltype = AA  length = 113
FEATURE                   Location/Qualifiers
REGION                    1..113
                          note = antibody light chain variable region
source                    1..113
                          mol_type = protein
                          organism = synthetic construct
SEQUENCE: 179
QTVLTQPPSV SGAPGQRVTI SCTGSSSNIG AGYDVHWYQQ LPGTAPKLLI AGRDNRPSGV   60
PDRFSGSKSG TSASLAITGL QAEDEADYYC QSYDSSSSGP HWVFGGGTKL TVL         113

SEQ ID NO: 180            moltype = AA  length = 113
FEATURE                   Location/Qualifiers
REGION                    1..113
                          note = antibody light chain variable region
source                    1..113
                          mol_type = protein
```

```
                              organism = synthetic construct
SEQUENCE: 180
QTVLTQPPSV SGAPGQRVTI SCTGSSSNIG AGYDVHWYQQ LPGTAPKLLI SGRDNRPSGV     60
PDRFSGSKSG TSASLAITGL QAEDEADYYC QSYDSSSSGP HWVFGGGTKL TVL           113

SEQ ID NO: 181          moltype = AA   length = 113
FEATURE                 Location/Qualifiers
REGION                  1..113
                        note = antibody light chain variable region
source                  1..113
                        mol_type = protein
                        organism = synthetic construct
SEQUENCE: 181
QTVLTQPPSV SGAPGQRVTI SCTGSSSNIG AGYDVHWYQQ LPGTAPKLLI YGRDNRPSGV     60
PDRFSGSKSG TSASLAITGL QAEDEADYYC QSYDSSSSGP HWVFGGGTKL TVL           113

SEQ ID NO: 182          moltype = AA   length = 113
FEATURE                 Location/Qualifiers
REGION                  1..113
                        note = antibody light chain variable region
source                  1..113
                        mol_type = protein
                        organism = synthetic construct
SEQUENCE: 182
QTVLTQPPSV SGAPGQRVTI SCTGSSSNIG AGYRVHWYQQ LPGTAPKLLI CGRSNRPSGV     60
PDRFSGSKSG TSASLAITGL QAEDEADYYC QSYDSSLFDP HWVFGGGTKL TVL           113

SEQ ID NO: 183          moltype = AA   length = 113
FEATURE                 Location/Qualifiers
REGION                  1..113
                        note = antibody light chain variable region
source                  1..113
                        mol_type = protein
                        organism = synthetic construct
SEQUENCE: 183
QTVLTQPPSV SGAPGQRVTI SCTGSSSNIG AGYRVHWYQQ LPGTAPKLLI AGRSNRPSGV     60
PDRFSGSKSG TSASLAITGL QAEDEADYYC QSYDSSLFDP HWVFGGGTKL TVL           113

SEQ ID NO: 184          moltype = AA   length = 113
FEATURE                 Location/Qualifiers
REGION                  1..113
                        note = antibody light chain variable region
source                  1..113
                        mol_type = protein
                        organism = synthetic construct
SEQUENCE: 184
QTVLTQPPSV SGAPGQRVTI SCTGSSSNIG AGYRVHWYQQ LPGTAPKLLI SGRSNRPSGV     60
PDRFSGSKSG TSASLAITGL QAEDEADYYC QSYDSSLFDP HWVFGGGTKL TVL           113

SEQ ID NO: 185          moltype = AA   length = 113
FEATURE                 Location/Qualifiers
REGION                  1..113
                        note = antibody light chain variable region
source                  1..113
                        mol_type = protein
                        organism = synthetic construct
SEQUENCE: 185
QTVLTQPPSV SGAPGQRVTI SCTGSSSNIG AGYRVHWYQQ LPGTAPKLLI YGRSNRPSGV     60
PDRFSGSKSG TSASLAITGL QAEDEADYYC QSYDSSLFDP HWVFGGGTKL TVL           113

SEQ ID NO: 186          moltype = AA   length = 113
FEATURE                 Location/Qualifiers
REGION                  1..113
                        note = antibody light chain variable region
source                  1..113
                        mol_type = protein
                        organism = synthetic construct
SEQUENCE: 186
QTVLTQPPSV SGAPGQRVTI SCTGSSSNIG AGYDVHWYQQ LPGTAPKLLI CGRSNRPSGV     60
PDRFSGSKSG TSASLAITGL QAEDEADYYC QSYDSSLSDP HWVFGGGTKL TVL           113

SEQ ID NO: 187          moltype = AA   length = 113
FEATURE                 Location/Qualifiers
REGION                  1..113
                        note = antibody light chain variable region
source                  1..113
                        mol_type = protein
                        organism = synthetic construct
SEQUENCE: 187
```

-continued

```
QTVLTQPPSV SGAPGQRVTI SCTGSSSNIG AGYDVHWYQQ LPGTAPKLLI AGRSNRPSGV  60
PDRFSGSKSG TSASLAITGL QAEDEADYYC QSYDSSLSDP HWVFGGGTKL TVL         113

SEQ ID NO: 188          moltype = AA  length = 113
FEATURE                 Location/Qualifiers
REGION                  1..113
                        note = antibody light chain variable region
source                  1..113
                        mol_type = protein
                        organism = synthetic construct
SEQUENCE: 188
QTVLTQPPSV SGAPGQRVTI SCTGSSSNIG AGYDVHWYQQ LPGTAPKLLI SGRSNRPSGV  60
PDRFSGSKSG TSASLAITGL QAEDEADYYC QSYDSSLSDP HWVFGGGTKL TVL         113

SEQ ID NO: 189          moltype = AA  length = 113
FEATURE                 Location/Qualifiers
REGION                  1..113
                        note = antibody light chain variable region
source                  1..113
                        mol_type = protein
                        organism = synthetic construct
SEQUENCE: 189
QTVLTQPPSV SGAPGQRVTI SCTGSSSNIG AGYDVHWYQQ LPGTAPKLLI YGRSNRPSGV  60
PDRFSGSKSG TSASLAITGL QAEDEADYYC QSYDSSLSDP HWVFGGGTKL TVL         113

SEQ ID NO: 190          moltype = AA  length = 113
FEATURE                 Location/Qualifiers
REGION                  1..113
                        note = antibody light chain variable region
source                  1..113
                        mol_type = protein
                        organism = synthetic construct
SEQUENCE: 190
QTVLTQPPSV SGAPGQRVTI SCTGSSSNIG AGYDVHWYQQ LPGTAPKLLI CGNDNRPSGV  60
PDRFSGSKSG TSASLAITGL QAEDEADYYC QSYDSSSSGP HWVFGGGTKL TVL         113

SEQ ID NO: 191          moltype = AA  length = 227
FEATURE                 Location/Qualifiers
REGION                  1..227
                        note = antibody heavy chain
source                  1..227
                        mol_type = protein
                        organism = synthetic construct
SEQUENCE: 191
EVQLVESGAE VKKPGESLKI SCKGSGYTFT RYWIGWVRQM PGKGLEWMGI IYPGDSDTRY  60
SPSFQGHVTI SADKSISTAY LQWNSLKASD TAMYYCARLP QYCSNGVCQR WFDPWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKS                227

SEQ ID NO: 192          moltype = AA  length = 213
FEATURE                 Location/Qualifiers
REGION                  1..213
                        note = antibody light chain
source                  1..213
                        mol_type = protein
                        organism = synthetic construct
SEQUENCE: 192
EIVLTQSPSS VSASVGDRVT ITCRASQGIS SWLAWYQQKP GKAPKLLIYA ASSLQSGVPS  60
RFSGSGSGTD FTLTISSLQP EDFATYYCQQ GNSFPYTFGQ GTNLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGE                               213

SEQ ID NO: 193          moltype = AA  length = 27
FEATURE                 Location/Qualifiers
REGION                  1..27
                        note = the C-terminal end of the SARS-CoV-2 spike S2 stem
                         helix
source                  1..27
                        mol_type = protein
                        organism = synthetic construct
SEQUENCE: 193
PLQPELDSFK EELDKYFKNH TSPDVDL                                      27

SEQ ID NO: 194          moltype = AA  length = 330
FEATURE                 Location/Qualifiers
REGION                  1..330
                        note = antibody heavy chain constant domain
source                  1..330
                        mol_type = protein
```

-continued

```
                        organism = synthetic construct
SEQUENCE: 194
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 195           moltype = AA   length = 107
FEATURE                  Location/Qualifiers
REGION                   1..107
                         note = antibody light chain constant domain
source                   1..107
                         mol_type = protein
                         organism = synthetic construct
SEQUENCE: 195
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 196           moltype = AA   length = 106
FEATURE                  Location/Qualifiers
REGION                   1..106
                         note = antibody light chain constant domain
source                   1..106
                         mol_type = protein
                         organism = synthetic construct
SEQUENCE: 196
GQPKANPTVT LFPPSSEELQ ANKATLVCLI SDFYPGAVTV AWKADGSPVK AGVETTKPSK    60
QSNNKYAASS YLSLTPEQWK SHRSYSCQVT HEGSTVEKTV APTECS                  106

SEQ ID NO: 197           moltype = AA   length = 19
FEATURE                  Location/Qualifiers
REGION                   1..19
                         note = SARS-CoV-2 spike S2 (aa 1149-1167)
source                   1..19
                         mol_type = protein
                         organism = synthetic construct
SEQUENCE: 197
KEELDKYFKN HTSPDVDLG                                                 19

SEQ ID NO: 198           moltype = AA   length = 1254
FEATURE                  Location/Qualifiers
REGION                   1..1254
                         note = BA.1 spike trimer
source                   1..1254
                         mol_type = protein
                         organism = synthetic construct
SEQUENCE: 198
VHSVSSQCVN LTTRTQLPPA YTNSFTRGVY YPDKVFRSSV LHSTQDLFLP FFSNVTWFHV    60
ISGTNGTKRF DNPVLPFNDG VYFASIEKSN IIRGWIFGTT LDSKTQSLLI VNNATNVVIK   120
VCEFQFCNDP FLDHKNNKSW MESEFRVYSS ANNCTFEYVS QPFLMDLEGK QGNFKNLREF   180
VFKNIDGYFK IYSKHTPIIV REPEDLPQGF SALEPLVDLP IGINITRFQT LLALHRSYLT   240
PGDSSSGWTA GAAAYYVGYL QPRTFLLKYN ENGTITDAVD CALDPLSETK CTLKSFTVEK   300
GIYQTSNFRV QPTESIVRFP NITNLCPFDE VFNATRFASV YAWNRKRISN CVADYSVLYN   360
LAPFFTFKCY GVSPTKLNDL CFTNVYADSF VIRGDEVRQI APGQTGNIAD YNYKLPDDFT   420
GCVIAWNSNK LDSKVSGNYN YLYRLFRKSN LKPFERDIST EIYQAGNKPC NGVAGFNCYF   480
PLRSYSFRPT YGVGHQPYRV VVLSFELLHA PATVCGPKKS TNLVKNKCVN FNFNGLKGTG   540
VLTESNKKFL PFQQFGRDIA DTTDAVRDPQ TLEILDITPC SFGGVSVITP GTNTSNQVAV   600
LYQGVNCTEV PVAIHADQLT PTWRVYSTGS NVFQTRAGCL IGAEYVNNSY ECDIPIGAGI   660
CASYQTQTKS HRAAASVASQ SIIAYTMSLG AENSVAYSNN SIAIPTNFTI SVTTEILPVS   720
MTKTSVDCTM YICGDSTECS NLLLQYGSFC TQLKRALTGI AVEQDKNTQE VFAQVKQIYK   780
TPPIKYFGGF NFSQILPDPS KPSKRSPIED LLFNKVTLAD AGFIKQYGDC LGDIAARDLI   840
CAQKFKGLTV LPPLLTDEMI AQYTSALLAG TITSGWTFGA GPALQIPFPM QMAYRFNGIG   900
VTQNVLYENQ KLIANQFNSA IGKIQDSLSS TPSALGKLQD VVNHNAQALN TLVKQLSSKF   960
GAISSVLNDI FSRLDPPEAE VQIDRLITGR LQSLQTYVTQ QLIRAAEIRA SANLAATKMS  1020
ECVLGQSKRV DFCGKGYHLM SFPQSAPHGV VFLHVTYVPA QEKNFTTAPA ICHDGKAHFP  1080
REGVFVSNGT HWFVTQRNFY EPQIITTDNT FVSGNCDVVI GIVNNTVYDP LQPELDSFKE  1140
ELDKYFKNHT SPDVDLGDIS GINASVVNIQ KEIDRLNEVA KNLNESLIDL QELGKYEQYI  1200
KWPGGYIPEA PRDGQAYVRK DGEWVLLSTF GGGSGGGSHH HHHHSAWSHP QFEK        1254

SEQ ID NO: 199           moltype = AA   length = 1240
FEATURE                  Location/Qualifiers
REGION                   1..1240
                         note = WIV1
source                   1..1240
                         mol_type = protein
                         organism = synthetic construct
SEQUENCE: 199
```

-continued

```
MKLLVLVFAT LVSSYTIEKC LDFDDRTPPA NTQFLSSHRG VYYPDDIFRS NVLHLVQDHF  60
LPFDSNVTRF ITFGLNFDNP IIPFKDGIYF AATEKSNVIR GWVFGSTMNN KSQSVIIMNN 120
STNLVIRACN FELCDNPFFV VLKSNNTQIP SYIFNNAFNC TFEYVSKDFN LDLGEKPGNF 180
KDLREFVFRN KDGFLHVYSG YQPISAASGL PTGFNALKPI FKLPLGINIT NFRTLLTAFP 240
PRPDYWGTSA AAYFVGYLKP TTFMLKYDEN GTITDAVDCS QNPLAELKCS VKSFEIDKGI 300
YQTSNFRVAP SKEVVRFPNI TNLCPFGEVF NATTFPSVYA WERKRISNCV ADYSVLYNST 360
SFSTFKCYGV SATKLNDLCF SNVYADSFVV KGDDVRQIAP GQTGVIADYN YKLPDDFTGC 420
VLAWNTRNID ATQTGNYNYK YRSLRHGKLR PFERDISNVP FSPDGKPCTP PAFNCYWPLN 480
DYGFYITNGI GYQPYRVVVL SFELLNAPAT VCGPKLSTDL IKNQCVNFNF NGLTGTGVLT 540
PSSKRFQPFQ QFGRDVSDFT DSVRDPKTSE ILDISPCSFG GVSVITPGTN TSSEVAVLYQ 600
DVNCTDVPVA IHADQLTPSW RVHSTGNNVF QTQAGCLIGA EHVDTSYECD IPIGAGICAS 660
YHTVSSLRST SQKSIVAYTM SLGADSSIAY SNNTIAIPTN FSISITTEVM PVSMAKTSVD 720
CNMYICGDST ECANLLLQYG SFCTQLNRAL SGIAVEQDRN TREVFAQVKQ MYKTPTLKDF 780
GGFNFSQILP DPLKPTKRSF IEDLLFNKVT LADAGFMKQY GECLGDINAR DLICAQKFNG 840
LTVLPPLLTD DMIAAYTAAL VSGTATAGWT FGAGAALQIP FAMQMAYRFN GIGVTQNVLY 900
ENQKQIANQF NKAISQIQES LTTTSTALGK LQDVVNQNAQ ALNTLVKQLS SNFGAISSVL 960
NDILSRLDPP EAEVQIDRLI TGRLQSLQTY VTQQLIRAAE IRASANLAAT KMSECVLGQS 1020
KRVDFCGKGY HLMSFPQAAP HGVVFLHVTY VPSQERNFTT APAICHEGKA YFPREGVFVF 1080
NGTSWFITQR NFFSPQIITT DNTFVSGSCD VVIGIINNTV YDPLQPELDS FKEELDKYFK 1140
NHTSPDVDLG DISGINASVV NIQKEIDRLN EVAKNLNESL IDLQELGKYE QGGYIPEAPR 1200
DGQAYVRKDG EWVLLSTFGG GSGGGSHHHH HHWSHPQFEK                       1240

SEQ ID NO: 200          moltype = AA  length = 1246
FEATURE                 Location/Qualifiers
REGION                  1..1246
                        note = SARS-CoV-2 BA.2_P1162L
source                  1..1246
                        mol_type = protein
                        organism = synthetic construct
SEQUENCE: 200
VNLITRTQSY TNSFTRGVYY PDKVFRSSVL HSTQDLFLPF FSNVTWFHAI HVSGTNGTKR  60
FDNPVLPFND GVYFASTEKS NIIRGWIFGT TLDSKTQSLL IVNNATNVVI KVCEFQFCND 120
PFLDVYYHKN NKSWMESEFR VYSSANNCTF EYVSQPFLMD LEGKQGNFKN LREFVFKNID 180
GYFKIYSKHT PINLGRDLPQ GFSALEPLVD LPIGINITRF QTLLALHRSY LTPGDSSSGW 240
TAGAAAYYVG YLQPRTFLLK YNENGTITDA VDCALDPLSE TKCTLKSFTV EKGIYQTSNF 300
RVQPTESIVR FPNITNLCPF DEVFNATRFA SVYAWNRKRI SNCVADYSVL YNFAPFFAFK 360
CYGVSPTKLN DLCFTNVYAD SFVIRGNEVS QIAPGQTGNI ADYNYKLPDD FTGCVIAWNS 420
NKLDSKVGGN YNYLYRLFRK SNLKPFERDI STEIYQAGNK PCNGVAGFNC YFPLRSYGFR 480
PTYGVGHQPY RVVVLSFELL HAPATVCGPK KSTNLVKNKC VNFNFNGLTG TGVLTESNKK 540
FLPFQQFGRD IADTTDAVRD PQTLEILDIT PCSFGGVSVI TPGTNTSNQV AVLYQGVNCT 600
EVPVAIHADQ LTPTWRVYST GSNVFQTRAG CLIGAEYVNN SYECDIPIGA GICASYQTQT 660
KSHRAAASVA SQSIIAYTMS LGAENSVAYS NNSIAIPTNF TISVTTEILP VSMTKTSVDC 720
TMYICGDSTE CSNLLLQYGS FCTQLKRALT GIAVEQDKNT QEVFAQVKQI YKTPPIKYFG 780
GFNFSQILPD PSKPSKRSPI EDLLFNKVTL ADAGFIKQYG DCLGDIAARD LICAQKFNGL 840
TVLPPLLTDE MIAQYTSALL AGTITSGWTF GAGPALQIPF PMQMAYRFNG IGVTQNVLYE 900
NQKLIANQFN SAIGKIQDSL SSTPSALGKL QDVVNHNAQA LNTLVKQLSS KFGAISSVLN 960
DILSRLDPPE AEVQIDRLIT GRLQSLQTYV TQQLIRAAEI RASANLAATK MSECVLGQSK 1020
RVDFCGKGYH LMSFPQSAPH GVVFLHVTYV PAQEKNFTTA PAICHDGKAH FPREGVFVSN 1080
GTHWFVTQRN FYEPQIITTD NTFVSGNCDV VIGIVNNTVY DPLQPELDSF KEELDKYFKN 1140
HTSLDVDLGD ISGINASVVN IQKEIDRLNE VAKNLNESLI DLQELGKYEQ YIKWPGGYIP 1200
EAPRDGQAYV RKDGEWVLLS TFGGGSGGGS HHHHHHSAWS HPQFEK                1246

SEQ ID NO: 201          moltype = AA  length = 1246
FEATURE                 Location/Qualifiers
REGION                  1..1246
                        note = SARS-CoV-2 BA.2_P1162S
source                  1..1246
                        mol_type = protein
                        organism = synthetic construct
SEQUENCE: 201
VNLITRTQSY TNSFTRGVYY PDKVFRSSVL HSTQDLFLPF FSNVTWFHAI HVSGTNGTKR  60
FDNPVLPFND GVYFASTEKS NIIRGWIFGT TLDSKTQSLL IVNNATNVVI KVCEFQFCND 120
PFLDVYYHKN NKSWMESEFR VYSSANNCTF EYVSQPFLMD LEGKQGNFKN LREFVFKNID 180
GYFKIYSKHT PINLGRDLPQ GFSALEPLVD LPIGINITRF QTLLALHRSY LTPGDSSSGW 240
TAGAAAYYVG YLQPRTFLLK YNENGTITDA VDCALDPLSE TKCTLKSFTV EKGIYQTSNF 300
RVQPTESIVR FPNITNLCPF DEVFNATRFA SVYAWNRKRI SNCVADYSVL YNFAPFFAFK 360
CYGVSPTKLN DLCFTNVYAD SFVIRGNEVS QIAPGQTGNI ADYNYKLPDD FTGCVIAWNS 420
NKLDSKVGGN YNYLYRLFRK SNLKPFERDI STEIYQAGNK PCNGVAGFNC YFPLRSYGFR 480
PTYGVGHQPY RVVVLSFELL HAPATVCGPK KSTNLVKNKC VNFNFNGLTG TGVLTESNKK 540
FLPFQQFGRD IADTTDAVRD PQTLEILDIT PCSFGGVSVI TPGTNTSNQV AVLYQGVNCT 600
EVPVAIHADQ LTPTWRVYST GSNVFQTRAG CLIGAEYVNN SYECDIPIGA GICASYQTQT 660
KSHRAAASVA SQSIIAYTMS LGAENSVAYS NNSIAIPTNF TISVTTEILP VSMTKTSVDC 720
TMYICGDSTE CSNLLLQYGS FCTQLKRALT GIAVEQDKNT QEVFAQVKQI YKTPPIKYFG 780
GFNFSQILPD PSKPSKRSPI EDLLFNKVTL ADAGFIKQYG DCLGDIAARD LICAQKFNGL 840
TVLPPLLTDE MIAQYTSALL AGTITSGWTF GAGPALQIPF AMQMAYRFNG IGVTQNVLYE 900
NQKLIANQFN SAIGKIQDSL SSTPSALGKL QDVVNHNAQA LNTLVKQLSS KFGAISSVLN 960
DILSRLDPPE AEVQIDRLIT GRLQSLQTYV TQQLIRAAEI RASANLAATK MSECVLGQSK 1020
RVDFCGKGYH LMSFPQSAPH GVVFLHVTYV PAQEKNFTTA PAICHDGKAH FPREGVFVSN 1080
GTHWFVTQRN FYEPQIITTD NTFVSGNCDV VIGIVNNTVY DPLQPELDSF KEELDKYFKN 1140
```

```
HTSSDVDLGD ISGINASVVN IQKEIDRLNE VAKNLNESLI DLQELGKYEQ YIKWPGGYIP  1200
EAPRDGQAYV RKDGEWVLLS TFGGGSGGGS HHHHHHSAWS HPQFEK              1246

SEQ ID NO: 202          moltype = AA  length = 1246
FEATURE                 Location/Qualifiers
REGION                  1..1246
                        note = SARS-CoV-2 BA.2 (parent)
source                  1..1246
                        mol_type = protein
                        organism = synthetic construct
SEQUENCE: 202
VNLITRTQSY TNSFTRGVYY PDKVFRSSVL HSTQDLFLPF FSNVTWFHAI HVSGTNGTKR  60
FDNPVLPFND GVYFASTEKS NIIRGWIFGT TLDSKTQSLL IVNNATNVVI KVCEFQFCND  120
PFLDVYYHKN NKSWMESEFR VYSSANNCTF EYVSQPFLMD LEGKQGNFKN LREFVFKNID  180
GYFKIYSKHT PINLGRDLPQ GFSALEPLVD LPIGINITRF QTLLALHRSY LTPGDSSSGW  240
TAGAAAYYVG YLQPRTFLLK YNENGTITDA VDCALDPLSE TKCTLKSFTV EKGIYQTSNF  300
RVQPTESIVR FPNITNLCPF DEVFNATRFA SVYAWNRKRI SNCVADYSVL YNFAPFFAFK  360
CYGVSPTKLN DLCFTNVYAD SFVIRGNEVS QIAPGQTGNI ADYNYKLPDD FTGCVIAWNS  420
NKLDSKVGGN YNYLYRLFRK SNLKPFERDI STEIYQAGNK PCNGVAGFNC YFPLRSYGFR  480
PTYGVGHQPY RVVVLSFELL HAPATVCGPK KSTNLVKNKC VNFNFNGLTG TGVLTESNKK  540
FLPFQQFGRD IADTTDAVRD PQTLEILDIT PCSFGGVSVI TPGTNTSNQV AVLYQGVNCT  600
EVPVAIHADQ LTPTWRVYST GSNVFQTRAG CLIGAEYVNN SYECDIPIGA GICASYQTQT  660
KSHRAAASVA SQSIIAYTMS LGAENSVAYS NNSIAIPTNF TISVTTEILP VSMTKTSVDC  720
TMYICGDSTE CSNLLLQYGS FCTQLKRALT GIAVEQDKNT QEVFAQVKQI YKTPPIKYFG  780
GFNFSQILPD PSKPSKRSPI EDLLFNKVTL ADAGFIKQYG DCLGDIAARD LICAQKFNGL  840
TVLPPLLTDE MIAQYTSALL AGTITSGWTF GAGPALQIPF AMQMAYRFNG IGVTQNVLYE  900
NQKLIANQFN SAIGKIQDSL SSTPSALGKL QDVVNHNAQA LNTLVKQLSS KFGAISSVLN  960
DILSRLDPPE AEVQIDRLIT GRLQSLQTYV TQQLIRAAEI RASANLAATK MSECVLGQSK  1020
RVDFCGKGYH LMSFPQSAPH GVVFLHVTYV PAQEKNFTTA PAICHDGKAH FPREGVFVSN  1080
GTHWFVTQRN FYEPQIITTD NTFVSGNCDV VIGIVNNTVY DPLQPELDSF KEELDKYFKN  1140
HTSPDVDLGD ISGINASVVN IQKEIDRLNE VAKNLNESLI DLQELGKYEQ YIKWPGGYIP  1200
EAPRDGQAYV RKDGEWVLLS TFGGGSGGGS HHHHHHSAWS HPQFEK              1246

SEQ ID NO: 203          moltype = AA  length = 15
FEATURE                 Location/Qualifiers
REGION                  1..15
                        note = SARS-CoV-2 S2 peptide 1133-1147
source                  1..15
                        mol_type = protein
                        organism = synthetic construct
SEQUENCE: 203
VNNTVYDPLQ PELDS                                                   15

SEQ ID NO: 204          moltype = AA  length = 15
FEATURE                 Location/Qualifiers
REGION                  1..15
                        note = SARS-CoV-2 S2 peptide 1137-1151
source                  1..15
                        mol_type = protein
                        organism = synthetic construct
SEQUENCE: 204
VYDPLQPELD SFKEE                                                   15

SEQ ID NO: 205          moltype = AA  length = 15
FEATURE                 Location/Qualifiers
REGION                  1..15
                        note = SARS-CoV-2 S2 peptide 1141-1155
source                  1..15
                        mol_type = protein
                        organism = synthetic construct
SEQUENCE: 205
LQPELDSFKE ELDKY                                                   15

SEQ ID NO: 206          moltype = AA  length = 15
FEATURE                 Location/Qualifiers
REGION                  1..15
                        note = SARS-CoV-2 S2 peptide 1145-1159
source                  1..15
                        mol_type = protein
                        organism = synthetic construct
SEQUENCE: 206
LDSFKEELDK YFKNH                                                   15

SEQ ID NO: 207          moltype = AA  length = 15
FEATURE                 Location/Qualifiers
REGION                  1..15
                        note = SARS-CoV-2 S2 peptide 1149-1163
source                  1..15
                        mol_type = protein
```

```
                              -continued

SEQUENCE: 207
KEELDKYFKN HTSPD                                                   15

SEQ ID NO: 208          moltype = AA  length = 15
FEATURE                 Location/Qualifiers
REGION                  1..15
                        note = SARS-CoV-2 S2 peptide 1153-1167
source                  1..15
                        mol_type = protein
                        organism = synthetic construct
SEQUENCE: 208
DKYFKNHTSP DVDLG                                                   15

SEQ ID NO: 209          moltype = AA  length = 15
FEATURE                 Location/Qualifiers
REGION                  1..15
                        note = SARS-CoV-2 S2 peptide 1157-1171
source                  1..15
                        mol_type = protein
                        organism = synthetic construct
SEQUENCE: 209
KNHTSPDVDL GDISG                                                   15

SEQ ID NO: 210          moltype = AA  length = 19
FEATURE                 Location/Qualifiers
REGION                  1..19
                        note = SARS-CoV-2 S2 peptide 1149-1167
source                  1..19
                        mol_type = protein
                        organism = synthetic construct
SEQUENCE: 210
KEELDKYFKN HTSPDVDLG                                               19

SEQ ID NO: 211          moltype = AA  length = 19
FEATURE                 Location/Qualifiers
REGION                  1..19
                        note = SARS-CoV-2 S2 peptide 1149-1167
source                  1..19
                        mol_type = protein
                        organism = synthetic construct
SEQUENCE: 211
KEELDKYFKN HTSPDVDLG                                               19

SEQ ID NO: 212          moltype = AA  length = 20
FEATURE                 Location/Qualifiers
REGION                  1..20
                        note = SARS-CoV-2 S2 peptide 1143-1162
source                  1..20
                        mol_type = protein
                        organism = synthetic construct
SEQUENCE: 212
PELDSFKEEL DKYFKNHTSP                                              20

SEQ ID NO: 213          moltype = AA  length = 20
FEATURE                 Location/Qualifiers
REGION                  1..20
                        note = SARS-CoV-2 S2 peptide 1143-1162
source                  1..20
                        mol_type = protein
                        organism = synthetic construct
SEQUENCE: 213
PELDSFKEEL DKYFKNHTSP                                              20

SEQ ID NO: 214          moltype = AA  length = 15
FEATURE                 Location/Qualifiers
REGION                  1..15
                        note = HIV-1 Env peptide
source                  1..15
                        mol_type = protein
                        organism = synthetic construct
SEQUENCE: 214
NMWKNDMVDQ MHEDI                                                   15
```

ANTIGEN BINDING MOLECULES TARGETING SARS-COV-2

RELATED APPLICATIONS

This application claims the benefit of U.S. Provisional Application No. 63/364,331, filed on May 6, 2022, U.S. Provisional Application No. 63/364,328, filed on May 6, 2022, U.S. Provisional Application No. 63/381,131, filed on Oct. 26, 2022, U.S. Provisional Application No. 63/381,132, filed on Oct. 26, 2022, U.S. Provisional Application No. 63/424,945, filed on Nov. 13, 2022, U.S. Provisional Application No. 63/383,695, filed on Nov. 14, 2022, U.S. Provisional Application No. 63/385,957, filed on Dec. 2, 2022, U.S. Provisional Application No. 63/478,650, filed on Jan. 5, 2023, U.S. Provisional Application No. 63/480,903, filed on Jan. 20, 2023, and U.S. Provisional Application No. 63/492,206, filed on Mar. 24, 2023. The entire teachings of the above applications are incorporated herein by reference.

INCORPORATION BY REFERENCE OF MATERIAL IN XML

This application incorporates by reference the Sequence Listing contained in the following eXtensible Markup Language (XML) file being submitted concurrently herewith:
  a) File name: 57081065007.xml; created May 4, 2023, 306,431 Bytes in size.

BACKGROUND

The SARS-Coronavirus-2 (SARS-CoV-2), a novel coronavirus, first caused a cluster of pneumonia cases (COVID-19) in Wuhan, China. As of Mar. 1, 2020, 79,968 patients in China had tested positive for COVID-19, 2,873 deaths had occurred, equivalent to a mortality rate of 3.6% (95% CI 3.5-3.7) (Baud et al. *Real estimates of mortality following COVID-19 infection*, Lancet Infect Dis. 20(7):773 (2020)). This figure, however, may be an underestimate of the potential threat of COVID-19 in symptomatic patients (Id.).

COVID-19 has been spreading rapidly throughout the world, resulting in a pandemic. The Coronavirus disease (COVID-2019) situation report released from the World Health Organization on Apr. 21, 2020 reported 2,397,216 confirmed infections and 162,956 deaths. Among them, 83,006 new cases and 5,109 deaths were added within the previous 24 hours. Quarantine, isolation, and infection-control measures have been relied on to prevent disease spread, and supportive care for those who become ill (Baden & Rubin, *Covid-19 —The Search for Effective Therapy*, N Engl J Med. 382(19):1851-52 (2020)).

Despite development and use of vaccines and therapeutics, SARS-CoV2 outbreaks continue and mutants of SARS-CoV2 continue to develop and evade these prophylactics and treatments. Accordingly, a need exists for additional therapeutics that can be rapidly deployed, preferably therapeutics that counter escape mutants and retain therapeutic efficacy, e.g., through broadly neutralizing activity.

SUMMARY

There is a critical need to develop specific antiviral therapeutic agents for preventing transmission of COVID-19 as well as treating COVID-19 patients, preferably where such therapeutic agents retain activity against new and emerging variants, with broadly neutralizing activity. The disclosure provides such therapeutics.

The disclosure provided herein is based, in part, on the discovery that polypeptides disclosed herein specifically bind to the Spike glycoprotein of severe acute respiratory syndrome coronavirus 2 (SARS-CoV-2-Spike). The disclosure provided herein is based, in part, on the discovery that polypeptides disclosed herein display robust neutralizing activity against SARS-CoV-2 variants in vitro and in vivo. Accordingly, the disclosure generally relates to compositions (e.g., polypeptides, pharmaceutical compositions) and methods that are useful for reducing Spike (e.g., SARS-CoV-2-Spike) mediated viral entry into a cell.

Provided herein, among other things, are polypeptides (e.g., antibodies and antigen binding fragments thereof) that specifically bind an S2 domain epitope of a betacoronavirus Spike glycoprotein (e.g., an S2 domain epitope of a severe acute respiratory syndrome coronavirus 2 (SARS-CoV-2) Spike glycoprotein). In some embodiments, the polypeptides have one or more properties selected from: a broadly neutralizing activity against a plurality of known and predicted betacoronaviruses (e.g., past, present, emergent, and future betacoronaviruses), and a binding affinity for an S2 domain epitope that is highly conserved across a plurality of betacoronaviruses. In some embodiments, a polypeptide has a broadly neutralizing activity against a plurality of known and predicted betacoronaviruses, and a binding affinity for an S2 domain epitope that is highly conserved across a plurality of betacoronaviruses.

The disclosure provides, among other things, polypeptides that specifically bind SARS-CoV-2-Spike, wherein the polypeptide comprises a paratope that is substantially similar to a paratope of an antibody comprising a $V_H/V_L$ pair selected from:
  SEQ ID NO:4 and SEQ ID NO:51 (AB-1);
  SEQ ID NO:5 and SEQ ID NO:52 (AB-2);
  SEQ ID NO:6 and SEQ ID NO:53 (AB-3);
  SEQ ID NO:7 and SEQ ID NO:54 (AB-4);
  SEQ ID NO:8 and SEQ ID NO:51 (AB-5);
  SEQ ID NO:9 and SEQ ID NO:55 (AB-6);
  SEQ ID NO:10 and SEQ ID NO:56 (AB-7);
  SEQ ID NO:11 and SEQ ID NO:57 (AB-8);
  SEQ ID NO:12 and SEQ ID NO:58 (AB-9);
  SEQ ID NO:13 and SEQ ID NO:59 (AB-10);
  SEQ ID NO:14 and SEQ ID NO:60 (AB-11);
  SEQ ID NO:15 and SEQ ID NO:56 (AB-12);
  SEQ ID NO:16 and SEQ ID NO:51 (AB-13);
  SEQ ID NO:10 and SEQ ID NO:50 (AB-14);
  SEQ ID NO:17 and SEQ ID NO:61 (AB-15);
  SEQ ID NO:18 and SEQ ID NO:62 (AB-16);
  SEQ ID NO:6 and SEQ ID NO:63 (AB-17);
  SEQ ID NO:19 and SEQ ID NO:64 (AB-18);
  SEQ ID NO:4 and SEQ ID NO:61 (AB-19);
  SEQ ID NO:20 and SEQ ID NO:61 (AB-20);
  SEQ ID NO:21 and SEQ ID NO:65 (AB-21);
  SEQ ID NO:22 and SEQ ID NO:66 (AB-22);
  SEQ ID NO:4 and SEQ ID NO:67 (AB-23);
  SEQ ID NO:23 and SEQ ID NO:56 (AB-24);
  SEQ ID NO:24 and SEQ ID NO:68 (AB-25);
  SEQ ID NO:25 and SEQ ID NO:51 (AB-26);
  SEQ ID NO:26 and SEQ ID NO:56 (AB-27);
  SEQ ID NO:27 and SEQ ID NO:61 (AB-28);
  SEQ ID NO:28 and SEQ ID NO:56 (AB-29);
  SEQ ID NO:28 and SEQ ID NO:69 (AB-30);
  SEQ ID NO:29 and SEQ ID NO:70 (AB-31);
  SEQ ID NO:30 and SEQ ID NO:71 (AB-32);
  SEQ ID NO:31 and SEQ ID NO:72 (AB-33);
  SEQ ID NO:32 and SEQ ID NO:67 (AB-34);
  SEQ ID NO:33 and SEQ ID NO:56 (AB-35);

SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51), or
any combination of the foregoing.

The disclosure also provides, among other things, a polypeptide that specifically binds SARS-CoV-2-Spike, wherein the polypeptide comprises:

an immunoglobulin heavy chain variable domain ($V_H$) amino acid sequence comprising a heavy chain complementarity determining region 1 (HCDR1), a heavy chain complementarity determining region 2 (HCDR2) and a heavy chain complementarity determining region 3 (HCDR3) that are substantially similar to a HCDR1, a HCDR2 and/or a HCDR3, respectively, of the amino acid sequence of any one of SEQ ID NOs:4-48; and an immunoglobulin light chain variable domain ($V_L$) amino acid sequence comprising a light chain complementarity determining region 1 (LCDR1), a light chain complementarity determining region 2 (LCDR2) and a light chain complementarity determining region 3 (LCDR3) that are substantially similar to a LCDR1, a LCDR2 and/or a LCDR3, respectively, of the amino acid sequence of any one of SEQ ID NOs:51-76.

In some embodiments, a polypeptide disclosed herein comprises a HCDR1, HCDR2 and/or HCDR3, and/or a LCDR1, LCDR2 and/or LCDR3, of an antibody comprising an amino acid sequence selected from:
SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);
SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51).

In some embodiments, a polypeptide disclosed herein comprises a paratope that is identical to a paratope of an antibody comprising an amino acid sequence selected from:
SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);
SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);

SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51).

The disclosure further provides, among other things, a polypeptide that comprises a $V_H$ comprising SEQ ID NO:2, wherein:
$X_1$ is not S;
$X_2$ is not D;
$X_3$ is not T;
$X_4$ is not L;
$X_5$ is not S;
$X_6$ is not N;
$X_7$ is not G;
$X_8$ is not V; or
$X_9$ is not Q,
or any combination of the foregoing.

In some embodiments, a polypeptide disclosed herein comprises a $V_L$ comprising SEQ ID NO:49, wherein:
$X_{10}$ is not Q;
$X_{11}$ is not G;
$X_{12}$ is not S;
$X_{13}$ is not S;
$X_{14}$ is not N;
$X_{15}$ is not S;
$X_{16}$ is not F; or
$X_{17}$ is not Y,
or any combination of the foregoing.

In some embodiments, the disclosure provides a polypeptide that specifically binds SARS-CoV-2-Spike, comprising:
a $V_H$ sequence that has at least 70% sequence identity to SEQ ID NO:3;
a $V_L$ sequence that has at least 70% sequence identity to SEQ ID NO:50; or
a combination thereof,
wherein the $V_H$ sequence does not comprise SEQ ID NO:3, the $V_L$ sequence does not comprise SEQ ID NO:50, or both.

In some embodiments, a polypeptide disclosed herein is a fusion protein.

In some embodiments, the disclosure provides a polynucleotide encoding a polypeptide disclosed herein, a vector comprising such polynucleotide, and a host cell comprising such polynucleotide and/or vector.

In some embodiments, the disclosure provides methods of treating a patient and/or subject in need thereof (e.g., a subject having a SARS-CoV infection, such as COVID-19), comprising administering to the subject an effective amount (e.g., a therapeutically effective amount) of one or more polypeptides disclosed herein and/or a composition (e.g., pharmaceutical composition) comprising one or more polypeptides disclosed herein.

In some embodiments, the disclosure provides methods of neutralizing SARS-CoV-2 variants in a cell (e.g., a cell in a subject), comprising contacting the cell with an effective amount of a composition comprising a polypeptide disclosed herein and/or a composition (e.g., pharmaceutical composition) comprising a polypeptide disclosed herein.

In some embodiments, the disclosure provides methods of neutralizing SARS-CoV-2 variants in a subject, comprising providing the subject with an effective amount of a composition comprising a polypeptide disclosed herein and/or a composition (e.g., pharmaceutical composition) comprising a polypeptide disclosed herein.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

In the drawings, "Reference" refers to the Reference Antibody.

FIG. 1 depicts the amino acid sequence of an epitope (bold letters) within the S2 domain (underlined) of SARS-CoV-2-Spike (SEQ ID NO:1). The epitope residues bound by the Reference Antibody disclosed herein are indicated by asterisks.

FIG. 2 depicts an alignment of the heavy chain variable domain ($V_H$) amino acid sequences of the Reference Antibody and AB-1. The heavy chain complementarity determining region (HCDR) amino acid sequences as determined by ImMunoGeneTics (IMGT) numbering are indicated using underlining. The bold letters indicate variable residues (designated throughout this disclosure by "Xn") in the Reference Antibody and AB-1 to AB-51. "*" indicates paratope residues. Also see $V_H$ consensus sequences in Table 1. Paratope positions were defined as antibody residues in the Reference that, when bound to the S2 domain of SARS-CoV-2-Spike, are within 5 angstroms of the antigen.

FIG. 3 depicts an alignment of the light chain variable domain ($V_L$) amino acid sequences of the Reference Antibody and AB-1. The light chain complementarity determining region (LCDR) amino acid sequences as determined by IMGT numbering are indicated using underlining. The bold letters indicate variable residues (designated throughout this disclosure by "Xn") in the Reference Antibody and AB-1 to AB-51. "*" indicates paratope residues. Also see $V_L$ consensus sequences in Table 2. Paratope positions were defined as antibody residues in the Reference Antibody that, when bound to the S2 domain of SARS-CoV-2-Spike, are within 5 angstroms of the antigen.

FIGS. 4A-4B show binding data expressed as composite scores across the indicated viruses. "Designs" refer to test antibodies, and "Seeds" refer to test antibodies that have been selected for project learning. ADG20, REGN10933 and REGN10987 are control antibodies.

FIGS. 6A-6B show tables summarizing data for screening hits, clinical stage molecule and the Reference Antibody. Composite neutralization score: score that accounts for all neutralization data for each antibody and express them as single value. The higher the value, the better the overall neutralization profile of that specific antibody. Composite binding score: score that accounts for all binding data for each antibody and express them as single value. The higher the value, the better the overall binding profile of that specific antibody. Neutralization delta lenti luminescence 3: percentage neutralization of Delta pseudovirus by each antibody at 0.16 ug/ml. Neutralization Omicron BA.2 lenti luminescence 3: percentage neutralization of Omicron BA.2 pseudovirus by each antibody at 0.16 ug/ml. Pseudovirus neutralization data were obtained as described in materials and methods.

FIG. 12 is a chart presenting developability study data obtained for AB-1, AB-15, and AB-17.

FIGS. 14A-14C are graphs (14A, 14B) and a chart (14C) showing that a combination of class 4 anti-RBD monoclonal antibody and AB-1 improves neutralization profiles against Omicron variants.

FIGS. 15A-15H are graphs showing that AB-1 protects against SARS-CoV-2 Delta infection in hamsters. Two hamster studies with prophylactic administration (day-1) of AB-1 expressed as human IgG1 (FIGS. 15A-15D) or hamster IgG2a (FIGS. 15E-15H) and challenged with SARS-CoV-2 Delta (day 0). Both AB-1 formats show dose-dependent protection against Delta-induced weight loss (FIGS. 15A-15B & 15E-15F), dose-dependent protection against Delta-induced increase in lung weight (a proxy for lung inflammation, FIGS. 15C & 15G), and effects on viral titer (FIGS. 15D & 15H). The effect is more pronounced at day 7 compared to earlier timepoints and seems slightly lower in magnitude compared to Sotrovimab. 15A & 15E) Hamster weights were recorded up to 7 days post-challenge and expressed as percentage change over Day 0 (pre-challenge) weights. Isotype control delivered at 25 mg/kg, Sotrovimab at 5 mg/kg. Results are shown as mean±SEM. 15B & 15F) Representations of percentage body weight change on Day 7. Each dot represents an individual hamster and horizontal lines represent median values. 15C & 15G) Lung weights on Day 7. 15D & 15H) Lung viral titers on Day 4. Each dot represents an individual hamster and horizontal lines represent median values. N=12 (day 0 to 4) or 6 (day 5 to 7) hamsters per group. Data were analyzed by one-way ANOVA corrected for multiple comparisons (Dunnett's test). Black asterisks indicate comparison to Isotype control-treated hamsters. **p<0.01.

Figure 17A:
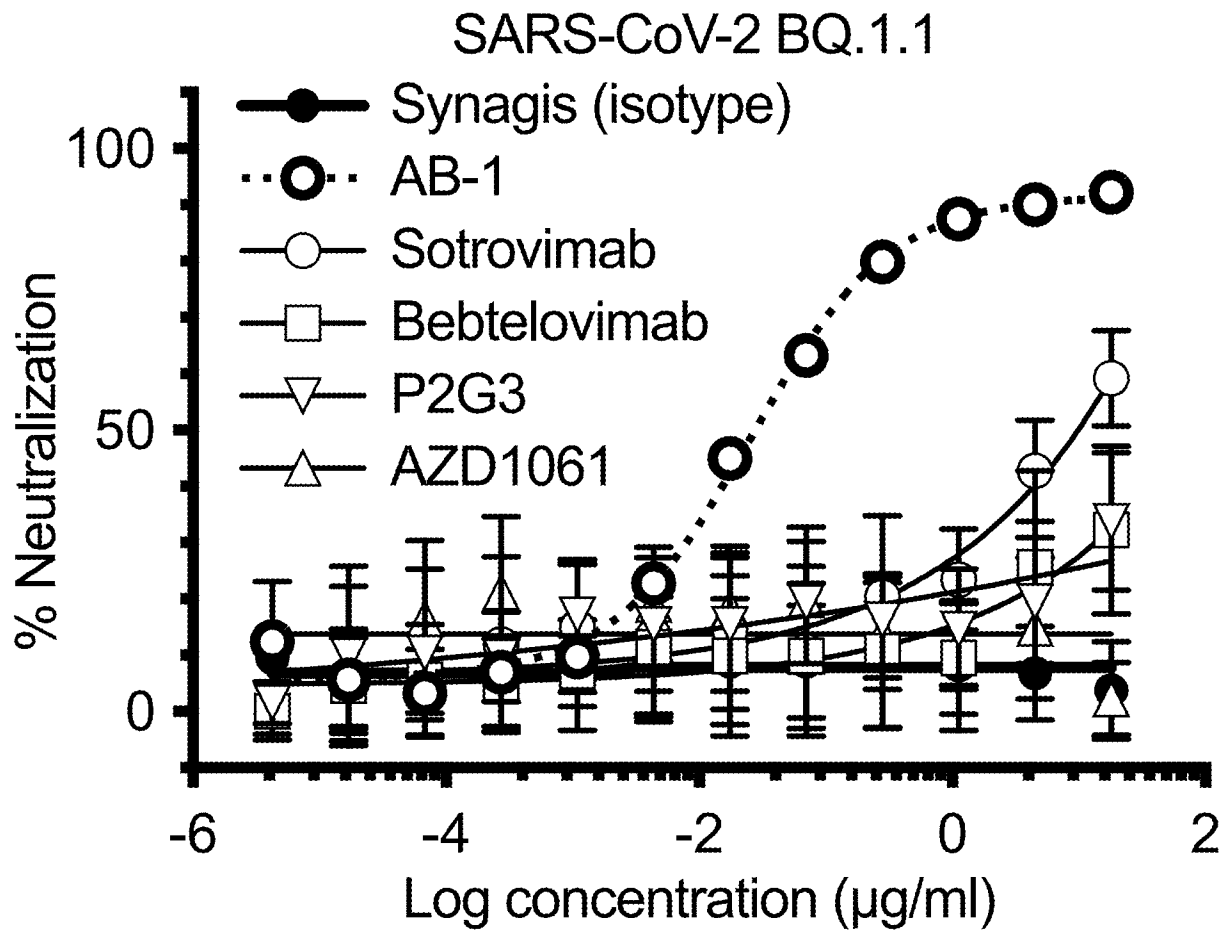

FIGS. 17A-17D are graphs, and FIG. 17E is a chart, showing that AB-1 combined with a class 4 anti-RBD antibody 3a ("RD Class 4 mAb-3a" or "R-AB-3a") demonstrates improved neutralization potency and efficacy against Omicron BQ.1.1 pseudovirus. FIGS. 17A-17C show neutralization profiles. Synagis was used as isotype control. FIG. 17D shows results of the neutralization profiles shown in FIG. 17B, and reported as efficacy (% neutralization at 18 µg/ml). FIG. 17E reports results shown in FIG. 17B as $EC_{50}$ (95% CI) and % median neutralization at 18 µg/ml (95% CI) values. Standard deviation (SD) is applied as error bars in FIG. 17B, and standard error of the mean (SEM) is applied as error bars in FIG. 17C.

FIGS. 18A and 18B are graphs, and FIG. 18C is a chart, showing that combinations of AB-1 and class 4 anti-RBD antibody 4a ("RD Class 4 mAb-4a" or "R-AB-4a") or Sotrovimab improve neutralization profiles against Delta and Omicron BA.5 live viruses. FIGS. 18A and 18B show neutralization profiles against SARS-CoV-2 Delta and BA.5 live viruses, respectively. Synagis was used as isotype control. FIG. 18C reports results shown in FIG. 18A-18B as $EC_{50}$ (95% CI) and % median neutralization at 18 µg/ml (95% CI) values. Standard deviation (SD) is applied as error bars in FIG. 18A-18B.

FIGS. 23A-23D. Sensorgrams of Fabs of AB-1 and the Reference Antibody binding to SARS-CoV-2 spike S2 (aa 1149-1167) peptide by SPR. Sensorgrams of Fabs of AB-1 (FIG. 23A) and the Reference Antibody (FIG. 23B) binding to SARS-CoV-2 spike S2 (aa 1149-1167) peptide, and Fabs of AB-1 (FIG. 23C) and the Reference Antibody (FIG. 23D) binding to HIV-1 Env negative control peptide obtained by SPR. The real-time binding sensorgrams are shown as black curves, while the fits generated by globally fitting the data to a 1:1 binding model with mass transport limitation are shown as dashed curves. The results are representative of one experiment without technical replicates.

FIG. 24A Low-pass filtered Cryo-EM map of the SARS-CoV-2 BA.1 spike trimer with R-AB-3a Fab binding RBD and AB-1 binding S2 stem helix. Map is shown from a side profile and from below. Each of the presumptive Fabs is labeled. FIG. 24B Density-docked atomic model of the SARS-CoV-2 spike assembly with bound Fabs. Spike trimer: a high-resolution structure of the SARS-CoV-2 spike with the S2 stem helix resolved. R-AB-3a: the designed model for R-AB-3a Fab. Bottom: three AB-1 Fabs docked into the propeller shaped density around the S2 stem helix. FIG. 24C Published cryo-electron tomography map of the SARS-CoV-2 spike trimer in virus-like particles bound to a Fab of Reference Antibody. Map was low-pass filtered identically as in FIG. 24A. Two copies of the Fabs of the Reference Antibody are apparent in the map.

DETAILED DESCRIPTION

Figure 5A:
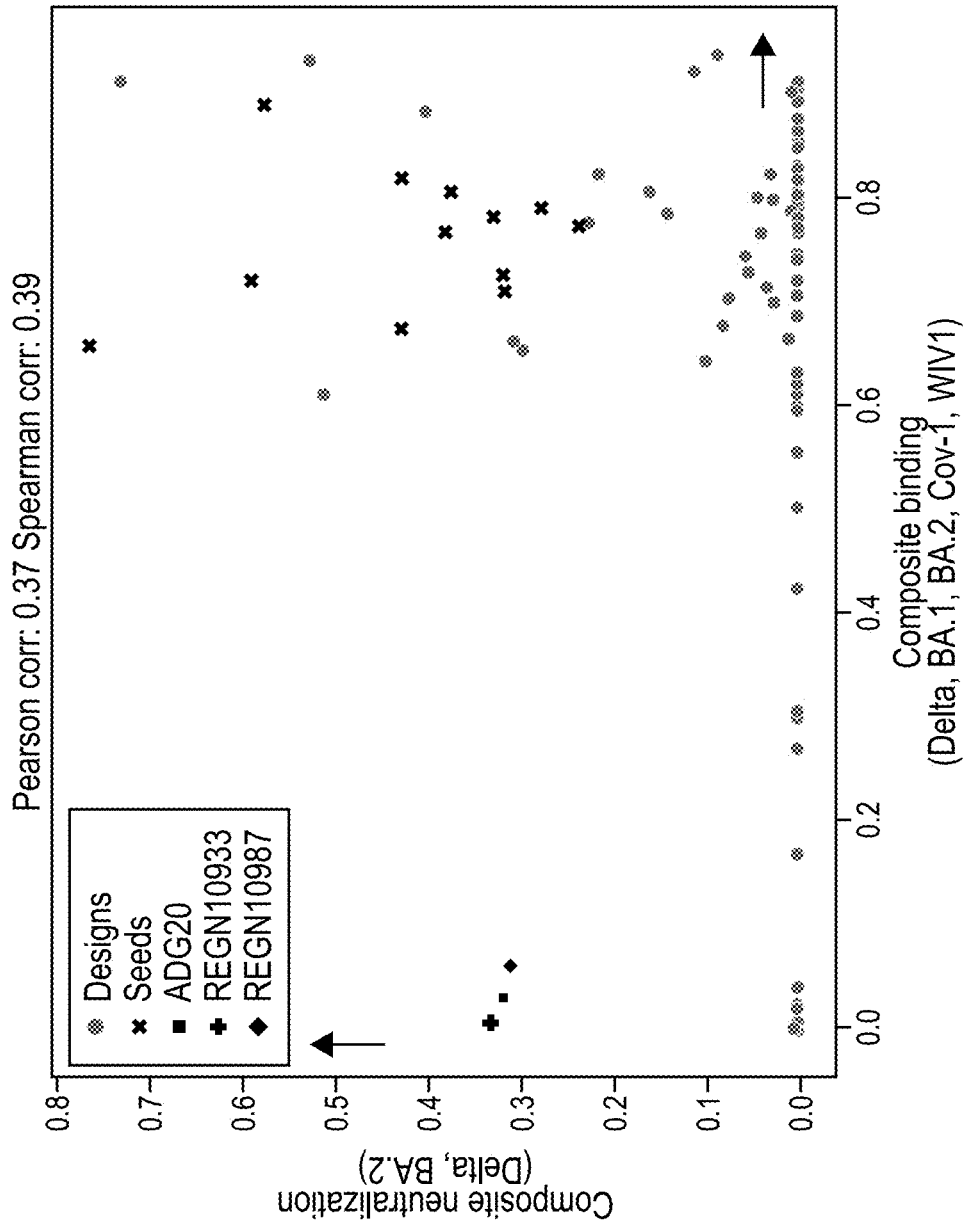
FIGS. 5A-5B show binding and neutralization data expressed as composite scores across the indicated viruses.

A description of example embodiments follows.

Several aspects of the disclosure are described below, with reference to examples for illustrative purposes only. It should be understood that numerous specific details, relationships, and methods are set forth to provide a full understanding of the disclosure. One having ordinary skill in the relevant art, however, will readily recognize that the disclosure can be practiced without one or more of the specific details or practiced with other methods, protocols, reagents, cell lines and animals. The disclosure is not limited by the illustrated ordering of acts or events, as some acts may occur in different orders and/or concurrently with other acts or events. Furthermore, not all illustrated acts, steps or events are required to implement a methodology in accordance with the disclosure.

Polypeptides that Specifically Bind Betacoronavirus Spike Proteins

Provided herein, among other things, are polypeptides that specifically bind to S2 domain of betacoronavirus Spike glycoprotein. In some embodiments, a polypeptide has one or more properties selected from: a broadly neutralizing activity against a plurality of known and predicted betacoronaviruses (e.g., past, present, emergent, and future betacoronaviruses), a binding affinity for an S2 domain epitope that is highly conserved across a plurality of betacoronaviruses, and an inhibitory activity against potential emerging betacoronavirus escape variants. In some embodiments, a polypeptide specifically binds the S2 domain of a sarbecovirus (e.g., a SARS-CoV-1 virus, a SARS-CoV-2 virus) Spike protein. In some embodiments, a polypeptide specifically binds the S2 domain of a SARS-CoV-1 virus (e.g., a plurality of SARS-CoV-1 variants) Spike protein. In some embodiments, a polypeptide specifically binds S2 domain of a SARS-CoV-2 virus (e.g., a plurality of SARS-CoV-2 variants) Spike protein. In some embodiments, a polypeptide specifically binds the S2 domain of a SARS-CoV-1 virus (e.g., a plurality of SARS-CoV-1 variants) Spike protein and the S2 domain of a SARS-CoV-2 virus (e.g., a plurality of SARS-CoV-2 variants) spike protein.

In some embodiments, a polypeptide disclosed herein has a broadly neutralizing activity (e.g., as measured using a neutralization assay described herein or otherwise known to those of ordinary skill the art) against a plurality of betacoronaviruses. In some embodiments, a polypeptide has neutralizing activity against a plurality of sarbecoviruses (e.g., SARS-CoV-1 viruses, SARS-CoV-2 viruses). In some embodiments, a polypeptide has neutralizing activity against a plurality of SARS-CoV-1 viruses (e.g., a plurality of SARS-CoV-1 variants). In some embodiments, a polypeptide has neutralizing activity against a plurality of SARS-CoV-2 viruses (e.g., a plurality of SARS-CoV-2 variants). In some embodiments, a polypeptide has neutralizing activity against a plurality of SARS-CoV-1 viruses (e.g., a plurality of SARS-CoV-1 variants) and a plurality of SARS-CoV-2 viruses (e.g., a plurality of SARS-CoV-2 variants).

In some embodiments, a polypeptide disclosed herein has a binding affinity for an S2 domain epitope that is conserved (e.g., highly conserved) across a plurality of betacoronaviruses. In some embodiments, the S2 domain epitope is highly conserved across a plurality of sarbecoviruses (e.g., SARS-CoV-1 viruses, SARS-CoV-2 viruses). In some embodiments, the S2 domain epitope is highly conserved across a plurality of SARS-CoV-1 viruses (e.g., a plurality of SARS-CoV-1 variants). In some embodiments, the S2 domain epitope is highly conserved across a plurality of SARS-CoV-2 viruses (e.g., a plurality of SARS-CoV-2 variants). In some embodiments, the S2 domain epitope is highly conserved across a plurality of SARS-CoV-1 viruses (e.g., a plurality of SARS-CoV-1 variants) and a plurality of SARS-CoV-2 viruses (e.g., a plurality of SARS-CoV-2 variants).

SARS-CoV-2 is the causative agent of COVID-19. The genome of SARS-CoV-2 encodes the nucleoprotein (N), the membrane glycoprotein (M), the small envelope glycoprotein (E), and the spike protein (S), in addition to 16 non-structural proteins (Song et al., Cytokine storm induced by SARS-CoV-2, Clin Chim Acta. 509:280-7 (2020)). SARS-CoV-2-Spike, or S of the SARS-CoV-2 facilitates entry of the SARS-CoV-2 virus into a host cell, such as a human host cell. S is a trimer with protomers composed of S1 and S2 subunits. S1 contains a receptor-binding domain (RBD) that binds ACE2 receptors, and S2 is necessary for fusion of viral and host membranes.

A non-limiting example of a wildtype SARS-CoV-2-Spike (S) sequence is NCBI RefSeq YP_009724390 (SEQ ID NO:1).

(SEQ ID NO: 1)

MFVFLVLLPLVSSQCVNLTTRTQLPPAYTNSFTRGVYYPDKVFRSSVLHSTQD

LFLPFFSNVTWFHAIHVSGTNGTKRFDNPVLPFNDGVYFASTEKSNIIRGWIFGTTLDSKT

QSLLIVNNATNVVIKVCEFQFCNDPFLGVYYHKNNKSWMESEFRVYSSANNCTFEYVSQ

PFLMDLEGKQGNFKNLREFVFKNIDGYFKIYSKHTPINLVRDLPQGFSALEPLVDLPIGINI

TRFQTLLALHRSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFNATRFASVYAWNRK

RISNCVADYSVLYNSASFSTFKCYGVSPTKLNDLCFTNVYADSFVIRGDEVRQIAPGQTG

KIADYNYKLPDDFTGCVIAWNSNNLDSKVGGNYNYLYRLFRKSNLKPFERDISTEIYQA

GSTPCNGVEGFNCYFPLQSYGFQPTNGVGYQPYRVVVLSFELLHAPATVCGPKKSTNLV

KNKCVNFNFNGLTGTGVLTESNKKFLPFQQFGRDIADTTDAVRDPQTLEILDITPCSFGGV

SVITPGTNTSNQVAVLYQDVNCTEVPVAIHADQLTPTWRVYSTGSNVFQTRAGCLIGAEH

VNNSYECDIPIGAGICASYQTQTNSPRRARSVASQSIIAYTMSLGAENSVAYSNNSIAIPTN

FTISVTTEILPVSMTKTSVDCTMYICGDSTECSNLLLQYGSFCTQLNRALTGIAVEQDKNT

QEVFAQVKQIYKTPPIKDFGGFNFSQILPDPSKPSKRSFIEDLLFNKVTLADAGFIKQYGD

CLGDIAARDLICAQKFNGLTVLPPLLTDEMIAQYTSALLAGTITSGWTFGAGAALQIPFA

MQMAYRFNGIGVTQNVLYENQKLIANQFNSAIGKIQDSLSSTASALGKLQDVVNQNAQ

ALNTLVKQLSSNFGAISSVLNDILSRLDKVEAEVQIDRLITGRLQSLQTYVTQQLIRAAEI

RASANLAATKMSECVLGQSKRVDFCGKGYHLMSFPQSAPHGVVFLHVTYVPAQEKNFT

TAPAICHDGKAHFPREGVFVSNGTHWFVTQRNFYEPQUITTDNTFVSGNCDVVIGIVNNT

VYDPLQPELDSFKEELDKYFKNHTSPDVDLGDISGINASVVNIQKEIDRLNEVAKNLNES

LIDLQELGKYEQYIKWPWYIWLGFIAGLIAIVMVTIMLCCMTSCCSCLKGCCSCGSCCKF

DEDDSEPVLKGVKLHYT.

As used herein, SARS-CoV-2 Spike includes wild-type SARS-CoV-2 Spike proteins (e.g., SEQ ID NO:1 (RefSeq YP_009724390) or homologs thereof) and truncated forms thereof, mutant and engineered versions of full-length and truncated SARS-CoV-2 Spike proteins, and modified forms (e.g., post-translationally modified forms) of full-length and truncated SARS-CoV-2 Spike proteins.

In some embodiments, a polypeptide disclosed herein binds to a SARS-CoV-2 Spike protein comprising SEQ ID NO:1.

In some embodiments, a polypeptide binds to a mutant, engineered and/or modified form of SARS-CoV-2-Spike. In some embodiments, the mutant, engineered and/or modified form of SARS-CoV-2-Spike comprises an amino acid sequence that has at least about 90% sequence identity to the wildtype SARS-CoV-2-Spike sequence (e.g., SEQ ID NO:1), for example, having at least about: 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence identity to the wildtype SARS-CoV-2-Spike sequence. In some embodiments, the sequence identity is about: 90-99.9%, 90-99.8%, 92-99.8%, 92-99.6%, 94-99.6%, 94-99.5%, 95-99.5%, 95-99.4%, 96-99.4%, 96-99.2%, 97-99.2% or 97-99%.

In some embodiments, a mutant, engineered and/or modified form of SARS-CoV-2-Spike comprises, relative to SEQ ID NO:1, one or more mutations selected from: L5F, S13I, T19R, A67V, del69, del70, del69-70, D80G, T95I, G142D, del142-144, del144, Y145D, W152C, E154K, F157S, del211, L212I, ins214EPE, A222V, D253G, G261D, G339D, V367F, S371L, S371L, S373P, S375F, K417N, N439K, N440K, G446S, L452R, Y453F, 5477N, T478K, E484A, E484K, E484Q, F486L, 5494P, Q493R, G496S, Q498R, N501T, N501Y, Y505H, T547K, F565L, A570D, H655Y, D614G, Q677H, N679K, P681H, P681R, A701V, T716I, N764K, D796Y, T859N, N856K, F888L, D950N, Q954H, Q957R, N969K, L981F, S982A, Q1071H, V1176F, D1118H, K1191N, or a combination thereof, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or more.

In some embodiments, a mutant, engineered and/or modified form of SARS-CoV-2-Spike comprises, relative to SEQ ID NO:1, one or more mutations selected from: 69del, 70del, 144del, E484K, 5494P, N501Y, A570D, D614G, P681H, T716I, S982A, D1118H or K1191N, or a combination thereof. In some embodiments, a mutant, engineered and/or modified form of SARS-CoV-2-Spike comprises 69del, 70del, 144del, N501Y, A570D, D614G, P681H, T716I, S982A, and D1118H. In some embodiments, a mutant, engineered and/or modified form of SARS-CoV-2-Spike further comprises E484K, S494P or K1191N, or a combination thereof.

In some embodiments, a mutant, engineered and/or modified form of SARS-CoV-2-Spike comprises, relative to SEQ ID NO:1, one or more mutations selected from: D80A, D215G, 241del, 242del, 243del, K417N, E484K, N501Y, D614G or A701V, or a combination thereof. In some embodiments, a mutant, engineered and/or modified form of SARS-CoV-2-Spike comprises D80A, D215G, 241del, 242del, 243del, K417N, E484K, N501Y, D614G, and A701V.

In some embodiments, a mutant, engineered and/or modified form of SARS-CoV-2-Spike comprises, relative to SEQ ID NO:1, one or more mutations selected from: T19R, G142D, 156del, 157del, R158G, L452R, T478K, D614G, P681R or D950N, or a combination thereof. In some embodiments, a mutant, engineered and/or modified form of SARS-CoV-2-Spike comprises T19R, 156del, 157del, R158G, L452R, T478K, D614G, P681R, and D950N. In some embodiments, a mutant, engineered and/or modified form of SARS-CoV-2-Spike further comprises G142D.

In some embodiments, the modified SARS-CoV-2 Spike protein comprises, relative to SEQ ID NO:1, one or more mutations selected from: A67V, del69-70, T95I, del142-144, Y145D, del211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K or L981F, or a combination thereof.

In some embodiments, the modified SARS-CoV-2 Spike protein comprises, relative to SEQ ID NO:1, one or more mutations selected from: T19I, del24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, or N969K, or a combination thereof.

In some embodiments, the modified SARS-CoV-2 Spike protein comprises, relative to SEQ ID NO:1, one or more mutations selected from: T19I, del24-26, A27S, del69-70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, or N969K, or a combination thereof.

In some embodiments, a mutant, engineered and/or modified form of SARS-CoV-2-Spike comprises, relative to SEQ ID NO:1, one or more mutations selected from: 69del, 70del, 144del, A222V, G261D, V367F, K417N, N439K, Y453F, S477N, E484K, F486L, N501T, N501Y, A570D or D614G, or a combination thereof.

In some embodiments, a mutant, engineered and/or modified form of SARS-CoV-2-Spike comprises, relative to SEQ ID NO:1, one or more mutations selected from: E484K, N501Y or D614G, or a combination thereof.

In some embodiments, a mutant, engineered and/or modified form of SARS-CoV-2 Spike protein comprises, relative to SEQ ID NO:1, one or more mutations selected from: F817P, A892P, A899P, A942P, K986P or V987P, or a combination thereof.

In some embodiments, a mutant, engineered and/or modified form of SARS-CoV-2 Spike protein comprises, relative to SEQ ID NO:1, one or more mutations selected from: L452R, F486V or R493Q, or a combination thereof.

In some embodiments, a mutant, engineered and/or modified form of SARS-CoV-2 Spike protein comprises, relative to SEQ ID NO:1, one or more mutations selected from: A67V, del69-70, T95I, del142-144, Y145D, del211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K or L981F, or a combination thereof.

In some embodiments, the modified SARS-CoV-2 Spike protein comprises, relative to SEQ ID NO:1, one or more mutations selected from: T19I, del24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, or N969K, or a combination thereof.

In some embodiments, the modified SARS-CoV-2 Spike protein comprises, relative to SEQ ID NO:1, one or more mutations selected from: T19I, del24-26, A27S, del69-70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, or N969K, or a combination thereof.

In some embodiments, the modified SARS-CoV-2 Spike protein comprises, relative to SEQ ID NO:1, one or more mutations selected from: T19I, del24-26, A27S, del69-70, G142D, V213G, G339D, S371F, S373P, S375F, T376A, D405N, R408S, K417N, N440K, K444T, L452R, S477N, T478K, E484A, F486V, Q498R, N501Y, Y505H, D614G, H655Y, N679K, P681H, N764K, D796Y, Q954H, or N969K, or a combination thereof.

In some embodiments, the modified SARS-CoV-2 Spike protein comprises, relative to SEQ ID NO:1, one or more mutations selected from: T19I, del24-26, A27S, del69-70, G142D, V213G, G339D, R346T, S371F, S373P, S375F, T376A, D405N, R408S, K417N, N440K, K444T, L452R, N460K, S477N, T478K, E484A, F486V, Q498R, N501Y, Y505H, D614G, H655Y, N679K, P681H, N764K, D796Y, Q954H, or N969K, or a combination thereof.

Additional modified SARS-CoV-2 Spike proteins can be found at https://covariants.org/shared-mutations, the contents of which are incorporated herein by reference. Non-limiting examples include Alpha, Beta, Gamma, Delta, Kappa, Epsilon, Eta, Iota, Lambda, Mu, and/or Omicron, for example, AY3, AY4, AY.41, AY.44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1.

In some embodiments, a polypeptide disclosed herein binds to the S2 domain of the SARS-CoV-2 Spike (S) protein. As used herein, S2 domain includes full-length S2 domain (e.g., having the amino acid sequence of SEQ ID NO:193 or homologs thereof) and truncated forms thereof, mutant and engineered versions of full-length and trunctated S2 domains (e.g., an epitope within the S2 domains (e.g., S2 (FIG. 1)), and modified forms (e.g., post-translationally modified forms) of full-length and truncated S2 domains.

PLQPELDSFKEELDKYFKNHTSPDVDL (SEQ ID NO:193).

In some embodiments, a polypeptide disclosed herein binds to a mutant, engineered and/or modified form of an S2 domain. In some embodiments, the mutant, engineered and/or modified form of an S2 domain comprises an amino acid sequence that has at least about 90% sequence identity to a wild-type full length S2 domain (e.g., SEQ ID NO:193), for example, having at least about: 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence identity. In some embodiments, the sequence identity is about: 90-99.9%, 90-99.8%, 92-99.8%, 92-99.6%, 94-99.6%, 94-99.5%, 95-99.5%, 95-99.4%, 96-99.4%, 96-99.2%, 97-99.2% or 97-99%.

In some embodiments, a polypeptide disclosed herein binds to a SARS-CoV-2 Spike protein (e.g., SEQ ID NO:1 or SEQ ID NO:193) and comprises an immunoglobulin light chain variable domain, an immunoglobulin heavy chain variable domain, or an immunoglobulin light chain variable domain and an immunoglobulin heavy chain variable domain, wherein the polypeptide does not comprise SEQ ID NO:3 or SEQ ID NO:50 or both SEQ ID NO:3 and SEQ ID NO:50.

In some embodiments, a polypeptide disclosed herein does not comprise all 6 CDRs of an antibody comprising a $V_H$ amino acid sequence of SEQ ID NO:3 and a $V_L$ amino acid sequence of SEQ ID NO:50. In some embodiments, a polypeptide disclosed herein comprises 1, 2, 3, 4 or 5 CDRs selected from SEQ ID NO:77, SEQ ID NO:79, SEQ ID NO:90, SEQ ID NO:133, SEQ ID NO:141 and SEQ ID NO:143. In some embodiments, a polypeptide disclosed herein comprises 1, 2 or 3 CDRs selected from SEQ ID NO:79, SEQ ID NO:90, SEQ ID NO:133 and SEQ ID NO:143.

In some embodiments, an antibody disclosed herein does not comprise all 6 CDRs of an antibody comprising a $V_H$ amino acid sequence of SEQ ID NO:3 and a $V_L$ amino acid sequence of SEQ ID NO:50. In some embodiments, an antibody disclosed herein comprises 1, 2, 3, 4 or 5 CDRs selected from SEQ ID NO:77, SEQ ID NO:79, SEQ ID NO:90, SEQ ID NO:133, SEQ ID NO:141 and SEQ ID NO:143. In some embodiments, an antibody disclosed herein comprises 1, 2 or 3 CDRs selected from SEQ ID NO:79, SEQ ID NO:90, SEQ ID NO:133 and SEQ ID NO:143.

In some embodiments, the disclosure provides a polypeptide that specifically binds an SARS-CoV-2 Spike protein, wherein the polypeptide comprises:
  a) an immunoglobulin heavy chain variable domain ($V_H$) comprising an amino acid sequence that has at least 55% (e.g., at least 60, 65, 70, 75, 80, 85, 90, 95, 98, or 99%) sequence identity to SEQ ID NO:3;
  b) an immunoglobulin light chain variable domain ($V_L$) comprising an amino acid sequence that has at least 55% (e.g., at least 60, 65, 70, 75, 80, 85, 90, 95, 98, or 99%) sequence identity to SEQ ID NO:50; or both a) and b),
wherein the polypeptide does not comprise all 6 CDRs of an antibody comprising a $V_H$ amino acid sequence of SEQ ID NO:3 and a $V_L$ amino acid sequence of SEQ ID NO:50.

In some embodiments, a polypeptide disclosed herein does not comprise all four sequences of SEQ ID NO:79, SEQ ID NO:90, SEQ ID NO:133 and SEQ ID NO:143. In some embodiments, a polypeptide disclosed herein comprises 1, 2 or 3 CDRs selected from SEQ ID NO:79, SEQ ID NO:90, SEQ ID NO:133 and SEQ ID NO:143.

In some embodiments, a polypeptide disclosed herein binds to a wildtype SARS-CoV-2 Spike protein (e.g., SEQ ID NO:1). In some embodiments, a polypeptide disclosed herein binds to one or more epitope residues of a wildtype SARS-CoV-2 Spike protein (e.g., one or more epitope residues in the SARS-CoV-2 S2 subunit).

As used herein, the term "comparator" or "comparator polypeptide" refers to a polypeptide (e.g., immunoglobulin molecule) that specifically binds to SARS-CoV-2, and is not a polypeptide disclosed herein. The sequence of a comparator polypeptide and a polypeptide disclosed herein may be compared to illustrate structural differences between them (e.g., differences at one or more amino acid positions, such as amino acid substitutions). Polypeptides disclosed herein have more than insubstantial differences (e.g., one or more substantial differences) in comparison to a comparator polypeptide, such that, polypeptides disclosed herein will, under controlled conditions, exhibit one or more (i.e., one, two, or all three) of: a different function, in a different way, to achieve a different result, in comparison to a comparator polypeptide. Comparator polypeptides will vary by one or more amino acids from a polypeptide disclosed herein, e.g., in some embodiments by 1, 2, 3, 4, 5, 6, 7, 8, 9, 10, 11, 12, 13, 14, 15, 16, 17, 18, 19, 20 or more amino acids. In some embodiments, a comparator polypeptide diverges from a polypeptide provided by the disclosure by at least about: 0.4, 0.8, 1, 2, 3, 4, 5, 6, 7, 8, 9, 10, 15, 20, 25, 30, 35, 40, 45, 50, 55% or more amino acid identity.

In some embodiments, the comparator polypeptide is an antibody, referred to herein as "the Reference Antibody," which comprises a $V_H$ domain comprising the amino acid sequence of SEQ ID NO:3, a V$_L$ domain comprising the amino acid sequence of SEQ ID NO:50, a heavy chain comprising the amino acid sequence of SEQ ID NO:191, and a light chain comprising the amino acid sequence of SEQ ID NO:192. The Reference Antibody is an antibody that binds SARS-CoV-2 S2 and neutralizes against SARS-CoV-2 variants. For additional information about the Reference Antibody, see, e.g., PDB: 7NAB_A, PDB: 7NAB_B, 7NAB_C, and Jennewein et al., *Isolation and characterization of cross-neutralizing coronavirus antibodies from COVID-19+subjects*, Cell Rep. 36(2):109353 (2021). The Reference Antibody has the following heavy and light chain amino acid sequences:

```
                                         (SEQ ID NO: 191)
EVQLVESGAEVKKPGESLKISCKGSGYTFTRYWIGWVRQMPGKGLEWMG

IIYPGDSDTRYSPSFQGHVTISADKSISTAYLQWNSLKASDTAMYYCAR

LPQYCSNGVCQRWFDPWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKS (SEQ ID NO: 192)
EIVLTQSPSSVSASVGDRVTITCRASQGISSWLAWYQQKPGKAPKLLIY

AASSLQSGVPSRFSGSGSGTDFTLTISSLQPEDFATYYCQQGNSFPYTF

GQGTNLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGE
```

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequence is compared. The sequence identity is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

The term "polypeptide" "peptide" or "protein" denotes a polymer of at least two amino acids covalently linked by an amide bond, regardless of length or post-translational modification (e.g., glycosylation or phosphorylation). A protein, peptide or polypeptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitrulline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*," John Wiley and Sons, 1991. The functional groups of a protein, peptide or polypeptide can also be derivatized (e.g., alkylated) or labeled (e.g., with a detectable label, such as a fluorogen or a hapten) using methods known in the art. A protein, peptide or polypeptide can comprise one or more modifications (e.g., amino acid linkers, acylation, acetylation, amidation, methylation, terminal modifiers (e.g., cyclizing modifications), N-methyl-□-amino group substitution), if desired. In addition, a protein, peptide or polypeptide can be an analog of a known and/or naturally-occurring peptide, for example, a peptide analog having conservative amino acid residue substitution(s).

In some embodiments, the disclosure provides a polypeptide that specifically binds SARS-CoV-2-Spike, wherein the polypeptide comprises a paratope that is substantially similar to a paratope of an antibody comprising a V$_H$/V$_L$ pair selected from:

SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);

SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51), or
any combination thereof.

In some embodiments, the disclosure provides a polypeptide that specifically binds SARS-CoV-2-Spike, wherein the polypeptide comprises a paratope that is identical to a paratope of an antibody comprising a $V_H/V_L$ pair selected from:
SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);
SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51).

See Table 1 for SEQ ID NOs:4-48, Table 2 for SEQ ID NOs:51-76, and FIG. 2 for the paratope residues of antibodies comprising SEQ ID Nos:4-48, and FIG. 3 for paratope residues of antibodies comprising SEQ ID Nos: 51-76.

Amino acid residues of a paratope contribute to an antibody's interaction with an epitope of its target protein. An interaction can be a hydrogen bond, a salt bridge, a van der Waals interaction, an electrostatic interaction, a hydrophobic interaction, pi-interaction effects, an ionic bond, and/or any combination thereof. An interaction can be direct, or indirect, e.g., via a coordinated intermediate molecule, such as an ion or water. The residues of a paratope, in some embodiments, comprise only residues that are part of a defined CDR. In some embodiments, the residues of a paratope further comprise one or more residues that are not part of a defined CDR (e.g., residues within a defined framework region).

In some embodiments, a paratope is oriented less than about 5.0 angstroms from an epitope on a target antigen when a polypeptide is bound to the target antigen, e.g., less than about: 4.5, 4.0, 3.5, 3.0, 2.5, 2.4, 2.3, 2.2, 2.1, 2.0, 1.9, 1.8, 1.7, 1.6, 1.5, 1.4, 1.3, 1.2, 1.1, 1.0 or 0.9 angstroms, or about: 0.9-5.0, 0.9-4.8. 1.0-5, 1.0-4.5, 1.0-4.0, 1.0-3.5, 1.1-3.5, 1.1-3.0, 1.2-3.0, 1.2-2.5, 1.3-2.5, 1.3-2.4, 1.4-2.4, 1.4-2.3, 1.5-2.3, 1.5-2.2, 1.6-2.2, 1.6-2.1, 1.7-2.1, 1.7-2.0 or 1.8-2.0 angstroms, from the epitope. In some embodiments, less than all of the amino acid residues constituting a paratope (e.g., about 40%, about 50%, about 60%, about 70%, about 80%, about 90%, about 95%, about 96%, about 97%, about 98%, or about 99% of the amino acid residues) in the paratope are oriented less than about 5.0 angstroms from an epitope on a target antigen when a polypeptide is bound to the target antigen.

As used herein, the term "substantially similar to" refers to a polypeptide disclosed herein that is substantially similar in amino acid sequence (e.g., has at least about 80%, at least about 90%, at least about 95%, at least about 96%, at least about 97%, at least about 98%, or at least about 99% of the amino acid residues amino acid sequence identity) and substantially preserves one or more functional properties of a specified polypeptide disclosed herein. In some embodiments, the one or more functional properties are selected from, without limitation, a substantially similar binding affinity, a substantially similar binding specificity, a substantially similar inhibitory activity, a substantially similar neutralization activity, and a substantially similar self-association property.

In some embodiments, a polypeptide disclosed herein comprises a paratope that is substantially similar to a paratope of a polypeptide selected from any one of AB-1 to AB-51. In some embodiments, a polypeptide comprises a paratope comprising only conservative substitutions (e.g., only highly conservative substitutions) relative a paratope of a polypeptide selected from any one of AB-1 to AB-51. In some embodiments, a polypeptide comprises a paratope comprising up to 1, 2, 3, 4, 5, 6, 7, 8, 9, 10, 11, 12, 13, 14 or 15 conservative substitutions (e.g., up to 1, 2, 3, 4, 5, 6, 7, 8, 9, 10, 11, 12, 13, 14 or 15 highly conservative substitutions), relative a paratope of a polypeptide selected from any one of AB-1 to AB-51. In some embodiments, a polypeptide comprises a paratope having 100% sequence identity to a paratope of a polypeptide selected from any one of AB-1 to AB-51.

In some embodiments, a paratope comprises amino acid residues corresponding to each of T28, T30, R31, Y32, W33, Y52, G54, D55, $X_1$ (position 57), K74, R98, $X_4$ (position 99), P100, Q101, Y102, C103, $X_7$ (position 106), C108, R110, and W111 of SEQ ID NO:2 and L46 of SEQ ID NO:49, or a subset thereof.

In some embodiments, a polypeptide comprising a paratope disclosed herein comprises an immunoglobulin heavy chain variable domain ($V_H$) and an immunoglobulin light chain variable domain ($V_L$). In some embodiments, paratope residues are contained within the $V_H$ and $V_L$ of a polypeptide.

In some embodiments, a polypeptide comprises an immunoglobulin light chain variable region, an immunoglobulin heavy chain variable region, or an immunoglobulin light chain variable region and an immunoglobulin heavy chain variable region. In some embodiments, a polypeptide comprises six CDRs of a polypeptide disclosed herein. In some embodiments, a polypeptide has fewer than six (e.g., 1, 2, 3, 4 or 5) of the CDRs of a polypeptide disclosed herein.

In some embodiments, the disclosure provides a polypeptide that specifically binds SARS-CoV-2-Spike, wherein the polypeptide comprises:
- a $V_H$ amino acid sequence comprising a heavy chain complementarity determining region 1 (HCDR1), a heavy chain complementarity determining region 2 (HCDR2) and a heavy chain complementarity determining region 3 (HCDR3) that are substantially similar in amino acid sequence to a HCDR1, a HCDR2 and a HCDR3, respectively, of a $V_H$ amino acid sequence set forth in any of SEQ ID NOs:4-48; and
- a $V_L$ amino acid sequence comprising a light chain complementarity determining region 1 (LCDR1), a light chain complementarity determining region 2 (LCDR2) and a light chain complementarity determining region 3 (LCDR3) that are substantially similar in amino acid sequence to a LCDR1, a LCDR2 and a LCDR3, respectively, of a $V_L$ amino acid sequence set forth in any of SEQ ID NOs:51-76.

In some embodiments, a polypeptide comprises a HCDR1, a HCDR2, a HCDR3, a LCDR1, a LCDR2 and a LCDR3 that substantially preserve one or more functional properties of a HCDR1, a HCDR2, a HCDR3, a LCDR1, a LCDR2 and a LCDR3 of a polypeptide selected from any one of AB-1 to AB-51.

In some embodiments, a polypeptide comprises a HCDR1, a HCDR2, a HCDR3, a LCDR1, a LCDR2 and a LCDR3 comprising only one or more conservative substitutions (e.g., only one or more highly conservative substitutions), relative a HCDR1, a HCDR2, a HCDR3, a LCDR1, a LCDR2 and a LCDR3 of a polypeptide selected from any one of AB-1 to AB-51.

In some embodiments, a polypeptide comprises a HCDR1, a HCDR2, a HCDR3, a LCDR1, a LCDR2 and a LCDR3 comprising up to 1, 2, or 3 conservative substitutions (e.g., up to 1, 2, or 3 highly conservative substitutions), relative a HCDR1, a HCDR2, a HCDR3, a LCDR1, a LCDR2 and a LCDR3 of a polypeptide selected from any one of AB-1 to AB-51.

In some embodiments, a polypeptide disclosed herein comprises a HCDR1, a HCDR2, a HCDR3, a LCDR1, a LCDR2 and a LCDR3 having 100% sequence identity to a HCDR1, a HCDR2, a HCDR3, a LCDR1, a LCDR2 and a LCDR3 of a polypeptide selected from any one of AB-1 to AB-51.

In some embodiments, a polypeptide comprises the HCDR1, HCDR2 and HCDR3, and LCDR1, LCDR2 and LCDR3, of an antibody comprising an amino acid sequence selected from:
SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);
SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);

SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51).

A CDR (e.g., HCDR1, HCDR2, HCDR3, LCDR1, LCDR2 and/or LCDR3) can be a CDR defined by any art-recognized method for identifying CDR residues of an antibody, as described further herein (e.g., a CDR as defined by Kabat, a CDR as defined by Chothia, or a CDR as defined by ImMunoGeneTics (IMGT) numbering (www.imgt.org/IMGTScientificChart/Nomenclature/IMGT-FRCDRdefinition.html, also accessible at www.imgt.org/)). In particular embodiments, a CDR is defined by IMGT numbering. Examples of CDRs defined by IMGT numbering include CDRs disclosed herein for polypeptides of the disclosure.

In some embodiments, a polypeptide comprises a paratope that is substantially similar to a paratope of an antibody comprising a $V_H/V_L$ pair selected from:
SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);
SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51), or
any combination thereof.

In some embodiments, a polypeptide comprises a paratope that is identical to a paratope of an antibody comprising a $V_H/V_L$ pair selected from:
SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);
SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51).

In some embodiments, the disclosure provides a polypeptide that specifically binds SARS-CoV-2-Spike, comprising a $V_H$ comprising the amino acid sequence of SEQ ID NO:2, wherein:
$X_1$ is not S;
$X_2$ is not D;
$X_3$ is not T;
$X_4$ is not L;
$X_5$ is not S;

$X_6$ is not N;
$X_7$ is not G;
$X_8$ is not V; or
$X_9$ is not Q,
or any combination of the foregoing.

The sequence identified as SEQ ID NO:2 is shown in Table 1, which is a consensus $V_H$ sequence for SEQ ID Nos:3-48 herein.

In some embodiments, polypeptides disclosed herein further comprise a $V_L$. In some embodiments, a polypeptide comprises a $V_L$ comprising the amino acid sequence of SEQ ID NO:49, wherein:
$X_{10}$ is not Q;
$X_{11}$ is not G;
$X_{12}$ is not S;
$X_{13}$ is not S;
$X_{14}$ is not N;
$X_{15}$ is not S;
$X_{16}$ is not F; or
$X_{17}$ is not Y,
or any combination of the foregoing.

The sequence identified as SEQ ID NO:49 is shown in Table 2, which is a consensus $V_L$ sequence for SEQ ID Nos:50-76 herein.

In some embodiments:
$X_1$ is S, N, A, R, L or F;
$X_2$ is D or E;
$X_3$ is T or V;
$X_4$ is L or V;
$X_5$ is S, Q, R, K, Y, D or E;
$X_6$ is N, K, A, S, R or E;
$X_7$ is G, N or L;
$X_8$ is V, S or K; or
$X_9$ is Q, Y, K, F or H,
or any combination of the foregoing.

In some embodiments:
$X_1$ is N, A, R, L or F;
$X_2$ is E;
$X_3$ is V;
$X_4$ is V;
$X_5$ is Q, R, K, Y, D or E;
$X_6$ is K, A, S, R or E;
$X_7$ is N or L;
$X_8$ is I, S or K; or
$X_9$ is Y, K, F or H,
or any combination of the foregoing.

In some embodiments, $X_1$ is not S. In some embodiments, $X_1$ is S, N, A, R, L or F. In some embodiments, $X_1$ is N, A, R, L or F. In some embodiments, $X_1$ is S. In some embodiments, $X_1$ is N. In some embodiments, $X_1$ is A. In some embodiments, $X_1$ is R. In some embodiments, $X_1$ is L. In some embodiments, $X_1$ is F.

In some embodiments, $X_2$ is not D. In some embodiments, $X_2$ is D or E. In some embodiments, $X_2$ is D. In some embodiments, $X_2$ is E.

In some embodiments, $X_3$ is not T. In some embodiments, $X_3$ is T or V. In some embodiments, $X_3$ is T. In some embodiments, $X_3$ is V.

In some embodiments, $X_4$ is not L. In some embodiments, $X_4$ is L or V. In some embodiments, $X_4$ is L. In some embodiments, $X_4$ is V.

In some embodiments, $X_5$ is not S. In some embodiments, $X_5$ is S, Q, R, K, Y, D or E. In some embodiments, $X_5$ is Q, R, K, Y, D or E. In some embodiments, $X_5$ is S. In some embodiments, $X_5$ is Q. In some embodiments, $X_5$ is R. In some embodiments, $X_5$ is K. In some embodiments, $X_5$ is Y. In some embodiments, $X_5$ is D. In some embodiments, $X_5$ is E.

In some embodiments, $X_6$ is not N. In some embodiments, $X_6$ is N, K, A, S, R or E. In some embodiments, $X_6$ is K, A, S, R or E. In some embodiments, $X_6$ is N. In some embodiments, $X_6$ is K. In some embodiments, $X_6$ is A. In some embodiments, $X_6$ is S. In some embodiments, $X_6$ is R. In some embodiments, $X_6$ is E.

In some embodiments, $X_7$ is not G. In some embodiments, $X_7$ is G, N or L. In some embodiments, $X_7$ is N or L. In some embodiments, $X_7$ is G. In some embodiments, $X_7$ is N. In some embodiments, $X_7$ is L.

In some embodiments, $X_8$ is not V. In some embodiments, $X_8$ is V, I, S or K. In some embodiments, $X_8$ is I, S or K. In some embodiments, $X_8$ is V. In some embodiments, $X_8$ is I. In some embodiments, $X_8$ is S. In some embodiments, $X_8$ is K.

In some embodiments, $X_9$ is not Q. In some embodiments, $X_9$ is Q, Y, K, F or H. In some embodiments, $X_9$ is Y, K, F or H. In some embodiments, $X_9$ is Q. In some embodiments, $X_9$ is Y. In some embodiments, $X_9$ is K. In some embodiments, $X_9$ is F. In some embodiments, $X_9$ is H.

In some embodiments:
$X_{10}$ is Q, K or I;
$X_{11}$ is G or S;
$X_{12}$ is S, R or V;
$X_{13}$ is S or N;
$X_{14}$ is N, H, D, Y or S;
$X_{15}$ is S or Q;
$X_{16}$ is F, Y, L, V, T or D; or
$X_{17}$ is Y or L,
or any combination of the foregoing.

In some embodiments:
$X_{10}$ is K or I;
$X_{11}$ is S;
$X_{12}$ is R or V;
$X_{13}$ is N;
$X_{14}$ is H, D, Y or S;
$X_{15}$ is Q;
$X_{16}$ is Y, L, V, T or D; or
$X_{17}$ is L,
or any combination of the foregoing.

In some embodiments, $X_{10}$ is not Q. In some embodiments, $X_{10}$ is Q, K or I. In some embodiments, $X_{10}$ is K or I. In some embodiments, $X_{10}$ is Q. In some embodiments, $X_{10}$ is K. In some embodiments, $X_{10}$ is I.

In some embodiments, $X_{11}$ is not G. In some embodiments, $X_{11}$ is G or S. In some embodiments, $X_{11}$ is G. In some embodiments, $X_{11}$ is S.

In some embodiments, $X_{12}$ is not S. In some embodiments, $X_{12}$ is S, R or V. In some embodiments, $X_{12}$ is S. In some embodiments, $X_{12}$ is R. In some embodiments, $X_{12}$ is V.

In some embodiments, $X_{13}$ is not S. In some embodiments, $X_{13}$ is S or N. In some embodiments, $X_{13}$ is S. In some embodiments, $X_{13}$ is N.

In some embodiments, $X_{14}$ is not N. In some embodiments, $X_{14}$ is N, H, D, Y or S. In some embodiments, $X_{14}$ is H, D, Y or S. In some embodiments, $X_{14}$ is N. In some embodiments, $X_{14}$ is H. In some embodiments, $X_{14}$ is D. In some embodiments, $X_{14}$ is Y. In some embodiments, $X_{14}$ is S.

In some embodiments, $X_{15}$ is not S. In some embodiments, $X_{15}$ is S or Q. In some embodiments, $X_{15}$ is S. In some embodiments, $X_{15}$ is Q.

In some embodiments, $X_{16}$ is not F. In some embodiments, $X_{16}$ is F, Y, L, V, T or D. In some embodiments, $X_{16}$ is Y, L, V, T or D. In some embodiments, $X_{16}$ is F. In some embodiments, $X_{16}$ is Y. In some embodiments, $X_{16}$ is L. In some embodiments, $X_{16}$ is V. In some embodiments, $X_{16}$ is T. In some embodiments, $X_{16}$ is D.

In some embodiments, $X_{17}$ is not Y. In some embodiments, $X_{17}$ is Y or L. In some embodiments, $X_{17}$ is Y. In some embodiments, $X_{17}$ is L.

In some embodiments, $X_1$ is S, $X_2$ is D, $X_3$ is V, $X_4$ is L, $X_5$ is S, $X_6$ is K, $X_7$ is G, $X_8$ is V, $X_9$ is Y, $X_{10}$ is Q, $X_{11}$ is G, $X_{12}$ is S, $X_{13}$ is S, $X_{14}$ is H, $X_{15}$ is S, $X_{16}$ is F, or $X_{17}$ is Y, or a combination thereof (AB-1);

$X_1$ is S, $X_2$ is D, $X_3$ is T, $X_4$ is L, $X_5$ is Q, $X_6$ is N, $X_7$ is G, $X_8$ is I, $X_9$ is K, $X_{10}$ is Q, $X_{11}$ is G, $X_{12}$ is R, $X_{13}$ is S, $X_{14}$ is D, $X_{15}$ is Q, $X_{16}$ is Y, or $X_{17}$ is L, or a combination thereof (AB-2);

$X_1$ is N, $X_2$ is D, $X_3$ is V, $X_4$ is L, $X_5$ is R, $X_6$ is K, $X_7$ is G, $X_8$ is I, $X_9$ is K, $X_{10}$ is Q, $X_{11}$ is G, $X_{12}$ is S, $X_{13}$ is S, $X_{14}$ is D, $X_{15}$ is Q, $X_{16}$ is L, or $X_{17}$ is Y, or a combination thereof (AB-3);

$X_1$ is S, $X_2$ is D, $X_3$ is T, $X_4$ is L, $X_5$ is R, $X_6$ is N, $X_7$ is G, $X_8$ is V, $X_9$ is Y, $X_{10}$ is K, $X_{11}$ is G, $X_{12}$ is S, $X_{13}$ is S, $X_{14}$ is N, $X_{15}$ is Q, $X_{16}$ is V, or $X_{17}$ is Y, or a combination thereof (AB-4);

$X_1$ is S, $X_2$ is D, $X_3$ is T, $X_4$ is L, $X_5$ is R, $X_6$ is A, $X_7$ is N, $X_8$ is V, $X_9$ is F, $X_{10}$ is Q, $X_{11}$ is G, $X_{12}$ is S, $X_{13}$ is S, $X_{14}$ is H, $X_{15}$ is S, $X_{16}$ is F, or $X_{17}$ is Y, or a combination thereof (AB-5);

$X_1$ is S, $X_2$ is D, $X_3$ is V, $X_4$ is L, $X_5$ is K, $X_6$ is K, $X_7$ is L, $X_8$ is I, $X_9$ is K, $X_{10}$ is Q, $X_{11}$ is G, $X_{12}$ is R, $X_{13}$ is S, $X_{14}$ is D, $X_{15}$ is Q, $X_{16}$ is L, or $X_{17}$ is Y, or a combination thereof (AB-6);

$X_1$ is S, $X_2$ is D, $X_3$ is T, $X_4$ is L, $X_5$ is R, $X_6$ is N, $X_7$ is G, $X_8$ is V, $X_9$ is Q, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-7);

$X_1$ is N, $X_2$ is D, $X_3$ is V, $X_4$ is L, $X_5$ is S, $X_6$ is A, $X_7$ is G, $X_8$ is S, $X_9$ is F, $X_{10}$ is I, $X_{11}$ is G, $X_{12}$ is R, $X_{13}$ is N, $X_{14}$ is Y, $X_{15}$ is S, $X_{16}$ is Y, or $X_{19}$ is Y, or a combination thereof (AB-8);

$X_1$ is N, $X_2$ is D, $X_3$ is V, $X_4$ is L, $X_5$ is R, $X_6$ is S, $X_7$ is G, $X_8$ is I, $X_9$ is K, $X_{10}$ is Q, $X_{11}$ is G, $X_{12}$ is S, $X_{13}$ is S, $X_{14}$ is D, $X_{15}$ is Q, $X_{16}$ is F, or $X_{17}$ is Y, or a combination thereof (AB-9);

$X_1$ is S, $X_2$ is D, $X_3$ is V, $X_4$ is L, $X_5$ is S, $X_6$ is A, $X_7$ is G, $X_8$ is V, $X_9$ is F, $X_{10}$ is Q, $X_{11}$ is G, $X_{12}$ is S, $X_{13}$ is S, $X_{14}$ is N, $X_{15}$ is S, $X_{16}$ is Y, or $X_{17}$ is Y, or a combination thereof (AB-10);

$X_1$ is S, $X_2$ is D, $X_3$ is T, $X_4$ is L, $X_5$ is R, $X_6$ is N, $X_7$ is G, $X_8$ is V, $X_9$ is H, $X_{10}$ is Q, $X_{11}$ is G, $X_{12}$ is R, $X_{13}$ is S, $X_{14}$ is N, $X_{15}$ is Q, $X_{16}$ is F, or $X_{17}$ is Y, or a combination thereof (AB-11);

$X_1$ is S, $X_2$ is D, $X_3$ is T, $X_4$ is L, $X_5$ is S, $X_6$ is R, $X_7$ is G, $X_8$ is V, $X_9$ is K, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-12);

$X_1$ is S, $X_2$ is D, $X_3$ is V, $X_4$ is L, $X_5$ is R, $X_6$ is K, $X_7$ is G, $X_8$ is V, $X_9$ is H, $X_{10}$ is Q, $X_{11}$ is G, $X_{12}$ is S, $X_{13}$ is S, $X_{14}$ is H, $X_{15}$ is S, $X_{16}$ is F, or $X_{17}$ is Y, or a combination thereof (AB-13);

$X_1$ is S, $X_2$ is D, $X_3$ is T, $X_4$ is L, $X_5$ is R, $X_6$ is N, $X_7$ is G, $X_8$ is V, $X_9$ is Q, $X_{10}$ is Q, $X_{11}$ is G, $X_{12}$ is S, $X_{13}$ is S, $X_{14}$ is N, $X_{15}$ is S, $X_{16}$ is F, or $X_{17}$ is Y, or a combination thereof (AB-14);

$X_1$ is S, $X_2$ is D, $X_3$ is T, $X_4$ is L, $X_5$ is Y, $X_6$ is A, $X_7$ is G, $X_8$ is V, $X_9$ is H, $X_{10}$ is Q, $X_{11}$ is G, $X_{12}$ is R, $X_{13}$ is S, $X_{14}$ is H, $X_{15}$ is S, $X_{16}$ is F, or $X_{17}$ is Y, or a combination thereof (AB-15);

$X_1$ is S, $X_2$ is D, $X_3$ is V, $X_4$ is L, $X_5$ is R, $X_6$ is S, $X_7$ is G, $X_8$ is S, $X_9$ is H, $X_{10}$ is Q, $X_{11}$ is G, $X_{12}$ is R, $X_{13}$ is S, $X_{14}$ is Y, $X_{15}$ is S, $X_{16}$ is F, or $X_{17}$ is Y, or a combination thereof (AB-16);

$X_1$ is N, $X_2$ is D, $X_3$ is V, $X_4$ is L, $X_5$ is R, $X_6$ is K, $X_7$ is G, $X_8$ is I, $X_9$ is K, $X_{10}$ is Q, $X_{11}$ is G, $X_{12}$ is S, $X_{13}$ is S, $X_{14}$ is H, $X_{15}$ is Q, $X_{16}$ is F, or $X_{17}$ is Y, or a combination thereof (AB-17);

$X_1$ is S, $X_2$ is D, $X_3$ is T, $X_4$ is L, $X_5$ is R, $X_6$ is N, $X_7$ is G, $X_8$ is S, $X_9$ is K, $X_{10}$ is Q, $X_{11}$ is G, $X_{12}$ is R, $X_{13}$ is S, $X_{14}$ is D, $X_{15}$ is Q, $X_{16}$ is F, or $X_{17}$ is L, or a combination thereof (AB-18);

$X_1$ is S, $X_2$ is D, $X_3$ is V, $X_4$ is L, $X_5$ is S, $X_6$ is K, $X_7$ is G, $X_8$ is V, $X_9$ is Y, $X_{10}$ is Q, $X_{11}$ is G, $X_{12}$ is R, $X_{13}$ is S, $X_{14}$ is H, $X_{15}$ is S, $X_{16}$ is F, or $X_{17}$ is Y, or a combination thereof (AB-19); or $X_1$ is S, $X_2$ is D, $X_3$ is T, $X_4$ is L, $X_5$ is R, $X_6$ is A, $X_7$ is G, $X_8$ is V, $X_9$ is H, $X_{10}$ is Q, $X_{11}$ is G, $X_{12}$ is R, $X_{13}$ is S, $X_{14}$ is H, $X_{15}$ is S, $X_{16}$ is F, or $X_{17}$ is Y, or a combination thereof (AB-20);

$X_1$ is A, $X_2$ is D, $X_3$ is V, $X_4$ is L, $X_5$ is R, $X_6$ is K, $X_7$ is G, $X_8$ is V, $X_9$ is Y, $X_{10}$ is Q, $X_{11}$ is G, $X_{12}$ is V, $X_{13}$ is S, $X_{14}$ is H, $X_{15}$ is S, $X_{16}$ is F, or $X_{17}$ is Y, or a combination thereof (AB-21);

$X_1$ is S, $X_2$ is D, $X_3$ is T, $X_4$ is L, $X_5$ is R, $X_6$ is S, $X_7$ is G, $X_8$ is V, $X_9$ is Q, $X_{10}$ is Q, $X_{11}$ is S, $X_{12}$ is S, $X_{13}$ is S, $X_{14}$ is S, $X_{15}$ is Q, $X_{16}$ is T, or $X_{17}$ is Y, or a combination thereof (AB-22);

$X_1$ is S, $X_2$ is D, $X_3$ is V, $X_4$ is L, $X_5$ is S, $X_6$ is K, $X_7$ is G, $X_8$ is V, $X_9$ is Y, $X_{10}$ is Q, $X_{11}$ is G, $X_{12}$ is R, $X_{13}$ is S, $X_{14}$ is H, $X_{15}$ is S, $X_{16}$ is T, or $X_{17}$ is Y, or a combination thereof (AB-23);

$X_1$ is S, $X_2$ is D, $X_3$ is T, $X_4$ is L, $X_5$ is R, $X_6$ is S, $X_7$ is G, $X_8$ is S, $X_9$ is Y, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-24);

$X_1$ is S, $X_2$ is D, $X_3$ is T, $X_4$ is L, $X_5$ is Y, $X_6$ is A, $X_7$ is G, $X_8$ is V, $X_9$ is K, $X_{10}$ is Q, $X_{11}$ is G, $X_{12}$ is R, $X_{13}$ is S, $X_{14}$ is Y, $X_{15}$ is S, $X_{16}$ is V, or $X_{17}$ is Y, or a combination thereof (AB-25);

$X_1$ is S, $X_2$ is D, $X_3$ is T, $X_4$ is V, $X_5$ is R, $X_6$ is S, $X_7$ is G, $X_8$ is V, $X_9$ is F, $X_{10}$ is Q, $X_{11}$ is G, $X_{12}$ is S, $X_{13}$ is S, $X_{14}$ is H, $X_{15}$ is S, $X_{16}$ is F, or $X_{17}$ is Y, or a combination thereof (AB-26);

$X_1$ is S, $X_2$ is E, $X_3$ is T, $X_4$ is V, $X_5$ is S, $X_6$ is R, $X_7$ is G, $X_8$ is V, $X_9$ is Y, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-27);

$X_1$ is S, $X_2$ is D, $X_3$ is T, $X_4$ is L, $X_5$ is Y, $X_6$ is R, $X_7$ is G, $X_8$ is V, $X_9$ is K, $X_{10}$ is Q, $X_{11}$ is G, $X_{12}$ is R, $X_{13}$ is S, $X_{14}$ is H, $X_{15}$ is S, $X_{16}$ is F, or $X_{17}$ is Y, or a combination thereof (AB-28);

$X_1$ is R, $X_2$ is D, $X_3$ is T, $X_4$ is L, $X_5$ is S, $X_6$ is R, $X_7$ is G, $X_8$ is V, $X_9$ is F, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-29);

$X_1$ is R, $X_2$ is D, $X_3$ is T, $X_4$ is L, $X_5$ is S, $X_6$ is R, $X_7$ is G, $X_8$ is V, $X_9$ is F, $X_{10}$ is Q, $X_{11}$ is G, $X_{12}$ is S, $X_{13}$ is S, $X_{14}$ is N, $X_{15}$ is Q, $X_{16}$ is V, or $X_{17}$ is Y, or a combination thereof (AB-30);

$X_1$ is L, $X_2$ is D, $X_3$ is T, $X_4$ is L, $X_5$ is Y, $X_6$ is K, $X_7$ is G, $X_8$ is V, $X_9$ is K, $X_{10}$ is Q, $X_{11}$ is G, $X_{12}$ is R, $X_{13}$ is S, $X_{14}$ is H, $X_{15}$ is S, $X_{16}$ is V, or $X_{17}$ is Y, or a combination thereof (AB-31);

$X_1$ is S, $X_2$ is E, $X_3$ is T, $X_4$ is L, $X_5$ is R, $X_6$ is R, $X_7$ is G, $X_8$ is V, $X_9$ is K, $X_{10}$ is Q, $X_{11}$ is G, $X_{12}$ is S, $X_{13}$ is S, $X_{14}$ is N, $X_{15}$ is Q, $X_{16}$ is L, or $X_{17}$ is Y, or a combination thereof (AB-32);

$X_1$ is S, $X_2$ is D, $X_3$ is T, $X_4$ is L, $X_5$ is R, $X_6$ is A, $X_7$ is G, $X_8$ is K, $X_9$ is K, $X_{10}$ is Q, $X_{11}$ is G, $X_{12}$ is S, $X_{13}$ is S, $X_{14}$ is N, $X_{15}$ is Q, $X_{16}$ is Y, or $X_{17}$ is Y, or a combination thereof (AB-33);

$X_1$ is A, $X_2$ is D, $X_3$ is V, $X_4$ is L, $X_5$ is R, $X_6$ is K, $X_7$ is G, $X_8$ is V, $X_9$ is K, $X_{10}$ is Q, $X_{11}$ is G, $X_{12}$ is R, $X_{13}$ is S, $X_{14}$ is H, $X_{15}$ is S, $X_{16}$ is T, or $X_{17}$ is Y, or a combination thereof (AB-34);

$X_1$ is A, $X_2$ is D, $X_3$ is T, $X_4$ is L, $X_5$ is S, $X_6$ is R, $X_7$ is G, $X_8$ is V, $X_9$ is Q, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-35);

$X_1$ is A, $X_2$ is D, $X_3$ is T, $X_4$ is L, $X_5$ is S, $X_6$ is K, $X_7$ is G, $X_8$ is V, $X_9$ is Y, $X_{10}$ is Q, $X_{11}$ is G, $X_{12}$ is S, $X_{13}$ is S, $X_{14}$ is H, $X_{15}$ is S, $X_{16}$ is T, or $X_{17}$ is Y, or a combination thereof (AB-36);

$X_1$ is F, $X_2$ is D, $X_3$ is T, $X_4$ is L, $X_5$ is R, $X_6$ is R, $X_7$ is G, $X_8$ is I, $X_9$ is F, $X_{10}$ is Q, $X_{11}$ is G, $X_{12}$ is S, $X_{13}$ is S, $X_{14}$ is H, $X_{15}$ is S, $X_{16}$ is F, or $X_{17}$ is Y, or a combination thereof (AB-37);

$X_1$ is S, $X_2$ is D, $X_3$ is T, $X_4$ is L, $X_5$ is Q, $X_6$ is R, $X_7$ is G, $X_8$ is V, $X_9$ is Q, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-38);

$X_1$ is A, $X_2$ is D, $X_3$ is V, $X_4$ is L, $X_5$ is R, $X_6$ is K, $X_7$ is G, $X_8$ is K, $X_9$ is K, $X_{10}$ is Q, $X_{11}$ is G, $X_{12}$ is S, $X_{13}$ is S, $X_{14}$ is H, $X_{15}$ is Q, $X_{16}$ is F, or $X_{17}$ is Y, or a combination thereof (AB-39);

$X_1$ is S, $X_2$ is E, $X_3$ is T, $X_4$ is L, $X_5$ is R, $X_6$ is S, $X_7$ is G, $X_8$ is V, $X_9$ is Q, $X_{10}$ is Q, $X_{11}$ is G, $X_{12}$ is S, $X_{13}$ is S, $X_{14}$ is N, $X_{15}$ is Q, $X_{16}$ is V, or $X_{17}$ is Y, or a combination thereof (AB-40);

$X_1$ is N, $X_2$ is D, $X_3$ is V, $X_4$ is L, $X_5$ is S, $X_6$ is A, $X_7$ is G, $X_8$ is V, $X_9$ is F, $X_{10}$ is Q, $X_{11}$ is G, $X_{12}$ is S, $X_{13}$ is N, $X_{14}$ is Y, $X_{15}$ is S, $X_{16}$ is Y, or $X_{17}$ is Y, or a combination thereof (AB-41);

$X_1$ is S, $X_2$ is D, $X_3$ is T, $X_4$ is L, $X_5$ is Q, $X_6$ is S, $X_7$ is G, $X_8$ is V, $X_9$ is K, $X_{10}$ is Q, $X_{11}$ is G, $X_{12}$ is R, $X_{13}$ is S, $X_{14}$ is D, $X_{15}$ is Q, $X_{16}$ is Y, or $X_{17}$ is L, or a combination thereof (AB-42);

$X_1$ is S, $X_2$ is D, $X_3$ is T, $X_4$ is L, $X_5$ is S, $X_6$ is A, $X_7$ is G, $X_8$ is V, $X_9$ is F, $X_{10}$ is Q, $X_{11}$ is G, $X_{12}$ is S, $X_{13}$ is S, $X_{14}$ is H, $X_{15}$ is S, $X_{16}$ is F, or $X_{17}$ is Y, or a combination thereof (AB-43);

$X_1$ is L, $X_2$ is D, $X_3$ is V, $X_4$ is L, $X_5$ is R, $X_6$ is E, $X_7$ is G, $X_8$ is K, $X_9$ is H, $X_{10}$ is Q, $X_{11}$ is G, $X_{12}$ is R, $X_{13}$ is N, $X_{14}$ is D, $X_{15}$ is Q, $X_{16}$ is D, or $X_{17}$ is L, or a combination thereof (AB-44);

$X_1$ is S, $X_2$ is D, $X_3$ is T, $X_4$ is L, $X_5$ is S, $X_6$ is S, $X_7$ is G, $X_8$ is V, $X_9$ is Q, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-45);

$X_1$ is S, $X_2$ is D, $X_3$ is T, $X_4$ is L, $X_5$ is S, $X_6$ is S, $X_7$ is G, $X_8$ is V, $X_9$ is H, $X_{10}$ is Q, $X_{11}$ is G, $X_{12}$ is S, $X_{13}$ is S, $X_{14}$ is H, $X_{15}$ is S, $X_{16}$ is F, or $X_{17}$ is Y, or a combination thereof (AB-46);

$X_1$ is S, $X_2$ is D, $X_3$ is T, $X_4$ is L, $X_5$ is Q, $X_6$ is N, $X_7$ is G, $X_8$ is V, $X_9$ is H, $X_{10}$ is Q, $X_{11}$ is G, $X_{12}$ is R, $X_{13}$ is N, $X_{14}$ is D, $X_{15}$ is Q, $X_{16}$ is D, or $X_{17}$ is L, or a combination thereof (AB-47);

$X_1$ is N, $X_2$ is D, $X_3$ is V, $X_4$ is L, $X_5$ is D, $X_6$ is K, $X_7$ is G, $X_8$ is I, $X_9$ is K, $X_{10}$ is Q, $X_{11}$ is G, $X_{12}$ is S, $X_{13}$ is S, $X_{14}$ is D, $X_{15}$ is Q, $X_{16}$ is L, or $X_{17}$ is Y, or a combination thereof (AB-48);

$X_1$ is S, $X_2$ is D, $X_3$ is T, $X_4$ is L, $X_5$ is E, $X_6$ is N, $X_7$ is G, $X_8$ is I, $X_9$ is K, $X_{10}$ is Q, $X_{11}$ is G, $X_{12}$ is R, $X_{13}$ is S, $X_{14}$ is D, $X_{15}$ is Q, $X_{16}$ is Y, or $X_{17}$ is L, or a combination thereof (AB-49);

$X_1$ is A, $X_2$ is D, $X_3$ is V, $X_4$ is L, $X_5$ is S, $X_6$ is S, $X_7$ is G, $X_8$ is S, $X_9$ is F, $X_{10}$ is Q, $X_{11}$ is G, $X_{12}$ is S, $X_{13}$ is S, $X_{14}$ is Y, $X_{15}$ is S, $X_{16}$ is T, or $X_{17}$ is Y, or a combination thereof (AB-50); or $X_1$ is S, $X_2$ is D, $X_3$ is T, $X_4$ is L, $X_5$ is S, $X_6$ is N, $X_7$ is G, $X_8$ is V, $X_9$ is Q, $X_{10}$ is Q, $X_{11}$ is G, $X_{12}$ is S, $X_{13}$ is S, $X_{14}$ is N, $X_{15}$ is Q, $X_{16}$ is F, or $X_{17}$ is Y, or a combination thereof (AB-51).

In some embodiments, a polypeptide disclosed herein comprises a $V_H$ that comprises an HCDR1, an HCDR2 and an HCDR3 that are substantially similar in amino acid sequence to a HCDR1, a HCDR2 and a HCDR3, respectively, of a $V_H$ amino acid sequence set forth in any of SEQ ID NOs:4-48 (see Table 1 for SEQ ID NOs:4-48, and see Table 3 and FIG. 2 for non-limiting examples of corresponding HCDR1, HCDR2 and HCDR3 sequences).

In some embodiments, a polypeptide disclosed herein comprises a $V_L$ that comprises a LCDR1, a LCDR2 and a LCDR3 that are substantially similar in amino acid sequence to a LCDR1, a LCDR2 and a LCDR3, respectively, of a $V_L$ amino acid sequence set forth in any of SEQ ID NOs:51-76 (see Table 2 for SEQ ID NOs:51-76, and see Table 3 and FIG. 3 for non-limiting examples of corresponding LCDR1, LCDR2 and LCDR3 sequences).

In some embodiments, a polypeptide disclosed herein comprises a $V_H$ that comprises an HCDR1, an HCDR2 and an HCDR3 that are identical in amino acid sequence to a HCDR1, a HCDR2 and a HCDR3, respectively, of a $V_H$ amino acid sequence set forth in any of SEQ ID NOs:4-48.

In some embodiments, a polypeptide disclosed herein comprises a $V_L$ that comprises a LCDR1, a LCDR2 and a LCDR3 that are identical in amino acid sequence to a LCDR1, a LCDR2 and a LCDR3, respectively, of a $V_L$ amino acid sequence set forth in any of SEQ ID NOs:51-76.

In some embodiments, a polypeptide disclosed herein comprises a paratope that is substantially similar to a paratope of a $V_H/V_L$ combination selected from: SEQ ID NO:4/SEQ ID NO:51 (AB-1), SEQ ID NO:5/SEQ ID NO:52 (AB-2), SEQ ID NO:6/SEQ ID NO:53 (AB-3), SEQ ID NO:7/SEQ ID NO:54 (AB-4), SEQ ID NO:8/SEQ ID NO:51 (AB-5), SEQ ID NO:9/SEQ ID NO:55 (AB-6), SEQ ID NO:10/SEQ ID NO:56 (AB-7), SEQ ID NO:11/SEQ ID NO:57 (AB-8), SEQ ID NO:12/SEQ ID NO:58 (AB-9), SEQ ID NO:13/SEQ ID NO:59 (AB-10), SEQ ID NO:14/SEQ ID NO:60 (AB-11), SEQ ID NO:15/SEQ ID NO:56 (AB-12), SEQ ID NO:16/SEQ ID NO:51 (AB-13), SEQ ID NO:10/SEQ ID NO:50 (AB-14), SEQ ID NO:17/SEQ ID NO:61 (AB-15), SEQ ID NO:18/SEQ ID NO:62 (AB-16), SEQ ID NO:6/SEQ ID NO:63 (AB-17), SEQ ID NO:19/SEQ ID NO:64 (AB-18), SEQ ID NO:4/SEQ ID NO:61 (AB-19), SEQ ID NO:20/SEQ ID NO:61 (AB-20), SEQ ID NO:21/SEQ ID NO:65 (AB-21), SEQ ID NO:22/SEQ ID NO:66 (AB-22), SEQ ID NO:4/SEQ ID NO:67 (AB-23), SEQ ID NO:23/SEQ ID NO:56 (AB-24), SEQ ID NO:24/SEQ ID NO:68 (AB-25), SEQ ID NO:25/SEQ ID NO:51 (AB-26), SEQ ID NO:26/SEQ ID NO:56 (AB-27), SEQ ID NO:27/SEQ ID NO:61 (AB-28), SEQ ID NO:28/SEQ ID NO:56 (AB-29), SEQ ID NO:28/SEQ ID NO:69 (AB-30), SEQ ID NO:29/SEQ ID NO:70 (AB-31), SEQ ID NO:30/

SEQ ID NO:71 (AB-32), SEQ ID NO:31/SEQ ID NO:72 (AB-33), SEQ ID NO:32/SEQ ID NO:67 (AB-34), SEQ ID NO:33/SEQ ID NO:56 (AB-35), SEQ ID NO:34/SEQ ID NO:73 (AB-36), SEQ ID NO:35/SEQ ID NO:51 (AB-37), SEQ ID NO:36/SEQ ID NO:56 (AB-38), SEQ ID NO:37/SEQ ID NO:63 (AB-39), SEQ ID NO:38/SEQ ID NO:69 (AB-40), SEQ ID NO:39/SEQ ID NO:74 (AB-41), SEQ ID NO:40/SEQ ID NO:52 (AB-42), SEQ ID NO:41/SEQ ID NO:51 (AB-43), SEQ ID NO:42/SEQ ID NO:75 (AB-44), SEQ ID NO:43/SEQ ID NO:56 (AB-45), SEQ ID NO:44/SEQ ID NO:51 (AB-46), SEQ ID NO:45/SEQ ID NO:75 (AB-47), SEQ ID NO:46/SEQ ID NO:53 (AB-48), SEQ ID NO:47/SEQ ID NO:52 (AB-49), SEQ ID NO:48/SEQ ID NO:76 (AB-50), or SEQ ID NO:3/SEQ ID NO:56 (AB-51).

In some embodiments, a polypeptide disclosed herein comprises a paratope that is identical to a paratope of a $V_H/V_L$ combination selected from: SEQ ID NO:4/SEQ ID NO:51 (AB-1), SEQ ID NO:5/SEQ ID NO:52 (AB-2), SEQ ID NO:6/SEQ ID NO:53 (AB-3), SEQ ID NO:7/SEQ ID NO:54 (AB-4), SEQ ID NO:8/SEQ ID NO:51 (AB-5), SEQ ID NO:9/SEQ ID NO:55 (AB-6), SEQ ID NO:10/SEQ ID NO:56 (AB-7), SEQ ID NO:11/SEQ ID NO:57 (AB-8), SEQ ID NO:12/SEQ ID NO:58 (AB-9), SEQ ID NO:13/SEQ ID NO:59 (AB-10), SEQ ID NO:14/SEQ ID NO:60 (AB-11), SEQ ID NO:15/SEQ ID NO:56 (AB-12), SEQ ID NO:16/SEQ ID NO:51 (AB-13), SEQ ID NO:10/SEQ ID NO:50 (AB-14), SEQ ID NO:17/SEQ ID NO:61 (AB-15), SEQ ID NO:18/SEQ ID NO:62 (AB-16), SEQ ID NO:6/SEQ ID NO:63 (AB-17), SEQ ID NO:19/SEQ ID NO:64 (AB-18), SEQ ID NO:4/SEQ ID NO:61 (AB-19), SEQ ID NO:20/SEQ ID NO:61 (AB-20), SEQ ID NO:21/SEQ ID NO:65 (AB-21), SEQ ID NO:22/SEQ ID NO:66 (AB-22), SEQ ID NO:4/SEQ ID NO:67 (AB-23), SEQ ID NO:23/SEQ ID NO:56 (AB-24), SEQ ID NO:24/SEQ ID NO:68 (AB-25), SEQ ID NO:25/SEQ ID NO:51 (AB-26), SEQ ID NO:26/SEQ ID NO:56 (AB-27), SEQ ID NO:27/SEQ ID NO:61 (AB-28), SEQ ID NO:28/SEQ ID NO:56 (AB-29), SEQ ID NO:28/SEQ ID NO:69 (AB-30), SEQ ID NO:29/SEQ ID NO:70 (AB-31), SEQ ID NO:30/SEQ ID NO:71 (AB-32), SEQ ID NO:31/SEQ ID NO:72 (AB-33), SEQ ID NO:32/SEQ ID NO:67 (AB-34), SEQ ID NO:33/SEQ ID NO:56 (AB-35), SEQ ID NO:34/SEQ ID NO:73 (AB-36), SEQ ID NO:35/SEQ ID NO:51 (AB-37), SEQ ID NO:36/SEQ ID NO:56 (AB-38), SEQ ID NO:37/SEQ ID NO:63 (AB-39), SEQ ID NO:38/SEQ ID NO:69 (AB-40), SEQ ID NO:39/SEQ ID NO:74 (AB-41), SEQ ID NO:40/SEQ ID NO:52 (AB-42), SEQ ID NO:41/SEQ ID NO:51 (AB-43), SEQ ID NO:42/SEQ ID NO:75 (AB-44), SEQ ID NO:43/SEQ ID NO:56 (AB-45), SEQ ID NO:44/SEQ ID NO:51 (AB-46), SEQ ID NO:45/SEQ ID NO:75 (AB-47), SEQ ID NO:46/SEQ ID NO:53 (AB-48), SEQ ID NO:47/SEQ ID NO:52 (AB-49), SEQ ID NO:48/SEQ ID NO:76 (AB-50), or SEQ ID NO:3/SEQ ID NO:56 (AB-51).

In some embodiments, a polypeptide disclosed herein comprises a paratope that differs from a paratope of a $V_H/V_L$ combination selected from: SEQ ID NO:4/SEQ ID NO:51 (AB-1), SEQ ID NO:5/SEQ ID NO:52 (AB-2), SEQ ID NO:6/SEQ ID NO:53 (AB-3), SEQ ID NO:7/SEQ ID NO:54 (AB-4), SEQ ID NO:8/SEQ ID NO:51 (AB-5), SEQ ID NO:9/SEQ ID NO:55 (AB-6), SEQ ID NO:10/SEQ ID NO:56 (AB-7), SEQ ID NO:11/SEQ ID NO:57 (AB-8), SEQ ID NO:12/SEQ ID NO:58 (AB-9), SEQ ID NO:13/SEQ ID NO:59 (AB-10), SEQ ID NO:14/SEQ ID NO:60 (AB-11), SEQ ID NO:15/SEQ ID NO:56 (AB-12), SEQ ID NO:16/SEQ ID NO:51 (AB-13), SEQ ID NO:10/SEQ ID NO:50 (AB-14), SEQ ID NO:17/SEQ ID NO:61 (AB-15), SEQ ID NO:18/SEQ ID NO:62 (AB-16), SEQ ID NO:6/SEQ ID NO:63 (AB-17), SEQ ID NO:19/SEQ ID NO:64 (AB-18), SEQ ID NO:4/SEQ ID NO:61 (AB-19), SEQ ID NO:20/SEQ ID NO:61 (AB-20), SEQ ID NO:21/SEQ ID NO:65 (AB-21), SEQ ID NO:22/SEQ ID NO:66 (AB-22), SEQ ID NO:4/SEQ ID NO:67 (AB-23), SEQ ID NO:23/SEQ ID NO:56 (AB-24), SEQ ID NO:24/SEQ ID NO:68 (AB-25), SEQ ID NO:25/SEQ ID NO:51 (AB-26), SEQ ID NO:26/SEQ ID NO:56 (AB-27), SEQ ID NO:27/SEQ ID NO:61 (AB-28), SEQ ID NO:28/SEQ ID NO:56 (AB-29), SEQ ID NO:28/SEQ ID NO:69 (AB-30), SEQ ID NO:29/SEQ ID NO:70 (AB-31), SEQ ID NO:30/SEQ ID NO:71 (AB-32), SEQ ID NO:31/SEQ ID NO:72 (AB-33), SEQ ID NO:32/SEQ ID NO:67 (AB-34), SEQ ID NO:33/SEQ ID NO:56 (AB-35), SEQ ID NO:34/SEQ ID NO:73 (AB-36), SEQ ID NO:35/SEQ ID NO:51 (AB-37), SEQ ID NO:36/SEQ ID NO:56 (AB-38), SEQ ID NO:37/SEQ ID NO:63 (AB-39), SEQ ID NO:38/SEQ ID NO:69 (AB-40), SEQ ID NO:39/SEQ ID NO:74 (AB-41), SEQ ID NO:40/SEQ ID NO:52 (AB-42), SEQ ID NO:41/SEQ ID NO:51 (AB-43), SEQ ID NO:42/SEQ ID NO:75 (AB-44), SEQ ID NO:43/SEQ ID NO:56 (AB-45), SEQ ID NO:44/SEQ ID NO:51 (AB-46), SEQ ID NO:45/SEQ ID NO:75 (AB-47), SEQ ID NO:46/SEQ ID NO:53 (AB-48), SEQ ID NO:47/SEQ ID NO:52 (AB-49), SEQ ID NO:48/SEQ ID NO:76 (AB-50), or SEQ ID NO:3/SEQ ID NO:56 (AB-51), by substitution (e.g., conservative such as highly conservative substitution) of from 1 to 3 (e.g., 1, 2 or 3) residues.

In some embodiments, a polypeptide disclosed herein comprises a paratope that is identical to a paratope of a $V_H/V_L$ combination selected from: SEQ ID NO:3/SEQ ID NO:50.

In some embodiments, a polypeptide disclosed herein comprises a paratope that is identical to a paratope of a $V_H/V_L$ combination selected from: SEQ ID NO:4/SEQ ID NO:51 (AB-1).

In some embodiments, a polypeptide disclosed herein comprises a $V_H$ that has at least about 70% sequence identity to the amino acid sequence of SEQ ID NO:3. For example, the $V_H$ can has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:3. In some embodiments, the $V_H$ has at least about 85% or at least about 90% sequence identity to the amino acid sequence of SEQ ID NO:3. The sequence identified as SEQ ID NO:3 is shown in Table 1, which corresponds to a human $V_H$ domain.

In some embodiments, a polypeptide disclosed herein comprises a $V_L$ that has at least about 70% sequence identity to the amino acid sequence of SEQ ID NO:50. For example, the $V_L$ can has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:50. In some embodiments, the $V_L$ has at least about 85% or at least about 90% sequence identity to the amino acid sequence of SEQ ID NO:50. The sequence identified as SEQ ID NO:50 is shown in Table 2, which corresponds to a human $V_L$ domain.

In some embodiments, a polypeptide disclosed herein comprises a $V_H$ that has at least about 70% sequence identity to the amino acid sequence of any one or more of SEQ ID NOs:4-48. For example, the $V_H$ can has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:4-48. In some embodiments, the $V_H$ has at least about 85% or at least about 90% sequence identity to the amino acid sequence of any one or more of SEQ ID NOs:4-48.

In some embodiments, a polypeptide disclosed herein comprises a $V_L$ that has at least about 70% sequence identity to the amino acid sequence of any one or more of SEQ ID NOs:51-76. For example, the $V_L$ can has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:51-76. In some embodiments, the $V_L$ has at least about 85% or at least about 90% sequence identity to the amino acid sequence of any one or more of SEQ ID NOs:51-76.

In some embodiments, a polypeptide disclosed herein comprises a $V_H$ that has at least about 70% sequence identity to the amino acid sequence of SEQ ID NO:4. For example, the $V_H$ can has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:4. In some embodiments, the $V_H$ has at least about 85% or at least about 90% sequence identity to the amino acid sequence of SEQ ID NO:4. The sequence identified as SEQ ID NO:4 is shown in Table 1.

In some embodiments, a polypeptide disclosed herein comprises a $V_L$ that has at least about 70% sequence identity to the amino acid sequence of SEQ ID NO:51. For example, the $V_L$ can has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:51. In some embodiments, the $V_L$ has at least about 85% or at least about 90% sequence identity to the amino acid sequence of SEQ ID NO:51. The sequence identified as SEQ ID NO:51 is shown in Table 2.

In some embodiments, a polypeptide disclosed herein comprises a $V_H$ that comprises at least 1 amino acid substitution (e.g., at least 1 conservative substitution such as highly conservative amino acid substitution) relative to the amino acid sequence of SEQ ID NO:3. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_H$ comprises about 1-10 amino acid substitutions, relative to the amino acid sequence of SEQ ID NO:3. In some embodiments, the at least 1 amino acid substitution replaces only a HCDR1, a HCDR2 and/or a HCDR3 residue, of SEQ ID NO:3. In some embodiments, the at least 1 amino acid substitution replaces only a non-CDR residue (e.g., within a framework region), of SEQ ID NO:3.

In some embodiments, a polypeptide disclosed herein comprises a $V_L$ that comprises at least 1 amino acid substitution relative to the amino acid sequence of SEQ ID NO:50. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_L$ comprises about 1-10 amino acid substitutions, relative to the amino acid sequence of SEQ ID NO:50. In some embodiments, the at least 1 amino acid substitution replaces only a LCDR1, a LCDR2 and/or a LCDR3 residue, of SEQ ID NO:50. In some embodiments, the at least 1 amino acid substitution replaces only a non-CDR residue (e.g., within a framework region), of SEQ ID NO:50.

In some embodiments, the amino acid substitutions are conservative substitutions. The term "conservative amino acid substitution(s)" or "conservative substitution(s)" refers to an amino acid substitution having a value of 0 or greater in BLOSUM62.

In some embodiments, the amino acid substitutions are highly conservative substitutions. The term "highly conservative amino acid substitution(s)" or "highly conservative substitution(s)" refers to an amino acid substitution having a value of at least 1 (e.g., at least 2) in BLOSUM62.

In some embodiments, a polypeptide disclosed herein comprises a $V_H$ that comprises at least 1 amino acid substitution relative to the amino acid sequence of any one or more of SEQ ID NOs:4-48. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_H$ comprises about 1-10 amino acid substitutions, relative to the amino acid sequence of any one or more of SEQ ID NOs:4-48.

In some embodiments, the at least 1 amino acid substitution replaces only a HCDR1, a HCDR2 and/or a HCDR3 residue, of any one or more of SEQ ID NOs:4-48. In some embodiments, the at least 1 amino acid substitution replaces only a non-CDR residue (e.g., within a framework region), of any one or more of SEQ ID NOs:4-48.

In some embodiments, a polypeptide disclosed herein comprises a $V_L$ that comprises at least 1 amino acid substitution relative to the amino acid sequence of any one or more of SEQ ID NOs:51-76. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_L$ comprises about 1-10 amino acid substitutions, relative to the amino acid sequence of any one or more of SEQ ID NOs:51-76.

In some embodiments, the at least 1 amino acid substitution replaces only a LCDR1, a LCDR2 and/or a LCDR3 residue, of any one or more of SEQ ID NOs:51-76. In some embodiments, the at least 1 amino acid substitution replaces only a non-CDR residue (e.g., within a framework region), of any one or more of SEQ ID NOs:51-76.

In some embodiments, a polypeptide comprises:
a) a HCDR1 comprising at least 1 amino acid substitution relative to the amino acid sequence of SEQ ID NO:77;
b) a HCDR2 comprising at least 1 amino acid substitution relative to at least one amino acid sequence set forth in SEQ ID NOs:79-88 (e.g., at least one amino acid sequence set forth in SEQ ID NOs:80-88);
c) a HCDR3 comprising at least 1 amino acid substitution relative to at least one amino acid sequence set forth in SEQ ID NOs:90-131 (e.g., at least one amino acid sequence set forth in SEQ ID NOs:91-131);
d) a LCDR1 comprising at least 1 amino acid substitution relative to the amino acid sequence set forth in SEQ ID NOs:133-140 (e.g., at least one amino acid sequence set forth in SEQ ID NOs:134-140);
e) a LCDR2 comprising at least 1 amino acid substitution relative to the amino acid sequence of SEQ ID NO:141;
f) a LCDR3 comprising at least 1 amino acid substitution relative to at least one amino acid sequence set forth in SEQ ID NOs:143-162 (e.g., at least one amino acid sequence set forth in SEQ ID NOs:144-162);
or any combination of the foregoing.

In some embodiments, a polypeptide comprises:
a) a HCDR2 comprising at least 1 amino acid substitution relative to at least one amino acid sequence set forth in SEQ ID NOs:79-88 (e.g., at least one amino acid sequence set forth in SEQ ID NOs:80-88);
b) a HCDR3 comprising at least 1 amino acid substitution relative to at least one amino acid sequence set forth in SEQ ID NOs:90-131 (e.g., at least one amino acid sequence set forth in SEQ ID NOs:91-131);
c) a LCDR1 comprising at least 1 amino acid substitution relative to the amino acid sequence set forth in SEQ ID NOs:133-140 (e.g., at least one amino acid sequence set forth in SEQ ID NOs:134-140); or
d) a LCDR3 comprising at least 1 amino acid substitution relative to at least one amino acid sequence set forth in SEQ ID NOs:143-162 (e.g., at least one amino acid sequence set forth in SEQ ID NOs:144-162);
or any combination of the foregoing.

In some embodiments, a polypeptide disclosed herein comprises a $V_H$ that comprises the amino acid sequence of SEQ ID NO:3. In some embodiments, a polypeptide disclosed herein comprises a $V_H$ that comprises the amino acid sequence of any one of SEQ ID NOs:4-48. In some embodiments, a polypeptide disclosed herein comprises a $V_H$ that comprises the amino acid sequence of SEQ ID NO:4.

In some embodiments, a polypeptide disclosed herein comprises a $V_L$ that comprises the amino acid sequence of SEQ ID NO:50. In some embodiments, a polypeptide disclosed herein comprises a $V_L$ that comprises the amino acid sequence of any one of SEQ ID NOs:51-76. In some embodiments, a polypeptide disclosed herein comprises a $V_L$ that comprises the amino acid sequence of SEQ ID NO:51.

In some embodiments, a polypeptide disclosed herein comprises:
a $V_H$ comprising the amino acid sequence of any one of SEQ ID NOs:4-48; and
a $V_L$ comprising the amino acid sequence of SEQ ID NO:50.

In some embodiments, a polypeptide disclosed herein comprises:
a $V_H$ comprising the amino acid sequence of SEQ ID NO:3; and
a $V_L$ comprising the amino acid sequence of any one of SEQ ID NOs:51-76.

In some embodiments, a polypeptide disclosed herein comprises:
a $V_H$ comprising the amino acid sequence of any one of SEQ ID NOs:4-48; and
a $V_L$ comprising the amino acid sequence of any one of SEQ ID NOs:51-76.

In some embodiments, a polypeptide disclosed herein comprises:
a) the $V_H$ comprises the amino acid sequence of SEQ ID NO:4; and
b) the $V_L$ comprises the amino acid sequence of SEQ ID NO:51 (AB-1).

In some embodiments, a polypeptide disclosed herein comprises:
a) the $V_H$ comprises the amino acid sequence of SEQ ID NO:5; and
b) the $V_L$ comprises the amino acid sequence of SEQ ID NO:52 (AB-2).

In some embodiments, a polypeptide disclosed herein comprises:
a) the $V_H$ comprises the amino acid sequence of SEQ ID NO:6; and
b) the $V_L$ comprises the amino acid sequence of SEQ ID NO:53 (AB-3).

In some embodiments, a polypeptide disclosed herein comprises:
a) the $V_H$ comprises the amino acid sequence of SEQ ID NO:7; and
b) the $V_L$ comprises the amino acid sequence of SEQ ID NO:54 (AB-4).

In some embodiments, a polypeptide disclosed herein comprises:
a) the $V_H$ comprises the amino acid sequence of SEQ ID NO:8; and
b) the $V_L$ comprises the amino acid sequence of SEQ ID NO:51 (AB-5).

In some embodiments, a polypeptide disclosed herein comprises:
a) the $V_H$ comprises the amino acid sequence of SEQ ID NO:9; and
b) the $V_L$ comprises the amino acid sequence of SEQ ID NO:55 (AB-6).

In some embodiments, a polypeptide disclosed herein comprises:
a) the $V_H$ comprises the amino acid sequence of SEQ ID NO:10; and
b) the $V_L$ comprises the amino acid sequence of SEQ ID NO:56 (AB-7).

In some embodiments, a polypeptide disclosed herein comprises:
a) the $V_H$ comprises the amino acid sequence of SEQ ID NO:11; and
b) the $V_L$ comprises the amino acid sequence of SEQ ID NO:57 (AB-8).

In some embodiments, a polypeptide disclosed herein comprises:
a) the $V_H$ comprises the amino acid sequence of SEQ ID NO:13; and
b) the $V_L$ comprises the amino acid sequence of SEQ ID NO:59 (AB-10).

In some embodiments, a polypeptide disclosed herein comprises:
a) the $V_H$ comprises the amino acid sequence of SEQ ID NO:14; and
b) the $V_L$ comprises the amino acid sequence of SEQ ID NO:60 (AB-11).

In some embodiments, a polypeptide disclosed herein comprises:
a) the $V_H$ comprises the amino acid sequence of SEQ ID NO:15; and
b) the $V_L$ comprises the amino acid sequence of SEQ ID NO:56 (AB-12).

In some embodiments, a polypeptide disclosed herein comprises:
a) the $V_H$ comprises the amino acid sequence of SEQ ID NO:16; and
b) the $V_L$ comprises the amino acid sequence of SEQ ID NO:51 (AB-13).

In some embodiments, a polypeptide disclosed herein comprises:
a) the $V_H$ comprises the amino acid sequence of SEQ ID NO:10; and
b) the $V_L$ comprises the amino acid sequence of SEQ ID NO:50 (AB-14).

In some embodiments, a polypeptide disclosed herein comprises:
- a) the $V_H$ comprises the amino acid sequence of SEQ ID NO:17; and
- b) the $V_L$ comprises the amino acid sequence of SEQ ID NO:61 (AB-15).

In some embodiments, a polypeptide disclosed herein comprises:
- a) the $V_H$ comprises the amino acid sequence of SEQ ID NO:18; and
- b) the $V_L$ comprises the amino acid sequence of SEQ ID NO:62 (AB-16).

In some embodiments, a polypeptide disclosed herein comprises:
- a) the $V_H$ comprises the amino acid sequence of SEQ ID NO:6; and
- b) the $V_L$ comprises the amino acid sequence of SEQ ID NO:63 (AB-17).

In some embodiments, a polypeptide disclosed herein comprises:
- a) the $V_H$ comprises the amino acid sequence of SEQ ID NO:19; and
- b) the $V_L$ comprises the amino acid sequence of SEQ ID NO:64 (AB-18).

In some embodiments, a polypeptide disclosed herein comprises:
- a) the $V_H$ comprises the amino acid sequence of SEQ ID NO:4; and
- b) the $V_L$ comprises the amino acid sequence of SEQ ID NO:61 (AB-19).

In some embodiments, a polypeptide disclosed herein comprises:
- a) the $V_H$ comprises the amino acid sequence of SEQ ID NO:20; and
- b) the $V_L$ comprises the amino acid sequence of SEQ ID NO:61 (AB-20).

In some embodiments, a polypeptide disclosed herein comprises:
- a) the $V_H$ comprises the amino acid sequence of SEQ ID NO:21; and
- b) the $V_L$ comprises the amino acid sequence of SEQ ID NO:65 (AB-21).

In some embodiments, a polypeptide disclosed herein comprises:
- a) the $V_H$ comprises the amino acid sequence of SEQ ID NO:22; and
- b) the $V_L$ comprises the amino acid sequence of SEQ ID NO:66 (AB-22).

In some embodiments, a polypeptide disclosed herein comprises:
- a) the $V_H$ comprises the amino acid sequence of SEQ ID NO:4; and
- b) the $V_L$ comprises the amino acid sequence of SEQ ID NO:67 (AB-23).

In some embodiments, a polypeptide disclosed herein comprises:
- a) the $V_H$ comprises the amino acid sequence of SEQ ID NO:23; and
- b) the $V_L$ comprises the amino acid sequence of SEQ ID NO:56 (AB-24).

In some embodiments, a polypeptide disclosed herein comprises:
- a) the $V_H$ comprises the amino acid sequence of SEQ ID NO:24; and
- b) the $V_L$ comprises the amino acid sequence of SEQ ID NO:68 (AB-25).

In some embodiments, a polypeptide disclosed herein comprises:
- a) the $V_H$ comprises the amino acid sequence of SEQ ID NO:25; and
- b) the $V_L$ comprises the amino acid sequence of SEQ ID NO:51 (AB-26).

In some embodiments, a polypeptide disclosed herein comprises:
- a) the $V_H$ comprises the amino acid sequence of SEQ ID NO:26; and
- b) the $V_L$ comprises the amino acid sequence of SEQ ID NO:56 (AB-27).

In some embodiments, a polypeptide disclosed herein comprises:
- a) the $V_H$ comprises the amino acid sequence of SEQ ID NO:27; and
- b) the $V_L$ comprises the amino acid sequence of SEQ ID NO:61 (AB-28).

In some embodiments, a polypeptide disclosed herein comprises:
- a) the $V_H$ comprises the amino acid sequence of SEQ ID NO:28; and
- b) the $V_L$ comprises the amino acid sequence of SEQ ID NO:56 (AB-29).

In some embodiments, a polypeptide disclosed herein comprises:
- a) the $V_H$ comprises the amino acid sequence of SEQ ID NO:28; and
- b) the $V_L$ comprises the amino acid sequence of SEQ ID NO:69 (AB-30).

In some embodiments, a polypeptide disclosed herein comprises:
- a) the $V_H$ comprises the amino acid sequence of SEQ ID NO:29; and
- b) the $V_L$ comprises the amino acid sequence of SEQ ID NO:70 (AB-31).

In some embodiments, a polypeptide disclosed herein comprises:
- a) the $V_H$ comprises the amino acid sequence of SEQ ID NO:30; and
- b) the $V_L$ comprises the amino acid sequence of SEQ ID NO:71 (AB-32).

In some embodiments, a polypeptide disclosed herein comprises:
- a) the $V_H$ comprises the amino acid sequence of SEQ ID NO:31; and
- b) the $V_L$ comprises the amino acid sequence of SEQ ID NO:72 (AB-33).

In some embodiments, a polypeptide disclosed herein comprises:
- a) the $V_H$ comprises the amino acid sequence of SEQ ID NO:32; and
- b) the $V_L$ comprises the amino acid sequence of SEQ ID NO:67 (AB-34).

In some embodiments, a polypeptide disclosed herein comprises:
- a) the $V_H$ comprises the amino acid sequence of SEQ ID NO:33; and
- b) the $V_L$ comprises the amino acid sequence of SEQ ID NO:56 (AB-35).

In some embodiments, a polypeptide disclosed herein comprises:
- a) the $V_H$ comprises the amino acid sequence of SEQ ID NO:34; and
- b) the $V_L$ comprises the amino acid sequence of SEQ ID NO:73 (AB-36).

In some embodiments, a polypeptide disclosed herein comprises:
- a) the $V_H$ comprises the amino acid sequence of SEQ ID NO:35; and
- b) the $V_L$ comprises the amino acid sequence of SEQ ID NO:51 (AB-37).

In some embodiments, a polypeptide disclosed herein comprises:
- a) the $V_H$ comprises the amino acid sequence of SEQ ID NO:36; and
- b) the $V_L$ comprises the amino acid sequence of SEQ ID NO:56 (AB-38).

In some embodiments, a polypeptide disclosed herein comprises:
- a) the $V_H$ comprises the amino acid sequence of SEQ ID NO:37; and
- b) the $V_L$ comprises the amino acid sequence of SEQ ID NO:63 (AB-39).

In some embodiments, a polypeptide disclosed herein comprises:
- a) the $V_H$ comprises the amino acid sequence of SEQ ID NO:38; and
- b) the $V_L$ comprises the amino acid sequence of SEQ ID NO:69 (AB-40).

In some embodiments, a polypeptide disclosed herein comprises:
- a) the $V_H$ comprises the amino acid sequence of SEQ ID NO:39; and
- b) the $V_L$ comprises the amino acid sequence of SEQ ID NO:74 (AB-41).

In some embodiments, a polypeptide disclosed herein comprises:
- a) the $V_H$ comprises the amino acid sequence of SEQ ID NO:40; and
- b) the $V_L$ comprises the amino acid sequence of SEQ ID NO:52 (AB-42).

In some embodiments, a polypeptide disclosed herein comprises:
- a) the $V_H$ comprises the amino acid sequence of SEQ ID NO:41; and
- b) the $V_L$ comprises the amino acid sequence of SEQ ID NO:51 (AB-43).

In some embodiments, a polypeptide disclosed herein comprises:
- a) the $V_H$ comprises the amino acid sequence of SEQ ID NO:42; and
- b) the $V_L$ comprises the amino acid sequence of SEQ ID NO:75 (AB-44).

In some embodiments, a polypeptide disclosed herein comprises:
- a) the $V_H$ comprises the amino acid sequence of SEQ ID NO:43; and
- b) the $V_L$ comprises the amino acid sequence of SEQ ID NO:56 (AB-45).

In some embodiments, a polypeptide disclosed herein comprises:
- a) the $V_H$ comprises the amino acid sequence of SEQ ID NO:44; and
- b) the $V_L$ comprises the amino acid sequence of SEQ ID NO:51 (AB-46).

In some embodiments, a polypeptide disclosed herein comprises:
- a) the $V_H$ comprises the amino acid sequence of SEQ ID NO:45; and
- b) the $V_L$ comprises the amino acid sequence of SEQ ID NO:75 (AB-47).

In some embodiments, a polypeptide disclosed herein comprises:
- a) the $V_H$ comprises the amino acid sequence of SEQ ID NO:46; and
- b) the $V_L$ comprises the amino acid sequence of SEQ ID NO:53 (AB-48).

In some embodiments, a polypeptide disclosed herein comprises:
- a) the $V_H$ comprises the amino acid sequence of SEQ ID NO:47; and
- b) the $V_L$ comprises the amino acid sequence of SEQ ID NO:52 (AB-49).

In some embodiments, a polypeptide disclosed herein comprises:
- a) the $V_H$ comprises the amino acid sequence of SEQ ID NO:48; and
- b) the $V_L$ comprises the amino acid sequence of SEQ ID NO:76 (AB-50).

In some embodiments, a polypeptide disclosed herein comprises:
- a) the $V_H$ comprises the amino acid sequence of SEQ ID NO:3; and
- b) the $V_L$ comprises the amino acid sequence of SEQ ID NO:56 (AB-51).

In some embodiments, a polypeptide disclosed herein comprises a $V_H$ and $V_L$ that are humanized, contain human framework regions, or a combination thereof.

In some embodiments, a polypeptide disclosed herein is an immunoglobulin molecule, such as an antibody (e.g., a whole antibody, an intact antibody) or an antigen-binding fragment of an antibody (e.g., a Fab, F(ab')$_2$, Fab', scFv, or Fv). As used herein, the term "antibody" refers to an immunoglobulin molecule, or a portion thereof, capable of specific binding to a target, such as a carbohydrate, polynucleotide, lipid, polypeptide, etc., through at least one antigen recognition site, located in the variable domain of the immunoglobulin molecule. In some embodiments, an antibody is a whole, or intact, antibody.

In some embodiments, a polypeptide disclosed herein is a single-domain antibody or an antigen-binding fragment thereof. As used herein, the term "single-domain antibody (sdAb)" or "nanobody" refers to an immunoglobulin molecule consisting of a single monomeric variable antibody domain and capable of specific binding to a target. The single-domain antibody can be of any species, such as a murine antibody, a human antibody or a humanized antibody.

In some embodiments, a polypeptide disclosed herein is a heavy-chain antibody comprising two or more heavy chains, but lacking light chains, or an antigen-binding fragment thereof. Non-limiting examples of heavy chain antibodies include camelid Vhh (also referred to as VHH or $V_H$H) antibodies. Camelid antibodies are antibodies from the Camelidae family of mammals that include llamas, camels, and alpacas.

In some embodiments, a polypeptide disclosed herein is an antibody comprising two heavy (H) chains and two light (L) chains inter-connected by disulfide bonds or multimers thereof (for example, IgM). Each heavy chain comprises a heavy chain variable domain ($V_H$) and a heavy chain constant domain (comprising domains CH1, hinge CH2 and CH3). Each light chain comprises a light chain variable domain ($V_L$) and a light chain constant domain (CL). The $V_H$ and the $V_L$ regions may be further subdivided into regions of hypervariability, termed complementarity determining regions (CDR), interspersed within framework regions (FR). $V_H$ and $V_L$ each comprises three CDRs and four FR segments, arranged from the amino-terminus to the carboxy-terminus in the following order: FR1, CDR1, FR2, CDR2, FR3, CDR3, and FR4. The antibody can be of any species, such as a murine antibody, a human antibody or a humanized antibody.

The extent of the framework region and the CDRs of an antibody can be identified using one of several suitable methodologies that are well known in the art, for example, by the Kabat definition, the Chothia definition, the AbM definition, and/or the contact definition. Publicly and/or commercially available tools for identifying framework and/or CDR regions include, IgBlast (accessible at www.ncbi.nlm.nih.gov/igblast/), Scaligner (available from drugdesigntech at www.scaligner.com/), IMGT rules and/or tools (see, for example, www.imgt.org/IMGTScientific-Chart/Nomenclature/IMGT-FRCDRdefinition.html, also accessible at www.imgt.org/), Chothia Canonical Assignment (accessible at www.bioinforg.uk/abs/chothia.html), Antigen receptor Numbering And Receptor CalssificatiIon (ANARCI, accessible at opig.stats.ox.ac.uk/webapps/news-abdab/sabpred/anarci/), or the Paratome web server (accessible at www.ofranlab.org/paratome/, see Vered Kunik, et al, Nucleic Acids Research, Volume 40, Issue W1, 1 Jul. 2012, Pages W521-W524).

As used herein, a "CDR" encompasses any CDR defined by an art-recognized method for identifying the CDR residues on an antibody. See, e.g., Kabat, E. A., et al., (1991) Sequences of Proteins of Immunological Interest, Fifth Edition, U.S. Department of Health and Human Services, NIH Publication No. 91-3242, Chothia et al., (1989) Nature 342:877; Chothia, C. et al., (1987) J. Mol. Biol. 196:901-917; Al-lazikani et al., (1997) J. Molec. Biol. 273:927-948; and Almagro, J. Mol. Recognit. 17:132-143 (2004). See also hgmp.mrc.ac.uk and bioinforg.uk/abs. Two antibodies are determined to have the same CDR as one another with respect to a HCDR1, HCDR2, HCDR3, LCDR1, LCDR2 and/or LCDR3, when the identity of that CDR is determined for both antibodies using the same method.

In some embodiments, a polypeptide disclosed herein is an antigen-binding fragment of an antibody. The term "antigen-binding fragment" refers to a portion of an immunoglobulin molecule (e.g., antibody) that retains the antigen binding properties of the full-length the Reference Antibody. Non-limiting examples of antigen-binding fragments include a $V_H$ region, a $V_L$ region, an Fab fragment, an F(ab')2 fragment, an Fd fragment, an Fv fragment, and a domain antibody (dAb) consisting of one $V_H$ domain or one $V_L$ domain, etc. $V_H$ and $V_L$ domains may be linked together via a synthetic linker to form various types of single-chain antibody designs in which the $V_H$/$V_L$ domains pair intramolecularly, or intermolecularly in those cases when the $V_H$ and $V_L$ domains are expressed by separate chains, to form a monovalent antigen binding site, such as single chain Fv (scFv) or diabody. In some embodiments, a polypeptide disclosed herein is an antigen binding fragment selected from Fab, F(ab')$_2$, Fab', scFv, or Fv. In some embodiments, a polypeptide is a scFv.

In some embodiments, a polypeptide disclosed herein (e.g., an antibody or antigen-binding fragment) is incorporated into a cell-based therapy. In some embodiments, a polypeptide is an engineered T cell receptor. In some embodiments, a polypeptide is a chimeric antigen receptor (CAR) (e.g., expressed on a T (CAR-T) cell, natural killer (CAR-NK) cell, or macrophage (CAR-M) cell). In some embodiments, the CAR comprises a transmembrane domain and an antigen-recognition moiety, wherein the antigen-recognition moiety binds SARS-CoV-2 (e.g., for example, an epitope within S2).

In some embodiments, a polypeptide is an antibody mimetic. The term "antibody mimetic" refers to polypeptides capable of mimicking an antibody's ability to bind an antigen, but structurally differ from native antibody structures. Non-limiting examples of antibody mimetics include Adnectins, Affibodies, Affilins, Affimers, Affitins, Alphabodies, Anticalins, Avimers, DARPins, Fynomers, Kunitz domain peptides, monobodies, nanobodies, nanoCLAMPs, and Versabodies.

In some embodiments, a polypeptide disclosed herein competes with a comparator antibody (e.g., the Reference Antibody, Sotrovimab) for binding to the wildtype SARS-CoV-2-Spike, a SARS-CoV-2-Spike variant, or a combination thereof, wherein the comparator antibody specifically binds the wildtype SARS-CoV-2-Spike (e.g., S2). The term "specifically binding" or "specifically binds" refers to preferential interaction, i.e., significantly higher binding affinity, between an antibody, or an antigen-binding fragment thereof, and its epitope relative to other antigens or amino acid sequences.

In some embodiments, the comparator antibody comprises a $V_H$ sequence of SEQ ID NO:3 and a $V_L$ sequence of SEQ ID NO:50. In some embodiments, the comparator antibody comprises HCDR1, HCDR2 and HCDR3 sequences of SEQ ID NO:77, SEQ ID NO:79 and SEQ ID NO:90, respectively. In some embodiments, the reference antibody comprises LCDR1, LCDR2 and LCDR3 sequences of SEQ ID NO:133, SEQ ID NO:141 and SEQ ID NO:143, respectively. In some embodiments, the comparator antibody comprises HCDR1, HCDR2 and HCDR3 sequences of SEQ ID NO:77, SEQ ID NO:79 and SEQ ID NO:90, respectively; and LCDR1, LCDR2 and LCDR3 sequences of SEQ ID NO:133, SEQ ID NO:141 and SEQ ID NO:143, respectively.

In some embodiments, a polypeptide disclosed herein comprises:

a) an antibody heavy chain constant domain sequence;
b) an antibody light chain constant domain sequence; or
c) both an antibody heavy chain constant domain sequence and an antibody light chain constant domain sequence.

In some embodiments, a polypeptide disclosed herein comprises an antibody heavy chain constant domain sequence. In some embodiments, the antibody heavy chain constant domain is selected from the group consisting of an IgA constant domain, an IgD constant domain, an IgE constant domain, an IgG constant domain and an IgM constant domain. In some embodiments, the IgG constant domain is an IgG1 constant domain, an IgG2 constant domain, an IgG3 constant domain or an IgG4 constant domain. In some embodiments, the IgG2 constant domain is an IgG2a, an IgG2b constant domain or an IgG2c constant domain. In some embodiments, the IgA constant domain is an IgA1 constant domain or an IgA2 constant domain. In some embodiments, the antibody heavy chain constant domain is an IgG1 constant domain (e.g., IGHV1-5 or IGHV5-51).

In some embodiments, a polypeptide disclosed herein comprises an immunoglobulin light chain variable domain ($V_L$). The $V_H$ and $V_L$ domains may be linked together via a linker (e.g., a synthetic linker) to form various types of single-chain antibody designs in which the $V_H$/$V_L$ domains pair intramolecularly, or intermolecularly in those cases when the V$_H$ and V$_L$ domains are expressed by separate chains, to form a monovalent antigen binding site.

In some embodiments, a polypeptide disclosed herein comprises an antibody light chain constant domain sequence. In some embodiments, the antibody light chain constant domain is selected from the group consisting of a κ constant domain and a λ constant domain. In some embodiments, the antibody heavy chain constant domain is an IgG1 constant domain, and the antibody light chain constant domain is a κ constant domain.

In some embodiments, the antibody heavy chain constant domain sequence has at least about 60% sequence identity to the amino acid sequence of SEQ ID NO:194. For example, the antibody heavy chain constant domain sequence can has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:194. In some embodiments, the antibody heavy chain constant domain sequence has at least about 70% or at least about 80% sequence identity to the amino acid sequence of SEQ ID NO:194. The sequence identified as SEQ ID NO:194 is shown below:

(SEQ ID NO: 194)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK.

In some embodiments, the antibody light chain constant domain sequence has at least about 60% sequence identity to the amino acid sequence of SEQ ID NO:195 or SEQ ID NO:196. For example, the antibody light chain constant domain sequence can has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:195 or SEQ ID NO:196. In some embodiments, the antibody light chain constant domain sequence has at least about 70% or at least about 80% sequence identity to SEQ ID NO:195 or SEQ ID NO:196. The sequences identified as SEQ ID NO:195 and SEQ ID NO:196 are shown below:

(SEQ ID NO: 195)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC.

(SEQ ID NO: 196)
GQPKANPTVTLFPPSSEELQANKATLVCLISDFYPGAVTVAWKADGSPV

KAGVETTKPSKQSNNKYAASSYLSLTPEQWKSHRSYSCQVTHEGSTVEK

TVAPTECS.

In some embodiments, the antibody heavy chain constant domain sequence comprises at least 1 amino acid substitution relative to the amino acid sequence of SEQ ID NO:194. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the antibody heavy chain constant domain sequence comprises about 1-10 amino acid substitutions, relative to the amino acid sequence of SEQ ID NO:194.

In some embodiments, the antibody light chain constant domain sequence comprises at least 1 amino acid substitution relative to the amino acid sequence of SEQ ID NO:195 or SEQ ID NO:196. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the antibody light chain constant domain sequence comprises about 1-10 amino acid substitutions, relative to the amino acid sequence of SEQ ID NO:195 or SEQ ID NO:196.

In some embodiments, the amino acid substitutions are conservative substitutions. In some embodiments, the amino acid substitutions are highly conservative substitutions.

In some embodiments, a polypeptide disclosed herein is an isolated polypeptide. In some embodiments, the isolated polypeptide is recombinantly produced. In some embodiments, the isolated polypeptide is synthetically produced.

In some embodiments, a polypeptide disclosed herein is linked to a second polypeptide. The term "linked" means attached, via a covalent or noncovalent interaction. Conjugation can employ a suitable linking agent. Non-limiting examples include peptide linkers, compound linkers, and chemical cross-linking agents. In some embodiments, the linker is a disulfide bond.

In some embodiments, a polypeptide disclosed herein is conjugated to a heterologous moiety. The term "conjugated" refers to attached, via a covalent or noncovalent interaction. Conjugation can employ any of suitable linking agents. Non-limiting examples include peptide linkers, compound linkers, and chemical cross-linking agents.

In some embodiments, the heterologous moiety is a therapeutic agent, a diagnostic agent or a combination thereof. In some embodiments, the heterologous moiety is polyethylene glycol (PEG), hexadecanoic acid, hydrogels, nanoparticles, multimerization domains and carrier peptides.

In some embodiments, the nanoparticle is a lipid nanoparticle. In some embodiments, the nanoparticle is a polymer nanoparticle. In some embodiments, the polymer is an amphiphilic polymer. In some embodiments, the polymer is a hydrophobic or hydrophilic polymer. Non-limiting examples of polymers include poly(lactic acid)-poly(ethylene glycol), poly(lactic-co-glycolic acid)-poly(ethylene glycol), poly(lactic-co-glycolic) acid (PLGA), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), polycaprolactone-poly(ethylene glycol), or any salts thereof. In some embodiments, the polymer nanoparticle comprises poly(lactic-co-glycolic) acid (PLGA).

In some embodiments, the carrier polypeptide is albumin or an Fc polypeptide.

In some embodiments, a polypeptide:
a) is capable of binding to an epitope in the S2 domain of SARS-CoV-2-Spike;

b) binds SARS-CoV-1 and/or SARS-CoV-2 with a $K_D$ of 10 µM or less;
c) neutralizes SARS-CoV-1 and/or SARS-CoV-2 infection of human host cells;
d) has a weaker non-specific binding than the Reference Antibody;
e) has a weaker self-association than the Reference Antibody;
or a combination of any of the foregoing.

In some embodiments, a polypeptide is capable of binding to one or more epitope residues in the S2 domain of SARS-CoV-2-Spike, for example, 1, 2, 3, 4, 5, 6, 7, 8, 9, 10, 11, 12, 13, 14, 15, 16, 17 or 18 residues of the S2 domain. In some embodiments, a polypeptide is capable of binding to one or more epitope residues (e.g., 1, 2, 3, 4, 5, 6, 7, 8, 9, 10, 11, 12, 13, 14, 15 or all 16 residues) selected from F1148, K1149, E1150, L1152, D1153, K1154, F1156, K1157, N1158, H1159, T1160, S1161, P1162, D1163, V1164 and D1165 of SEQ ID NO: 1.

In some embodiments, a polypeptide binds SARS-CoV-2-Spike with a binding constant ($K_D$) of about 10 µM or less. As used herein the term "$K_D$," also referred to as "binding constant," "equilibrium dissociation constant" or "affinity constant," is a measure of the extent of a reversible association between two molecular species (e.g., antibody and target protein) and includes both the actual binding affinity as well as the apparent binding affinity. Binding affinity can be determined using methods known in the art including, for example, by measurement of surface plasmon resonance, e.g., using a Biolayer interferometry (Octet, ForteBio) or a surface plasmon resonance (Biacore) system and assay. A reference that compares various surface technologies for measuring binding affinity and kinetics is Yang, D., Singh, A., Wu, H., & Kroe-Barrett, R., *Comparison of biosensor platforms in the evaluation of high affinity antibody-antigen binding kinetics*, Analytical Biochemistry 508: 78-96 (2016), the contents of which are incorporated by reference herein in their entirety.

In some embodiments, a polypeptide binds SARS-CoV-1-Spike (e.g., of CoV-1 and/or WIV1) and/or SARS-CoV-2-Spike (e.g., of Alpha, Beta, Gamma, Delta, Kappa, Epsilon, Eta, Iota, Lambda, Mu, and/or Omicron, for example, AY.3, AY.4, AY.41, AY.44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1) or a fragment thereof (e.g., the S2 domain of SARS-CoV-2-Spike and/or the epitopes in FIG. 1) with a $K_D$ of about: 5 µM, 2 µM, 1 µM, 500 nM, 200 nM, 100 nM, 50 nM, 20 nM, 10 nM, 5 nM, 2 nM, 1 nM, 0.5 nM, 0.2 nM or 0.1 nM or less. In some embodiments, a polypeptide binds SARS-CoV-1-Spike (e.g., of CoV-1 and/or WIV1) and/or SARS-CoV-2-Spike (e.g. of Alpha, Beta, Gamma, Delta, Kappa, Epsilon, Eta, Iota, Lambda, Mu, and/or Omicron, for example, AY.3, AY.4, AY.41, AY.44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1) or a fragment thereof (e.g., the S2 domain of SARS-CoV-2-Spike and/or the epitopes in FIG. 1) with a $K_D$ of 100 nM or less.

In some embodiments, a polypeptide binds SARS-CoV-1-Spike (e.g., of CoV-1 and/or WIV1) and/or SARS-CoV-2-Spike (e.g. of Alpha, Beta, Gamma, Delta, Kappa, Epsilon, Eta, Iota, Lambda, Mu, and/or Omicron, for example, B.1, B.1.1, B.1.1.1, B.1.1.529, B.1.1.7, B.1.177, B.1.2, B.1.351, B.1.427/429, B.1.525, B.1.526, B.1.617.1, B.1.617.2, B.1.621, BA.1, BA.1.1, BA.2, BA.2.12.1, BA.2.75, BA.2.75.2, BA.3, BA.4, BA.4/5, BA.4/5+K444T, BA.4.6, BA.5, BA.5.2.6, BF.7, BF.11, BN.1, BQ.1, BQ.1.1, C.37, D.2, GA.5, GR/484A, P.1, P.3, and/or XBB) or a fragment thereof (e.g., the S2 domain of SARS-CoV-2-Spike and/or the epitopes in FIG. 1) with a $K_D$ of about: $10^{-10}$-$10^{-5}$ M, $10^{-10}$-$5\times10^{-6}$ M, $2\times10^{-10}$-$5\times10^{-6}$ M, $2\times10^{-10}$-$2\times10^{-6}$ M, $5\times10^{-10}$-$2\times10^{-6}$ M, $5\times10^{-10}$-$10^{-7}$ M, $10^{-9}$-$10^{-7}$ M, $10^{-9}$-$5\times10^{-8}$ M, $2\times10^{-9}$-$5\times10^{-8}$ M, $2\times10^{-9}$-$2\times10^{-8}$ M, $5\times10^{-9}$-$2\times10^{-8}$ M or $5\times10^{-9}$-$10^{-8}$ M.

In some embodiments, a polypeptide (e.g., full-length IgG1 antibody) binds SARS-CoV-1-Spike (e.g., of CoV-1 and/or WIV1) and/or SARS-CoV-2-Spike (e.g. of Alpha, Beta, Gamma, Delta, Kappa, Epsilon, Eta, Iota, Lambda, Mu, and/or Omicron, for example, AY.3, AY.4, AY.41, AY.44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1) or a fragment thereof (e.g., the S2 domain of SARS-CoV-2-Spike and/or the epitopes in FIG. 1) with a $K_D$ of about $10^{-6}$ M or less, e.g., about: 500 nM, 200 nM, 100 nM, 50 nM, 20 nM, 10 nM, 5 nM, 2 nM, 1 nM, 0.5 nM, 0.2 nM or 0.1 nM or less; or about: $10^{-10}$-$10^{-6}$ M, $10^{-10}$-$5\times10^{-7}$ M, $2\times10^{10}$-$5\times10^{-7}$ M, $2\times10^{-10}$-$2\times10^{-7}$ M, $5\times10^{-10}$-$2\times10^{-7}$ M, $5\times10^{-10}$-$10^{-7}$ M, $10^{-9}$-$10^{-7}$M, $10^{-9}$-$5\times10^{-8}$ M, $2\times10^{-9}$-$5\times10^{-8}$ M, $2\times10^{-9}$-$2\times10^{-8}$ M, $5\times10^{-9}$-$2\times10^{-8}$ M or $5\times10^{-9}$-$10^{-8}$ M.

In some embodiments, a polypeptide competes with the Reference Antibody for binding to a SARS-CoV-2-Spike (e.g., S2 domain). Techniques and assays for assessing competition between antibodies are known in the art.

In some embodiments, a polypeptide neutralizes SARS-CoV-1 (e.g., CoV-1 and/or WIV1) and/or SARS-CoV-2 (e.g. of Alpha, Beta, Gamma, Delta, Kappa, Epsilon, Eta, Iota, Lambda, Mu, and/or Omicron, for example, AY.3, AY.4, AY.41, AY.44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1) with an $IC_{50}$ of 10 µM or less.

In some embodiments, a polypeptide (e.g., full-length IgG1 antibody) neutralizes SARS-CoV-2 (e.g. of Alpha, Beta, Gamma, Delta, Kappa, Epsilon, Eta, Iota, Lambda, Mu, and/or Omicron, for example, AY.3, AY.4, AY.41, AY.44, AY64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1) infection of a human host cells with an $IC_{50}$ of about 25,000 ng/mL or less, e.g., about: 20,000 ng/mL, 15,000 ng/mL, 10,000 ng/mL, 5,000 ng/mL, 2,500 ng/mL, 1,000 ng/mL, 750 ng/mL, 500 ng/mL, 250 ng/mL, 100 ng/mL, 75 ng/mL, 50 ng/mL, 25 ng/mL or 10 ng/mL or less; e.g., about: 10-25,000 ng/mL, 10-20,000 ng/mL, 25-20,000 ng/mL, 25-15,000 ng/mL, 50-15,000 ng/mL, 50-10,000 ng/mL, 75-10,000 ng/mL, 75-5,000 ng/mL, 100-5,000 ng/mL, 100-2,500 ng/mL, 250-2,500 ng/mL, 250-1,000 ng/mL, 500-1,000 ng/mL or 500-750 ng/mL.

In some embodiments, a polypeptide (e.g., full-length IgG1 antibody) neutralizes SARS-CoV-2 (e.g. of Alpha, Beta, Gamma, Delta, Kappa, Epsilon, Eta, Iota, Lambda, Mu, and/or Omicron, for example, AY.3, AY.4, AY.41, AY.44, AY64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1) infection of human host cells with an $IC_{80}$ of about 50,000 ng/mL or less, e.g., about: 25,000 ng/mL, 15,000 ng/mL, 10,000 ng/mL, 5,000 ng/mL, 2,500 ng/mL, 1,000 ng/mL, 750 ng/mL, 500 ng/mL, 250 ng/mL, 100 ng/mL, 75 ng/mL, 50 ng/mL, 25 ng/mL or 10 ng/mL or less; e.g., about: 10-50,000 ng/mL, 10-25,000 ng/mL, 25-25,000 ng/mL, 25-15,000 ng/mL, 50-15,000 ng/mL, 50-10,000 ng/mL, 75-10,000 ng/mL, 75-5,000 ng/mL, 100-5,000 ng/mL, 100-2,500 ng/mL, 250-2,500 ng/mL, 250-1,000 ng/mL, 500-1,000 ng/mL or 500-750 ng/mL.

In some embodiments, a polypeptide (e.g., full-length IgG1 antibody) neutralizes SARS-CoV-1 (e.g., CoV-1 and/or WIV1) infection of human host cells with an $IC_{50}$ of about 25,000 ng/mL or less, e.g., about: 20,000 ng/mL, 15,000 ng/mL, 10,000 ng/mL, 5,000 ng/mL, 2,500 ng/mL, 1,000 ng/mL, 750 ng/mL, 500 ng/mL, 250 ng/mL, 100 ng/mL, 75 ng/mL, 50 ng/mL, 25 ng/mL or 10 ng/mL or less; e.g., about: 10-25,000 ng/mL, 10-20,000 ng/mL, 25-20,000 ng/mL, 25-15,000 ng/mL, 50-15,000 ng/mL, 50-10,000 ng/mL, 75-10,000 ng/mL, 75-5,000 ng/mL, 100-5,000 ng/mL, 100-2,500 ng/mL, 250-2,500 ng/mL, 250-1,000 ng/mL, 500-1,000 ng/mL or 500-750 ng/mL.

In some embodiments, a polypeptide (e.g., full-length IgG1 antibody) neutralizes SARS-CoV-1 (e.g., CoV-1 and/or WIV1) infection of human host cells with an $IC_{80}$ of about 50,000 ng/mL or less, e.g., about: 25,000 ng/mL, 15,000 ng/mL, 10,000 ng/mL, 5,000 ng/mL, 2,500 ng/mL, 1,000 ng/mL, 750 ng/mL, 500 ng/mL, 250 ng/mL, 100 ng/mL, 75 ng/mL, 50 ng/mL, 25 ng/mL or 10 ng/mL or less; e.g., about: 10-50,000 ng/mL, 10-25,000 ng/mL, 25-25,000 ng/mL, 25-15,000 ng/mL, 50-15,000 ng/mL, 50-10,000 ng/mL, 75-10,000 ng/mL, 75-5,000 ng/mL, 100-5,000 ng/mL, 100-2,500 ng/mL, 250-2,500 ng/mL, 250-1,000 ng/mL, 500-1,000 ng/mL or 500-750 ng/mL.

In some embodiments, a polypeptide reduces betacoronavirus (e.g., SARS-CoV-2) infectivity of host cells (e.g., human host cells). In some embodiments, a polypeptide reduces betacoronavirus (e.g., SARS-CoV-2) infectivity of host cells (e.g., human host cells) by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces betacoronavirus (e.g., SARS-CoV-2) infectivity of human cells by at least about 30%.

In some embodiments, a polypeptide reduces betacoronavirus (such as SARS-CoV-2 (e.g. of Alpha, Beta, Gamma, Delta, Kappa, Epsilon, Eta, Iota, Lambda, Mu, and/or Omicron, for example, AY3, AY.4, AY.41, AY.44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1)) re-infection of host cells (e.g., human host cells). In some embodiments, a polypeptide reduces betacoronavirus (such as SARS-CoV-2 (e.g. of Alpha, Beta, Gamma, Delta, Kappa, Epsilon, Eta, Iota, Lambda, Mu, and/or Omicron, for example, AY3, AY4, AY41, AY44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+ P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1)) re-infection of host cells (e.g., human host cells) by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces betacoronavirus (such as SARS-CoV-2 (e.g. of Alpha, Beta, Gamma, Delta, Kappa, Epsilon, Eta, Iota, Lambda, Mu, and/or Omicron, for example, AY.3, AY4, AY41, AY44, AY.64, AY.103, B.1, B.1.1, B.1.1.1, B.1.1.529, B.1.1.7, B.1.177, B.1.2, B.1.351, B.1.427/429, B.1.525, B.1.526, B.1.533, B.1.617.1, B.1.617.2, B.1.621, BA.1, BA.1.1, BA.1.15, BA.1.17.2, BA.2, BA.2+P1162L, and BA.2+P1162S, BA.2.3.20, BA.2.10, BA.2.12.1, BA.2.75, BA.2.75.2, BA.3, BA.4, BA.4/5, BA.4/5+K444T, BA.4.6, BA.5, BA.5.2.6, BA.5.8, BF.7, BF.11, BN.1, BQ.1, BQ.1.1, C.37, CH.1.1, CH.1.1.1, D.2, GA.5, GR/484A, P.1, P.1.17, P.1.10, P.2, P.3, Q.3, Q.4, Q.7, XBB, XBB.1.1, XBB.1.16, XBB.1.5, and/or XBB.1.9.1)) re-infection of human cells by at least about 30%.

Infectivity or re-infection can be measured using techniques such as a pseudovirus neutralization assay or a live virus neutralization assay (see, e.g., Pinto et al., *Cross-neutralization of SARS-CoV-2 by a human monoclonal SARS-CoV antibody*, Nature 583: 290-95 (2020), the contents of which are incorporated herein by reference). A kit, for example, the GenScript cPass™ SARS-CoV-2 neutralization antibody detection kit, can be used according to manufacturer's protocol.

In some embodiments, a polypeptide reduces SARS-CoV-1 (e.g., CoV-1 and/or WIV1) infectivity of host cells (e.g., human host cells). In some embodiments, a polypeptide reduces SARS-CoV-1 (e.g., CoV-1 and/or WIV1) infectivity of host cells (e.g., human host cells) by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces SARS-CoV-1 (e.g., CoV-1 and/or WIV1) infectivity of human cells by at least about 30%.

In some embodiments, a polypeptide reduces SARS-CoV-1 (e.g., CoV-1 and/or WIV1) re-infection of host cells (e.g., human host cells). In some embodiments, a polypeptide reduces SARS-CoV-1 (e.g., CoV-1 and/or WIV1) re-infection of host cells (e.g., human host cells) by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces SARS-CoV-1 (e.g., CoV-1 and/or WIV1) re-infection of human cells by at least about 30%.

In some embodiments, the host cells are selected from the group consisting of lung type II pneumocytes, ileal absorptive enterocytes, nasal goblet secretory cells, and combinations thereof.

In some embodiments, a polypeptide has a weaker self-association than the Reference Antibody, for example, as determined by an affinity-capture self-interaction nanoparticle spectroscopy (AC-SINS) value. The AC-SINS value is the change in maximum absorbance wavelength in the coated-nanoparticle absorption spectra compared to the spectra of the nanoparticle alone. Thus, the greater the change in maximum absorbance wavelength, the more self-interaction of the antibody coated on the nanoparticle. Self-association is an unwanted property that correlates with poor viscosity and poor PK properties. Techniques and assays for assessing self-association of proteins are known in the art. See, e.g., Patro & Przybycien, Biotechnol Bioeng. 52(2):193-203 (1996), the contents of which are incorporated herein in their entirety. In some embodiments, a polypeptide has a weaker self-association than the Reference Antibody.

In some embodiments, a polypeptide has an AC-SINS value of no more than about: 1, 2, 3, 4, 5, 6, 7, 8, 9, 10, 11, 12, 13, 14, 15, 16, 17, 18, 18, 20, 21, 22, 23, 24 or 25. In some embodiments, a polypeptide has an AC-SINS value of no more than about 14. In some embodiments, a polypeptide has an AC-SINS value of no more than about 8. In some embodiments, a polypeptide has an AC-SINS value of about: 1, 2, 3, 4, 5, 6, 7, 8, 9, 10, 11, 12, 13, 14, 15, 16, 17, 18, 18, 20, 21, 22, 23, 24 or 25. In some embodiments, a polypeptide has an AC-SINS value of about 0-25, e.g., 0-20, 0-15, 0-10, 0-8, 0-5, 2-20, 2-15, 2-10, 2-8, 2-5, 5-20, 5-15, 5-10, 5-8, 7-8 or 13-15. In some embodiments, a polypeptide has an AC-SINS value of about 13-14, 13-15, 7-9 or 7-8. In some embodiments, a polypeptide has an AC-SINS value of about: 8 or 14.

In some embodiments, a polypeptide has an improved developability (e.g., reduced AC-SINS) relative to the Reference Antibody. In some embodiments, the self-association of a polypeptide is at least about 10% lower than that of the Reference Antibody, for example, by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99% lower than that of the Reference Antibody. In some embodiments, the self-association of a polypeptide is at least about 30% lower than that of the Reference Antibody.

In some embodiments, the self-association of a polypeptide is less than about 90% of that of the Reference Antibody, for example, less than about: 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or 1% of that of the Reference Antibody.

In some embodiments, the self-association of a polypeptide is about 1-90% relative to that of the Reference Antibody, for example, about: 2-90%, 2-85%, 3-85%, 3-80%, 4-80%, 4-75%, 5-75%, 5-70%, 6-70%, 6-65%, 7-65%, 7-60%, 8-60%, 8-55%, 9-55%, 9-50%, 10-50%, 10-45%, 15-45%, 15-40%, 20-40%, 20-35%, 25-35% or 25-30%, relative to that of the Reference Antibody.

In some embodiments, the reduction in self-association relative to the Reference Antibody is at least about 10%, for example, by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%.

Fusion Proteins

In some embodiments, the disclosure provides a fusion protein comprising one or more of polypeptides described herein.

The term "fusion protein" refers to a synthetic, semi-synthetic or recombinant single protein molecule. A fusion protein can comprise all or a portion of two or more different proteins and/or polypeptides that are attached by covalent bonds (e.g., peptide bonds). For example, a fusion protein can comprise a full-length polypeptide disclosed herein (e.g., a whole antibody), or a fragment thereof (e.g., an antigen-binding fragment of an antibody). The heterologous partner can be a full-length protein or a fragment thereof (e.g., a truncated protein).

Fusion proteins can be produced recombinantly or synthetically, using routine methods and reagents that are well known in the art. For example, a fusion protein disclosed herein can be produced recombinantly in a suitable host cell (e.g., bacteria) according to methods known in the art. See, e.g., *Current Protocols in Molecular Biology*, Second Edition, Ausubel et al. eds., John Wiley & Sons, 1992; and *Molecular Cloning: a Laboratory Manual,* 2nd edition, Sambrook et al., 1989, Cold Spring Harbor Laboratory Press. For example, a nucleic acid molecule comprising a nucleotide sequence encoding a fusion protein described herein can be introduced and expressed in suitable host cell (e.g., *E. coli*), and the expressed fusion protein can be isolated/purified from the host cell (e.g., in inclusion bodies) using routine methods and readily available reagents. For example, DNA fragments coding for different protein sequences (e.g., a light-responsive domain, a heterologous peptide component) can be ligated together in-frame in accordance with conventional techniques. In another embodiment, the fusion gene can be synthesized by conventional techniques including automated DNA synthesizers. In some embodiments, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992).

Nucleic Acids, Vectors, Host Cells

In some embodiments, the disclosure provides one or more polynucleotides (e.g., DNA, RNA, or analogs of either, e.g., optionally including one or more modified nucleotides; the polynucleotide may be linear or circular, e.g., linear or circular RNA) encoding any one of polypeptides or fusion proteins described herein. In some embodiments, a polypeptide or fusion protein disclosed herein is encoded by a single polynucleotide. In some embodiments, a polypeptide or fusion protein disclosed herein is encoded by multiple polynucleotides.

In some embodiments, the polynucleotide comprises a nucleotide sequence that is codon-optimized for a chosen host cell.

In some embodiments, the disclosure provides a vector (e.g., an expression vector, including a viral-delivery vector) comprising any one or more of the polynucleotides described herein.

The term "expression vector" refers to a replicable nucleic acid from which one or more proteins can be expressed when the expression vector is transformed into a suitable expression host cell.

In some embodiments, the vector (e.g., expression vector) comprises an expression control polynucleotide sequence operably linked to the polynucleotide, a polynucleotide sequence encoding a selectable marker, or both. In some embodiments, the expression control polynucleotide sequence comprises a promoter sequence, an enhancer sequence, or both. In some embodiments, the expression control polynucleotide sequence comprises an inducible promoter sequence. The term "promoter" refers to a region of DNA to which RNA polymerase binds and initiates the transcription of a gene. The term "operably linked" means that the nucleic acid is positioned in the recombinant polynucleotide, e.g., vector, in such a way that enables expression of the nucleic acid under control of the element (e.g., promoter) to which it is linked. The term "selectable marker element" is an element that confers a trait suitable for artificial selection. Selectable marker elements can be negative or positive selection markers.

In some embodiments, the disclosure provides an expression host cell comprising any one or more of the polynucleotides or expression vectors described herein.

The term "expression host cell" refers to a cell useful for receiving, maintaining, reproducing and/or amplifying a vector.

Non-limiting examples of expression host cells include mammalian cells such as hybridoma cells, Chinese hamster ovary (CHO) cells, COS cells, human embryonic kidney (HEK), yeast cells such as *Pichia pastoris* cells, or bacterial cells such as *E. coli*, including DH5α, etc.

Compositions

In some embodiments, the disclosure provides a composition comprising any one of polypeptides or fusion proteins described herein. In some embodiments, the composition is a pharmaceutical composition.

In some embodiments, the composition (e.g., pharmaceutical composition) comprises pharmaceutically acceptable carriers, excipients, stabilizers, diluents or tonifiers (Remington's Pharmaceutical Sciences 16th edition, Osol, A. Ed. (1980)). Suitable pharmaceutically acceptable carriers, excipients, or stabilizers are nontoxic to recipients at the dosages and concentrations employed. Non-limiting examples of pharmaceutically acceptable carriers, excipients, stabilizers, diluents or tonifiers include buffers (e.g., phosphate, citrate, histidine), antioxidants (e.g., ascorbic acid or methionine), preservatives, proteins (e.g., serum albumin, gelatin or immunoglobulins); hydrophilic polymers, amino acids, carbohydrates (e.g., monosaccharides, disaccharides, glucose, mannose or dextrins); chelating agents (e.g., EDTA), sugars (e.g., sucrose, mannitol, trehalose or sorbitol), salt-forming counter-ions (e.g., sodium), metal complexes (e.g., Zn-protein complexes); non-ionic surfactants (e.g., Tween), PLURONICS™ and polyethylene glycol (PEG).

In some embodiments, the composition (e.g., pharmaceutical composition) disclosed herein is formulated for a suitable administration schedule and route. Non-limiting examples of administration routes include oral, rectal, mucosal, intravenous, intramuscular, subcutaneous and topical, etc. In some embodiments, the composition (e.g., pharmaceutical composition) disclosed herein is stored in the form of an aqueous solution or a dried formulation (e.g., lyophilized).

In some embodiments, the composition is formulated to be administered by infusion (e.g., intravenous infusion).

In some embodiments, the composition is formulated to be administered with a second therapeutic agent as a combination therapy. In some embodiments, the second therapeutic agent is any one of polypeptides described herein. In some embodiments, the second therapeutic agent comprises bamlanivimab, etesevimab, casirivimab, imdevimab, Cilgavimab, Tixagevimab, AZD7442 (Tixagevimab-Cilgavimab), Regdanvimab, Sotrovimab. In some embodiments, the second therapeutic agent comprises Sotrovimab.

Methods of Use

In some embodiments, the disclosure provides methods of neutralizing a SARS-CoV-2 infection in a subject, comprising administering to the subject an effective amount of a pharmaceutical composition comprising a pharmaceutically acceptable carrier and, wherein as an active ingredient, any one of polypeptides or fusion proteins described herein.

In some embodiments, the likelihood of SARS-CoV-2 infection in the subject is reduced by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%.

In some embodiments, the likelihood of SARS-CoV-2 infection in the subject in the presence of a polypeptide is about 1-90% relative to the likelihood in the absence of the polypeptide, for example, about: 2-90%, 2-85%, 3-85%, 3-80%, 4-80%, 4-75%, 5-75%, 5-70%, 6-70%, 6-65%, 7-65%, 7-60%, 8-60%, 8-55%, 9-55%, 9-50%, 10-50%, 10-45%, 15-45%, 15-40%, 20-40%, 20-35%, 25-35% or 25-30%.

The term "subject" and "patient" are used herein interchangeably to refer to an animal (e.g., a mammal, such as a human) who is to be treated according to a method disclosed herein. A subject to be treated according to methods described herein may be one who has been diagnosed with a particular condition (e.g., COVID-19), or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

In some embodiments, the subject has (e.g., confirmed by testing, such as by PCR or rapid test), or is suspected of having, COVID-19. In some embodiments, the subject has COVID-19. In some embodiments, the subject has been diagnosed with COVID-19. In some embodiments, the subject is at risk of developing COVID-19.

In some embodiments, the subject is a mammal. In some embodiments, the subject is a mammal selected from the group consisting of a dog, a cat, a mouse, a rat, a hamster, a guinea pig, a horse, a pig, a sheep, a cow, a chimpanzee, a macaque, a cynomolgus, and a human. In some embodiments, the subject is a primate. In some embodiments, the subject is a human.

In some embodiments, the subject has a heart disease. In some embodiments, the subject has a heart disease selected from the group consisting of a congenital heart disease, a coronary artery disease, a hypertensive heart disease, an inflammatory heart disease, a pulmonary heart disease, a rheumatic heart disease, a valvular heart disease, a cardiomyopathy, heart failure, and combinations thereof. In some embodiments, the subject has a congestive heart failure. In some embodiments, the subject has an inflammatory heart disease selected from the group consisting of endocarditis, cardiomegaly, myocarditis, and combinations thereof.

In some embodiments, the subject has diabetes.

In some embodiments, the subject has a lung disease. Non-limiting examples of lung diseases include acute respiratory distress syndromes, asthma, bronchitis, COPD, emphysema, lung tumors, pleural cavity diseases (e.g., pleural mesothelioma or tension pneumothorax), pulmonary vascular diseases (e.g., embolisms, edema, arterial hypertension or hemorrhage), respiratory tract infections (e.g., pneumonia or other upper or lower respiratory tract infections).

In some embodiments, the subject is a tobacco smoker.

In some embodiments, the subject is immune-compromised (e.g., has an underlying disorder or is on immunosuppressive therapy).

In some embodiments, the subject is 40 years or older, e.g., at least: 45, 50, 55, 60, 65, 70, 75, 80, 85, 90 years old.

"A therapeutically effective amount," "an effective amount" or "an effective dosage" is an amount effective, at dosages and for periods of time necessary, to achieve a desired therapeutic result (e.g., treatment, healing, inhibition or amelioration of physiological response or condition, reduced infectivity, reduced infection upon exposure, prophylaxis, reduced viral load, etc.). The therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual.

An effective amount of an agent to be administered can be determined by a clinician of ordinary skill using the guidance provided herein and other methods known in the art. Relevant factors include the given agent, the pharmaceutical formulation, the route of administration, the type of disease or disorder, the identity of the subject (e.g., age, sex, weight) or host being treated, and the like. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects.

Desired response or desired results include effects at the cellular level, tissue level, or clinical results. As such, "a therapeutically effective amount" or synonym thereto depends upon the context in which it is being applied. For example, in some embodiments it is an amount of the composition sufficient to achieve a treatment and/or prophylactic response as compared to the response obtained without administration of the composition. In some embodiments, it is an amount that results in a beneficial or desired result in a subject as compared to a control. As defined herein, a therapeutically effective amount of a composition disclosed herein may be readily determined by one of ordinary skill by routine methods known in the art. Dosage regimen and route of administration may be adjusted to provide the optimum therapeutic response.

In some embodiments, methods disclosed herein are used for prophylactic therapy. In some embodiments, the effective dosage is sufficient to prevent the subject of being infected by SARS-CoV-2.

In some embodiments, methods disclosed herein are used for treating SARS-CoV-2 infection.

The term "treating" or "treatment" refers to the medical management of a subject with the intent to improve, ameliorate, stabilize (i.e., not worsen), prevent or cure a disease, pathological condition, infection, or disorder—such as the particular indications exemplified herein. This term includes active treatment (treatment directed to improve the disease, pathological condition, infection, or disorder), causal treatment (treatment directed to the cause of the associated disease, pathological condition, infection, or disorder), palliative treatment (treatment designed for the relief of symptoms), preventative (e.g., prophylactic) treatment (treatment directed to minimizing or partially or completely inhibiting the development of the associated disease, pathological condition, infection, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition, infection, or disorder, as well as those prone to have the condition or disorder or those in which the condition, infection, or disorder is to be prevented.

In some embodiments, the effective dosage is sufficient to reduce viral load in the subject. In some embodiments, the reduction in viral load is by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the reduction in viral load is about $10^{-99}$%, e.g., about: $10^{-98}$%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, the effective dosage is sufficient to inhibit binding of the virus to its target proteins, target cells, or both. In some embodiments, the reduction in binding is by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the reduction in binding is about $10^{-99}$%, e.g., about: $10^{-98}$%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, the effective dosage is sufficient to inhibit virus mediated fusion with a target cell. In some embodiments, the reduction in fusion is by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the reduction in fusion is about $10^{-99}$%, e.g., about: $10^{-98}$%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, the effective dosage is sufficient to interfere with conformational changes in the viral envelope proteins necessary for cell infectivity.

A therapeutic agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound chosen.

In some embodiments, a polypeptide, composition, or pharmaceutical composition disclosed herein is administered to a subject as a monotherapy.

In some embodiments, a polypeptide, composition, or pharmaceutical composition disclosed herein is administered to a subject in combination with one or more additional therapeutic agents (e.g., concurrently or sequentially with one or more additional therapeutic agents) or prophylactic agents (e.g., concurrently or sequentially with one or more prophylactic agents). In some embodiments, a subject has been previously treated with one or more therapeutic agents prior to being administered a polypeptide, composition, or pharmaceutical composition disclosed herein. In some embodiments, methods disclosed herein comprise administering a therapeutically effective amount of one or more additional therapeutic agents to the subject at the same time as, or following administration of a polypeptide, composition, or pharmaceutical composition disclosed herein. In some embodiments, methods disclosed herein comprise administering a therapeutically effective amount of one or more prophylactic agents to the subject before, at the same time as, or following administration of a polypeptide, composition, or pharmaceutical composition disclosed herein. In some embodiments, the subject previously received a therapeutic or prophylactic agent. In some embodiments, the subject was previously infected with a betacoronavirus, such as SARS-CoV-2.

Non-limiting examples of additional therapeutic agents include antibiotics (e.g., azithromycin), antibodies or antigen-binding fragments thereof (e.g., other SARS-CoV-2-binding antibodies or antigen-binding fragments), antimalarial agents (e.g., chloroquine or hydroxychloroquine), antiviral agents (e.g., Molnupiravir (LAGEVRIO, Merck), PF-07817883 (Pfizer), STI-1558 (Sorrento Therapeutics), PBI-0451 (Pardes Biosciences), EDP-235 (Enanta Pharmaceuticals), favipiravir, lopinavir and/or ritonavir), cytokines (e.g., type 1 interferons such as interferon beta-1a), nucleotide analogs (e.g., remdesivir), protease inhibitors (e.g., danoprevir), Renin-Angiotensin-Aldosterone System Inhibitors (e.g., ACE2 inhibitors or angiotensin-receptor blockers (ARBs)).

In some embodiments, the antiviral agent is selected from the group consisting of Molnupiravir (LAGEVRIO, Merck), PF-07817883 (Pfizer), STI-1558 (Sorrento Therapeutics), PBI-0451 (Pardes Biosciences), EDP-235 (Enanta Pharmaceuticals), amantadine, favipiravir, lopinavir, oseltamivir (Tamiflu), pleconaril, rimantadine, ritonavir, an anti-sense RNA to SARS-CoV-2, a siRNA to SARS-CoV-2, an additional anti-SARS-CoV-2 monoclonal antibody, and combinations thereof.

In some embodiments, the antiviral agent is selected from the group consisting of Molnupiravir (LAGEVRIO, Merck), PF-07817883 (Pfizer), STI-1558 (Sorrento Therapeutics), PBI-0451 (Pardes Biosciences), EDP-235 (Enanta Pharmaceuticals), and combinations thereof.

In some embodiments, the additional anti-SARS-CoV-2 antibody targets the S1 domain of the Spike protein of SARS-CoV-2. In some embodiments, the additional anti-SARS-CoV-2 antibody targets the class 4 region of the S1 domain. In some embodiments, the additional anti-SARS-CoV-2 monoclonal antibody targets the RBD (e.g., RBD class 1, 2, 3 or 4 epitopes) of the S1 domain of SARS-CoV-2. In some embodiments, the additional anti-SARS-CoV-2 antibody targets the class 3 region of the RBD domain. In some embodiments, the additional anti-SARS-CoV-2 antibody targets the N-terminal domain (NTD)-nonsupersite region of the S1 domain. In some embodiments, the additional anti-SARS-CoV-2 antibody targets the SD1 region of the S1 domain.

In some embodiments, the additional anti-SARS-CoV-2 monoclonal antibody targets (e.g., binds) the S2 domain of the Spike protein of SARS-CoV-2. In some embodiments, the additional anti-SARS-CoV-2 monoclonal antibody is a neutralizing monoclonal antibody (e.g., as determined using a neutralization assay described herein or otherwise known in the art). Non-limiting examples of anti-SARS-CoV-2 monoclonal antibodies include Bamlanivimab (LY-CoV555 or LY3819253), Etesevimab (LY-CoV016 or LY3832479), Bebtelovimab (LY-CoV1404, LY3853113), Casirivimab (REGN10933), Imdevimab (REGN10987), Cilgavimab, Tixagevimab, AZD7442/Evusheld (Tixagevimab-Cilgavimab), Regdanvimab, Sotrovimab (Vir Biotechnology, Inc.), ADG20 (Adagio Therapeutics, Inc.), Ensovibep (MP0420) (DARPin, Novartis), P2G3 (Aerium Tx), and S2X259 (Tortorici M A, et al., Broad sarbecovirus neutralization by a human monoclonal antibody. Nature. 2021 September; 597 (7874):103-108. doi: 10.1038/s41586-021-03817-4. Epub 2021 Jul. 19 PMID: 34280951). Additional examples of anti-SARS-CoV-2 antibodies include those described in U.S. Pat. Nos. 11,168,128, 11,192,940, WO 2022/010912 A1, WO 2022/010921 A1, WO 2022/047033 A1, WO 2021/173753 A1, WO 2021/158521 A1, WO 2021/203053 A1, WO 2021/211775 A1, WO 2021/226560 A1, the contents of which are incorporated herein by reference. Further examples of anti-SARS-CoV-2 antibodies are provided at www.covid19treatmentguidelines.nih.gov/therapies/anti-sars-cov-2-antibody-products/anti-sars-cov-2-monoclonal-antibodies.

In some embodiments, the subject is further treated (previously, concurrently, or sequentially) with (e.g., an effective amount of) one or more RBD-class 4 antibodies (or antigen-binding fragments thereof), such as S2X259 or a variant thereof. Additional examples of SARS-CoV-2 RBD-class 4 antibodies include, for example, those described herein as RBD Class 4 mAb-1a, RBD Class 4 mAb-1b, RBD Class 4 mAb-1c, RBD Class 4 mAb-1d, RBD Class 4 mAb-2a, RBD Class 4 mAb-2b, RBD Class 4 mAb-2c, RBD Class 4 mAb-2d, RBD Class 4 mAb-3a, RBD Class 4 mAb-3b, RBD Class 4 mAb-3c, and RBD Class 4 mAb-3d, having the VH and VL sequences in Tables 10 and 11 herein, respectively, and those described in U.S. Patent Application Nos. 63/424,947 (filed on Nov. 13, 2022), 63/383,699 (filed on Nov. 14, 2022), 63/480,919 (filed on Jan. 20, 2023), and 63/492,211 (filed on Mar. 24, 2023), the entire contents of which are incorporated herein by reference. In some embodiments, the subject is treated with (e.g., an effective amount of) S2X259.

In some embodiments, the subject is further treated (previously, concurrently, or sequentially) with one or more SARS-CoV-2 RBD-class 3 antibodies (or antigen-binding fragments thereof), such as, for example, one or more of Sotrovimab, Bebtelovimab, AZD1061, P2G3 and Evusheld. In some embodiments, the subject is treated with (e.g., an effective amount of) Bebtelovimab. In some embodiments, the subject is treated with (e.g., an effective amount of) Evusheld. In some embodiments, the subject is treated with (e.g., an effective amount of) tixagevimab. In some embodiments, the subject is treated with (e.g., an effective amount of) cilgavimab.

In some embodiments, the subject is further treated (previously, concurrently, or sequentially) with one or more SARS-CoV-2 N-terminal domain (NTD)-nonsupersite antibodies (or antigen-binding fragments thereof), such as C1520 and C1717.

In some embodiments, the subject is further treated (previously, concurrently, or sequentially) with one or more SARS-CoV-2 SD1 antibodies (or antigen-binding fragments thereof), such as S3H3 and P008_60.

In some embodiments, the ACE2 inhibitor is selected from the group consisting of an RNAi to ACE2, a siRNA to ACE2, CRISPR-based inhibitor of ACE2, a soluble ACE2, a soluble ACE2 variant, an anti-ACE2 antibody, a vaccine, and combinations thereof. In some embodiments, the antibiotic is azithromycin. In some embodiments, the antimalarial agent comprises chloroquine or hydroxychloroquine. In some embodiments, the vaccine is a nucleic acid vaccine or an inactivated virus vaccine. In some embodiments, the vaccine is mrna-1273, BNT162, INO-4800, AZD1222, Ad5-nCoV, PiCoVacc, NVX-CoV2373, JNJ-78436735, or a combination thereof.

Administration of the two or more therapeutic agents encompasses co-administration of the therapeutic agents in a substantially simultaneous manner, such as in a pharmaceutical combination. In some embodiments, such administration encompasses co-administration in multiple containers, or separate containers (e.g., capsules, powders, and liquids) for each therapeutic agent. Such administration also encompasses use of each type of therapeutic agent in a sequential manner, either at approximately the same time or at different times. The composition described herein and the second therapeutic agent can be administered via the same administration route or via different administration routes.

In some embodiments, the disclosure provides methods of preventing a SARS-CoV-2 infection in a subject, comprising administering to the subject an effective amount of a pharmaceutical composition comprising a pharmaceutically acceptable carrier and, wherein as an active ingredient, any one of polypeptides or fusion proteins described herein.

In some embodiments, the disclosure provides methods of treating a SARS-CoV-2 infection in a subject, comprising administering to the subject an effective amount of a pharmaceutical composition comprising a pharmaceutically acceptable carrier and, wherein as an active ingredient, any polypeptide or fusion protein described herein.

In some embodiments, the disclosure provides methods of reducing viral load of SARS-CoV-2 in a subject, comprising administering to the subject an effective amount of a pharmaceutical composition comprising a pharmaceutically acceptable carrier and, wherein as an active ingredient, any polypeptide or fusion protein described herein.

In some embodiments, the disclosure provides methods of inhibiting binding of SARS-CoV-2 to a target cell, comprising contacting the target cell an effective amount of any polypeptide or fusion protein described herein.

In some embodiments, the disclosure provides methods of inhibiting binding of SARS-CoV-2 to a target protein on a target cell, comprising contacting the target cell an effective amount of any polypeptide or fusion protein described herein.

In some embodiments, the disclosure provides methods of inhibiting virus mediated fusion with a target cell, comprising contacting the target cell an effective amount of any polypeptide or fusion protein described herein.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting.

As used herein, the indefinite articles "a," "an" and "the" should be understood to include plural reference unless the context clearly indicates otherwise.

Throughout this specification and the claims which follow, unless the context requires otherwise, the word "comprise," and variations such as "comprises" and "comprising", will be understood to imply the inclusion of, e.g., a stated integer or step or group of integers or steps, but not the exclusion of any other integer or step or group of integer or step. When used herein, the term "comprising" can be substituted with the term "containing" or "including."

As used herein, "consisting of" excludes any element, step, or ingredient not specified in the claim element. When used herein, "consisting essentially of" does not exclude materials or steps that do not materially affect the basic and novel characteristics of the claim. Any of the terms "comprising," "containing," "including," and "having," whenever used herein in the context of an aspect or embodiment disclosed herein, can in some embodiments, be replaced with the term "consisting of" or "consisting essentially of" to vary scopes disclosed herein.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and, therefore, satisfy the requirement of the term "and/or" as used herein. Concurrent applicability of more than one of the options is also understood to fall within the meaning, and, therefore, satisfy the requirement of the term "and/or."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." For all numerical bounds describing some parameter in this application, such as "about," "at least," "less than," "fewer than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

Headings used in this application are for convenience only and do not affect the interpretation of this application.

Preferred features of each of the aspects or embodiments provided by the invention are applicable to all of the other aspects or embodiments of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

EMBODIMENTS

1. A polypeptide that specifically binds an S2 domain of a betacoronavirus Spike glycoprotein, wherein the polypeptide has one or more properties selected from:

a broadly neutralizing activity against a plurality of known and predicted betacoronaviruses;
a binding affinity for an S2 domain epitope that is highly conserved across a plurality of betacoronaviruses; and
an inhibitory activity against potential emerging betacoronavirus escape variants.

2. A polypeptide that specifically binds a severe acute respiratory syndrome coronavirus 2 Spike glycoprotein (SARS-CoV-2-Spike), comprising a paratope that is substantially similar to a paratope of an antibody comprising an amino acid sequence selected from:
SEQ ID NO:4 and SEQ ID NO:51 (AB-1);
SEQ ID NO:5 and SEQ ID NO:52 (AB-2);
SEQ ID NO:6 and SEQ ID NO:53 (AB-3);
SEQ ID NO:7 and SEQ ID NO:54 (AB-4);
SEQ ID NO:8 and SEQ ID NO:51 (AB-5);
SEQ ID NO:9 and SEQ ID NO:55 (AB-6);
SEQ ID NO:10 and SEQ ID NO:56 (AB-7);
SEQ ID NO:11 and SEQ ID NO:57 (AB-8);
SEQ ID NO:12 and SEQ ID NO:58 (AB-9);
SEQ ID NO:13 and SEQ ID NO:59 (AB-10);
SEQ ID NO:14 and SEQ ID NO:60 (AB-11);
SEQ ID NO:15 and SEQ ID NO:56 (AB-12);
SEQ ID NO:16 and SEQ ID NO:51 (AB-13);
SEQ ID NO:10 and SEQ ID NO:50 (AB-14);
SEQ ID NO:17 and SEQ ID NO:61 (AB-15);
SEQ ID NO:18 and SEQ ID NO:62 (AB-16);
SEQ ID NO:6 and SEQ ID NO:63 (AB-17);
SEQ ID NO:19 and SEQ ID NO:64 (AB-18);
SEQ ID NO:4 and SEQ ID NO:61 (AB-19);
SEQ ID NO:20 and SEQ ID NO:61 (AB-20);
SEQ ID NO:21 and SEQ ID NO:65 (AB-21);
SEQ ID NO:22 and SEQ ID NO:66 (AB-22);
SEQ ID NO:4 and SEQ ID NO:67 (AB-23);
SEQ ID NO:23 and SEQ ID NO:56 (AB-24);
SEQ ID NO:24 and SEQ ID NO:68 (AB-25);
SEQ ID NO:25 and SEQ ID NO:51 (AB-26);
SEQ ID NO:26 and SEQ ID NO:56 (AB-27);
SEQ ID NO:27 and SEQ ID NO:61 (AB-28);
SEQ ID NO:28 and SEQ ID NO:56 (AB-29);
SEQ ID NO:28 and SEQ ID NO:69 (AB-30);
SEQ ID NO:29 and SEQ ID NO:70 (AB-31);
SEQ ID NO:30 and SEQ ID NO:71 (AB-32);
SEQ ID NO:31 and SEQ ID NO:72 (AB-33);
SEQ ID NO:32 and SEQ ID NO:67 (AB-34);
SEQ ID NO:33 and SEQ ID NO:56 (AB-35);
SEQ ID NO:34 and SEQ ID NO:73 (AB-36);
SEQ ID NO:35 and SEQ ID NO:51 (AB-37);
SEQ ID NO:36 and SEQ ID NO:56 (AB-38);
SEQ ID NO:37 and SEQ ID NO:63 (AB-39);
SEQ ID NO:38 and SEQ ID NO:69 (AB-40);
SEQ ID NO:39 and SEQ ID NO:74 (AB-41);
SEQ ID NO:40 and SEQ ID NO:52 (AB-42);
SEQ ID NO:41 and SEQ ID NO:51 (AB-43);
SEQ ID NO:42 and SEQ ID NO:75 (AB-44);
SEQ ID NO:43 and SEQ ID NO:56 (AB-45);
SEQ ID NO:44 and SEQ ID NO:51 (AB-46);
SEQ ID NO:45 and SEQ ID NO:75 (AB-47);
SEQ ID NO:46 and SEQ ID NO:53 (AB-48);
SEQ ID NO:47 and SEQ ID NO:52 (AB-49);
SEQ ID NO:48 and SEQ ID NO:76 (AB-50); or
SEQ ID NO:3 and SEQ ID NO:56 (AB-51), or
any combination thereof.

3. The polypeptide of embodiment 1 or 2, comprising an immunoglobulin heavy chain variable domain ($V_H$) and an immunoglobulin light chain variable domain ($V_L$).
4. A polypeptide that specifically binds a severe acute respiratory syndrome coronavirus 2 Spike glycoprotein (SARS-CoV-2-Spike), comprising:
   a) an immunoglobulin heavy chain variable domain ($V_H$) amino acid sequence comprising a heavy chain complementarity determining region 1 (HCDR1), a heavy chain complementarity determining region 2 (HCDR2) and a heavy chain complementarity determining region 3 (HCDR3) that are substantially similar to a HCDR1, HCDR2 and HCDR3, respectively, of the amino acid sequence of any one of SEQ ID NOs:4-48; and
   b) an immunoglobulin light chain variable domain ($V_L$) amino acid sequence comprising a light chain complementarity determining region 1 (LCDR1), a light chain complementarity determining region 2 (LCDR2) and a light chain complementarity determining region 3 (LCDR3) that are substantially similar to a LCDR1, LCDR2 and LCDR3, respectively, of the amino acid sequence of any one of SEQ ID NOs:51-76.
5. The polypeptide of any one of embodiments 1-4, comprising the HCDR1, HCDR2 and HCDR3, and LCDR1, LCDR2 and LCDR3, of an antibody comprising an amino acid sequence selected from:
   SEQ ID NO:4 and SEQ ID NO:51 (AB-1);
   SEQ ID NO:5 and SEQ ID NO:52 (AB-2);
   SEQ ID NO:6 and SEQ ID NO:53 (AB-3);
   SEQ ID NO:7 and SEQ ID NO:54 (AB-4);
   SEQ ID NO:8 and SEQ ID NO:51 (AB-5);
   SEQ ID NO:9 and SEQ ID NO:55 (AB-6);
   SEQ ID NO:10 and SEQ ID NO:56 (AB-7);
   SEQ ID NO:11 and SEQ ID NO:57 (AB-8);
   SEQ ID NO:12 and SEQ ID NO:58 (AB-9);
   SEQ ID NO:13 and SEQ ID NO:59 (AB-10);
   SEQ ID NO:14 and SEQ ID NO:60 (AB-11);
   SEQ ID NO:15 and SEQ ID NO:56 (AB-12);
   SEQ ID NO:16 and SEQ ID NO:51 (AB-13);
   SEQ ID NO:10 and SEQ ID NO:50 (AB-14);
   SEQ ID NO:17 and SEQ ID NO:61 (AB-15);
   SEQ ID NO:18 and SEQ ID NO:62 (AB-16);
   SEQ ID NO:6 and SEQ ID NO:63 (AB-17);
   SEQ ID NO:19 and SEQ ID NO:64 (AB-18);
   SEQ ID NO:4 and SEQ ID NO:61 (AB-19);
   SEQ ID NO:20 and SEQ ID NO:61 (AB-20);
   SEQ ID NO:21 and SEQ ID NO:65 (AB-21);
   SEQ ID NO:22 and SEQ ID NO:66 (AB-22);
   SEQ ID NO:4 and SEQ ID NO:67 (AB-23);
   SEQ ID NO:23 and SEQ ID NO:56 (AB-24);
   SEQ ID NO:24 and SEQ ID NO:68 (AB-25);
   SEQ ID NO:25 and SEQ ID NO:51 (AB-26);
   SEQ ID NO:26 and SEQ ID NO:56 (AB-27);
   SEQ ID NO:27 and SEQ ID NO:61 (AB-28);
   SEQ ID NO:28 and SEQ ID NO:56 (AB-29);
   SEQ ID NO:28 and SEQ ID NO:69 (AB-30);
   SEQ ID NO:29 and SEQ ID NO:70 (AB-31);
   SEQ ID NO:30 and SEQ ID NO:71 (AB-32);
   SEQ ID NO:31 and SEQ ID NO:72 (AB-33);
   SEQ ID NO:32 and SEQ ID NO:67 (AB-34);
   SEQ ID NO:33 and SEQ ID NO:56 (AB-35);
   SEQ ID NO:34 and SEQ ID NO:73 (AB-36);
   SEQ ID NO:35 and SEQ ID NO:51 (AB-37);
   SEQ ID NO:36 and SEQ ID NO:56 (AB-38);
   SEQ ID NO:37 and SEQ ID NO:63 (AB-39);
   SEQ ID NO:38 and SEQ ID NO:69 (AB-40);
   SEQ ID NO:39 and SEQ ID NO:74 (AB-41);
   SEQ ID NO:40 and SEQ ID NO:52 (AB-42);
   SEQ ID NO:41 and SEQ ID NO:51 (AB-43);
   SEQ ID NO:42 and SEQ ID NO:75 (AB-44);
   SEQ ID NO:43 and SEQ ID NO:56 (AB-45);
   SEQ ID NO:44 and SEQ ID NO:51 (AB-46);
   SEQ ID NO:45 and SEQ ID NO:75 (AB-47);
   SEQ ID NO:46 and SEQ ID NO:53 (AB-48);
   SEQ ID NO:47 and SEQ ID NO:52 (AB-49);
   SEQ ID NO:48 and SEQ ID NO:76 (AB-50); or
   SEQ ID NO:3 and SEQ ID NO:56 (AB-51).
6. The polypeptide of embodiment 4 or 5, comprising a paratope that is identical to a paratope of an antibody comprising an amino acid sequence selected from:
   SEQ ID NO:4 and SEQ ID NO:51 (AB-1);
   SEQ ID NO:5 and SEQ ID NO:52 (AB-2);
   SEQ ID NO:6 and SEQ ID NO:53 (AB-3);
   SEQ ID NO:7 and SEQ ID NO:54 (AB-4);
   SEQ ID NO:8 and SEQ ID NO:51 (AB-5);
   SEQ ID NO:9 and SEQ ID NO:55 (AB-6);
   SEQ ID NO:10 and SEQ ID NO:56 (AB-7);
   SEQ ID NO:11 and SEQ ID NO:57 (AB-8);
   SEQ ID NO:12 and SEQ ID NO:58 (AB-9);
   SEQ ID NO:13 and SEQ ID NO:59 (AB-10);
   SEQ ID NO:14 and SEQ ID NO:60 (AB-11);
   SEQ ID NO:15 and SEQ ID NO:56 (AB-12);
   SEQ ID NO:16 and SEQ ID NO:51 (AB-13);
   SEQ ID NO:10 and SEQ ID NO:50 (AB-14);
   SEQ ID NO:17 and SEQ ID NO:61 (AB-15);
   SEQ ID NO:18 and SEQ ID NO:62 (AB-16);
   SEQ ID NO:6 and SEQ ID NO:63 (AB-17);
   SEQ ID NO:19 and SEQ ID NO:64 (AB-18);
   SEQ ID NO:4 and SEQ ID NO:61 (AB-19);
   SEQ ID NO:20 and SEQ ID NO:61 (AB-20);
   SEQ ID NO:21 and SEQ ID NO:65 (AB-21);
   SEQ ID NO:22 and SEQ ID NO:66 (AB-22);
   SEQ ID NO:4 and SEQ ID NO:67 (AB-23);
   SEQ ID NO:23 and SEQ ID NO:56 (AB-24);
   SEQ ID NO:24 and SEQ ID NO:68 (AB-25);
   SEQ ID NO:25 and SEQ ID NO:51 (AB-26);
   SEQ ID NO:26 and SEQ ID NO:56 (AB-27);
   SEQ ID NO:27 and SEQ ID NO:61 (AB-28);
   SEQ ID NO:28 and SEQ ID NO:56 (AB-29);
   SEQ ID NO:28 and SEQ ID NO:69 (AB-30);
   SEQ ID NO:29 and SEQ ID NO:70 (AB-31);
   SEQ ID NO:30 and SEQ ID NO:71 (AB-32);
   SEQ ID NO:31 and SEQ ID NO:72 (AB-33);
   SEQ ID NO:32 and SEQ ID NO:67 (AB-34);
   SEQ ID NO:33 and SEQ ID NO:56 (AB-35);
   SEQ ID NO:34 and SEQ ID NO:73 (AB-36);
   SEQ ID NO:35 and SEQ ID NO:51 (AB-37);
   SEQ ID NO:36 and SEQ ID NO:56 (AB-38);
   SEQ ID NO:37 and SEQ ID NO:63 (AB-39);
   SEQ ID NO:38 and SEQ ID NO:69 (AB-40);
   SEQ ID NO:39 and SEQ ID NO:74 (AB-41);
   SEQ ID NO:40 and SEQ ID NO:52 (AB-42);
   SEQ ID NO:41 and SEQ ID NO:51 (AB-43);
   SEQ ID NO:42 and SEQ ID NO:75 (AB-44);
   SEQ ID NO:43 and SEQ ID NO:56 (AB-45);
   SEQ ID NO:44 and SEQ ID NO:51 (AB-46);
   SEQ ID NO:45 and SEQ ID NO:75 (AB-47);
   SEQ ID NO:46 and SEQ ID NO:53 (AB-48);
   SEQ ID NO:47 and SEQ ID NO:52 (AB-49);
   SEQ ID NO:48 and SEQ ID NO:76 (AB-50); or
   SEQ ID NO:3 and SEQ ID NO:56 (AB-51).

7. A polypeptide that specifically binds a severe acute respiratory syndrome coronavirus 2 Spike glycoprotein (SARS-CoV-2-Spike), comprising an immunoglobulin heavy chain variable domain ($V_H$) comprising the amino acid sequence of SEQ ID NO:2, wherein:
$X_1$ is not S;
$X_2$ is not D;
$X_3$ is not T;
$X_4$ is not L;
$X_5$ is not S;
$X_6$ is not N;
$X_7$ is not G;
$X_8$ is not V; or
$X_9$ is not Q,
or any combination of the foregoing.

8. The polypeptide of embodiment 7, comprising an immunoglobulin light chain variable domain ($V_L$) comprising the amino acid sequence of SEQ ID NO:49, wherein:
$X_{10}$ is not Q;
$X_{11}$ is not G;
$X_{12}$ is not S;
$X_{13}$ is not S;
$X_{14}$ is not N;
$X_{15}$ is not S;
$X_{16}$ is not F; or
$X_{17}$ is not Y,
or any combination of the foregoing.

9. A polypeptide that specifically binds a severe acute respiratory syndrome coronavirus 2 Spike glycoprotein (SARS-CoV-2-Spike), comprising an immunoglobulin heavy chain variable domain ($V_H$) comprising the amino acid sequence of SEQ ID NO:2, wherein:
$X_1$ is S, N, A, R, L or F;
$X_2$ is D or E;
$X_3$ is T or V;
$X_4$ is L or V;
$X_5$ is S, Q, R, K, Y, D or E;
$X_6$ is N, K, A, S, R or E;
$X_7$ is G, N or L;
$X_8$ is V, I, S or K; or
$X_9$ is Q, Y, K, F or H,
or any combination of the foregoing.

10. The polypeptide of embodiment 9, wherein:
$X_1$ is N, A, R, L or F;
$X_2$ is E;
$X_3$ is V;
$X_4$ is V;
$X_5$ is Q, R, K, Y, D or E;
$X_6$ is K, A, S, R or E;
$X_7$ is N or L;
$X_8$ is I, S or K; or
$X_9$ is Y, K, F or H,
or any combination of the foregoing.

11. The polypeptide of embodiment 9 or 10, comprising an immunoglobulin light chain variable domain ($V_L$) comprising the amino acid sequence of SEQ ID NO:49, wherein:
$X_{10}$ is Q, K or I;
$X_{11}$ is G or S;
$X_{12}$ is S, R or V;
$X_{13}$ is S or N;
$X_{14}$ is N, H, D, Y or S;
$X_{15}$ is S or Q;
$X_{16}$ is F, Y, L, V, T or D; or
$X_{17}$ is Y or L,
or any combination of the foregoing.

12. The polypeptide of embodiment 11, wherein:
$X_{10}$ is K or I;
$X_{11}$ is S;
$X_{12}$ is R or V;
$X_{13}$ is N;
$X_{14}$ is H, D, Y or S;
$X_{15}$ is Q;
$X_{16}$ is Y, L, V, T or D; or
$X_{17}$ is L,
or any combination of the foregoing.

13. The polypeptide of any one of embodiments 1-4 and 6-12, wherein the $V_H$ comprises a heavy chain complementarity determining region 1 (HCDR1), a heavy chain complementarity determining region 2 (HCDR2) and a heavy chain complementarity determining region 3 (HCDR3) that are identical in amino acid sequence to the HCDR1, HCDR2 and HCDR3, respectively, of any one of SEQ ID NOs:4-48.

14. The polypeptide of any one of embodiments 1-4 and 6-13, wherein the $V_L$ comprises a light chain complementarity determining region 1 (LCDR1), light chain complementarity determining region 2 (LCDR2) and light chain complementarity determining region 3 (LCDR3) that are identical in amino acid sequence to the LCDR1, LCDR2 and LCDR3, respectively, of any one of SEQ ID NOs:51-76.

15. The polypeptide of any one of embodiments 1-5 and 7-14, wherein the polypeptide comprises a paratope that is identical to a paratope of a $V_H/V_L$ combination selected from the amino acid sequence of SEQ ID NO:4/SEQ ID NO:51 (AB-1), SEQ ID NO:5/SEQ ID NO:52 (AB-2), SEQ ID NO:6/SEQ ID NO:53 (AB-3), SEQ ID NO:7/SEQ ID NO:54 (AB-4), SEQ ID NO:8/SEQ ID NO:51 (AB-5), SEQ ID NO:9/SEQ ID NO:55 (AB-6), SEQ ID NO:10/SEQ ID NO:56 (AB-7), SEQ ID NO:11/SEQ ID NO:57 (AB-8), SEQ ID NO:12/SEQ ID NO:58 (AB-9), SEQ ID NO:13/SEQ ID NO:59 (AB-10), SEQ ID NO:14/SEQ ID NO:60 (AB-11), SEQ ID NO:15/SEQ ID NO:56 (AB-12), SEQ ID NO:16/SEQ ID NO:51 (AB-13), SEQ ID NO:10/SEQ ID NO:50 (AB-14), SEQ ID NO:17/SEQ ID NO:61 (AB-15), SEQ ID NO:18/SEQ ID NO:62 (AB-16), SEQ ID NO:6/SEQ ID NO:63 (AB-17), SEQ ID NO:19/SEQ ID NO:64 (AB-18), SEQ ID NO:4/SEQ ID NO:61 (AB-19), SEQ ID NO:20/SEQ ID NO:61 (AB-20), SEQ ID NO:21/SEQ ID NO:65 (AB-21), SEQ ID NO:22/SEQ ID NO:66 (AB-22), SEQ ID NO:4/SEQ ID NO:67 (AB-23), SEQ ID NO:23/SEQ ID NO:56 (AB-24), SEQ ID NO:24/SEQ ID NO:68 (AB-25), SEQ ID NO:25/SEQ ID NO:51 (AB-26), SEQ ID NO:26/SEQ ID NO:56 (AB-27), SEQ ID NO:27/SEQ ID NO:61 (AB-28), SEQ ID NO:28/SEQ ID NO:56 (AB-29), SEQ ID NO:28/SEQ ID NO:69 (AB-30), SEQ ID NO:29/SEQ ID NO:70 (AB-31), SEQ ID NO:30/SEQ ID NO:71 (AB-32), SEQ ID NO:31/SEQ ID NO:72 (AB-33), SEQ ID NO:32/SEQ ID NO:67 (AB-34), SEQ ID NO:33/SEQ ID NO:56 (AB-35), SEQ ID NO:34/SEQ ID NO:73 (AB-36), SEQ ID NO:35/SEQ ID NO:51 (AB-37), SEQ ID NO:36/SEQ ID NO:56 (AB-38), SEQ ID NO:37/SEQ ID NO:63 (AB-39), SEQ ID NO:38/SEQ ID NO:69 (AB-40), SEQ ID NO:39/SEQ ID NO:74 (AB-41), SEQ ID NO:40/SEQ ID NO:52 (AB-42), SEQ ID NO:41/SEQ ID NO:51 (AB-43), SEQ ID NO:42/SEQ ID NO:75 (AB-44), SEQ ID NO:43/SEQ ID NO:56 (AB-45), SEQ ID NO:44/SEQ ID NO:51 (AB-46), SEQ ID NO:45/SEQ ID NO:75 (AB-47), SEQ ID NO:46/SEQ ID NO:53 (AB-48), SEQ ID NO:47/SEQ ID NO:52 (AB-49), SEQ ID NO:48/SEQ ID NO:76 (AB-50), or SEQ ID NO:3/SEQ ID NO:56 (AB-51).

16. The polypeptide of any one of embodiments 1-15, wherein the $V_H$ has at least 85% sequence identity to the amino acid sequence of any one or more of SEQ ID NOs:4-48.

17. The polypeptide of any one of embodiments 1-16, wherein the $V_H$ comprises about 1-10 amino acid substitutions, relative to the amino acid sequence of any one or more of SEQ ID NOs:4-48.

18. The polypeptide of any one of embodiments 1-17, wherein the $V_L$ has at least 85% sequence identity to the amino acid sequence of any one or more of SEQ ID NOs: 51-76.

19. The polypeptide of any one of embodiments 1-18, wherein the $V_L$ comprises about 1-10 amino acid substitutions, relative to the amino acid sequence of any one or more of SEQ ID NOs:51-76.

20. The polypeptide of embodiment 17 or 19, wherein the amino acid substitutions are conservative substitutions.

21. The polypeptide of embodiment 20, wherein the amino acid substitutions are highly conservative substitutions.

22. The polypeptide of any one of embodiments 1-20, wherein:
    a) the $V_H$ comprises the amino acid sequence of SEQ ID NO:4; and
    b) the $V_L$ comprises the amino acid sequence of SEQ ID NO:51 (AB-1).

23. The polypeptide of any one of embodiments 1-20, wherein:
    a) the $V_H$ comprises the amino acid sequence of SEQ ID NO:5; and
    b) the $V_L$ comprises the amino acid sequence of SEQ ID NO:52 (AB-2).

24. The polypeptide of any one of embodiments 1-20, wherein:
    a) the $V_H$ comprises the amino acid sequence of SEQ ID NO:6; and
    b) the $V_L$ comprises the amino acid sequence of SEQ ID NO:53 (AB-3).

25. The polypeptide of any one of embodiments 1-20, wherein:
    a) the $V_H$ comprises the amino acid sequence of SEQ ID NO:7; and
    b) the $V_L$ comprises the amino acid sequence of SEQ ID NO:54 (AB-4).

26. The polypeptide of any one of embodiments 1-20, wherein:
    a) the $V_H$ comprises the amino acid sequence of SEQ ID NO:8; and
    b) the $V_L$ comprises the amino acid sequence of SEQ ID NO:51 (AB-5).

27. The polypeptide of any one of embodiments 1-20, wherein:
    a) the $V_H$ comprises the amino acid sequence of SEQ ID NO:9; and
    b) the $V_L$ comprises the amino acid sequence of SEQ ID NO:55 (AB-6).

28. The polypeptide of any one of embodiments 1-20, wherein:
    a) the $V_H$ comprises the amino acid sequence of SEQ ID NO:10; and
    b) the $V_L$ comprises the amino acid sequence of SEQ ID NO:56 (AB-7).

29. The polypeptide of any one of embodiments 1-20, wherein:
    a) the $V_H$ comprises the amino acid sequence of SEQ ID NO:11; and
    b) the $V_L$ comprises the amino acid sequence of SEQ ID NO:57 (AB-8).

30. The polypeptide of any one of embodiments 1-20, wherein:
    a) the $V_H$ comprises the amino acid sequence of SEQ ID NO:12; and
    b) the $V_L$ comprises the amino acid sequence of SEQ ID NO:30 (AB-9).

31. The polypeptide of any one of embodiments 1-20, wherein:
    a) the $V_H$ comprises the amino acid sequence of SEQ ID NO:13; and
    b) the $V_L$ comprises the amino acid sequence of SEQ ID NO:59 (AB-10).

32. The polypeptide of any one of embodiments 1-20, wherein:
    a) the $V_H$ comprises the amino acid sequence of SEQ ID NO:14; and
    b) the $V_L$ comprises the amino acid sequence of SEQ ID NO:60 (AB-11).

33. The polypeptide of any one of embodiments 1-20, wherein:
    a) the $V_H$ comprises the amino acid sequence of SEQ ID NO:15; and
    b) the $V_L$ comprises the amino acid sequence of SEQ ID NO:56 (AB-12).

34. The polypeptide of any one of embodiments 1-20, wherein:
    a) the $V_H$ comprises the amino acid sequence of SEQ ID NO:16; and
    b) the $V_L$ comprises the amino acid sequence of SEQ ID NO:51 (AB-13).

35. The polypeptide of any one of embodiments 1-20, wherein:
    a) the $V_H$ comprises the amino acid sequence of SEQ ID NO:10; and
    b) the $V_L$ comprises the amino acid sequence of SEQ ID NO:50 (AB-14).

36. The polypeptide of any one of embodiments 1-20, wherein:
    a) the $V_H$ comprises the amino acid sequence of SEQ ID NO:17; and
    b) the $V_L$ comprises the amino acid sequence of SEQ ID NO:61 (AB-15).

37. The polypeptide of any one of embodiments 1-20, wherein:
    a) the $V_H$ comprises the amino acid sequence of SEQ ID NO:18; and
    b) the $V_L$ comprises the amino acid sequence of SEQ ID NO:62 (AB-16).

38. The polypeptide of any one of embodiments 1-20, wherein:
    a) the $V_H$ comprises the amino acid sequence of SEQ ID NO:6; and
    b) the $V_L$ comprises the amino acid sequence of SEQ ID NO:63 (AB-17).

39. The polypeptide of any one of embodiments 1-20, wherein:
    a) the $V_H$ comprises the amino acid sequence of SEQ ID NO:19; and
    b) the $V_L$ comprises the amino acid sequence of SEQ ID NO:64 (AB-18).

40. The polypeptide of any one of embodiments 1-20, wherein:
   a) the $V_H$ comprises the amino acid sequence of SEQ ID NO:4; and
   b) the $V_L$ comprises the amino acid sequence of SEQ ID NO:61 (AB-19).

41. The polypeptide of any one of embodiments 1-20, wherein:
   a) the $V_H$ comprises the amino acid sequence of SEQ ID NO:20; and
   b) the $V_L$ comprises the amino acid sequence of SEQ ID NO:61 (AB-20).

42. The polypeptide of any one of embodiments 1-20, wherein:
   a) the $V_H$ comprises the amino acid sequence of SEQ ID NO:21; and
   b) the $V_L$ comprises the amino acid sequence of SEQ ID NO:65 (AB-21).

43. The polypeptide of any one of embodiments 1-20, wherein:
   a) the $V_H$ comprises the amino acid sequence of SEQ ID NO:22; and
   b) the $V_L$ comprises the amino acid sequence of SEQ ID NO:66 (AB-22).

44. The polypeptide of any one of embodiments 1-20, wherein:
   a) the $V_H$ comprises the amino acid sequence of SEQ ID NO:4; and
   b) the $V_L$ comprises the amino acid sequence of SEQ ID NO:67 (AB-23).

45. The polypeptide of any one of embodiments 1-20, wherein:
   a) the $V_H$ comprises the amino acid sequence of SEQ ID NO:23; and
   b) the $V_L$ comprises the amino acid sequence of SEQ ID NO:56 (AB-24).

46. The polypeptide of any one of embodiments 1-20, wherein:
   a) the $V_H$ comprises the amino acid sequence of SEQ ID NO:24; and
   b) the $V_L$ comprises the amino acid sequence of SEQ ID NO:68 (AB-25).

47. The polypeptide of any one of embodiments 1-20, wherein:
   a) the $V_H$ comprises the amino acid sequence of SEQ ID NO:25; and
   b) the $V_L$ comprises the amino acid sequence of SEQ ID NO:51 (AB-26).

48. The polypeptide of any one of embodiments 1-20, wherein:
   a) the $V_H$ comprises the amino acid sequence of SEQ ID NO:26; and
   b) the $V_L$ comprises the amino acid sequence of SEQ ID NO:56 (AB-27).

49. The polypeptide of any one of embodiments 1-20, wherein:
   a) the $V_H$ comprises the amino acid sequence of SEQ ID NO:27; and
   b) the $V_L$ comprises the amino acid sequence of SEQ ID NO:61 (AB-28).

50. The polypeptide of any one of embodiments 1-20, wherein:
   a) the $V_H$ comprises the amino acid sequence of SEQ ID NO:28; and
   b) the $V_L$ comprises the amino acid sequence of SEQ ID NO:56 (AB-29).

51. The polypeptide of any one of embodiments 1-20, wherein:
   a) the $V_H$ comprises the amino acid sequence of SEQ ID NO:28; and
   b) the $V_L$ comprises the amino acid sequence of SEQ ID NO:69 (AB-30).

52. The polypeptide of any one of embodiments 1-20, wherein:
   a) the $V_H$ comprises the amino acid sequence of SEQ ID NO:29; and
   b) the $V_L$ comprises the amino acid sequence of SEQ ID NO:70 (AB-31).

53. The polypeptide of any one of embodiments 1-20, wherein:
   a) the $V_H$ comprises the amino acid sequence of SEQ ID NO:30; and
   b) the $V_L$ comprises the amino acid sequence of SEQ ID NO:71 (AB-32).

54. The polypeptide of any one of embodiments 1-20, wherein:
   a) the $V_H$ comprises the amino acid sequence of SEQ ID NO:31; and
   b) the $V_L$ comprises the amino acid sequence of SEQ ID NO:72 (AB-33).

55. The polypeptide of any one of embodiments 1-20, wherein:
   a) the $V_H$ comprises the amino acid sequence of SEQ ID NO:32; and
   b) the $V_L$ comprises the amino acid sequence of SEQ ID NO:67 (AB-34).

56. The polypeptide of any one of embodiments 1-20, wherein:
   a) the $V_H$ comprises the amino acid sequence of SEQ ID NO:33; and
   b) the $V_L$ comprises the amino acid sequence of SEQ ID NO:56 (AB-35).

57. The polypeptide of any one of embodiments 1-20, wherein:
   a) the $V_H$ comprises the amino acid sequence of SEQ ID NO:34; and
   b) the $V_L$ comprises the amino acid sequence of SEQ ID NO:73 (AB-36).

58. The polypeptide of any one of embodiments 1-20, wherein:
   a) the $V_H$ comprises the amino acid sequence of SEQ ID NO:35; and
   b) the $V_L$ comprises the amino acid sequence of SEQ ID NO:51 (AB-37).

59. The polypeptide of any one of embodiments 1-20, wherein:
   a) the $V_H$ comprises the amino acid sequence of SEQ ID NO:36; and
   b) the $V_L$ comprises the amino acid sequence of SEQ ID NO:56 (AB-38).

60. The polypeptide of any one of embodiments 1-20, wherein:
   a) the $V_H$ comprises the amino acid sequence of SEQ ID NO:37; and
   b) the $V_L$ comprises the amino acid sequence of SEQ ID NO:63 (AB-39).

61. The polypeptide of any one of embodiments 1-20, wherein:
   a) the $V_H$ comprises the amino acid sequence of SEQ ID NO:38; and
   b) the $V_L$ comprises the amino acid sequence of SEQ ID NO:69 (AB-40).

62. The polypeptide of any one of embodiments 1-20, wherein:
   a) the $V_H$ comprises the amino acid sequence of SEQ ID NO:39; and
   b) the $V_L$ comprises the amino acid sequence of SEQ ID NO:74 (AB-41).
63. The polypeptide of any one of embodiments 1-20, wherein:
   a) the $V_H$ comprises the amino acid sequence of SEQ ID NO:40; and
   b) the $V_L$ comprises the amino acid sequence of SEQ ID NO:52 (AB-42).
64. The polypeptide of any one of embodiments 1-20, wherein:
   c) the $V_H$ comprises the amino acid sequence of SEQ ID NO:41; and
   d) the $V_L$ comprises the amino acid sequence of SEQ ID NO:51 (AB-43).
65. The polypeptide of any one of embodiments 1-20, wherein:
   e) the $V_H$ comprises the amino acid sequence of SEQ ID NO:42; and
   f) the $V_L$ comprises the amino acid sequence of SEQ ID NO:75 (AB-44).
66. The polypeptide of any one of embodiments 1-20, wherein:
   g) the $V_H$ comprises the amino acid sequence of SEQ ID NO:43; and
   h) the $V_L$ comprises the amino acid sequence of SEQ ID NO:56 (AB-45).
67. The polypeptide of any one of embodiments 1-20, wherein:
   i) the $V_H$ comprises the amino acid sequence of SEQ ID NO:44; and
   j) the $V_L$ comprises the amino acid sequence of SEQ ID NO:51 (AB-46).
68. The polypeptide of any one of embodiments 1-20, wherein:
   k) the $V_H$ comprises the amino acid sequence of SEQ ID NO:45; and
   l) the $V_L$ comprises the amino acid sequence of SEQ ID NO:75 (AB-47).
69. The polypeptide of any one of embodiments 1-20, wherein:
   m) the $V_H$ comprises the amino acid sequence of SEQ ID NO:46; and
   n) the $V_L$ comprises the amino acid sequence of SEQ ID NO:53 (AB-48).
70. The polypeptide of any one of embodiments 1-20, wherein:
   o) the $V_H$ comprises the amino acid sequence of SEQ ID NO:47; and
   p) the $V_L$ comprises the amino acid sequence of SEQ ID NO:52 (AB-49).
71. The polypeptide of any one of embodiments 1-20, wherein:
   q) the $V_H$ comprises the amino acid sequence of SEQ ID NO:48; and
   r) the $V_L$ comprises the amino acid sequence of SEQ ID NO:76 (AB-50).
72. The polypeptide of any one of embodiments 1-20, wherein:
   s) the $V_H$ comprises the amino acid sequence of SEQ ID NO:3; and
   t) the $V_L$ comprises the amino acid sequence of SEQ ID NO:56 (AB-51).
73. The polypeptide of any one of embodiments 3-72, wherein the $V_H$ and $V_L$ are humanized, contain human framework regions, or a combination thereof.
74. The polypeptide of any one of embodiments 1-73, wherein the polypeptide is an antibody or an antigen-binding fragment thereof.
75. The polypeptide of embodiment 74, wherein the antigen binding fragment is selected from Fab, F(ab')$_2$, Fab', scFv, or Fv.
76. The polypeptide of embodiment 74, comprising an antibody heavy chain constant domain sequence, an antibody light chain constant domain sequence, or both an antibody heavy chain constant domain sequence and an antibody light chain constant domain sequence.
77. The polypeptide of embodiment 76, wherein the antibody heavy chain constant domain is selected from the group consisting of an IgA constant domain, an IgD constant domain, an IgE constant domain, an IgG constant domain and an IgM constant domain.
78. The polypeptide of embodiment 77, wherein the antibody heavy chain constant domain is an IgG1 heavy chain constant domain.
79. The polypeptide of any one of embodiments 76-78, comprising an antibody light chain constant domain selected from the group consisting of a κ constant domain or a λ constant domain.
80. The polypeptide of embodiment 79, wherein the antibody light chain constant domain is a κ light chain constant domain.
81. The polypeptide of any one of embodiments 1-80, wherein the polypeptide is conjugated to a heterologous moiety.
82. The polypeptide of embodiment 81, wherein the heterologous moiety is a therapeutic agent, a diagnostic agent or a combination thereof.
83. The polypeptide of embodiment 81, wherein the heterologous moiety is selected from the group consisting of polyethylene glycol (PEG), hexadecanoic acid, a hydrogel, a lipid nanoparticle, a polymer nanoparticle, and a heterologous polypeptide sequence, or a combination thereof.
84. The polypeptide of embodiment 83, wherein the polymer nanoparticle comprises poly(lactic-co-glycolic) acid (PLGA).
85. The polypeptide of embodiment 81, wherein the heterologous polypeptide sequence comprises a carrier polypeptide.
86. The polypeptide of embodiment 85, wherein the carrier polypeptide is albumin or an Fc polypeptide.
87. The polypeptide of any one of embodiments 1-86, wherein the polypeptide:
   a) binds SARS-CoV-2 with a $K_D$ of 1 μM or less;
   b) neutralizes SARS-CoV-2 infection of human host cells with an $IC_{50}$ of about 25,000 ng/mL or less;
   c) reduces infectivity of SARS-CoV-2 in human cells, or any combination of the foregoing.
88. The polypeptide of embodiment 87, wherein the SARS-CoV-2 is a variant comprising T19R, 156del, 157del, R158G, L452R, T478K, D614G, P681R and D950N, and optionally comprising G142D.
89. The polypeptide of embodiment 87 or 88, wherein the polypeptide binds SARS-CoV-2 with a $K_D$ of 100 nM or less.
90. The polypeptide of embodiment 87, wherein the polypeptide neutralizes SARS-CoV-2 infection of human host cells with an $IC_{50}$ of about 25,000 ng/mL or less.

91. The polypeptide of embodiment 87, wherein the polypeptide reduces infectivity of SARS-CoV-2 in human cells by at least about 30%.
92. A fusion protein comprising the polypeptide of any one of embodiments 1-91.
93. A polynucleotide (e.g., DNA or RNA; linear or circular; optionally containing one or more modified nucleotides) comprising a sequence encoding the polypeptide of any one of embodiments 1-80 or the fusion protein of embodiment 92.
94. A vector (e.g., an expression vector, including a viral-delivery vector) comprising the polynucleotide of embodiment 93.
95. A host cell comprising the polynucleotide of embodiment 93 or the vector of embodiment 94.
96. A composition comprising the polypeptide of any one of embodiments 1-91 or the fusion protein of embodiment 92 or the polynucleotide of embodiment 93.
97. The composition of embodiment 96, comprising one or more pharmaceutical excipients, diluents, or carriers.
98. A method of treating a subject in need thereof, comprising administering an effective amount of the composition of embodiment 96 or 97 to the subject.
99. A method of reducing infectivity of a betacoronavirus, such as SARS-CoV-2, of a cell in a subject, comprising contacting the cell with an effective amount of the composition of embodiment 96 or 97.
100. The method of embodiment 98 or 99, wherein the subject has (e.g., confirmed by testing, such as by PCR or rapid test), or is suspected of having, COVID-19.
101. The method of embodiment 98 or 99, wherein the subject is at risk of developing COVID-19.
102. The method of any one of embodiments 98-101, wherein the subject is a human.
103. The method of any one of embodiments 98-102, wherein the subject has a heart disease.
104. The method of embodiment 103, wherein the heart disease is selected from the group consisting of a congestive heart disease, a coronary artery disease, a hypertensive heart disease, an inflammatory heart disease, a pulmonary heart disease, a rheumatic heart disease, a valvular heart disease, a cardiomyopathy, heart failure, and combinations thereof.
105. The method of embodiment 104, wherein the heart failure is a congestive heart failure.
106. The method of embodiment 104, wherein the inflammatory heart disease is selected from the group consisting of endocarditis, cardiomegaly, myocarditis, and combinations thereof.
107. The method of any one of embodiments 98-106, wherein the subject has diabetes.
108. The method of any one of embodiments 98-107, wherein the subject has a lung disease.
109. The method of embodiment 108, wherein the lung disease is selected from the group consisting of acute respiratory distress syndrome, asthma, bronchitis, COPD, emphysema, a lung tumor, a pleural cavity disease, a pulmonary vascular disease, a respiratory tract infection, and combinations thereof.
110. The method of embodiment 109, wherein:
a) the respiratory tract infection is an upper respiratory tract infection, a lower respiratory tract infection, or pneumonia;
b) the pleural cavity disease is pleural mesothelioma or tension pneumothorax;
c) the pulmonary vascular disease is embolisms, edema, arterial hypertension or hemorrhages; or
d) a combination thereof.
111. The method of any one of embodiments 98-110, wherein the subject is a tobacco smoker.
112. The method of any one of embodiments 98-111, wherein the subject is immune-compromised.
113. The method of embodiment 112, wherein the subject is on immunosuppressive therapy.
114. The method of any one of embodiments 98-113, wherein the subject is 40 years or older.
115. The method of any one of embodiments 98-114, comprising administering a therapeutically effective amount of an additional therapeutic or prophylactic agent to the subject.
116. The method of embodiment 115, wherein the additional therapeutic agent is selected from the group consisting of an antiviral agent, an ACE2 inhibitors, an additional SARS-CoV-2-Spike-binding antibody, an antibiotic, an antimalarial agent, a vaccine, and combinations thereof.
117. The method of embodiment 116, wherein:
a) the additional SARS-CoV-2-Spike-binding antibody is selected from the group consisting of bamlanivimab, etesevimab, bebtelovimab, casirivimab, imdevimab, Cilgavimab, Tixagevimab, AZD7442 (Tixagevimab-Cilgavimab), Regdanvimab, Sotrovimab and combinations thereof;
b) the antiviral agent is selected from the group consisting of Molnupiravir (LAGEVRIO, Merck), PF-07817883 (Pfizer), STI-1558 (Sorrento Therapeutics), PBI-0451 (Pardes Biosciences), EDP-235 (Enanta Pharmaceuticals), oseltamivir (Tamiflu), favipiravir, amantadine, remdesivir, rimantadine, pleconaril, an anti-sense RNA to SARS-CoV-2, a siRNA to SARS-CoV-2, and combinations thereof;
c) the ACE2 inhibitor is selected from the group consisting of an RNAi to ACE2, a siRNA to ACE2, CRISPR-based inhibitor of ACE2, a soluble ACE2, a soluble ACE2 variant, an anti-ACE2 antibody, and combinations thereof;
d) the antibiotic comprises azithromycin;
e) the antimalarial agent comprises a chloroquine;
f) the vaccine is a nucleic acid vaccine or an inactivated virus vaccine; or
g) a combination thereof.
118. The method of embodiment 117, wherein the vaccine is mrna-1273, BNT162, INO-4800, AZD1222, Ad5-nCoV, PiCoVacc, NVX-CoV2373, JNJ-78436735, or a combination thereof. 119. The method of any one of embodiments 98-118, wherein the subject is further treated (previously, concurrently, or sequentially) with one or more RBD-class 4 antibodies (or antigen-binding fragments thereof).
120. The method of embodiment 119, wherein the one or more RBD-class 4 antibodies are selected from the group consisting of S2X259, RBD Class 4 mAb-1a having a VH comprising SEQ ID NO:174 and a VL comprising SEQ ID NO:178, RBD Class 4 mAb-1b having a VH comprising SEQ ID NO:174 and a VL comprising SEQ ID NO:179, RBD Class 4 mAb-1c having a VH comprising SEQ ID NO:174 and a VL comprising SEQ ID NO:180, RBD Class 4 mAb-1d having a VH comprising SEQ ID NO:174 and a VL comprising SEQ ID NO:181, RBD Class 4 mAb-2a having a VH comprising SEQ ID NO:175 and a VL comprising SEQ ID NO:182, RBD Class 4 mAb-2b having a VH comprising SEQ ID NO:175 and a VL comprising SEQ ID NO:183, RBD Class 4 mAb-2c having a VH comprising SEQ ID NO:175 and a VL comprising SEQ ID NO:184, RBD Class 4 mAb-2d having a VH comprising SEQ ID NO:175 and a VL comprising SEQ ID NO:185, RBD Class 4 mAb-3a having a VH comprising SEQ ID NO:176 and a VL comprising SEQ ID NO:186, RBD Class 4 mAb-3b having a VH comprising SEQ ID NO:176 and a VL comprising SEQ ID NO:187, RBD Class 4 mAb-3c having a VH comprising SEQ ID NO:176 and a VL comprising SEQ ID NO:188, RBD Class 4 mAb-3d having a VH comprising SEQ ID NO:176 and a VL comprising SEQ ID NO:189, and RBD Class 4 mAb-4a having a VH comprising SEQ ID NO:177 and a VL comprising SEQ ID NO:190, a variant of any of the foregoing, or a combination of any of the foregoing.

121. The method of any one of embodiments 98-120, wherein the subject previously received a therapeutic or prophylactic agent.
122. The method of any one of embodiments 98-121, wherein the subject was previously infected with a betacoronavirus, such as SARS-CoV-2.
123. The method of any one of embodiments 98-122, comprising administering an effective amount of a combination of AB-1 and Sotrovimab to the subject.
124. The method of any one of embodiments 98-122, comprising administering an effective amount of a combination of AB-1 and Bebtelovimab to the subject.
125. The method of any one of embodiments 98-122, comprising administering an effective amount of a combination of AB-1 and Evusheld to the subject.
126. The method of any one of embodiments 98-122, comprising administering an effective amount of a combination of AB-1 and AZD-1061 to the subject.
127. The method of any one of embodiments 98-122, comprising administering an effective amount of a combination of AB-1 and P2G3 to the subject.
128. The method of any one of embodiments 98-122, comprising administering an effective amount of a combination of AB-1 and RBD Class 4 mAb-1a to the subject.

EXEMPLIFICATION

Example 1. Materials and Methods

Binding Assay (DELFIA)

Polystyrene MaxiSorp plates (ThermoFisher, Waltham, MA, Cat #460372) were coated with phosphate buffered saline (PBS)-diluted Spike proteins at 5 µg/ml, and incubated overnight at 4° C. Plates were washed with the Tris-buffered saline Tween® 20 buffer (TBS-T) (ThermoFisher, Waltham, MA, Cat #28360) and blocked with an assay diluent (BioLegend, San Diego, CA, Cat #421205) for 1 hour at room temperature. Serial dilutions (1:4) of the antibodies were made in PBS/bovine serum albumin (BSA) starting from 4.5 µg/ml. After one wash with TBS-T, the serially diluted antibodies were transferred to the pre-coated plates and incubated for 1 hour at room temperature. Next, the plates were washed 3 times with TBS-T, and a Europium-labeled secondary antibody (PerkinElmer, Waltham, MA, Cat #1244-330) was added for 30 minutes at room temperature. Following the incubation, the plates were washed 3 times in TBS-T, and an enhancement solution (PerkinElmer, Waltham, MA, Cat #4001-0010) was applied. Time-resolved fluorescence was read at 615 nm with the EnVision plate reader (PerkinElmer, Waltham, MA).

Pseudovirus Neutralization Assay

For pseudovirus neutralization, Vero-TMPRSS2 cells were plated in tissue culture treated 384-well plate (ThermoFisher, Waltham, MA, Cat #164610) at density of $3.5 \times 10^3$ cells/per well in volume of 20 µl. Plates were briefly spun down at <50 g and incubated at 37° C., 5% $CO_2$ for 2-4 hours. To generate 5-, 10- or 12-point titration curves, the antibodies were 3-, 4- or 6-fold serially diluted in PBS/0.2% BSA/1× Penicillin-Streptomycin (Pen-Strep) buffer, starting from 72 µg/ml or 18 µg/ml (4× final concentration), in round bottom 96-well plates (ThermoFisher, Waltham, MA, Cat #268200). The antibodies were mixed with equal volumes of diluted SARS-CoV-2 pseudoviruses (lentiviruses pseudo-typed with SARS-CoV-2 Delta, BA.1, SARS-CoV-1 or WIV1 Spike, and VSV-dG pseudotyped with SARS-CoV-2 D614G, Delta, BA.2, BA.2.12.1, BA.4/5, BA.4/5+K444T, BQ.1, BQ.1.1, XBB.1.5, SARS-CoV-1 or WIV1 Spike). Antibody-virus mixtures were incubated at 37 C, 5% $CO_2$ for 30-60 minutes. 20 µl of antibody-virus mixture was then transferred to 384 well plates pre-seeded with Vero-TMPRSS2 cells. The 384-well plates were briefly spun down at <50 g and incubated at 37° C., 5% $CO_2$ for 24 (VSV-dG) or 72 (lentiviruses) hours. At the end of incubation, 40 µl of luciferase detection buffer (BPS Bioscience ONE-Step™ Luciferase Assay System, BPS Bioscience, San Diego, CA Cat #60690-3) was added to each well of the cell culture plates. The plates were centrifuged for <5 seconds at 50 g, incubated for 15 minutes with gentle rocking. The luminescence signals were recorded with an Envision plate reader. The results were expressed as percentage neutralization and analyzed with Prism 9. The curves were generated by fitting the data using the following equation: Log(inhibitor) vs normalized response-variable slope (four parameters).

In Vivo SARS-CoV-2 Infection

In vivo experiments were performed at Bioqual. Male hamsters were injected intraperitoneally with the indicated antibodies (variable regions [VH/VL] expressed as human IgG1 [huIgG1] or hamster IgG2a [hamIgG2a]) one day before intranasal inoculation of SARS-CoV-2 Delta. Weights were recorded daily up to day 7 and reported as percentage change over day 0 weights. On day 7, the hamsters were sacrificed, their lungs were collected, and their weights were recorded. Viral titers in nares and lungs (day 4 post-infection) were recorded, and lung histopathology (day 7 post-infection) was performed.

Live Virus Neutralization Assay

Live virus neutralization assays were performed at Virology Research Services. SARS-CoV-2 Delta, BA.1 or BA.5 live viruses were incubated with a 3-fold or a 4-fold serial dilution of each antibody for 1 hour, after which the mix were added to Vero cells. Antiviral activity was determined 6 hours later using an immunofluorescence-based assay. The results were expressed as percentage neutralization and analyzed with Prism 9. The curves were generated by fitting the data using the following equation: Log(inhibitor) vs normalized response-variable slope (four parameters).

Example 2. Generating and Characterizing S2-Binding Polypeptides

The S2 domain of the SARS-CoV-2 Spike protein contains the fusion machinery and comprises sequences that are conserved across SARS-CoV-2 variants and the entire sarbecovirus subgenus as well. One of this sequence is the stem helix peptide targeted by antibodies with neutralizing activity that nevertheless show low neutralization potency in vitro and efficacy at a relatively high dose in in vivo models of SARS-CoV-2 infection. Of note, these antibodies bind the stem helix peptide from different angles therefore providing the opportunity to probe the impact of both sequence variation and binding pose on antibody function.

The generation campaign chose a human IgG1 antibody isolated from a convalescent donor and targeting the stem helix peptide targeted by the Reference Antibody. The target epitope of the Reference Antibody is highly conversed across the SARS-CoV-2 genomes sequenced so far, with mutations appearing at very low frequencies (the most frequent mutations over the past 3 months were P1162L and P1162S, and they were detected only in 0.4% and 0.2% of SARS-CoV-2 genome sequences respectively). A variant set of 182 antibodies was generated, and the following datasets were acquired: (1) developability: PSR, AC-SINS, SEC; (2) binding of Spike proteins: SARS-CoV-2-related viruses (Delta, BA.1, BA.2), SARS-CoV-1-related viruses (SARS-CoV-1, WIV1); and (3) neutralization of pseudotyped viruses: SARS-CoV-2-related viruses (Delta, BA.2), SARS-CoV-1-related viruses (SARS-CoV-1, WIV1).

Figure 4A:
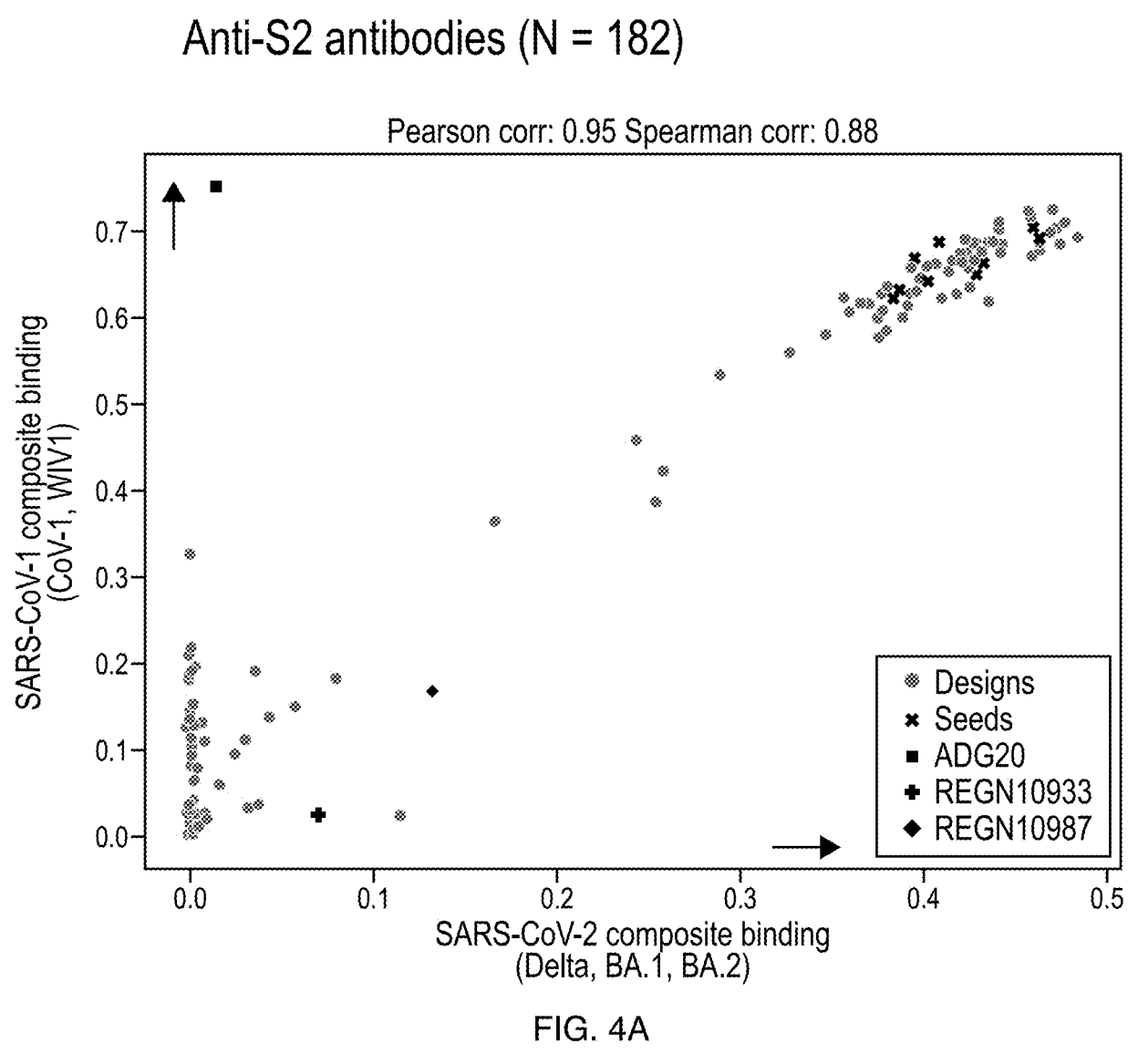
Figure 4B:
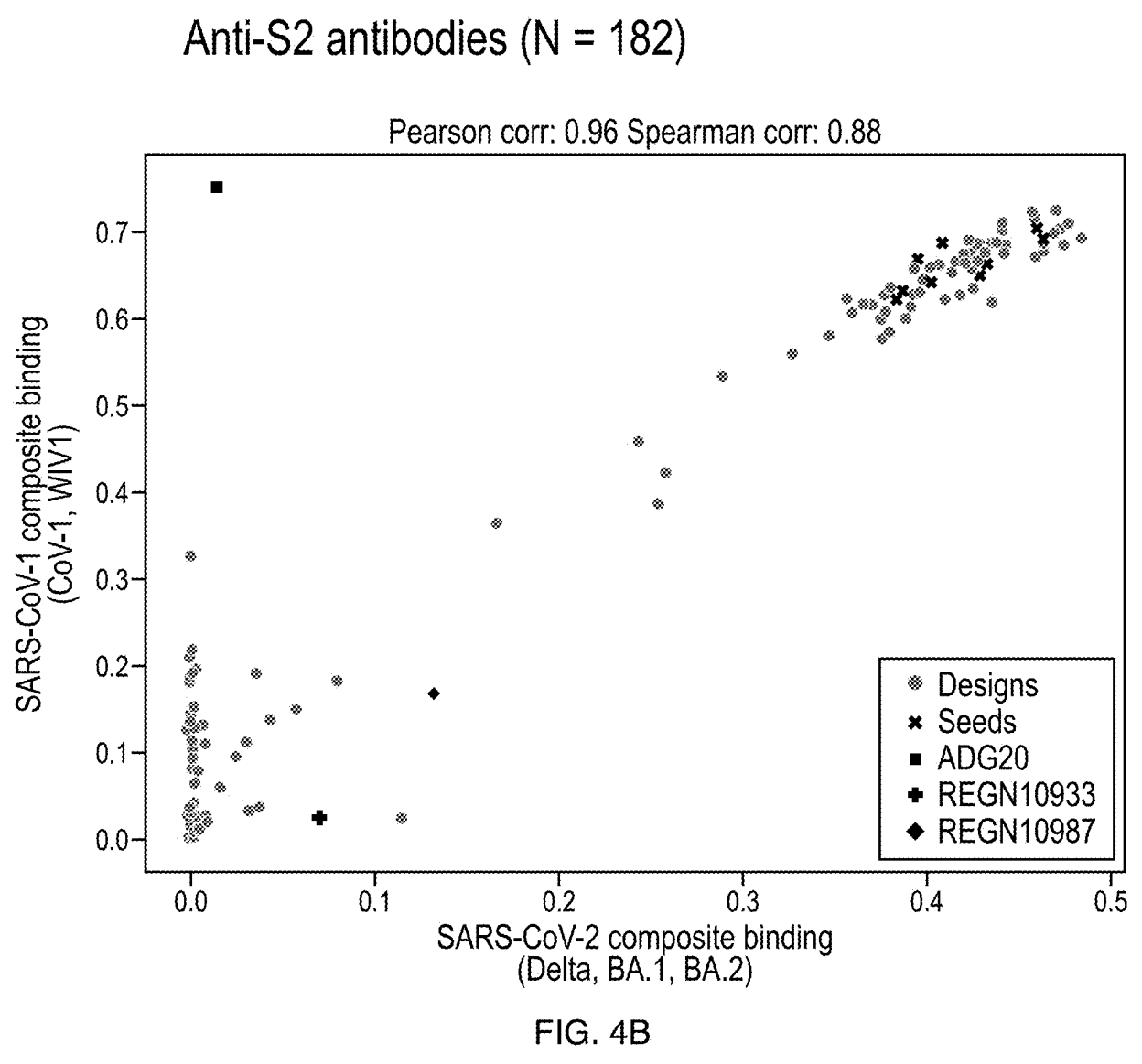
Figure 5B:
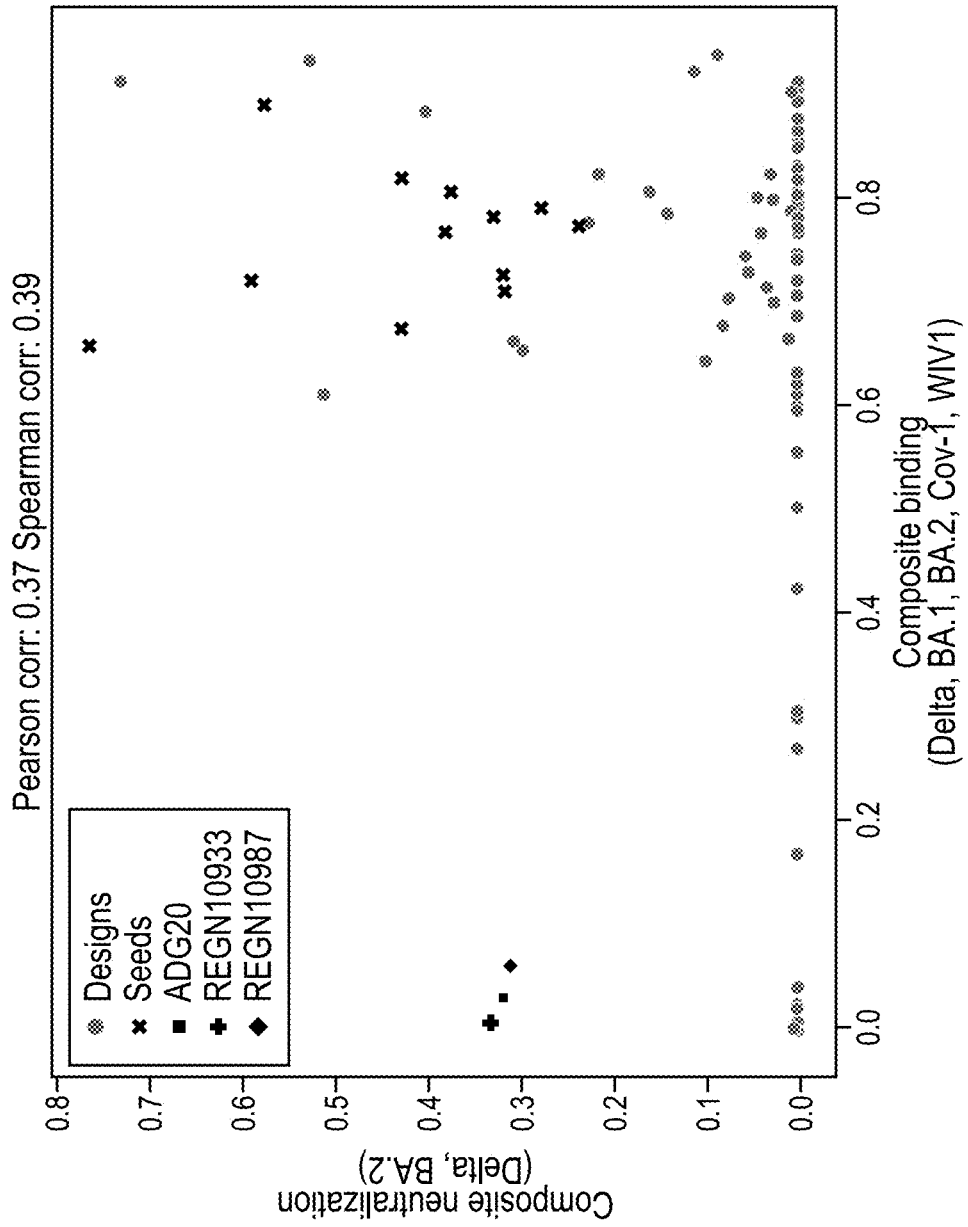
Figure 21:
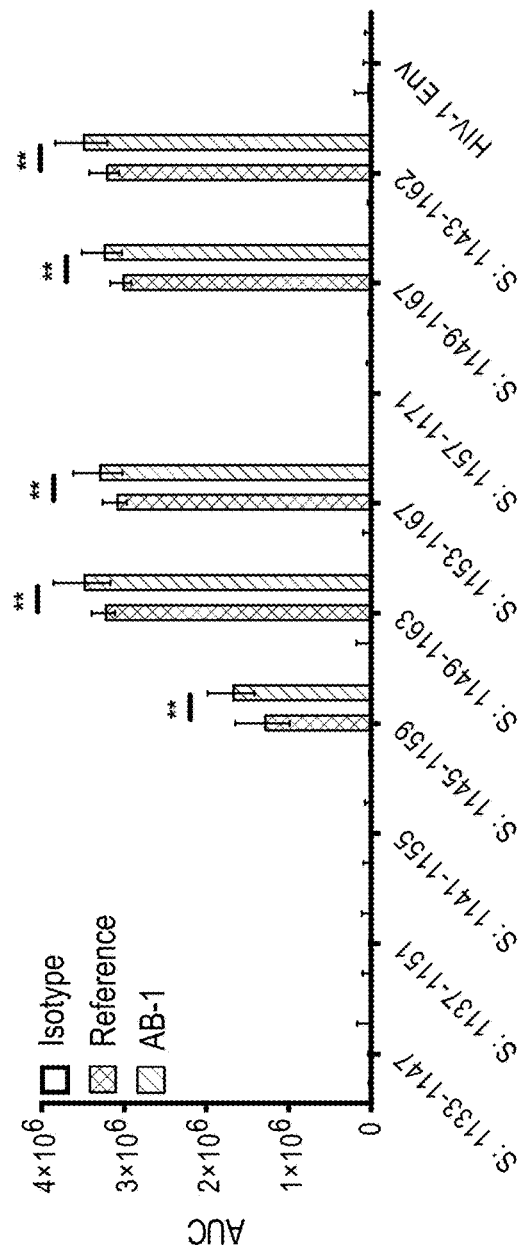
FIG. 21. Binding of AB-1 and the Reference Antibody to SARS-CoV-2 spike S2 peptides by DELFIA. Binding of AB-1, the Reference Antibody and isotype control to SARS-CoV-2 spike S2 peptides (indicated as "S:" followed by amino acid positions) and HIV-1 Env negative control peptide was assessed by DELFIA. Results are expressed as AUC values and shown as bars representing mean±standard deviation (representative of two independent experiments, three technical replicates each). Statistical comparisons between AB-1 and the Reference Antibody AUC values were performed with 2-way ANOVA corrected for multiple comparisons (** indicates P≤0.01).

Many generated antibodies bound Spike proteins of SARS-CoV-1- and SARS-CoV-2-related viruses with high affinity (FIGS. 4A-4B), and some of them also neutralized SARS-CoV-2 Delta, BA.2 (FIGS. 5A-5B), XBB.1.5, and BQ.1.1 (FIG. 21). Compared to the clinical-stage molecule, the Sotrovimab used in these experiments does not have the LS mutation and has 3 additional amino acid mutations due to a differential use of the IgG allele. ADG20 used in these experiments has the LS mutation in the Fc region, while the clinical-stage molecule has the LA mutation.

Binding and neutralization data were combined in a composite fitness score to rank-order the top 20 screening hits. Then 12 molecules with acceptable developability parameters (AC-SINS<20, SEC>90%, PSR<10) were further down-selected as seeds for the next round of project learning. Of note, the Reference Antibody expresses 6 sequence liabilities (4, if the 2 cysteines were not considered since they form a bond) posing low-to-moderate risk for process development, and some of the seeds already show a reduced number of liabilities. As part of our project learning campaign, the aim was to improve antibody function and further reduce the number of sequence liabilities.

Figure 7A:
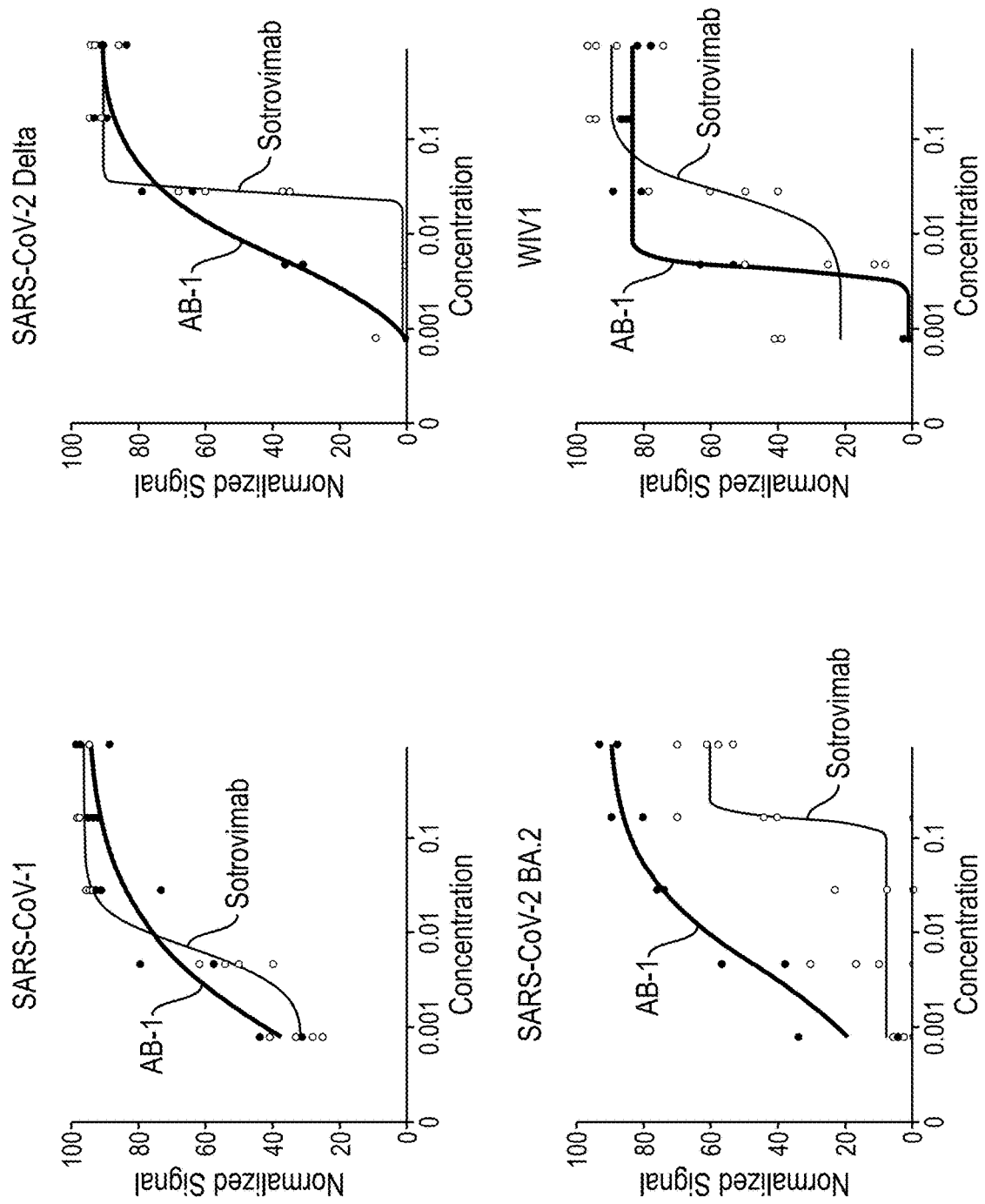
FIGS. 7A-7B show neutralization curves of AB-1 and the clinical-stage control antibody Sotrovimab for the indicated pseudoviruses. Y-axis, % neutralization. X-axis, antibody concentration expressed as µg/ml.
Figure 7B:
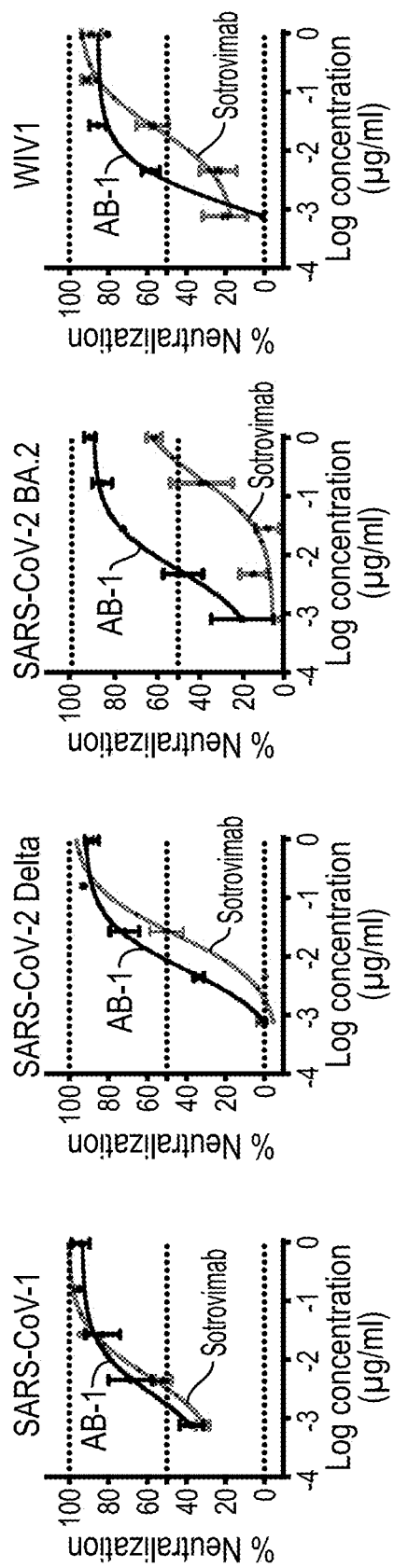

A handful of seeds also showed promising characteristics as lead molecules. AB-1 potently neutralized past (SARS-CoV-1), present (SARS-CoV-2 Delta, BA.2) and potentially emergent (WIV1) sarbecoviruses (FIGS. 6A-6B), is 4 mutations away from the Reference Antibody and has only 1 sequence liability outside of the 2 cysteines. AB-2 is less potent than AB-1 (FIGS. 7A-7B) but is 7 mutations away from the Reference Antibody, has optimal AC-SINS (<10) and no liabilities outside of the 2 cysteines.

Figure 8A:
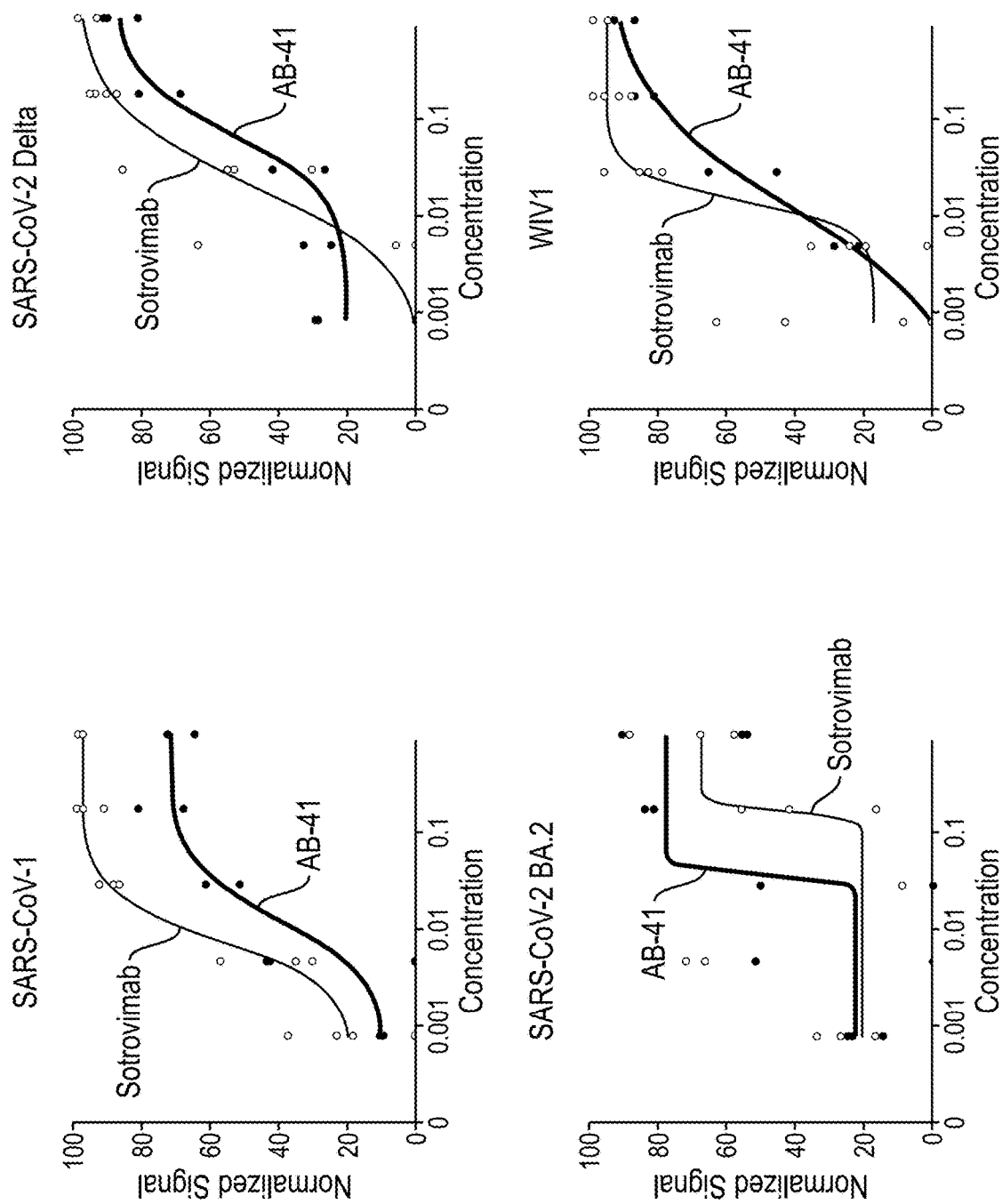
FIGS. 8A-8B show neutralization curves of AB-41 and the clinical-stage control antibody Sotrovimab for the indicated pseudoviruses. Y-axis, % neutralization. X-axis, antibody concentration expressed as µg/ml.
Figure 8B:
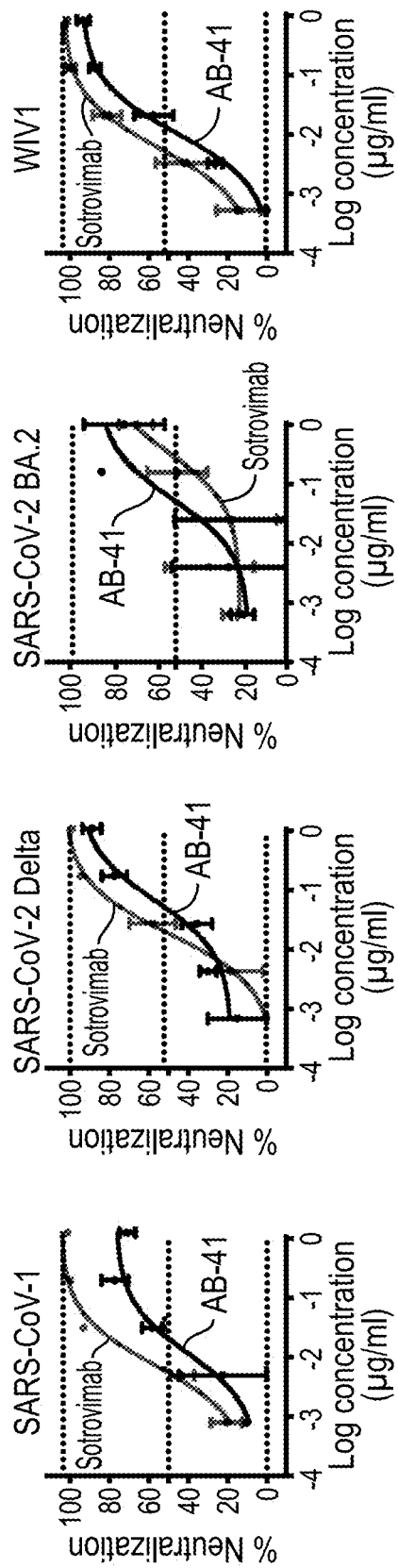
Figure 9A:
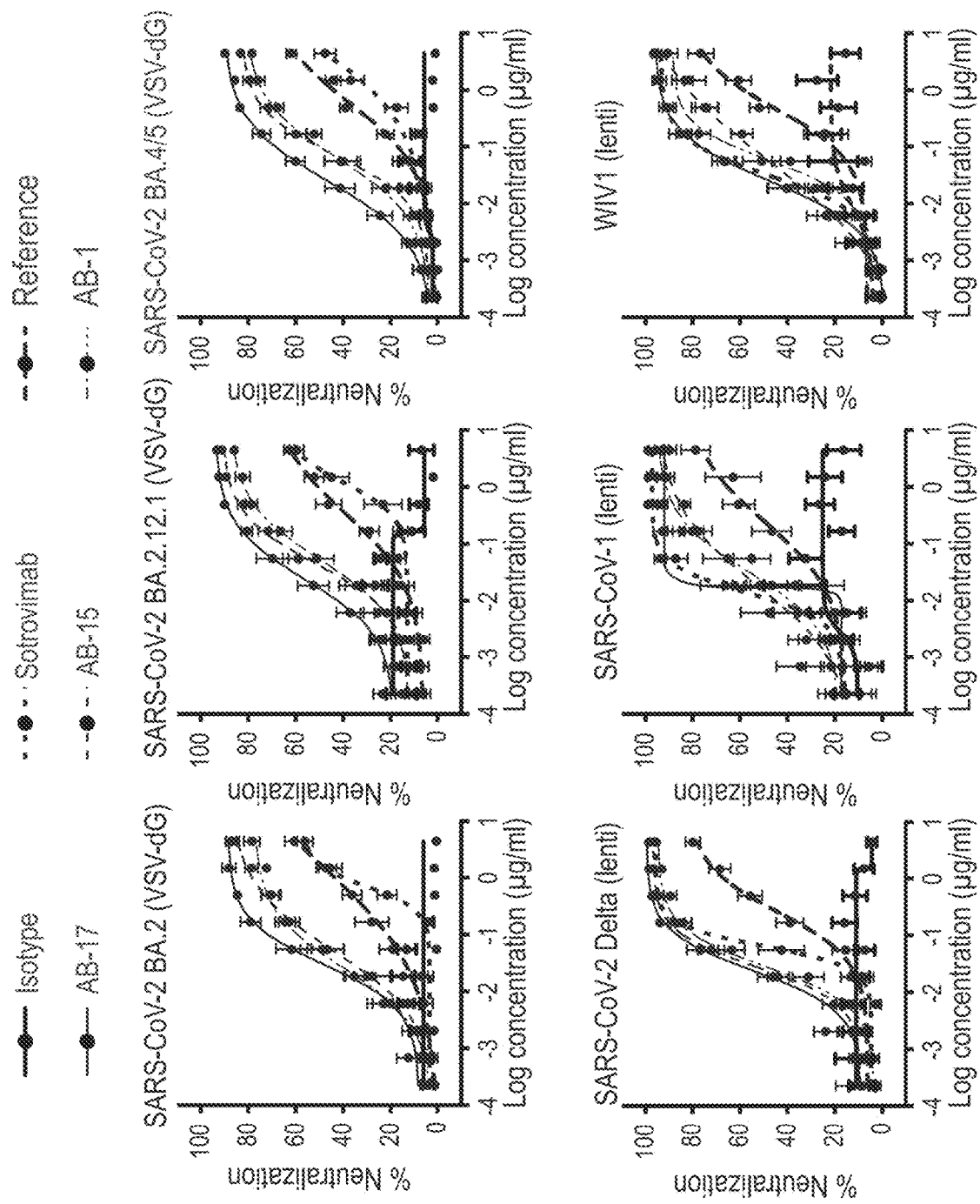
FIGS. 9A-9B show neutralization curves of AB-17, AB-15, AB-1, and Reference Antibody from high-throughput production, and the clinical-stage control antibody Sotrovimab for the indicated pseudoviruses. Y-axis, % neutralization. X-axis, antibody concentration expressed as µg/ml.
Figure 9B:
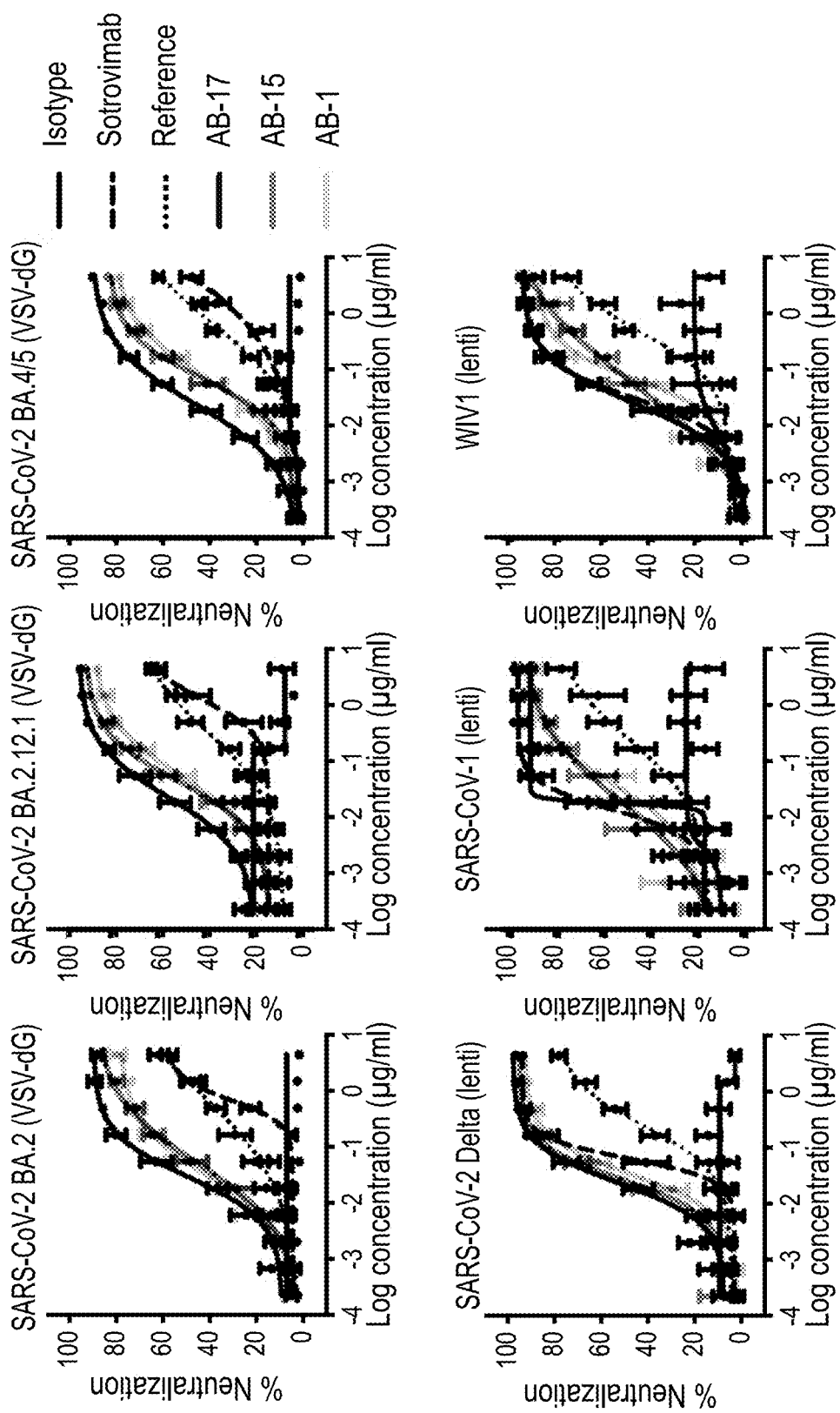

Seed molecules identified by screening this variant set such as the ones indicated in FIGS. 6 and 7 were used to generate a new variant set of 364 antibodies, and the following datasets were acquired as part of the screening campaign: (1) developability: PSR, AC-SINS, SEC; (2) binding of Spike proteins: SARS-CoV-2-related viruses (Delta, BA.1, BA.2), SARS-CoV-1-related viruses (SARS-CoV-1, WIV1); and (3) neutralization of pseudotyped viruses: SARS-CoV-2-related viruses (Delta, BA.2). Antibodies were ranked based on composite neutralization score, and the top 20 were selected (FIGS. 8A-8B). Among these, 3 antibodies (AB-17, AB-15 and AB-1) were further down selected based on optimal binding, neutralization and developability profiles (FIGS. 9A-9B and Table 4). These antibodies were then tested in additional neutralization assays (SARS-CoV-2 BA.2, BA.2.12.1 and BA.4/5 VSV-dG; SARS-CoV-2 Delta, SARS-CoV-1 and WIV1 pseudotyped lentiviruses) and benchmarked against the Reference Antibody (Reference Ab) and Sotrovimab (Synagis was used as isotype control) (FIGS. 9A-9B and Table 4). AB-17, AB-15 and AB-1 exhibited increased neutralization potency and efficacy compared to the Reference Antibody across all neutralization assays. They also showed neutralization activities greater than (SARS-CoV-2 BA.2, BA.2.12.1 and BA.4/5 VSV-dG) or comparable to (SARS-CoV-2 Delta, SARS-CoV-1 and WIV1) Sotrovimab. The isotype control was inactive across all the assays.

Example 3. Development Candidate Selection and Characterization

Monoclonal antibodies (mAbs) targeting the Spike protein of SARS-CoV-2 have proved effective for the prophylaxis and treatment of COVID-19. Several mAbs targeting distinct regions of the Spike protein (receptor binding domain [RBD], N-terminal domain [NTD], S2) have been characterized to date, and some anti-RBD mAbs have received emergency use authorization over the past two years based on the ability to neutralize circulating SARS-CoV-2 variants in vitro and in vivo. However, SARS-CoV-2 variants have accrued several mutations in the RBD leading to escape from many mAbs. Therefore, there is a need to develop mAbs targeting conserved regions of the Spike protein with robust neutralizing activity against multiple SARS-CoV-2 variants.

The S2 domain contains highly conserved epitopes, namely the fusion peptide and the stem helix peptide. Antibodies targeting these epitopes have been isolated from convalescent/vaccinated donors and immunized animals and show neutralizing activities albeit with low potencies. However, if an anti-S2 neutralizing antibody with sufficient potency were to be found, it would be potentially very valuable due to the broad conservation of the S2 epitopes across coronaviruses. The Reference Antibody is a human IgG1 anti-S2 antibody isolated from a convalescent donor and showed neutralization of coronaviruses of the Sarbecovirus subgenus with promising neutralization potencies (Li et al., *Structural Basis and Mode of Action for Two Broadly Neutralizing Antibodies Against SARS-CoV-2 Emerging Variants of Concern*, Cell Reports 38(2):110210 (2021)). The binding mode was known from a co-crystal structure with the stem helix peptide. In addition, the target epitope of Reference Antibody is highly conversed across the SARS-CoV-2 genomes sequenced so far, with only two mutations occurring at position P1162 at very low frequencies (P1162L and P1162S, respectively 0.4% and 0.2% of SARS-CoV-2 genomes sequences over the last 3 months). It was hypothesized that by exploring the antibody sequence space compatible with this binding mode, it may be possible to identify sequences with improved neutralization potencies compared to the Reference Antibody.

Novel anti-S2 stem helix binders were generated using an in-house computational protein design protocol. Beginning with the co-crystal structure of Reference Antibody bound to the S2 stem helix peptide, an in-house machine-learning (ML) model was used to predict the sequence landscape compatible with the binding conformation (Ingraham et al., *Generative models for graph-based protein design*, 33rd Conference on Neural Information Processing Systems (NeurIPS 2019), Vancouver, Canada; Zhou et al., *A general-purpose protein design framework based on mining sequence-structure relationships in known protein struc-*

*tures*, Proc Natl Acad Sci USA. 117(2):1059-68 (2020)), from which 182 diverse sequences were sampled for experimental testing.

To test these designs, the antibody variants were generated in a human IgG1 format and screened for function (pseudovirus neutralization), affinity (Sarbecovirus Spike protein binding estimated with DELFIA), and developability properties (self-association propensity [AC-SINS], monomericity [aSEC], and polyspecific reactivity [PSR]). Pseudovirus neutralization of SARS-CoV-2 variants Delta, BA.1, BA.2 as well as SARS-CoV-1 and WIV1 was measured across five different titration concentrations. Affinities to Spike proteins of SARS-CoV-1, WIV1, and SARS-CoV-2 variants Delta, BA.1, and BA.2 were measured across eight different titration concentrations. Based on these experiments, a subset of antibodies with promising neutralization and binding profiles were identified.

To further improve the neutralization potency of candidate sequences, a second round of computational design was performed. Here, experimental measurements were used to train models that predicted potency and affinity from sequence. Using the resulting models, predicted potency and affinity were then co-optimized in the context of the sequence landscape described above to produce a set of 364 second-round sequences.

After experimental characterization of all antibody variants, the lead antibody sequences were selected based on function, binding, and developability properties as measured across 533 unique sequences generated from the two rounds of sequence design.

Figure 10A:
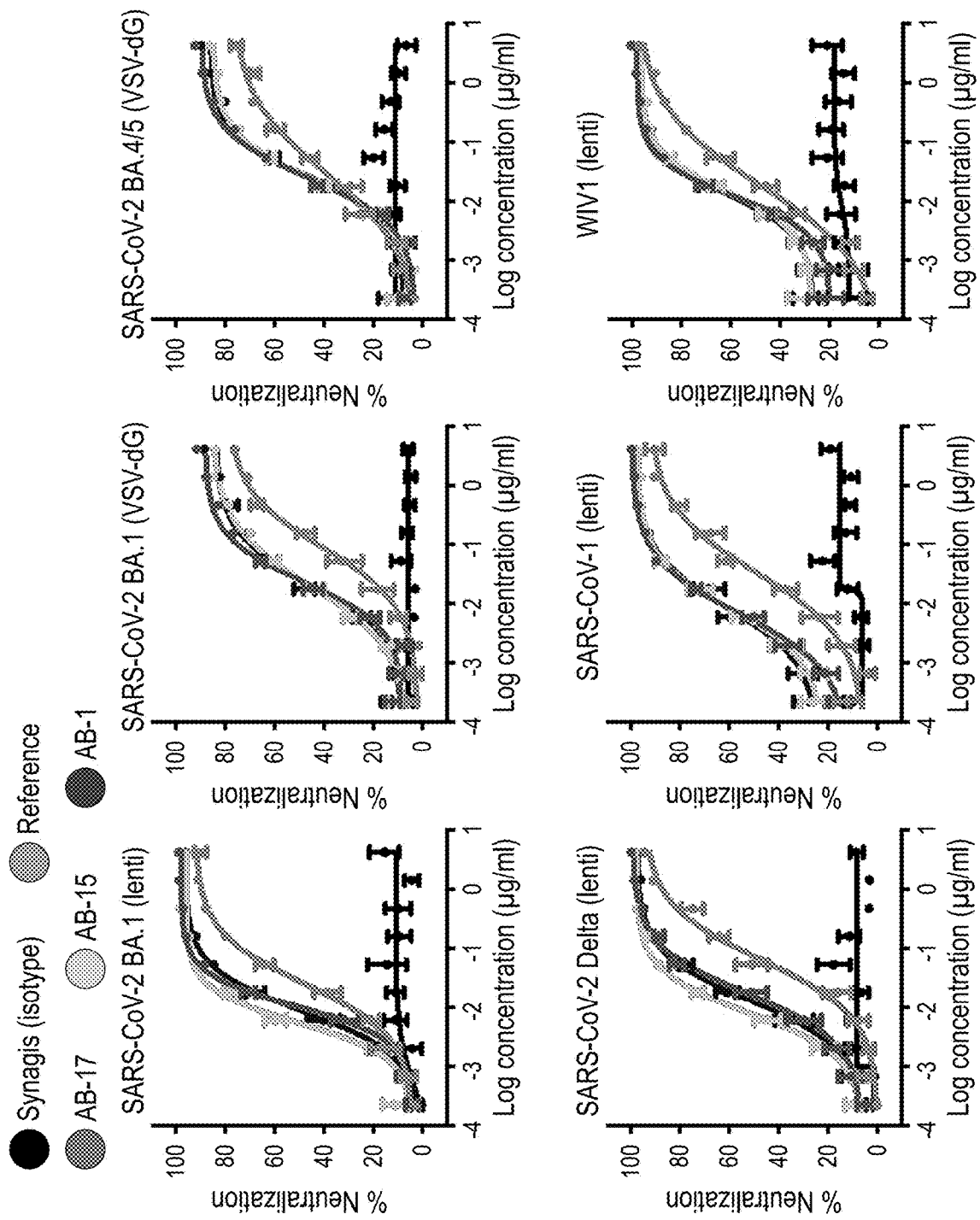
FIGS. 10A-10B. The three lead molecules show robust and comparable neutralization of multiple pseudoviruses. Neutralization experiments were performed with the indicated pseudoviruses and the following antibodies: isotype control (Synagis), the Reference Antibody, clinical-stage controls (a human IgG1 molecule expressing the same variable regions of Sotrovimab, the two antibodies that compose Evusheld [AZD1061 and AZD8895]), leads molecules (AB-1, AB-17, AB-15) from large scale production. Results are representative of at least 8 technical replicates across at least 2 biological replicates and shown as mean±SEM.
Figure 10B:
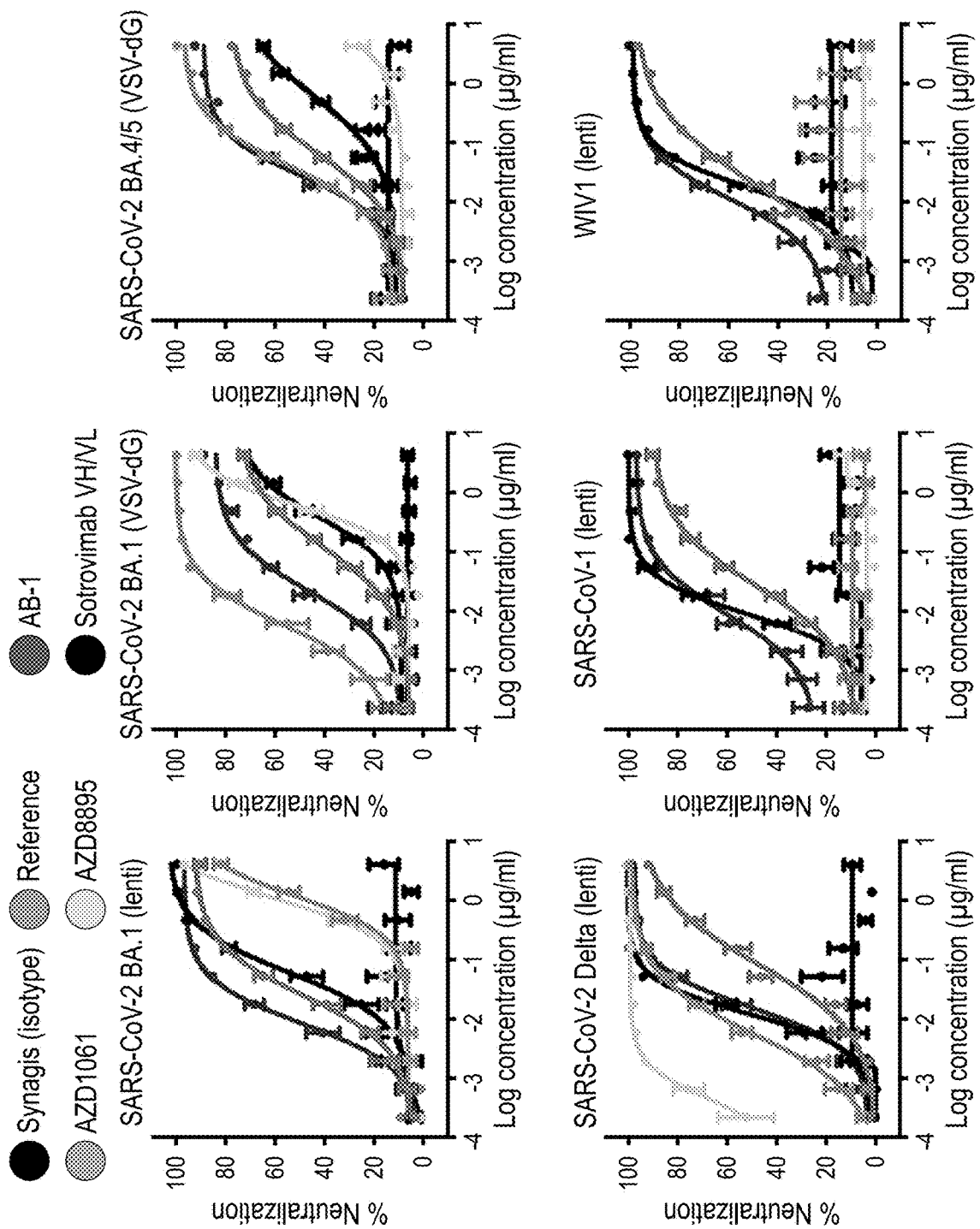
Figure 11:
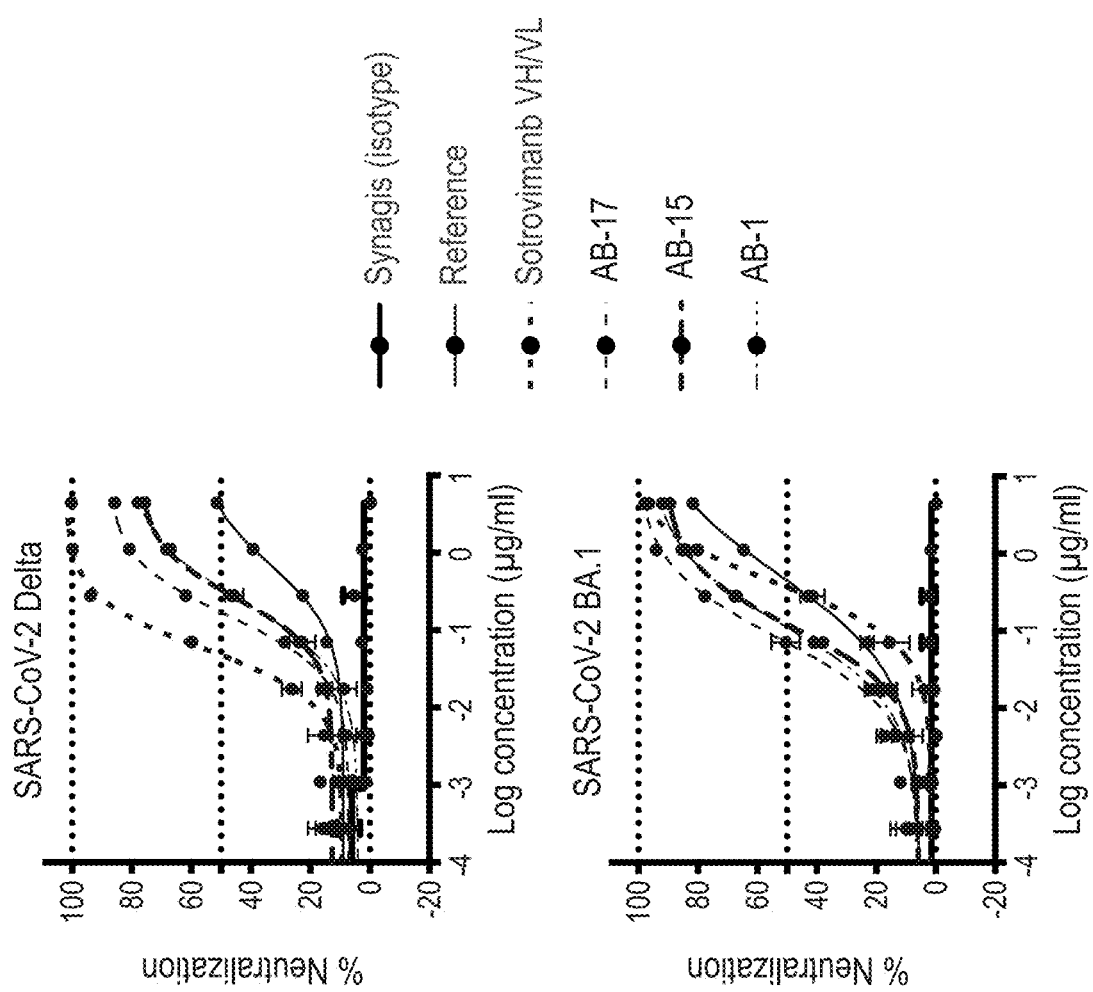
FIG. 11 are graphs showing that AB-1, AB-17, and AB-15 neutralize live viruses. Neutralization experiments were performed with the indicated live viruses and the following antibodies: isotype control (Synagis), the Reference Antibody, clinical-stage controls (a human IgG1 molecule expressing the same variable regions of Sotrovimab, AB-1, AB-17, AB-15. Results are representative of 3 replicates and shown as mean±SEM.

Based on the screening data, three lead molecules with optimal functional profiles were selected: AB-1, AB-17 and AB-15 that respectively exhibited 4, 8 and 5 mutations compared to the Reference Antibody. These molecules were tested against a panel of pseudoviruses representative of SARS-CoV-2 variants (Delta, Omicron BA.1, BA.2, BA.2.12.1 and BA.4/5) and other sarbecoviruses (SARS-CoV-1, WIV1) along with an isotype control (Synagis), the Reference Antibody, and clinical-stage benchmarks (an IgG1 molecule expressing the variable region of Sotrovimab and the two molecules that compose Evusheld [AZD8895, AZD1061]) (FIGS. 10A-10B). The three lead molecules exhibited comparable neutralization profiles across all pseudoviruses and overall improved neutralization potencies (as measured by $IC_{50}$) and/or efficacies (maximum neutralization) compared to the Reference Antibody. Interestingly, the three lead molecules showed improved neutralization potencies and efficacies against BA.2 sublineages (BA.2, BA.2.12.1, BA.4/5) compared to Sotrovimab, and BA.4/5 neutralization profiles comparable to AZD1061 (FIGS. 10A-10B, Tables 5 and 6). Preliminary experiments with live viruses also confirmed neutralization of SARS-CoV-2 Delta and Omicron BA.1 by the three lead molecules (FIG. 11, Table 7).

FDA factsheets of clinical-stage antibodies report that when ratios between neutralization potencies against two viruses are <5, then those neutralization profiles are considered comparable. To compare neutralization potencies across experiments, neutralization potencies of the three lead molecules against each virus were expressed as ratio over neutralization potency of Sotrovimab against SARS-CoV-2 Delta. Ratios <5 were interpreted as comparable neutralization to Sotrovimab neutralization of SARS-CoV-2 Delta. This may be a relevant metric since Sotrovimab showed clinical efficacy against SARS-CoV-2 Delta and therefore a ratio <5 may indicate human efficacy for our lead molecules at Sotrovimab clinical dose (500 mg, IV). Of note, ratios calculated for the three lead molecules across all viruses were <5 confirming comparable neutralization potencies to Sotrovimab neutralization of Delta (Table 8).

Overall, the three lead candidates showed robust and comparable neutralization profiles against a range of coronaviruses. To select a development candidate out of the three lead candidates, developability parameters were assessed. AB-1 exhibited optimal PSR and acceptable AC-SISN, and therefore it was selected as development candidate (FIG. 12).

The neutralization activity of AB-1 was further validated in a hamster model of SARS-CoV-2 Delta challenge. For these in vivo experiments variable regions ($V_H/V_L$) of AB-1, isotype (Synagis) and clinical-stage (Sotrovimab) controls were expressed as human IgG1 (huIgG1, FIGS. 15A-15D) and hamster IgG2a (hamIgG2a, FIGS. 15E-15H) to account for interaction with hamster Fcγ receptors. Hamsters were injected with the indicated antibodies one day before infection with SARS-CoV-2 Delta. Body weights were recorded daily and expressed as percentage change over day 0 (pre-infection) body weights. On day 7, the hamsters were sacrificed, their lungs were collected, and their weights were recorded (as proxy for lung inflammation). AB-1 expressed as human IgG1 or hamster IgG2a protected from weight loss in a dose-dependent manner (FIGS. 15A-B & E-F), and these results correlated with a reduction in lung weights (FIGS. 15C & G).

Figures 16A, 16B, 16C, 16D:
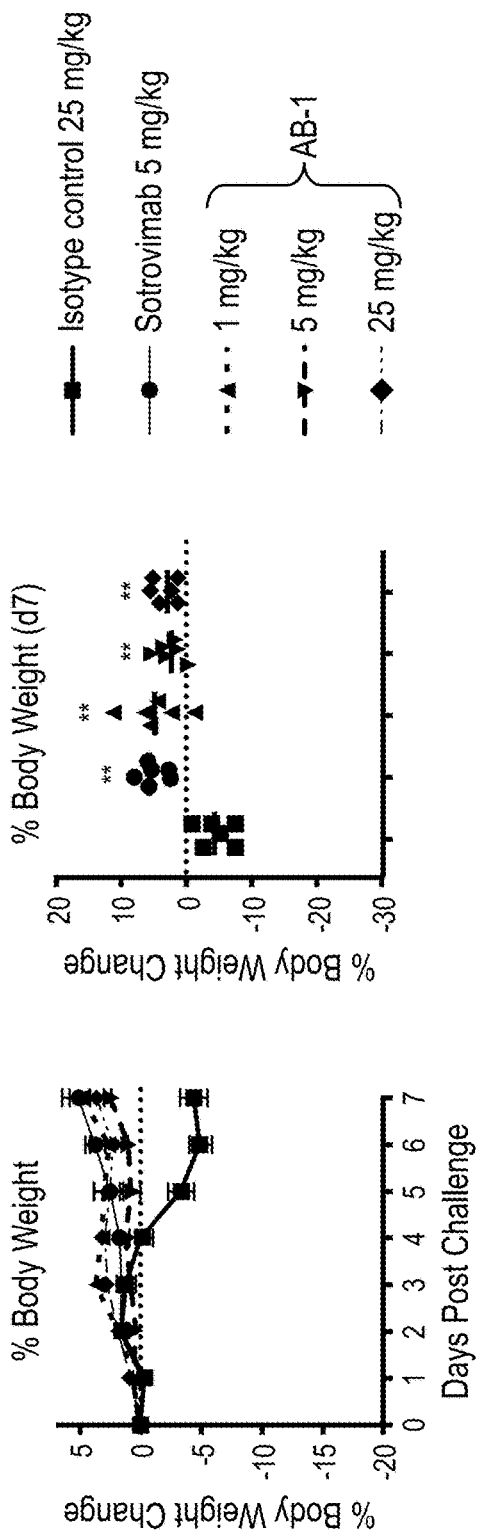
FIGS. 16A-16D are graphs showing that AB-1 protects against SARS-CoV-2 Omicron BA.2 infection in hamsters. A hamster study with prophylactic administration (day-1) of AB-1 expressed as hamster IgG2a and challenged with SARS-CoV-2 Omicron BA.2 (day 0). AB-1 shows dose-dependent protection against Omicron BA.2-induced weight loss (FIGS. 16A-16B), dose-dependent protection against Omicron BA.2-induced increase in lung weight (a proxy for lung inflammation, FIG. 16C), and effects on viral titer (FIG. 16D). 16A) Hamster weights were recorded up to 7 days post-challenge and expressed as percentage change over Day 0 (pre-challenge) weights. Isotype control delivered at 25 mg/kg, Sotrovimab at 5 mg/kg. Results are shown as mean±SEM. 16B) Representations of percentage body weight change on Day 7. Each dot represents an individual hamster and horizontal lines represent median values. 16C) Lung weights on Day 7. 16D) Lung viral titers on Day 4. Each dot represents an individual hamster and horizontal lines represent median values. N=12 (day 0 to 4) or 6 (day 5 to 7) hamsters per group. Data were analyzed by one-way ANOVA corrected for multiple comparisons (Dunnett's test). Black asterisks indicate comparison to Isotype control-treated hamsters. **p<0.01.
Figure 17B:
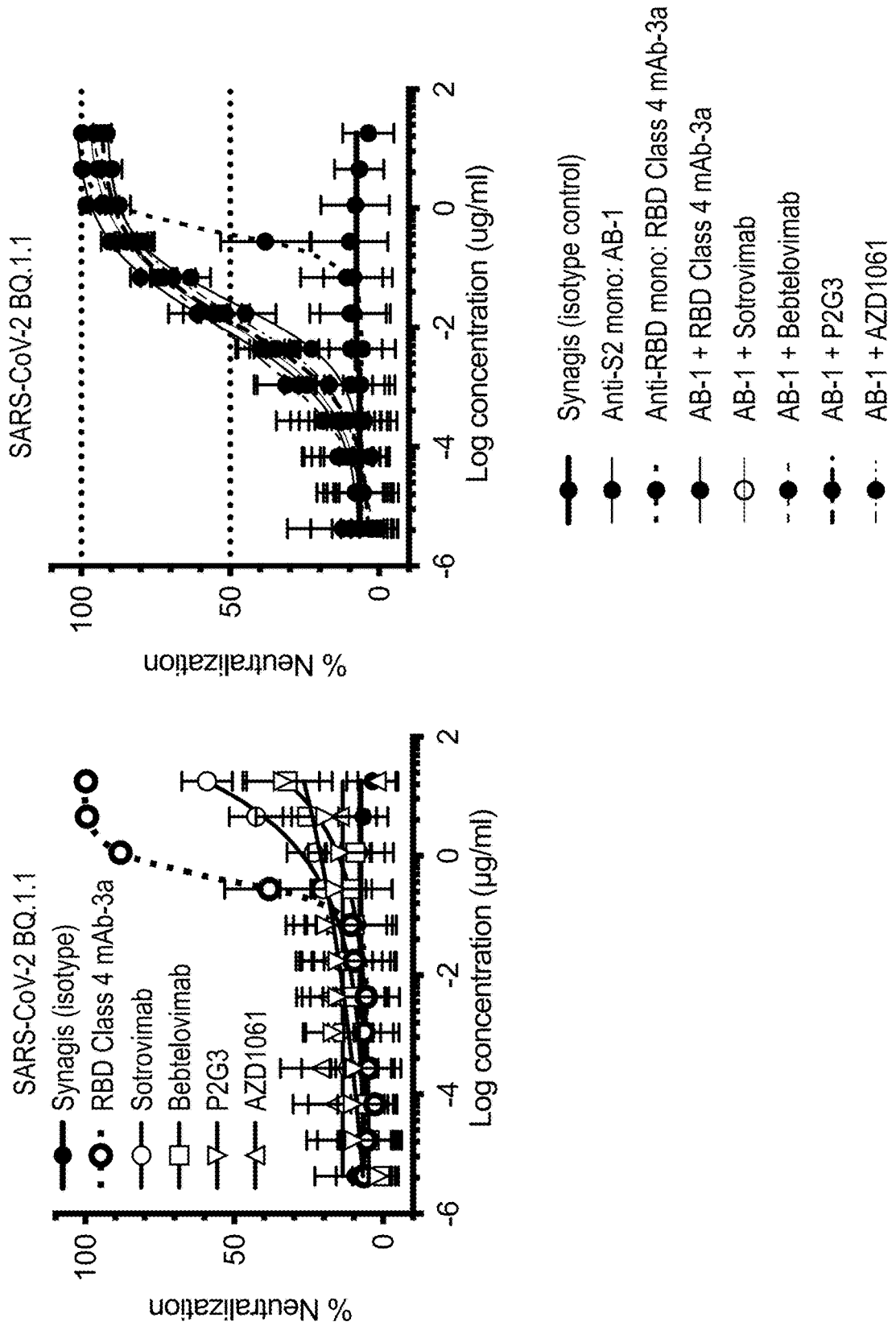
Figure 17C:
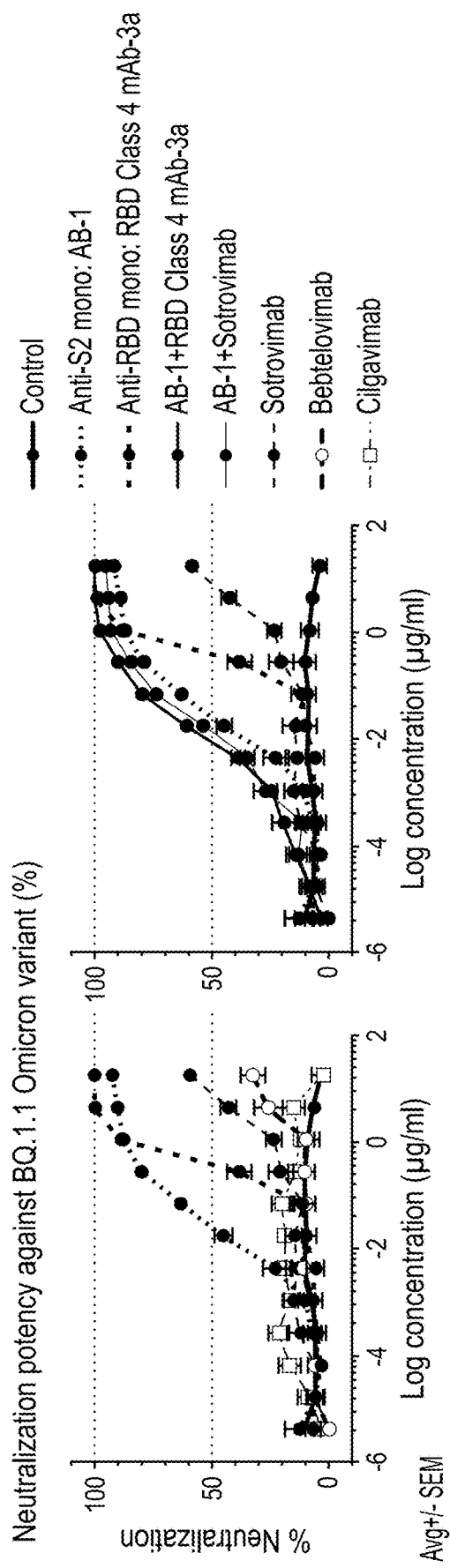
Figure 17D:
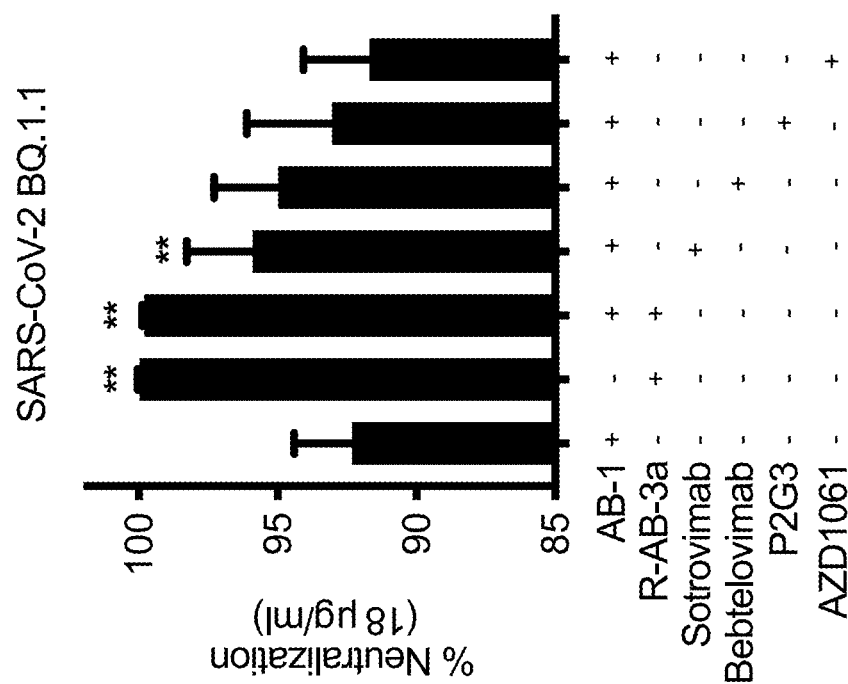

The neutralization activity of AB-1 was further validated in a hamster model of SARS-CoV-2 Omicron BA.2 challenge. For these in vivo experiments variable regions ($V_H/V_L$) of AB-1, isotype (Synagis) and clinical-stage (Sotrovimab) controls were expressed as hamster IgG2a (hamIgG2a, FIGS. 16A-16D) to account for interaction with hamster Fcγ receptors. Hamsters were injected with the indicated antibodies one day before infection with SARS-CoV-2 Omicron BA.2. Body weights were recorded daily and expressed as percentage change over day 0 (pre-infection) body weights. On day 7, the hamsters were sacrificed, their lungs were collected, and their weights were recorded (as proxy for lung inflammation). AB-1 expressed as hamster IgG2a protected from weight loss in a dose-dependent manner (FIGS. 16A-16B), and these results correlated with a reduction in lung weights (FIG. 16C). Thus, further in vivo characterization of AB-1 confirms protection from weight loss in Omicron BA.2 model of infection, and protection by measuring weight loss is not correlated to a reduction in viral load in lung FIGS. 15D & H and 16D).

FIGS. 17A-17D, 18A-18C, and 19 show that AB-1 demonstrated significant neutralization potency and efficacy against multiple variants, such as Omicron BQ.1.1, Omicron BA.5, and Delta, either alone or in combined with another antibody (e.g., a class 4 anti-RBD antibody).

Overall, these results demonstrate that AB-1 has robust neutralizing activity against SARS-CoV-2 variants in vitro and in vivo.

Recently many SARS-CoV-2 variants have emerged with marked escape from clinical-stage antibodies. Some of these variants show signs of convergent evolution such as mutations at position K444. Therefore, neutralization of BA.4/5 pseudoviruses without and with K444T mutations (BA.4/5+K444T) by AB-1 and clinical-stage antibodies Sotrovimab and Bebtelovimab was assessed. Sotrovimab poorly neutralizes both pseudoviruses, while Bebtelovimab shows marked neutralization impairment of the BA.4/5+K444T pseudovirus as measured by $IC_{50}$. AB-1 neutralization BA.4/5 and BA.4/5+K444T pseudoviruses with comparable neutralization potencies (Table 9).

Figure 13B:
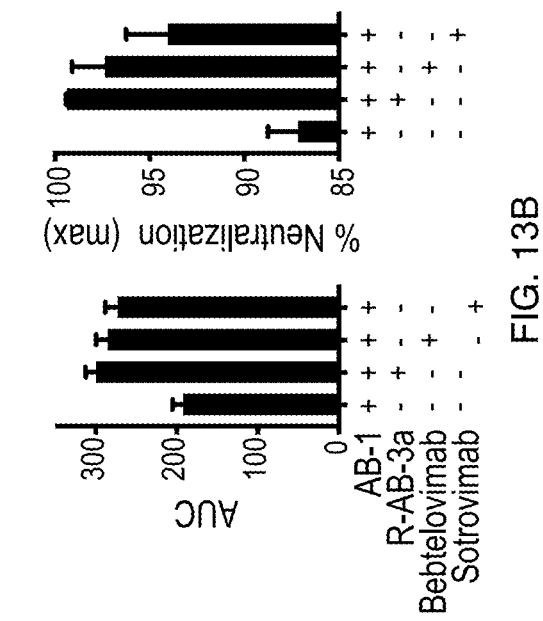
FIGS. 13A and 13B are graphs showing improvement in neutralization profiles by combining AB-1 with clinical-stage class 3 anti-RBD antibodies or a class 4 anti-RBD monoclonal antibody. Combination of AB-1 with clinical-stage class 3 anti-RBD antibodies (Sotrovimanb or Bebtelovimab) or a class 4 anti-RBD monoclonal antibody (anti-RBD4 mAb) shows enhanced neutralization profiles compared to AB-1 alone (as measured by area under the curve (AUC) and efficacy (max neutralization)).
Figure 13A:
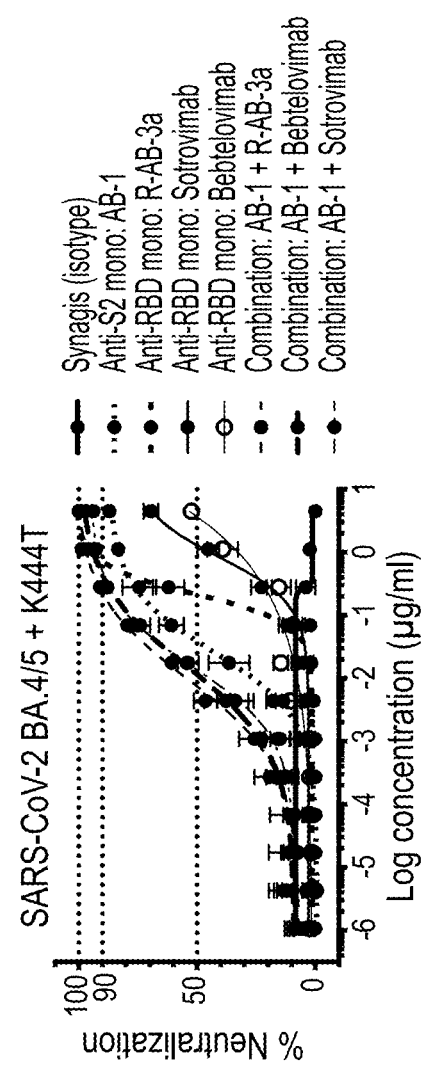
Figure 14C:

AB-1 targets the S2 stem helix epitope that does not overlap with epitopes targeted by anti-RBD antibodies. Combinations of AB-1 and clinical-stage class 3 anti-RBD antibodies (Sotrovimab, Bebtelovimab) or a class 4 anti-RBD antibody (anti-RBD4) were tested in a neutralization assay using the BA.4/5+K444T pseudovirus (which impairs neutralization activity of Sotrovimab and Bebtelovimab). All combinations show enhanced neutralization profiles compared to AB-1 alone, as assessed by AUC (area under the curve) and efficacy (% neutralization at max concentration) (FIGS. 13A-13B).

Example 4. Pseudovirus Neutralization Assay

Vero-TMPRSS2 cells were plated in tissue culture treated 384-well plate (ThermoFisher, Waltham, MA, Cat #164610) at density of $3.5 \times 10^3$ cells/per well in volume of 20 µl. Plates were briefly spun down for <5 seconds at 50 g and incubated at 37° C., 5% $CO_2$ for 2-4 hours. To generate 12-point titration curves, the antibodies (alone or in combinations) were 4-fold serially diluted in PBS/0.2% BSA/1× Penicillin-Streptomycin (Pen-Strep) buffer, starting from 72 µg/ml (4× final concentration), in round bottom 96-well plates (ThermoFisher, Waltham, MA, Cat #268200). The antibodies were mixed with equal volumes of diluted SARS-CoV-2 pseudoviruses (VSV-dG pseudotyped with SARS-CoV-2 BQ.1.1 Spike). Antibody-virus mixtures were incubated at 37C, 5% $CO_2$ for 30-60 minutes. 20 µl of antibody-virus mixture was then transferred to 384-well plates pre-seeded with Vero-TMPRSS2 cells. The 384-well plates were briefly spun down for <5 seconds at 50 g and incubated at 37° C., 5% $CO_2$ for 24 hours. At the end of incubation, 40 µl of luciferase detection buffer (BPS Bioscience ONE-Step™ Luciferase Assay System, BPS Bioscience, San Diego, CA Cat #60690-3) was added to each well of the cell culture plates. The plates were centrifuged for <5 seconds at 50 g, incubated for 15 minutes with gentle rocking. The luminescence signals were recorded with an Envision plate reader. The results were expressed as percentage neutralization and analyzed with Prism 9. The curves were generated by fitting the data using the following equation: Log(inhibitor) vs normalized response-variable slope (four parameters).

Figure 19:
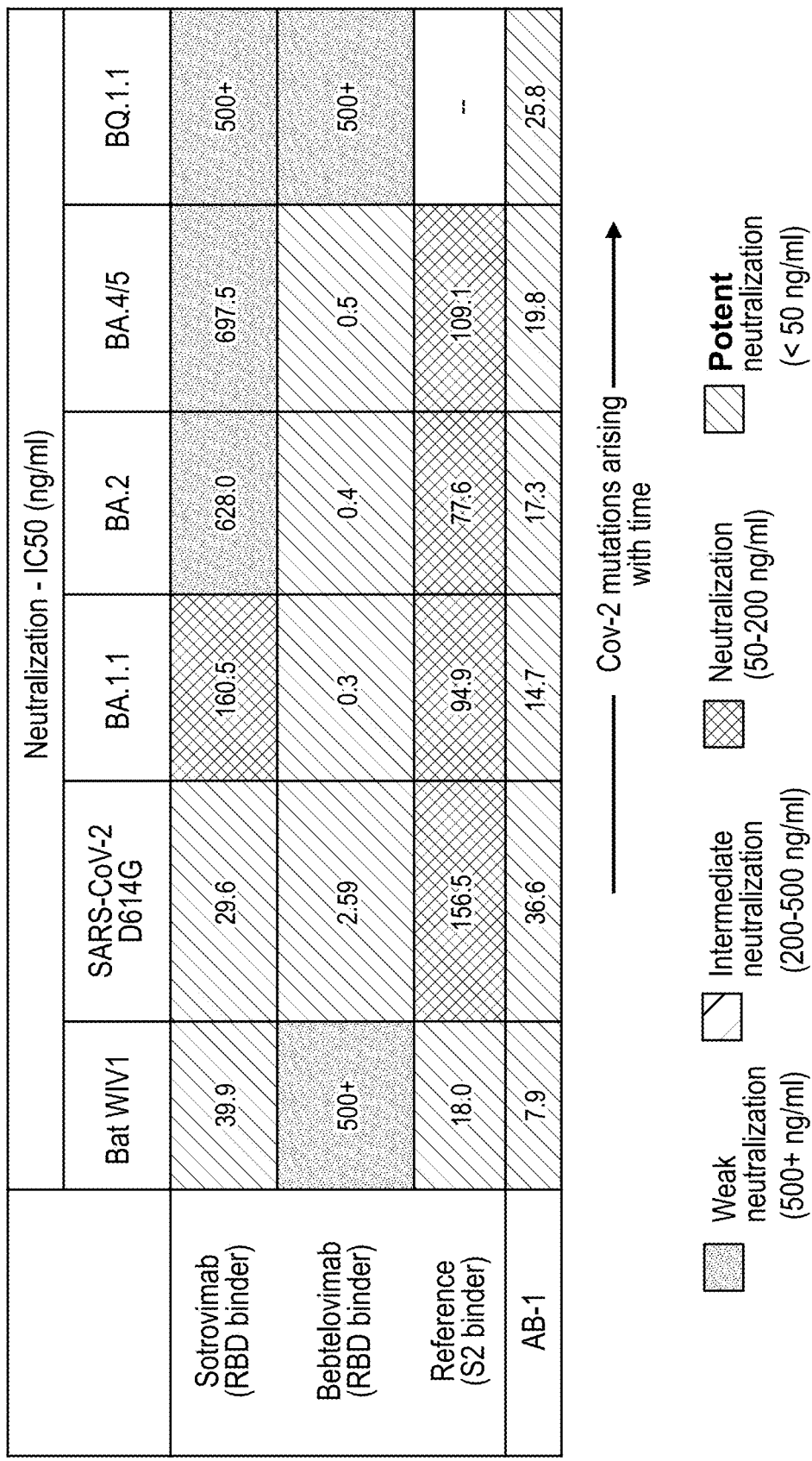
FIG. 19 is a chart showing in vitro neutralization potency of AB-1 against multiple variants of SARS-CoV-2. The results were obtained from a pseudovirus neutralization assay.
Figure 20:
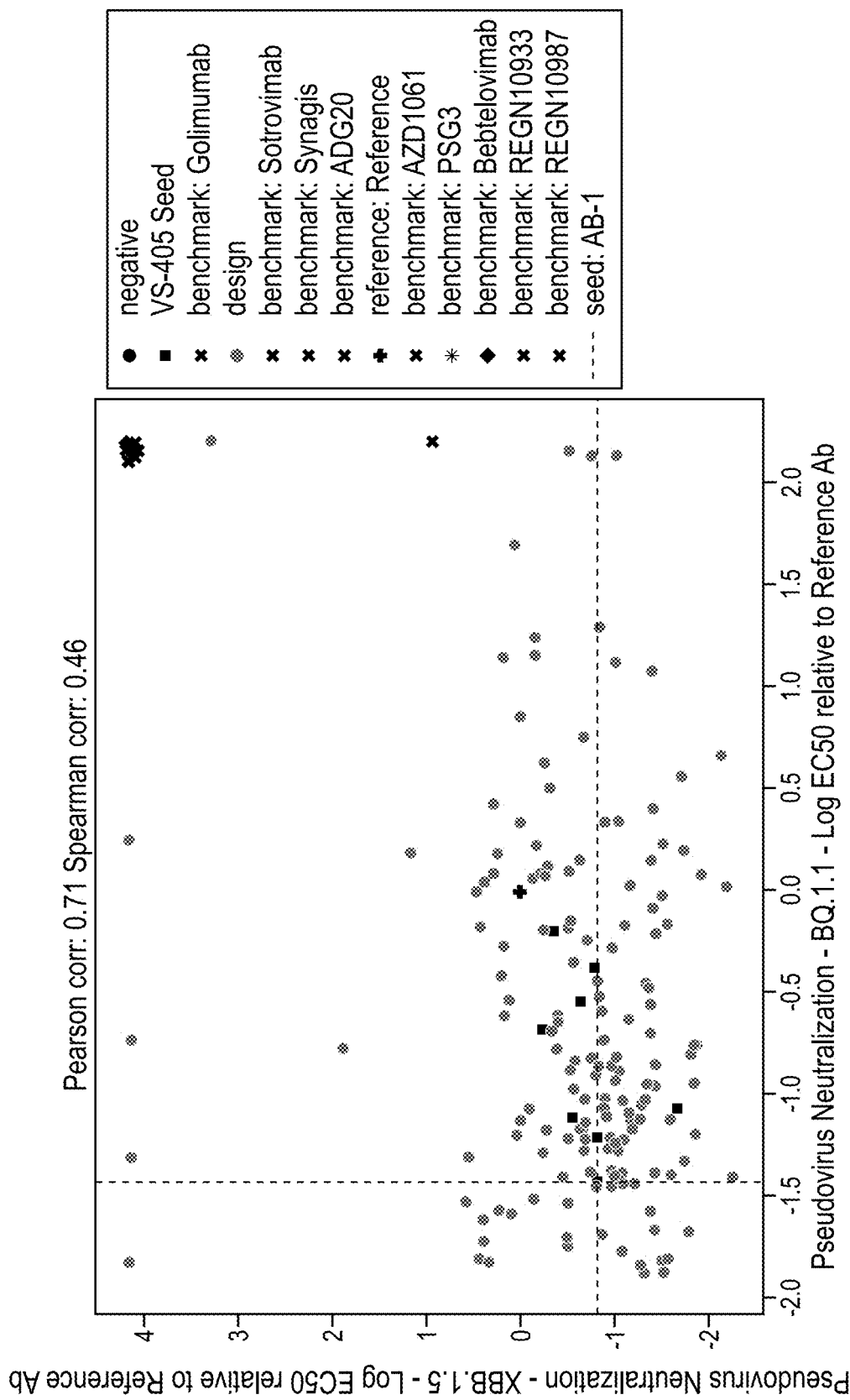
FIG. 20 shows neutralization $IC_{50}$ data expressed as log fold change over Reference Antibody against BQ.1.1 (x axis) and XBB.1.5 (y axis) VSV-dG pseudoviruses. "Design" refers to test antibodies, "Seed" refers to test antibodies that have been selected for project learning, and "Benchmark" refers to control antibodies.

As shown in FIG. 19, AB-1 displays therapeutically meaningful in vitro neutralization potency across multiple variants, suggesting that it can be used to tackle different variants by binding to a low immunogenic, highly conserved region of SARS-CoV-2.

Pseudoviruses (VSV-dG pseudotyped with Spike proteins) representative of SARS-CoV-2 variants tracked by the CDC or increasing in prevalence worldwide, such as Delta, BA.1, BA.1.1, BA.2, BA.2.12.1, BA.4/5, BA.2.75, BA.2.75.2, BA.4.6, BA.5.2.6, BF.7, BF.11, BN.1, BQ.1, BQ.1.1, XBB, as well as the non-SARS-CoV-2 Sarbecoviruses SARS-CoV-1 and WIV1 will be produced. The pseudotyping system will be used to assess neutralizing activity of a polypeptide disclosed herein (e.g., AB-1) against current and novel SARS-CoV-2 variants that may arise. These results will be confirmed with live viruses. Pseudoviruses bearing mutations in Spike epitopes that may lead to impaired neutralization activity of the polypeptide (e.g., AB-1) will be developed and evaluated. These mutations will be selected based on structural and/or biochemical assessment of binding epitope, analysis of mutations in selected sequences reported in public databases and escape experiments with replication-competent VSV, or a combination of the foregoing. Finally, neutralization activity of the polypeptide (e.g., AB-1) against pseudoviruses bearing mutations that lead to impaired neutralization activity against clinical-stage monoclonal antibodies will be tested. For mutations already represented in Omicron sublineages, neutralization activity against Omicron sublineages will be tested, instead of pseudoviruses generated with selected escape mutations.

Example 5. Biochemical Characterization of AB-1 Epitope

Monoclonal antibody (mAb) AB-1 was developed using in-house machine learning models and leveraging the co-crystal structure of the human-derived Reference Antibody (Hurlburt 2022, Jennewein 2021, Ullah 2021, Li 2022). AB-1 is a human IgG1 mAb targeting the spike S2 stem helix peptide of SARS-CoV-2 with an LS mutation in the Fc region to extend the half-life and promote translocation to mucosal tissue. AB-1 demonstrates robust neutralization against all major SARS-CoV-2 variants as well as other sarbecoviruses associated with previous epidemics (SARS-CoV-1) or pandemic potential (WIV1, bat SARS-like coronavirus). AB-1 is hypothesized to be effective for prophylaxis of COVID-19 in high-risk populations across all current Omicron sublineages and future variants of concern as a single agent and potentially, in combination with one or more other anti-spike mAbs.

The goal of Example 5 was to assess binding properties of AB-1 to SARS-CoV-2 spike S2 stem helix peptide (target epitope of the Reference Antibody). Dissociation-enhanced lanthanide fluorescence immunoassay (DELFIA) and surface plasmon resonance (SPR) were employed to assess binding of AB-1 and the Reference Antibody to biotinylated peptides reported in Hurlburt 2022 (partially overlapping peptides spanning the Reference Antibody target epitope (aa 1133-1162), a peptide representing the C-terminal end of the stem helix (aa 1149-1167), and a control 15-mer peptide derived from HIV-1 Env protein). An additional biotinylated peptide was designed to encompass the SARS-CoV-2 spike S2 stem helix (aa 1143-1162).

A. Biochemical Characterization of AB-1 Epitope by DELFIA

Biotinylated peptides: SARS-CoV-2 spike S2 peptides 1133-1147 (Biosynth, Gardner, MA, lot #LP10933), 1137-1151 (Biosynth, lot #LP10934), 1141-1155 (Biosynth, lot #LP10935), 1145-1159 (Biosynth, lot #LP10936), 1149-1163 (Biosynth, lot #LP10945), 1153-1167 (Biosynth, lot #LP10938), 1157-1171 (Biosynth, lot #LP10939), 1149-1167 (Biosynth, lot #LP10937), 1143-1162 (Biosynth, lot #BU17943); HIV-1 Env peptide (Biosynth, lot #LP10940). See, e.g., Table 36.

Antibodies: AB-1 (Lonza, lot #1100-130922-01), the Reference Antibody (GenScript USA, Inc., Piscataway, NJ, lot #U737NHI220, the Reference Antibody variable regions expressed as human IgG1 with LS mutation in the Fc region), isotype (GenScript USA, Inc., lot #U799WHJ270-3, palivizumab variable regions targeting RSV F protein and expressed as human IgG1 with LS mutation in the Fc region).

Neutravidin: NeutrAvidin Protein (Thermo Fisher Scientific, Waltham, MA, catalog #31000).

Dilution plates: 96 well plate round bottom, non-treated, polypropylene (Corning, Corning, NY, catalog #3365; Greiner, Kremsmünster, Austria, catalog #650201).

DELFIA plates: 384 well plate white, MaxiSorp, polystyrene (Thermo Fisher Scientific, catalog #460372).

TBS-T: 20×TBS Tween-20 (Thermo Fisher Scientific, catalog #28360) diluted 1:20 in ddH$_2$O.

Blocking solution: ELISA Assay Diluent B (5×) (BioLegend, San Diego, CA, catalog #421205) diluted 1:5 in PBS.

Secondary antibody: DELFIA Eu-N1 Anti-Human IgG (PerkinElmer, Waltham, MA, catalog #1244-330).

Enhancement solution: DELFIA Enhancement Solution (PerkinElmer, catalog #4001-0010).

DELFIA, a time-resolved fluorescence (TRF) intensity technology, was used to determine binding of AB-1 to different SARS-CoV-2 spike S2 stem helix peptides. DELFIA assays are designed to detect the presence of an analyte of interest using lanthanide (e.g., Europium [Eu]) chelate labeled reagents. When the immunoreaction is complete, the Eu ion is dissociated from the labeled immunocomponent bound to the solid phase by adding Enhancement solution. Then Eu fluorescence is measured by TRF.

384 well plates were coated with neutravidin (2 μg/mL) overnight at room temperature. The plates were washed and coated with biotinylated peptides (50 nM) for 1 hour at room temperature. The plates were then washed and incubated with blocking solution for 2 hours at room temperature, washed again and incubated with antibodies (AB-1, the Reference Antibody, and isotype control) for 1 hour at room temperature. Antibody binding was assessed using a 12-point titration curve in technical triplicate (1:4 serial dilutions prepared in blocking solution and starting at 18 μg/mL). Following this, the plates were washed and incubated with Eu-labeled anti-human IgG secondary antibody (0.1 μg/mL) for 30 minutes at room temperature. Finally, the plates were washed and incubated with DELFIA Enhancement solution for 15 minutes. TRF was recorded at 615 nm with a PerkinElmer EnVision plate reader.

Statistical analysis was performed with Prism 9.5.0 software using data from two independent replicates. Area Under the Curve (AUC) values and 95% confidence intervals were derived for Log-transformed antibody titration curves using the trapezoid rule. Statistical comparisons between AUC values of AB-1 and the Reference Antibody were performed as reported in the software documentation (https://www.graphpad.com/support/faqid/2031/) using 2-way ANOVA corrected for multiple comparisons.

B. Biochemical Characterization of AB-1 Epitope by SPR

Biacore 8K+ (Cytiva, Marlborough, MA, serial #2873569).

Biacore 8K Control Software (Cytiva, version 4.0.8.19879).

Biacore Insight Evaluation Software (Cytiva, version 4.0.8.19879).

GraphPad Prism (version 9.5.0).

Biotinylated peptides: SARS-CoV-2 spike S2 peptides 1133-1147 (Biosynth, lot #LP10933), 1137-1151 (Biosynth, lot #LP10934), 1141-1155 (Biosynth, lot #LP10935), 1145-1159 (Biosynth, lot #LP10936), 1149-1163 (Biosynth, lot #LP10945), 1153-1167 (Biosynth, lot #LP10938), 1157-1171 (Biosynth, lot #LP10939), 1149-1167 (Biosynth, lot #LP10937), 1143-1162 (Biosynth, lot #BU17943); HIV-1 Env peptide (Biosynth, lot #LP10940). See, e.g., Table 36.

Fabs: AB-1 (in-house preparation), the Reference Antibody (in-house preparation).

Antibodies: AB-1 (in-house production), the Reference Antibody variable domain (GenScript USA, Inc., lot #U3767HH180-11, the Reference Antibody variable regions expressed as human IgG1 with LS mutation in the Fc region).

Series S Biotin CAPture kit (Cytiva, catalog #28920234) containing Biotin CAPture reagent, 50 μg/mL in HBS-EP, Regeneration Stock 1 (8 M guanidine hydrochloride) and Regeneration Stock 2 (1 M sodium hydroxide).

20×HBS-EP+, pH 7.6 (Teknova, Hollister, CA, catalog #H8022) composed of 0.2 M HEPES pH 7.4, 3 M NaCl, 60 mM EDTA, 1% Surfactant P20 and prepared at 1×.

Microplate, 96W, deep-well, U-bottom, PP, 2 mL (Porvair, Ashland, VA, catalog #219020).

Microplate foil 96W (Cytiva, catalog #28975816).

Biacore is a label-free platform that uses SPR to measure binding interactions in real-time. Kinetic and affinity parameters are extracted from experimental data by an iterative process that finds the best fit for a set of equations describing the interaction. The association rate constant $k_a$ ($M^{-1}s^{-1}$) governs the rate at which a complex is formed. The dissociation rate constant $k_d$ ($s^{-1}$) governs the rate at which a complex dissociates. The equilibrium dissociation constant $K_D$ (M) describes the strength of the interaction.

To evaluate the response units (RU) of AB-1 and the Reference Antibody binding to peptides spanning the SARS-CoV-2 spike S2 stem helix region, a multi-cycle kinetics approach was implemented using a Biacore 8K+. The biotinylated peptides were captured using the Biotin CAPture kit. The Biotin CAPture reagent was injected for 180 s at a flow rate of 2 μL $min^{-1}$. The biotinylated peptides (referred to as the ligands) were injected for 10 s at a flow rate of 10 $min^{-1}$ to achieve a capture level of approximately 10 to 20 RU. AB-1 and the Reference Antibody (referred to as the analytes) were injected over the surface at 100 nM for 180 s at a flow rate of 30 μL $min^{-1}$ and the complex was allowed to dissociate for 900 s using 1×HBS-EP+ as the running buffer. The surface was regenerated by injecting a solution of 3 parts Regeneration Stock 1 with 1 part Regeneration Stock 2 for 120 s at a flow rate of 10 μL $min^{-1}$. The assay was performed at 25° C. Capture level report points were obtained 25 s after ligand injection end, and binding response report points were obtained 5 s before analyte injection end. The binding responses were normalized to the ligand capture level using GraphPad Prism and are reported as normalized binding responses.

To evaluate the kinetics of Fabs of AB-1 and the Reference Antibody binding to peptides spanning the SARS-CoV-2 spike S2 stem helix region, a single-cycle kinetics approach was implemented using a Biacore 8K+. The biotinylated peptides were captured using the Biotin CAPture kit. The Biotin CAPture reagent was injected for 180 s at a flow rate of 2 μL $min^{-1}$. The biotinylated peptides (referred to as the ligands) were injected for 10 s at a flow rate of 10 $min^{-1}$ to achieve a capture level of approximately 10 to 20 RU. Fabs of AB-1 and the Reference Antibody (referred to as the analytes) were injected sequentially over the surface starting from low to high analyte concentration for 180 s at a flow rate of 30 μL $min^{-1}$ and the complex was allowed to dissociate for 900 s using 1×HBS-EP+ as the running buffer. The concentration series consisted of a 3-fold serial dilution starting from 300 nM for a total of six concentrations. The surface was regenerated by injecting a solution of 3 parts Regeneration Stock 1 with 1 part Regeneration Stock 2 for 120 s at a flow rate of 10 μL $min^{-1}$. The assay was performed at 25° C. Kinetic parameters for the concentration series were obtained by double referencing and globally fitting the data to a 1:1 binding model with mass transport limitation using the Biacore Insight Evaluation software. The kinetics of Fabs of AB-1 and the Reference Antibody binding to the SARS-CoV-2 spike S2 peptide, representing the C-terminal end of the stem helix (aa 1149-1167), are reported and the resulting sensorgrams are shown.

C. Results

Figure 22:
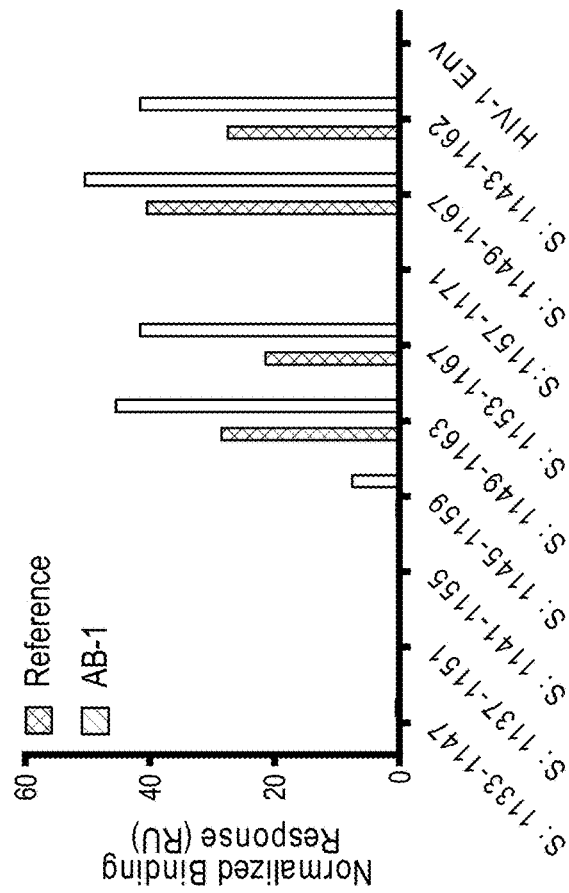
FIG. 22. Binding of AB-1 and the Reference Antibody to SARS-CoV-2 spike S2 peptides by SPR. Binding of AB-1 and the Reference Antibody to SARS-CoV-2 spike S2 peptides (indicated as "S:" followed by amino acid positions) and HIV-1 Env negative control peptide were assessed by SPR at 25° C. Antibody binding responses were normalized to biotinylated peptide capture levels and are reported as normalized binding responses. Results are representative of one experiment without technical replicates.

DELFIA and SPR data show binding profiles of AB-1 to SARS-CoV-2 spike S2 peptides (FIG. 21, FIG. 22, Table 13). The specificity of these results is confirmed by a lack of binding of the isotype control in the DELFIA experiment, and a lack of binding of AB-1 and the Reference Antibody to the HIV-1 Env peptide used as negative control in both DELFIA and SPR experiments. Of note, AB-1 Fab binds to the SARS-CoV-2 spike S2 peptide representative of the C-terminal end of the stem helix (aa 1149-1167) with higher affinity as compared to the Reference Antibody ($K_D$ values: AB-1, 0.9 nM; the Reference Antibody, 5.4 nM (Table 14, FIGS. 23A-23D)).

In conclusion, Example 5 shows that AB-1 binds to SARS-CoV-2 spike S2 stem helix of the Reference Antibody with a higher affinity.

Example 6. Structural Characterization of AB-1 Epitope

The goal of Example 6 was to collect structural information on AB-1 in complex with both the SARS-CoV-2 BA.1 spike trimer and the spike S2 (aa 1149-1167) stem helix peptide and to define its binding site.

X-ray crystallography was used to determine the structure of AB-1 Fab in complex with spike S2 (aa 1149-1167) stem helix peptide at high resolution. Cryo-electron microscopy (Cryo-EM) was used to determine the structure of AB-1 Fab in complex with the SARS-CoV-2 BA.1 spike trimer. As observed in previous structure determination attempts, the coil-coil S2 stem helix peptide of SARS-CoV-2 BA.1 spike trimer is highly flexible and can be prohibitively challenging to resolve by Cryo-EM. To stabilize the motion in this region, the Fab region of an internally discovered monoclonal antibody (R-AB-3a), targeting the class 4 epitope of spike receptor binding domain (RBD), was used in complex with SARS-CoV-2 BA.1 spike trimer bound to AB-1 Fab.

A. Structural Characterization of AB-1 Epitope by Cryo-EM

Antigens: SARS-CoV-2 BA.1 spike trimer (in-house production)
Fabs: AB-1 (in-house production), R-AB-3a (in-house production)
Expi293F™ Cells (Thermo Fisher Scientific, catalog #A14527)
Gibco Expi293™ Expression Medium (Thermo Fisher Scientific, catalog #A14351-01)
ExpiFectamine™ 293 Transfection Kit (Thermo Fisher Scientific, catalog #A14525)
Nickel Sepharose Excel (Cytiva, catalog #17371201, lot #10313877)
LambdaFabSelect (Cytiva, catalog #17548201, lot #10302825)
Capto™ L (Cytiva, catalog #17547802, lot #10305645)
Quantifoil Gold R1.2/3 grids (Electron Microscopy Sciences, catalog #261655 lot #Q82801)
Instruments:
Kuhner Shaker (Kuhner, model: ISF1-ZC Peltier)
Äkta Pure (Cytiva)
SRT-C SEC-500 (Sepax, PN: 235500-4630)
Superose 6 Increase 10/300 GL (Cytiva, catalog #29091596, lot #10325571)
Nanodrop One (Thermo Fisher Scientific, Model Nanodrop One)
HPLC 1260 Infinity II (Agilent, TT No.: 1581T8)
Pelco easiGLOW (Pelco, Model No.: 91000)
Vitrobot Mark IV (Thermo Fisher Scientific, serial #220301059)
Glacios (Thermo Fisher Scientific, serial #9956936)
Software:
EPU (Thermo Fisher Scientific, v3.2)
cryoSPARC (Structura Biotechnology, v4.1.1)
ChimeraX (UCSF RVBI, v1.5)

a. Expression and Purification of SARS-CoV-2 BA.1 Spike Trimer

SARS-CoV-2 BA.1 spike trimer was expressed in Expi293™ cells following the Gibco™ Expi293™ Expression System protocol. In brief, three million cells were transfected with approximately 1 mg of plasmid DNA. The cells were incubated at 37° C., with 80% relative humidity and 8% $CO_2$ on an orbital shaker at 150 RPM. Four days post-transfection, the cells were harvested and pelleted at 3,900×g for 30 mins at 4° C. The supernatant was decanted into 0.22 μm filter units and stored at 4° C. until purification. The SARS-CoV-2 BA.1 spike trimer was purified using Nickel Sepharose Excel resin. The supernatant was incubated with 2 mL of Nickel Sepharose Excel resin overnight at 4° C. and purified by gravity flow.

b. Expression and Purification of AB-1 and R-AB-3a Fabs

AB-1 and R-AB-3a Fabs were expressed in Expi293™ cells following the same protocol used for SARS-CoV-2 BA.1 spike trimer. The supernatant for both Fabs were incubated with either Capto™ L resin (AB-1 Fab), or LambdaFabSelect resin (R-AB-3a Fab) overnight at 4° C. The mixtures of supernatant and resin were loaded onto a 10 mL disposable column equilibrated in 1×PBS (pH 7.4). The column was then washed with 10 CV of 1×PBS (pH 7.4). AB-1 and R-AB-3a were eluted with 50 mM Glycine (pH 2.5). The proteins were immediately neutralized with 1M Tris-HCl (pH8.0). Each protein was buffer exchanged using a PD-10 desalting column and eluted with 1×PBS (pH 7.4). The purified proteins were concentrated and kept at 4° C. until complexation with the SARS-CoV-2 BA.1 spike trimer.

c. Complexation of SARS-CoV-2 BA.1 Spike Trimer with AB-1 and R-AB-3a Fabs

The SARS-CoV-2 BA.1 spike trimer was incubated with AB-1 and R-AB-3a Fabs at a 1:2:2 molar ratio at 4° C. overnight with gentle mixing. The complex was purified by size exclusion chromatography on a Superose 6 Increase 10/300GL column equilibrated in 50 mM HEPES (pH 8.0), 150 mM NaCl. Prior to injection, the incubated sample was spun at 1699×g. One mL of the complex was injected on the column via a 1 mL loop; the flow rate throughout the run was 0.5 mL/min. Each eluted peak was analyzed by SDS-PAGE to confirm which fraction contains a complex between the SARS-CoV-2 BA.1 spike trimer and AB-1 and R-AB-3a Fabs. These fractions were further analyzed by aSEC on an SRT-C SEC-500 column equilibrated in 50 mM HEPES (pH 8.0), 150 mM NaCl.

d. Cryo EM Sample Preparation

Four microliters of sample were applied to Quantifoil gold grids which were glow-discharged for 30 seconds at a plasma current of 0.15 mA with negative polarity.

e. Cryo-EM Data Collection

Cryo-EM images were acquired on a Glacios cryo-TEM using EPU software (v3.2). The Glacios was operated at 200 kV with a Falcon4i direct electron detector and a Selectris energy filter with a zero-loss slit width of 10 eV. 5160 movies were collected at 130,000× magnification at a pixel size of 0.876 Å. The total dose per movie was 51.3 electrons per square angstrom. The targeted defocus range was between 0.5-2.4 μm.

f. Cryo-EM Data Processing

All computational steps were performed using the cryoSPARC (v4.1.1) software suite and ChimeraX (v1.5) molecular visualization software. The movies in EER format were imported and fractionated into 40 frames and sampled at the physical pixel size. Beam-induced motion correction, per-frame dose-weighting, and CTF estimation were performed using the patch motion correction and patch CTF jobs in cryoSPARC (v4.1.1). The exposures were selected semi-automatically using the interactive exposure curation tool. After setting stringent cut-offs on CTF fit resolution, defocus, and relative ice thickness, 2,921 images were selected for subsequent processing.

Template-based particle picking was performed with projections from a 3D map of the SARS-CoV-2 BA.1 spike trimer low-passed filtered to 20 Å. 466,074 particles were extracted from 2921 micrographs. 2D classification was performed with 200 classes to identify incorrectly picked or broken particles, retaining 87,564 particles for subsequent processing.

Ab initio reconstruction with three classes was performed, yielding an initial 3D map with the expected size and shape of the SARS-CoV-2 BA.1 spike trimer from a subset of 51,996 particles. Subsequent non-uniform 3D refinement in cryoSPARC of these particles yielded a 'consensus map' at 3.6 Å resolution by gold-standard FSC criteria.

g. Focused Classification and Model Fitting

An atomic model of the SARS-CoV-2 BA.1 spike trimer without bound Fabs was computationally docked into the consensus map with the 'fit in map' tool in ChimeraX (v1.5). The map fits snugly into the density, except for several unaccounted densities at the RBD and S2 stem helix regions of the map. Gaussian low-pass filtering of the map revealed these densities to be dumbbell shaped with a hole in the center, as expected for Fab molecules. The 'Segment Map' tool in ChimeraX and cryoSPARC's volume tools were used to produce a focused mask around the S2 stem helix that enclosed the propeller-shaped putative Fab densities. Focused 3D classification without alignment in cryoSPARC was performed with ten classes to identify a subset of 9,822 particles with stronger density of the putative S2 stem helix bound Fabs. This subset was refined without applying symmetry using non-uniform refinement to 5.7 Å resolution by gold-standard FSC criteria.

A local resolution estimation in cryoSPARC showed that the S2 stem helix binding Fabs have lower local resolution than the core of the SARS-CoV-2 BA.1 spike trimer. The CDR-containing domains of the Fabs were approximately 8 Å local resolution, while the flexibly-associated framework domains of the Fabs were approximately 14-20 Å local resolution. For this reason, a Gaussian low-pass filter in ChimeraX (v1.5) with a width of 3 Å was applied. One Fab is distinctly weaker than the other two. Nevertheless, these densities were sufficient to unambiguously dock three copies of AB-1 Fab-S2 stem helix complex crystal structure (described below) into each of the three S2 stem helix Fab densities using ChimeraX's 'fit in map' tool. The structure of the RBD-binding R-AB-3a Fab was also docked into dumbbell-shaped density at the spike RBD.

B. Structural Characterization of AB-1 Epitope by X-ray Crystallography

Fab: AB-1 (in-house preparation).
Fabalactica Midispin Fab digestion kit (Genovis, cat #A2-AFK-100).
Peptide: SARS-CoV-2 spike S2 peptide 1149-1167 (Biosynth, lot #LP10941).
MCSG-3 crystallization screen (Anatrace, part #MCSG-3).
16/900 Superdex 200 pg column (custom).

a. Production of AB-1 Fab and SARS-CoV-2 Spike S2 (Aa 1149-1167) Peptide

AB-1 was produced by Lonza, and the monomeric content was assessed by SE-HPLC. The Fab was digested and purified from the IgG using Genovis's Fabalactica Midispin Fab digestion kit per the manufacturer's instructions. SARS-CoV-2 spike S2 (aa 1149-1167) peptide (H2N-KEELDKYFKNHTSPDVDLG-OH) (SEQ ID NO:197) was synthesized at Biosynth and was verified for quality using HPLC, Mass Spectrometry, and Amino Acid Analysis. Binding of AB-1 to SARS-CoV-2 spike S2 (aa 1149-1167) peptide was assessed in AB-1-001-PD.

b. AB-1 Fab:SARS-CoV-2 Spike S2 (Aa 1149-1167) Peptide Co-Crystallization Trials:

AB-1 Fab and SARS-CoV-2 spike S2 (aa 1149-1167) peptide were added in a 1:1 molar ratio, incubated on ice for 20 minutes, concentrated and injected on to a 16/900 Superdex 200 pg column (buffer: 25 mM HEPES, pH 7.5, 150 mM NaCl). Peak fractions were analyzed by SDS-PAGE and combined and concentrated to 10 mg/mL. An ARI Crystal Gryphon drop-setting robot used 96-3 Intelliplates to set crystallization drops for the complex at 10 mg/mL at three ratios (1:1, 2:1, and 3:1) of complex to the crystallization condition. The 96-well MCSG-3 commercial screen was set and incubated at 4 and 20° C.

c. AB-1 Fab:SARS-CoV-2 Spike S2 (Aa 1149-1167) Peptide Data Collection and Structure Determination Crystals from the MCSG-2 A2 (1:1 ratio) at 4° C. were harvested and cryoprotected in 20% glycerol. The crystals were sent to the NSLS2 synchrotron, and X-ray data sets were collected on AMX beamline with an Eiger X 9M detector. The data was processed using DIALS and XDS to 1.93 Å. Once processed, the data set was phased by molecular replacement using Phaser_MR with an AlphaFold model of Fabs of AB-1 and the Reference Antibody for the peptide. Several rounds of refinement were performed using Phenix and Coot.

C. Results

Figures 24A, 24B, 24C:
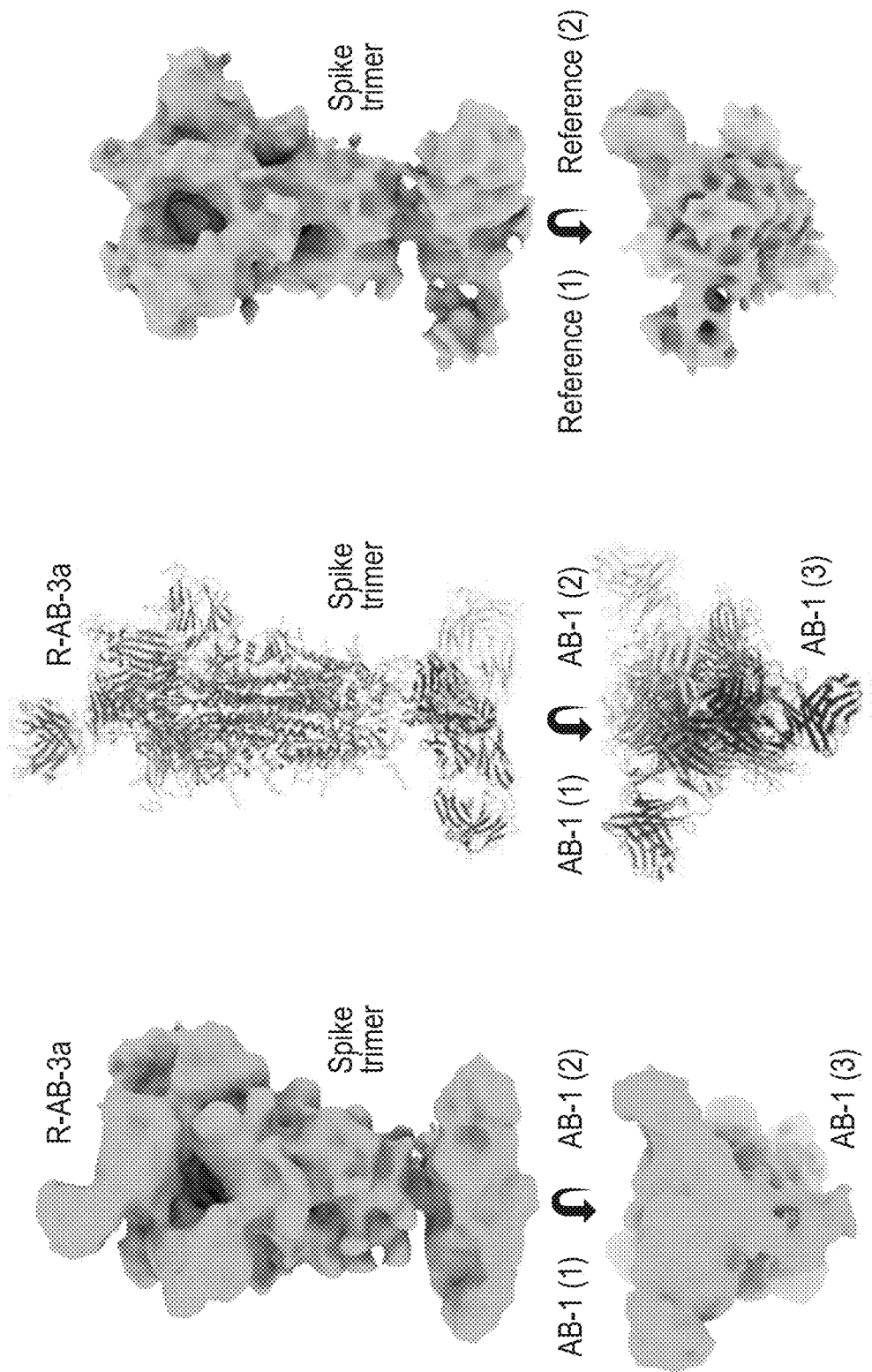
FIGS. 24A-24C. AB-1 Fab binds to SARS-CoV-2 spike with an apparent stoichiometry of three Fabs per spike.

Structural characterization of the AB-1 Fab:SARS-CoV-2 BA.1 spike trimer complex by Cryo-EM and the AB-1 Fab: SARS-CoV-2 spike S2 (aa 1149-1167) peptide complex by X-ray crystallography reveals that AB-1 binds the S2 peptide (FIGS. 24A-24C). Additionally, the results show that three copies of AB-1 Fab can bind the SARS-CoV-2 BA.1 spike trimer.

In conclusion, structural characterization of AB-1 Fab in complex with the SARS-CoV-2 BA.1 spike trimer and SARS-CoV-2 spike S2 (aa 1149-1167) peptide revealed that AB-1 binds to the SARS-CoV-2 spike S2 stem helix peptide.

Example 7. Mutational Analysis of AB-1 Epitope and Adjacent Sequences

The goal of Example 7 was to assess sequence conservation of regions of the SARS-CoV-2 spike protein that can potentially impact the neutralization efficacy of AB-1 by defining relative frequencies of mutations in the AB-1 epitope, epitope adjacent regions (within 5 angstroms of the epitope in the protein structure), Heptad Repeat 1 (HR1) and Heptad Repeat 2 (HR2) among publicly reported SARS-CoV-2 spike protein sequences over the course of the pandemic (Jan. 6, 2020 to Mar. 1, 2023).

A. Definition of Regions of Interest

In this study, the four regions of interest of the SARS-CoV-2 spike protein are: the AB-1 epitope (referred to as "Epitope"), residues adjacent to the epitope (referred to as "Epitope Adjacent"), HR1, and HR2. Using the epitope residues and a publicly available structure of the SARS-CoV-2 spike protein (PDB ID: 6VSB), the "Epitope Adjacent" residues were defined as residues containing any atom within 5 angstroms of any epitope-residue atom. Residues corresponding to HR1 and HR2 are defined in the NCBI entry for the SARS-CoV-2 surface glycoprotein YP_009724390.1. The positions of each of these four regions in the SARS-CoV-2 spike sequence are summarized in Table 15. As the epitope intersects with HR2, to avoid double counting residues falling in both regions, the intersecting region was defined to be part of the "Epitope" category and excluded from the HR2 category throughout the analysis. Similarly, Epitope Adjacent positions also intersect with HR2; this intersection is defined to be part of HR2 and excluded from the Epitope Adjacent category for analysis.

B. Identification of Relevant Mutations in the AB-1 Epitope, Adjacent Regions, and Heptad Repeats The covSPECTRUM API (Application Programming Interface) was used to query the GenBank database for mutations occurring in each of the four regions of interest (Chen 2021). For each mutation, the relative frequency of the mutation was calculated for periods ending each month from Jan. 6, 2020, through Mar. 1, 2023, using three different lookback periods per month: 1 month, 3 months, and all time (since Jan. 6, 2020). The relative frequency was determined by dividing the number of sequences with a mutation of interest observed during a given time interval by the total number of sequences observed during the same time interval.

The mutations were identified that meet the following criteria:

Falls within either "Epitope", "Epitope Adjacent", "HR1" or "HR2."

Satisfies a), b) or both:
  a) All-time relative frequency: has relative frequency at least 0.001 among all sequences deposited since the start of data availability (Jan. 6, 2020) through Mar. 1, 2023.
  b) Recent relative frequency: has relative frequency of at least 0.01 among all sequences deposited from Jan. 1, 2023, to Mar. 1, 2023, and has been observed at least 100 times in that period.

The relative frequency data was plotted throughout the course of the pandemic to observe whether a mutation appears to be currently increasing or decreasing in prevalence.

C. Identification of Most Prevalent Lineages Amongst Sequences Harboring Mutations To identify the most prevalent strains amongst sequences harboring each mutation of interest, covSPECTRUM was queried for the set of sequences with each mutation that had been observed from the start of data availability, Jan. 6, 2020, to Mar. 1, 2023. For each mutation, the lineage assignments were tallied for all sequences harboring the mutation (the nextcladePangoLineage assignment reported by covSPECTRUM) and ranked the lineages according to absolute count. For each mutation and lineage, to convert the count to the relative frequency of the strain among all sequences with the mutation, the count of lineage sequences with the mutation was divided by the total number of sequences with the mutation observed from Jan. 6, 2020, to Mar. 1, 2023. In this analysis, the four most frequent lineages associated with each mutation are reported.

D. Relative Frequency of Mutations of Interest in Most Prevalent Lineages

The five most prevalent lineages were determined for each of three time periods ending on Mar. 1, 2023 (1 month, 3 months, and since Jan. 6, 2020) by querying the covSPECTRUM API for the frequency of observed lineages over each of these periods. The overall prevalence of each lineage was determined by converting counts to relative frequency: lineage counts observed in each time interval were divided by the total number of sequences observed in that same time interval.

For the five most prevalent lineages over each time period, relative frequency of a mutation within each lineage was determined as follows: the number of sequences belonging to the lineage with the mutation within the time interval was queried, and then divided by the number of all sequences belonging to the lineage in that same time interval. These relative frequencies enable assessment of the prevalence of the mutations of interest in the most prevalent lineages.

E. Software for Analysis

Figure 25:
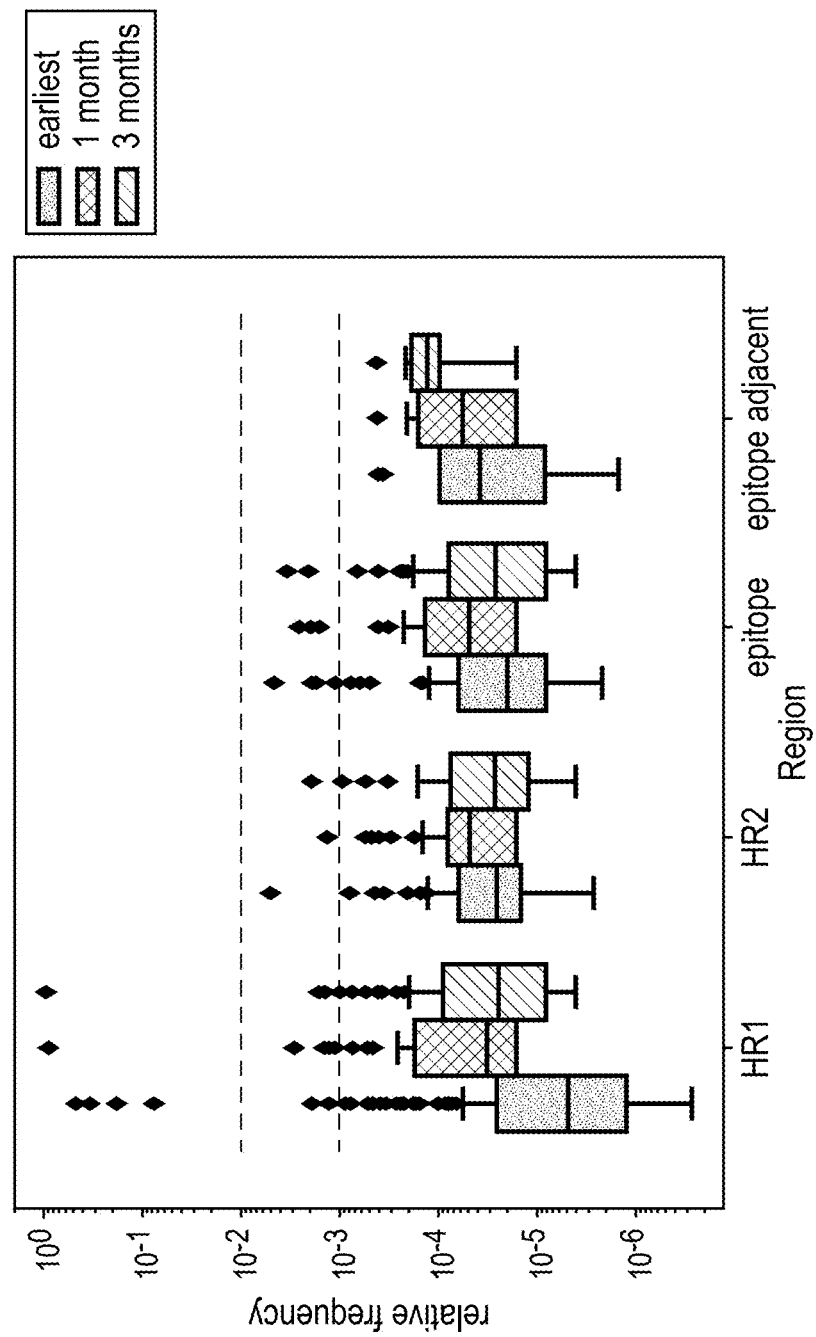
FIG. 25. The observed frequencies of mutations in the regions of interest. Distributions of the observed relative frequencies for mutations falling within "HR1," "HR2," "the Epitope," and "Epitope Adjacent residues," over three different time intervals ending on Mar. 1, 2023 (earliest [Jan. 6, 2

Custom python scripts used to retrieve data and complete the analysis are stored in a versioned repository at GitLab: https://gitlab.com/generatebio/computational_sciences/projects/sars-mutation-tracking F. Results FIG. 25 shows the relative frequency distribution for all mutations occurring within the four regions of interest (HR1, HR2, Epitope, Epitope Adjacent) over the three different time intervals. Dashed lines indicate the threshold for all-time relative frequency (0.001) and the threshold for recent relative frequency (0.01). Within the AB-1 epitope, no mutation exceeds 0.01 relative frequency in any of the time intervals. Overall, the vast majority of mutations that were observed in these four regions of interest occurred at low frequencies.

Each individual mutation meeting the criteria for mutations of interest was examined. For each mutation, the relative frequency profile over the course of the pandemic was assessed to potentially infer future relevance of the mutation.

Figure 26:
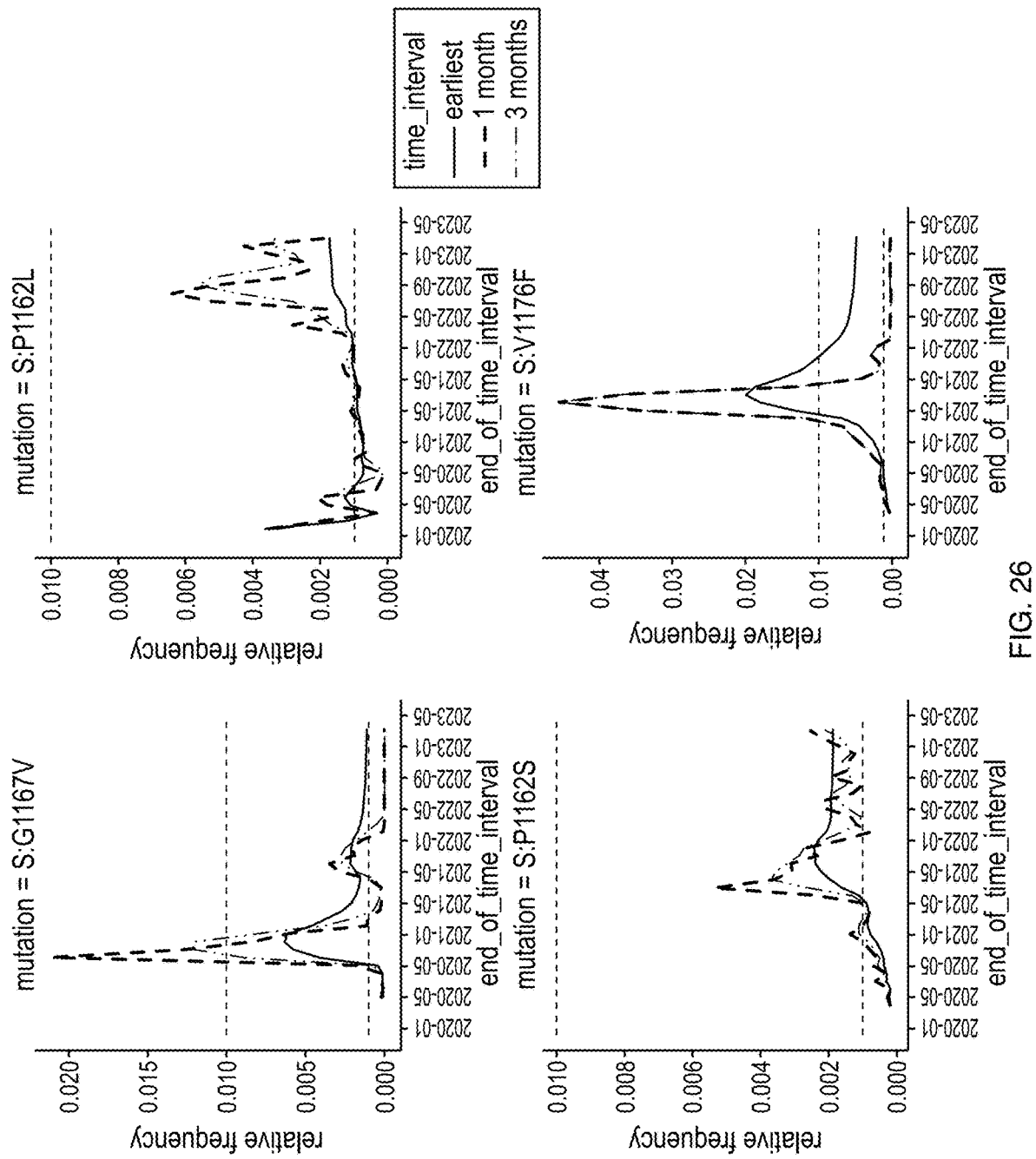

FIG. 26 shows mutations of interest within the AB-1 epitope. Only one of these mutations, V1176F, has exceeded a relative frequency of 0.01 at any point in the pandemic. V1176F was most often observed in the P.1 (Gamma) lineage (Table 15), which is no longer a prevalent lineage in circulation. Mutations that have recently shown a trend toward an increase in relative frequency are P1162L and P1162S. However, their relative frequencies never exceeded 0.01.

Figure 27A:
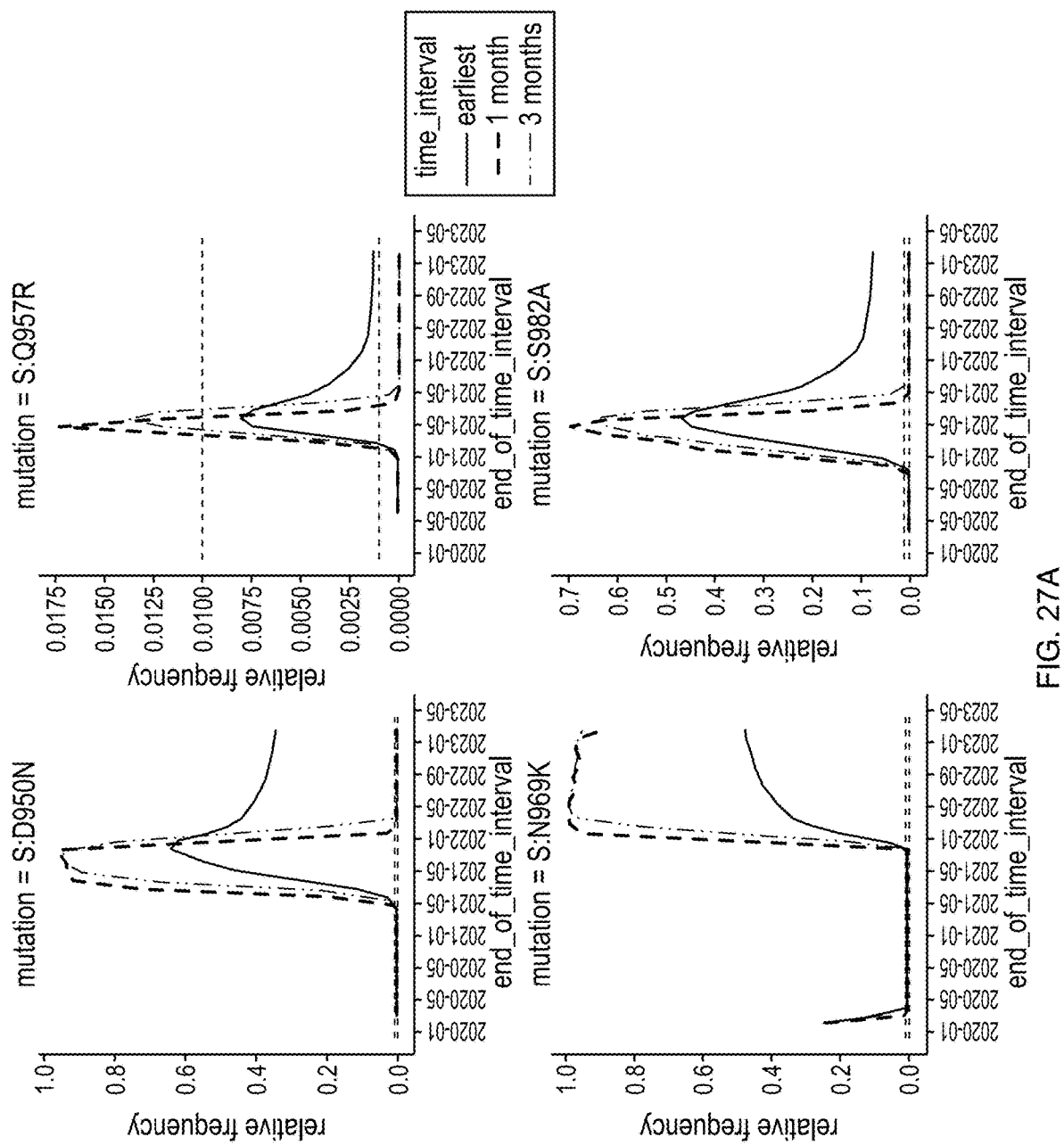
Figure 27B:
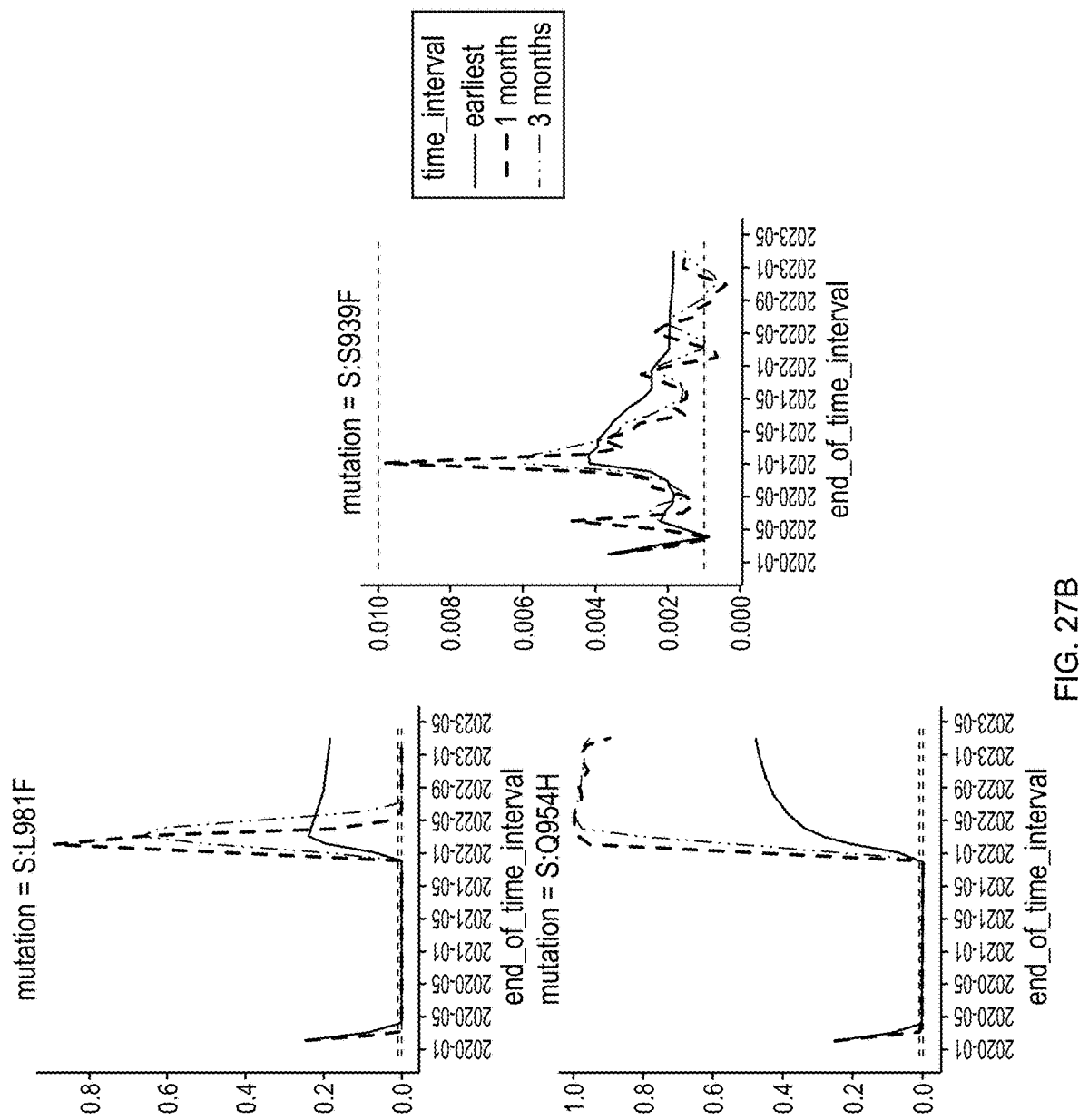

FIG. 27 shows mutations of interest within the HR1 region. Several mutations in the region such as L981F, N969K and Q954H have become prevalent in recently circulating Omicron lineages (FIG. 30), while other mutations such as D950N and S982A are associated with previously circulating lineages and no longer prevalent in recently circulating ones (FIG. 30) (https://covariants.org/shared-mutations). The remaining mutations (Q957R, S939F) have shown low relative frequencies and no upward trends. The relative frequency of each of these mutations, as well as the most prevalent lineage harboring each mutation, is summarized in Table 16.

Figure 28:
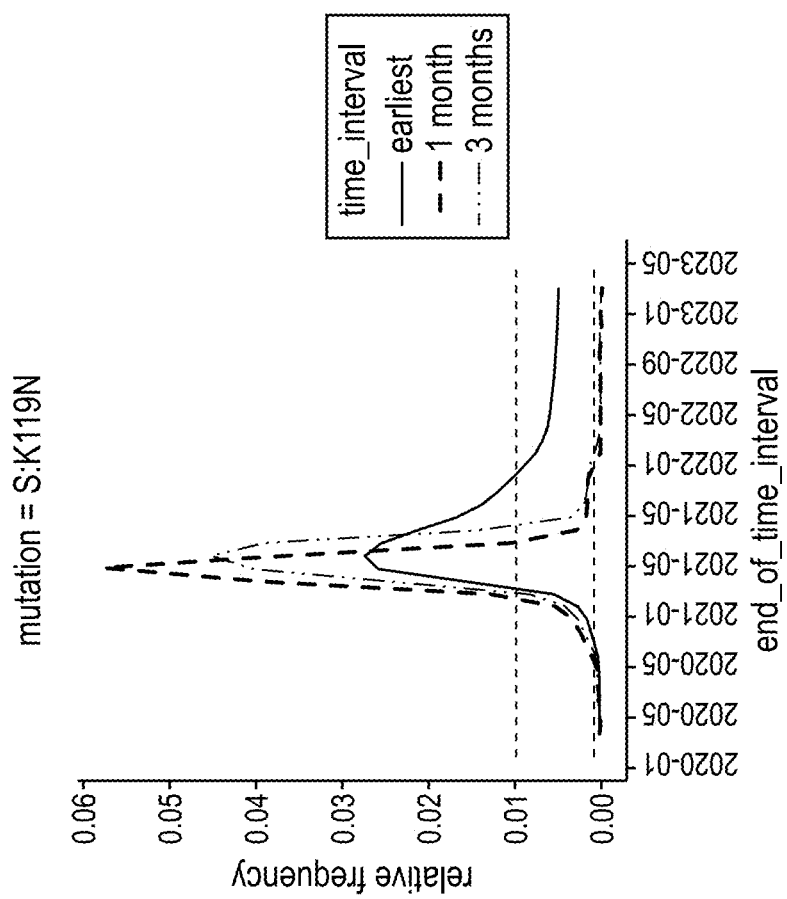

Analysis of mutations within the HR2 region revealed only one mutation that satisfies the indicated criteria:

K1191N, which is no longer prevalent in currently circulating lineages (FIG. 28, Table 16).

No additional mutations were observed in residues adjacent to AB-1 epitope (within 5 angstroms) satisfying the criteria, other than the one that was already analyzed within HR2.

Table 16 lists all mutations satisfying the criteria (for all-time relative frequency or recent relative frequency and count), along with relative frequency data and the four most prevalent lineages amongst the sequences with each given mutation (from the start of data availability to Mar. 1, 2023). For more frequent variants that have become fixed within a lineage (FIG. 30), such as D950N, Q954H, N969K, and L981F, the most frequent lineages are closely related. Q954H, N969K, and L981F appear fixed in the Omicron lineage and are shared between recent Omicron related lineages; D950N was prevalent amongst Delta related lineages (covariants.org/shared-mutations).

Within the AB-1 epitope, V1176F was observed primarily in P.1 (Gamma) related lineages and has not been observed frequently in the more recent time intervals. The remaining mutations, P1162L, P1162S, and G1167V are less frequent across all three time-intervals and are observed in a mix of lineages. The two mutations that have been recently detected with higher frequencies, P1162S and P1162L, have both been observed in Delta and Omicron related lineages.

Figure 29:
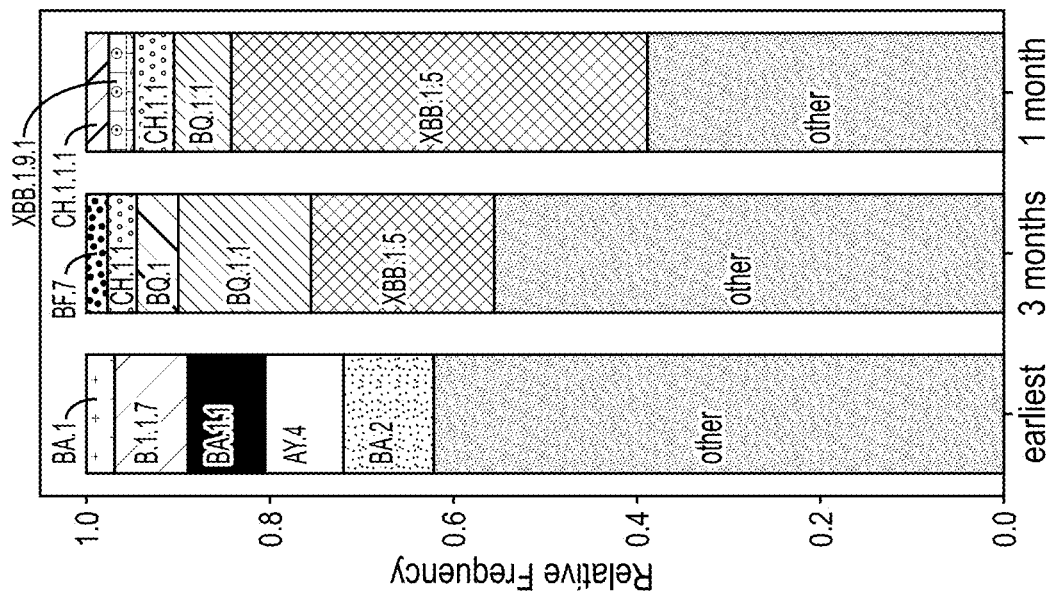
Figure 30:
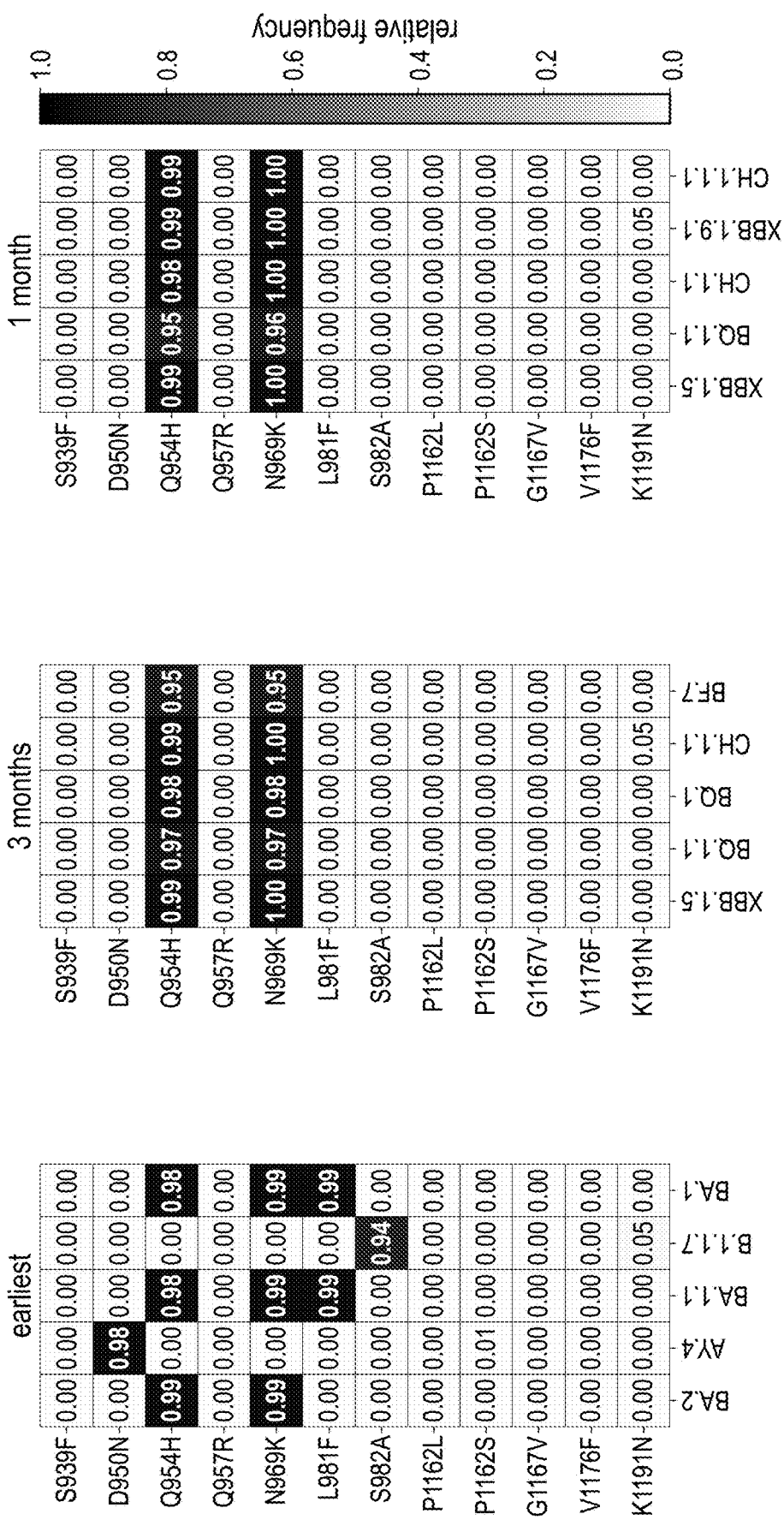

The relative frequencies of the mutations of interest summarized in Table 16 were assessed in the most prevalent lineages. FIG. 29 shows the relative prevalence of predominant lineages during the three time-intervals ending on Mar. 1, 2023. For the five most prevalent lineages over each time interval, the relative frequencies of mutations of interest were calculated within each of these lineages (FIG. 30). Q954H and N969K, which are common mutations in Omicron lineages, are the only mutations that occur with any appreciable frequency amongst the most prevalent lineages, but they do not reside in the AB-1 epitope. Mutations within the AB-1 epitope (G1167V, P1162L, P1162S, and V1176F) all occur with low frequency in the most prevalent lineages.

In conclusion, Example 7 categorizes the mutations detected at indicated relative frequencies in the regions of interest of the SARS-CoV-2 spike protein (AB-1 epitope, epitope adjacent regions, HR1 and HR2). Some of these mutations were detected in circulating strains such as Omicron variants (Q954H, N969, L981F), while others were associated with formerly circulating strains such as Alpha variant (S982A) and Delta variant (D950N). In comparison to these, mutations that appear in the AB-1 epitope occurred at very low frequency over the course of the pandemic.

Example 8. AB-1 Binding to SARS-CoV-2 Spike Trimers

The goal of Example 8 was to assess binding properties of AB-1 to spike trimers representative of SARS-CoV-2 variants and non-SARS-CoV-2 sarbecoviruses.

DELFIA and SPR were employed to assess binding of AB-1 and the Reference Antibody to a panel of spike trimers representative of:
a) SARS-CoV-2 pre-Omicron variants (D614G (ancestral strain with D614G mutation), and Delta (B.1.617.2));
b) major SARS-CoV-2 Omicron variants (BA.1, BA.1.1, BA.2, BA.2.12.1, BA.2.3.20, BA.2.75, BA.2.75.2, BA.4, BA.5, BA.4.6, BF.7, BN.1, BQ.1, BQ.1.1, XBB, XBB.1, and XBB.1.5);
c) non-SARS-CoV-2 sarbecoviruses (WIV1, and SARS-CoV-1); and
d) SARS-CoV-2 Omicron variants with polymorphisms in the AB-1 epitope (P1162S and P1162L) as identified in the mutational analysis studies.

Of note, recombinant SARS-CoV-2 BA.2+P1162L, SARS-CoV-2 BA.2+P1162S and SARS-CoV-2 BA.2 (parent (BA.2 spike sequence with no mutation in the AB-1 epitope)) spike trimers were produced internally in a single batch, while all other spike trimers (with the exception of WIV1) were commercially purchased from a single source and reconstituted based on vendor recommendations. To account for inherent differences in recombinant protein production between each source, the data obtained for SARS-CoV-2 BA.2+P1162L and SARS-CoV-2 BA.2+P1162S spike trimers were compared to SARS-CoV-2 BA.2 (parent), whereas the data generated with other spike trimers were compared to SARS-CoV-2 D614G.

A. AB-1 Binding to SARS-CoV-2 and Non-SARS-CoV-2 Spike Trimers by DELFIA

Recombinant spike trimers: WIV1 (in-house production); SARS-CoV-1 (ACRO Biosystems, catalog #SPN-S52H6, lot #4102-223VF1-12M); SARS-CoV-2 D614G (ACRO Biosystems, catalog #SPN-052H3, lot #3841-216YF1-Y8); SARS-CoV-2 Delta, (Pango lineage B.1.617.2, ACRO Biosystems, catalog #SPN-052He, lot #4961-222HF1-11X); SARS-CoV-2 BA.1 (ACRO Biosystems, catalog #SPN-052 Hz, lot #5714a-21CCR1-Z4); SARS-CoV-2 BA.1.1 (ACRO Biosystems, #SPN-05224, lot #6222-224EF1-12M); SARS-CoV-2 BA.2 (ACRO Biosystems #SPN-05223, lot #5910-2232F1-11S); SARS-CoV-2 BA.2.12.1 (ACRO Biosystems, #SPN-0522d, lot #6307-224UF1-12T); SARS-CoV-2 BA.2.3.20 (ACRO Biosystems, #SPN-0522n, lot #7111-22B9F1-176); SARS-CoV-2 BA.2.75 (ACRO Biosystems, cat #SPN-0522f, lot #6764a-227DF1-15C); SARS-CoV-2 BA.2.75.2 (ACRO Biosystems, #SPN-0522r, lot #7198-22BFF1-178); SARS-CoV-2 BA.4 (ACRO Biosystems, #SPN-05229, lot #6292-2255F1-132); SARS-CoV-2 BA.4.6 (ACRO Biosystems, #SPN-0522m, lot #6992-229MF1-162); SARS-CoV-2 BF.7 (ACRO Biosystems, #SPN-0522Q, lot #7159-22ANF1-16V); SARS-CoV-2 BN.1 (ACRO Biosystems, #SPN-0524b, lot #7459-22CHF1-17X); SARS-CoV-2 BQ.1 (ACRO Biosystems, #SPN-0524a, lot #7433-2315F1-188); SARS-CoV-2 BQ.1.1 (ACRO Biosystems, #SPN-0522s, lot #7199-22B3F1-171); SARS-CoV-2 XBB (ACRO Biosystems, #SPN-05248, lot #7367a-22C6F1-17P); SARS-CoV-2 XBB.1 (ACRO Biosystems, #SPN-0522t, lot #7256-22B7F1-182); SARS-CoV-2 XBB.1.5 (ACRO Biosystems, #SPN-0524i, lot #7643-231AF1-188); SARS-CoV-2 BA.2+P1162L (BA.2_P1162L_EPI_ISL_10027138, in-house production); SARS-CoV-2 BA.2+P1162S (BA.2_P1162S_EPI_ISL_10014673, in-house production); SARS-CoV-2 BA.2 (parent) (Omicron_BA.2_EPI_ISL_10000005, in-house production).

Antibodies: AB-1 (Lonza, lot #1100-130922-01), the Reference Antibody (GenScript USA, Inc., lot #U737NHI220-3, the Reference Antibody variable regions expressed as human IgG1 with LS mutation in the Fc region), isotype control (GenScript USA, Inc., lot #U799WHJ270-3, palivizumab variable regions targeting RSV F protein and expressed as human IgG1 with LS mutation in the Fc region).

Dilution plates: 96 well plate round bottom, non-treated, polypropylene (Corning, #3365; Greiner, #650201).

DELFIA plates: 384 well plate white, MaxiSorp, polystyrene (Thermo Fisher Scientific, #460372).

TBS-T: 20×TBS Tween-20 (Thermo Fisher Scientific, #28360) diluted 1:20 in ddH$_2$O.

Blocking solution: ELISA Assay Diluent B (5X) (BioLegend, #421205) diluted 1:5 in PBS.

Secondary antibody: DELFIA Eu-N1 Anti-Human IgG (PerkinElmer, #1244-330).

Enhancement solution: DELFIA Enhancement Solution (PerkinElmer, #4001-0010).

DELFIA, a time-resolved fluorescence (TRF) intensity technology, was used to determine binding of AB-1 to different SARS-CoV-2 spike trimers. DELFIA assays are designed to detect the presence of an analyte of interest using lanthanide (e.g., Europium [Eu]) chelate labeled reagents. When the immunoreaction is complete, the Eu ion is dissociated from the labeled immunocomponent bound to the solid phase by adding Enhancement solution. Then Eu fluorescence is measured by TRF.

Three hundred and eighty four (384) well plates were coated with spike trimers (5 μg/ml) overnight at 4° C. The plates were washed, incubated with blocking solution for 1 hour at room temperature, washed again and incubated with antibodies for 1 hour at room temperature. Antibody binding was assessed using a 12-point titration curve in technical quadruplicate (1:4 serial dilutions prepared in blocking solution and starting at 18 μg/ml). Then, the plates were washed and incubated with Eu-labeled anti-human IgG secondary antibody (0.1 μg/ml) for 30 minutes at room temperature. Finally, the plates were washed and incubated with DELFIA Enhancement solution for 15 minutes. TRF was recorded at 615 nm with a PerkinElmer EnVision plate reader.

Statistical analysis was performed with Prism 9.5.0 software. Half maximal effective concentration (EC$_{50}$) values and 95% confidence intervals were derived for each Log-transformed antibody titration curve using log(inhibitor) vs. response-Variable slope (four parameters) equation.

B. AB-1 Binding Kinetics to SARS-CoV-2 Spike Trimers by SPR

Biacore 8K+(Cytiva, serial #2873569).

Biacore 8K Control Software (Cytiva, version 4.0.8.19879).

Biacore Insight Evaluation Software (Cytiva, version 4.0.8.19879).

Recombinant spike trimer, His-tagged: SARS-CoV-2 D614G (ACRO Biosystems, #SPN-052H3, lot #3841-216YF1-Y8); SARS-CoV-2 Delta (Pango lineage B.1.617.2, ACRO Biosystems, #SPN-052He, lot #4961-2189F1-YF); SARS-CoV-2 BA.4 (ACRO Biosystems, #SPN-05229, lot #6292-2255F1-132); SARS-CoV-2 BA.5 (ACRO Biosystems, catalog #SPN-0522e, lot #6371-225RF1-144); SARS-CoV-2 BQ.1.1 (ACRO Biosystems, #SPN-0522s, lot #7199-22B3F1-17L); SARS-CoV-2 XBB.1.5 (ACRO Biosystems, #SPN-0524i, lot #7643-231AF1-188); SARS-CoV-2 BA.2+ P1162L (BA.2_P1162L_EPI_ISL_10027138, in-house production); SARS-CoV-2 BA.2+P1162S (BA.2_P1162S_EPI_ISL_10014673, in-house production); SARS-CoV-2 BA.2 (parent, Omicron_BA.2_EPI_ISL_10000005, in-house production); MERS (ACRO Biosystems, #SPN-M52H4, lot #4103a-212GF1-YV).

Fabs: AB-1 (in-house preparation), the Reference Antibody (in-house preparation).

Series S sensor chip CM4 (Cytiva, #29104989).

Amine-coupling kit, type 2 (Cytiva, #BR100633) composed of N-hydroxysuccinimide (NHS), 1-ethyl-3-(3-dimethylaminopropyl) carbodiimide hydrochloride (EDC) and 1 M ethanolamine hydrochloride, pH 8.5.

THE His tag antibody (anti-His, Genscript, #A00186).

10 mM sodium acetate, pH 4.5 (Cytiva, #BR100350).

10 mM glycine-HCl, pH 2.1 (Cytiva, #29234601).

20× HBS-EP+, pH 7.6 (Teknova, #H8022) composed of 0.2 M HEPES pH 7.4, 3 M NaCl, 60 mM EDTA, 1% Surfactant P20 and prepared at 1×.

Microplate, 96W, deep-well, U-bottom, PP, 1 mL (Greiner, #780201)

Microplate foil 96W (Cytiva, #28975816)

Biacore is a label-free platform that uses SPR to measure binding interactions in real-time. Kinetic and affinity parameters are extracted from experimental data by an iterative process that finds the best fit for a set of equations describing the interaction. The association rate constant $k_a$ (M$^{-1}$s$^{-1}$) governs the rate at which a complex is formed. The dissociation rate constant $k_d$ (s$^{-1}$) governs the rate at which a complex dissociates. The equilibrium dissociation constant $K_D$ (M) describes the strength of the interaction.

To evaluate the kinetics of Fabs of AB-1 and the Reference Antibody binding to a panel of SARS-CoV-2 spike trimers, a multi-cycle kinetics approach was implemented using a Biacore 8K+. An anti-His capture sensor surface was prepared across flow cells 1 and 2 and all 8 channels in series by activating a CM4 sensor chip with a 1:1 (v/v) mixture of 400 mM EDC and 100 mM NHS, injecting 25 μg/mL of the His tag antibody diluted in sodium acetate, pH 4.5 and deactivating the surface using 1 M ethanolamine, pH 8.5 for 420 s at a flow rate of 10 μL min$^{-1}$ for each command to attain approximately 5000 response units (RU) of immobilized anti-His. The panel of His-tagged SARS-CoV-2 spike trimers (referred to as the ligands) were injected for 30 sat a flow rate of 10 μL min$^{-1}$ to achieve a capture level of approximately 250 RU. Fabs of AB-1 and the Reference Antibody (referred to as the analytes) were injected over the surface starting from 600 nM to 0.8 nM using a 3-fold serial dilution. Each analyte concentration was injected in a separate cycle for 120 s at a flow rate of 30 μL min$^{-1}$ and the complex was allowed to dissociate for 600 s using 1× HBS-EP+ as the running buffer. The surface was regenerated by injecting 10 mM glycine-HCl, pH 2.1 for 20 s at a flow rate of 10 μL min$^{-1}$ in between each cycle. The assay was performed at 25° C. and 37° C. with technical replicates. Kinetic parameters for the concentration series were obtained by double referencing and globally fitting the data to a 1:1 binding model with mass transport limitation using the Biacore Insight Evaluation software. The kinetics of Fabs of AB-1 and the Reference Antibody binding to the panel of SARS-CoV-2 spike trimers are reported, and the resulting sensorgrams are shown. For interactions exhibiting biphasic binding profiles, specifically SARS-CoV-2 BA.2 spike trimers (parent, BA.2+P1162L and BA.2+P1162S), the dissociation time was cropped to allow for more robust curve fitting and improved residuals. As a result, the affinity values obtained for SARS-CoV-2 BA.2+P1162L and BA.2+ P1162S spike trimers were compared to the affinity value of SARS-CoV-2 BA.2 (parent) spike trimer, whereas the affinity values obtained for SARS-CoV-2 Delta, BA.4, BA.5, BQ.1.1 and XBB.1.5 spike trimers were compared to the affinity value of SARS-CoV-2 D614G spike trimer.

C. Results

Figures 31A, 31B, 31C:
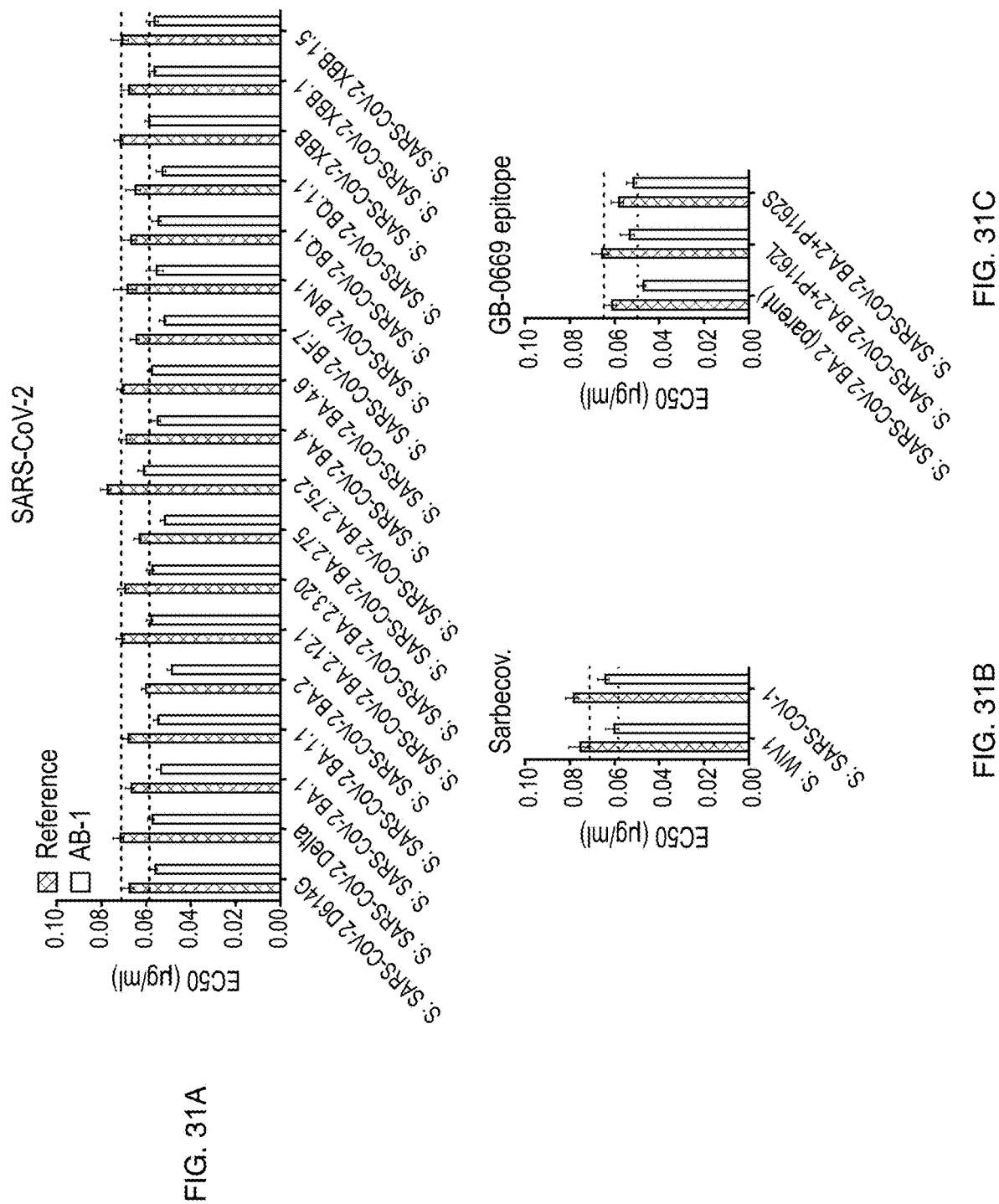
Figure 32A:
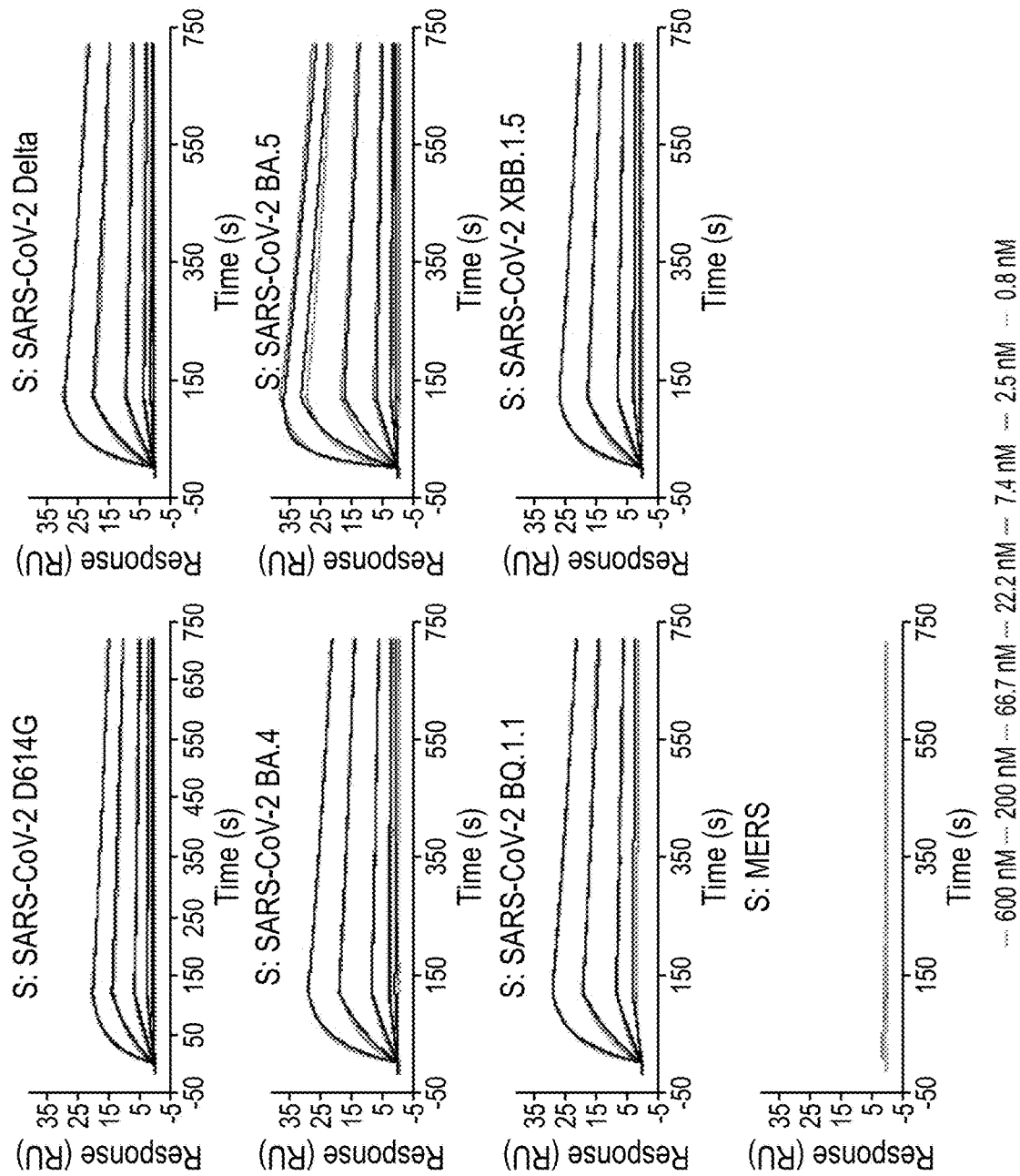
Figure 32B:
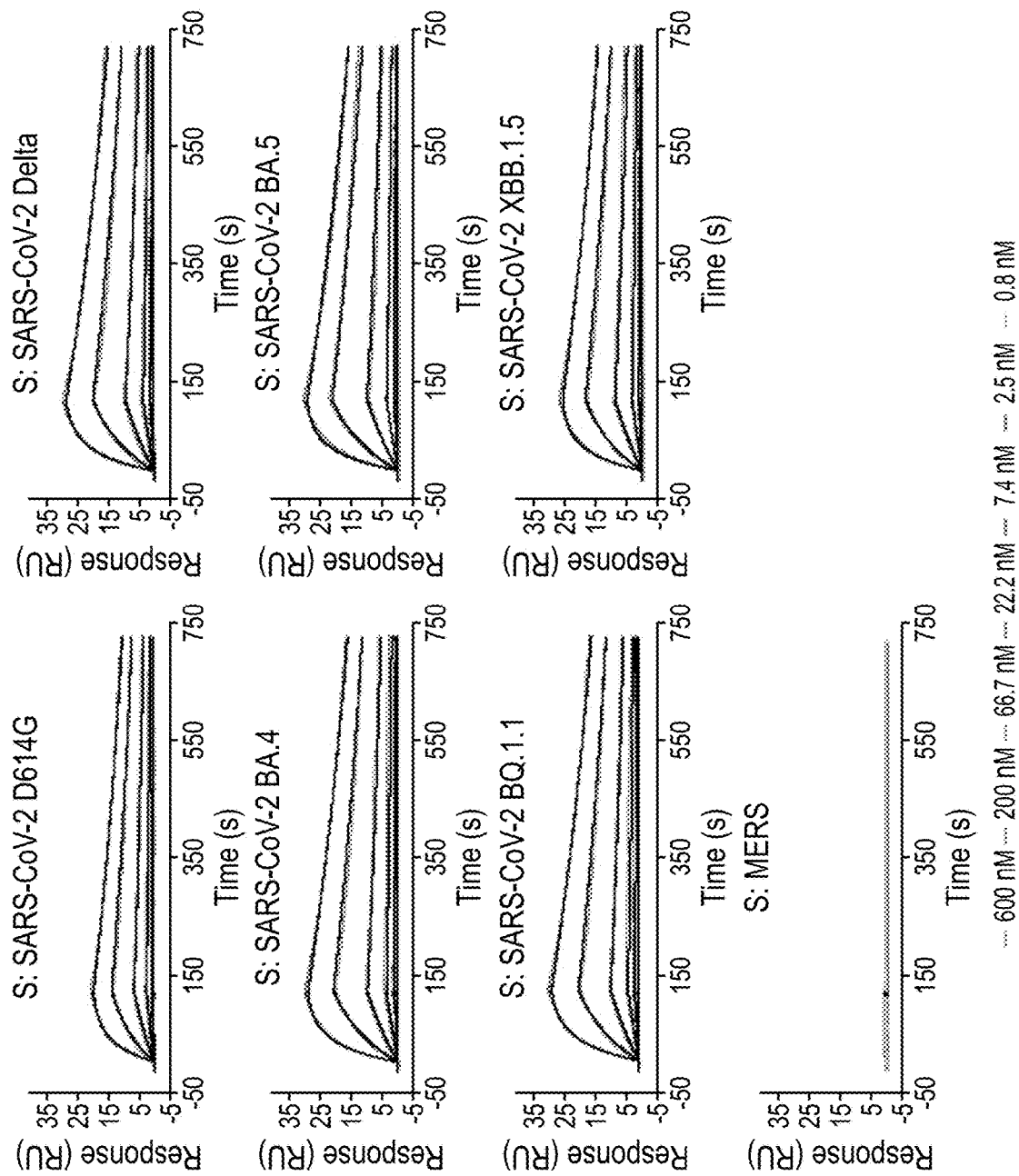
Figure 32C:
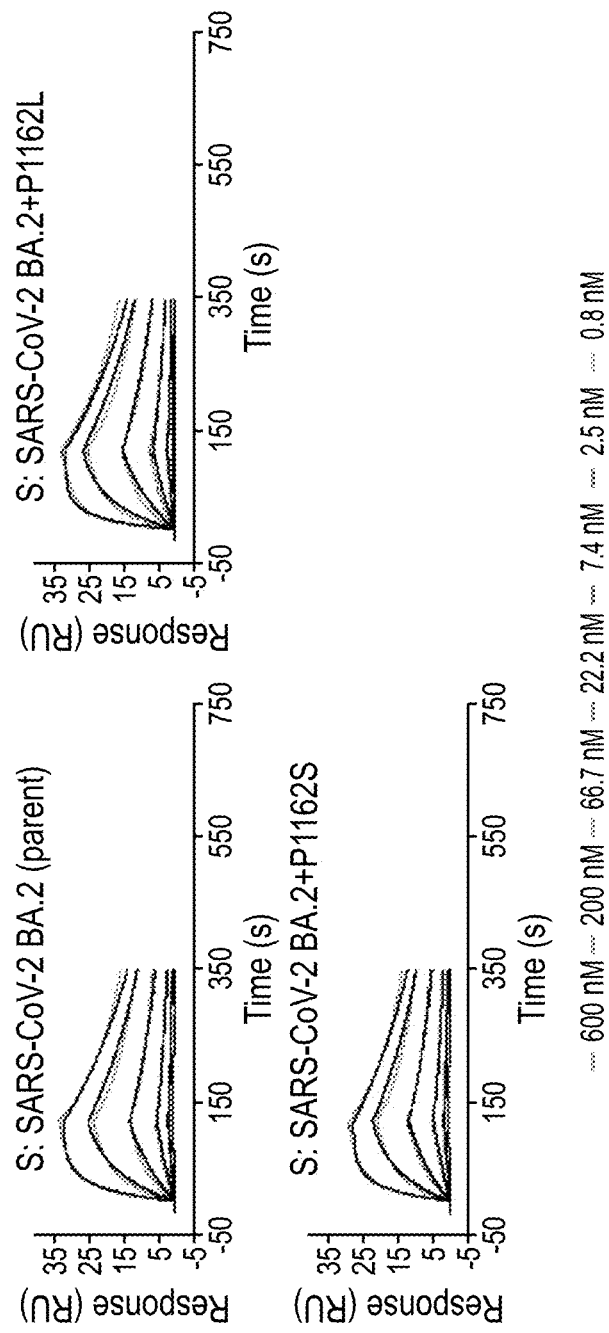
Figure 32D:
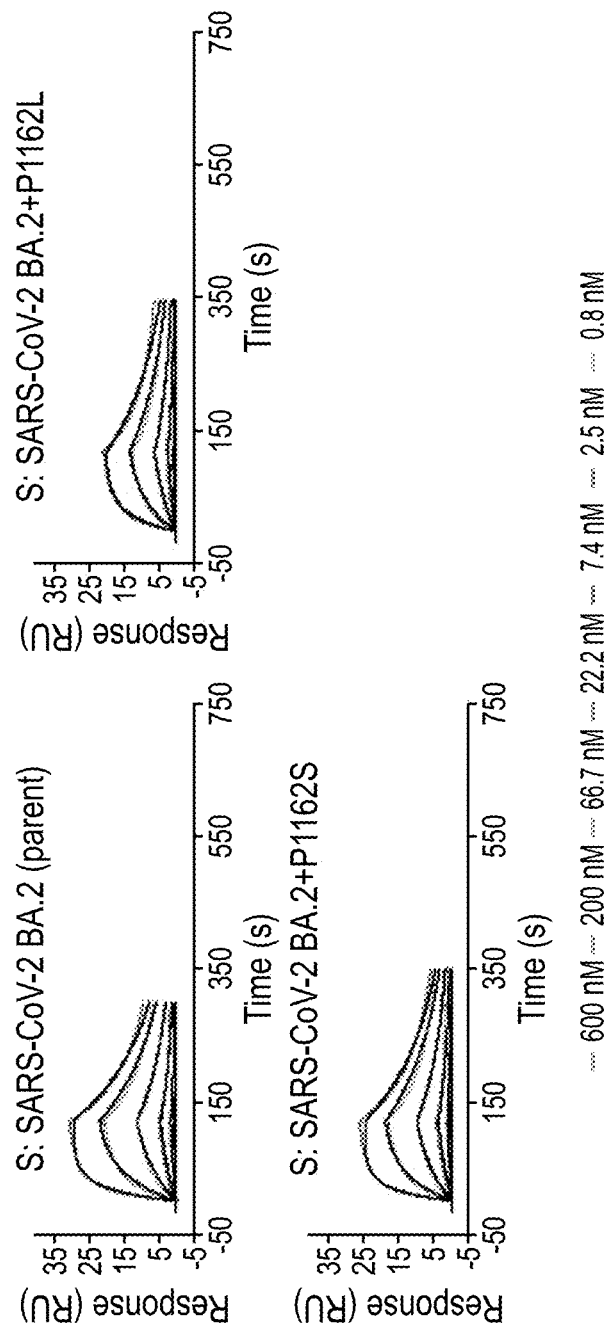
Figure 33A:
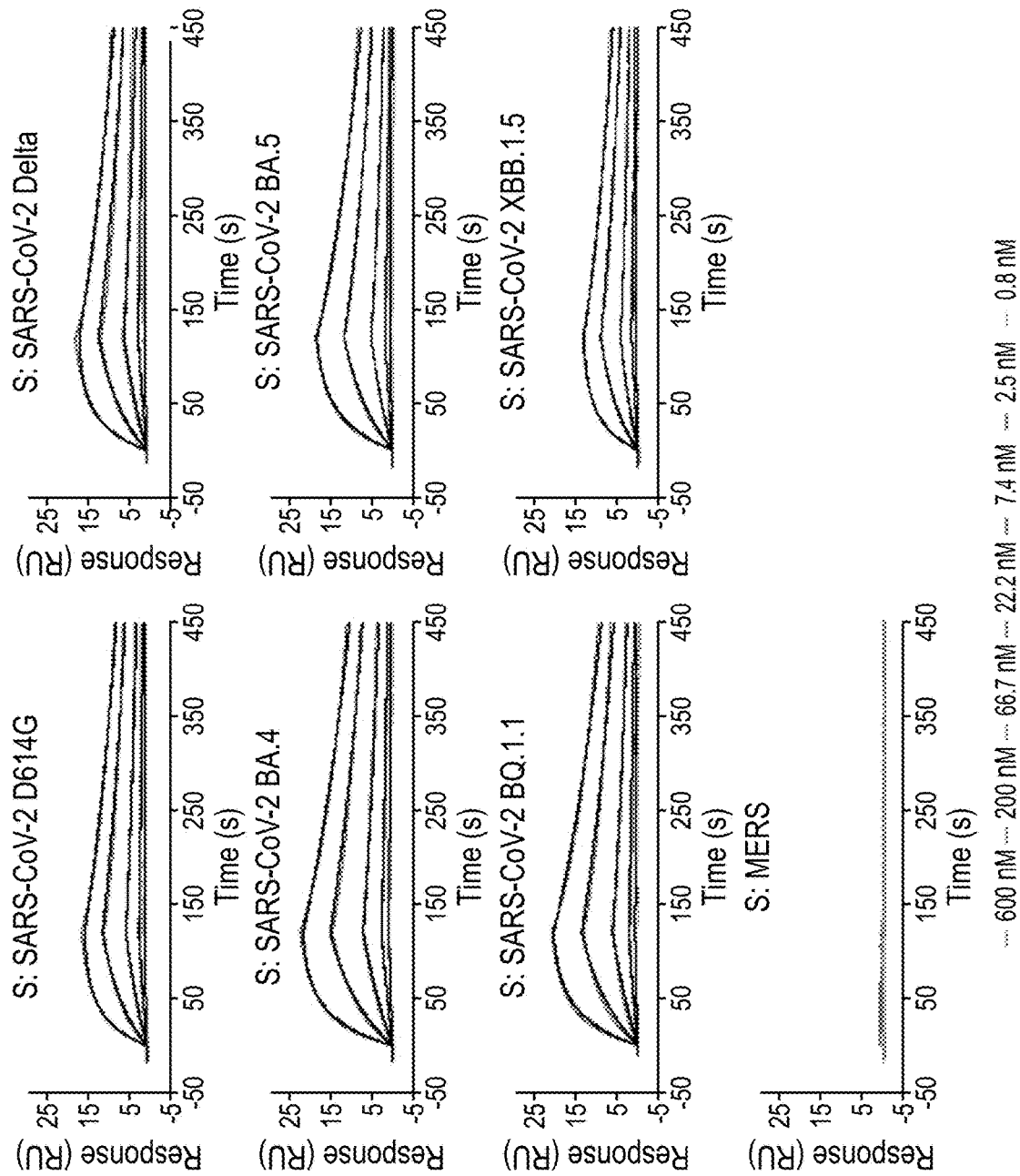
FIGS. 33A-33D. Sensorgrams of Fabs of AB-1 and the Reference Antibody binding to a panel of SARS-CoV-2 spike trimers by SPR at 37° C. Sensorgrams of Fabs of AB-1 (FIG. 33A) and the Reference Antibody (FIG. 33B) binding to SARS-CoV-2 spike trimers D614G, delta, BA.4, BA.5, BQ.1.1, XBB.1.5 and MERS spike trimer (negative control) at 37° C., from one independent experiment, are shown. Sensorgrams of Fabs of AB-1 (FIG. 33C) and the Reference Antibody (FIG. 33D) binding to SARS-CoV-2 spike trimers BA.2 (parent), BA.2+P1162L and BA.2+P1162S at 37° C., from one independent experiment, are shown. Shown are the real-time binding sensorgrams at different concentrations, and the fits generated by globally fitting the data to a 1:1 binding model with mass transport limitation.
Figure 33B:
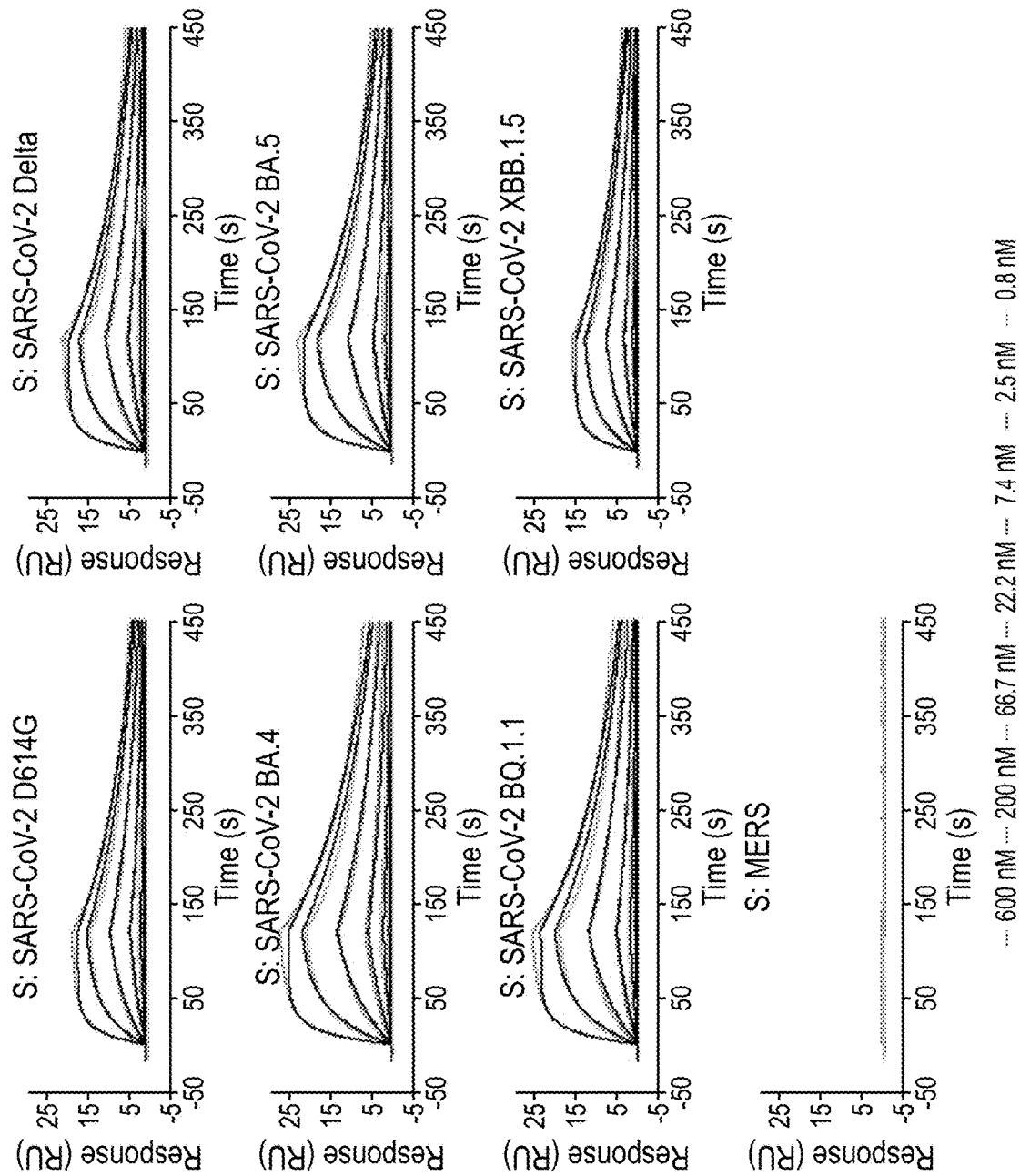
Figure 33C:
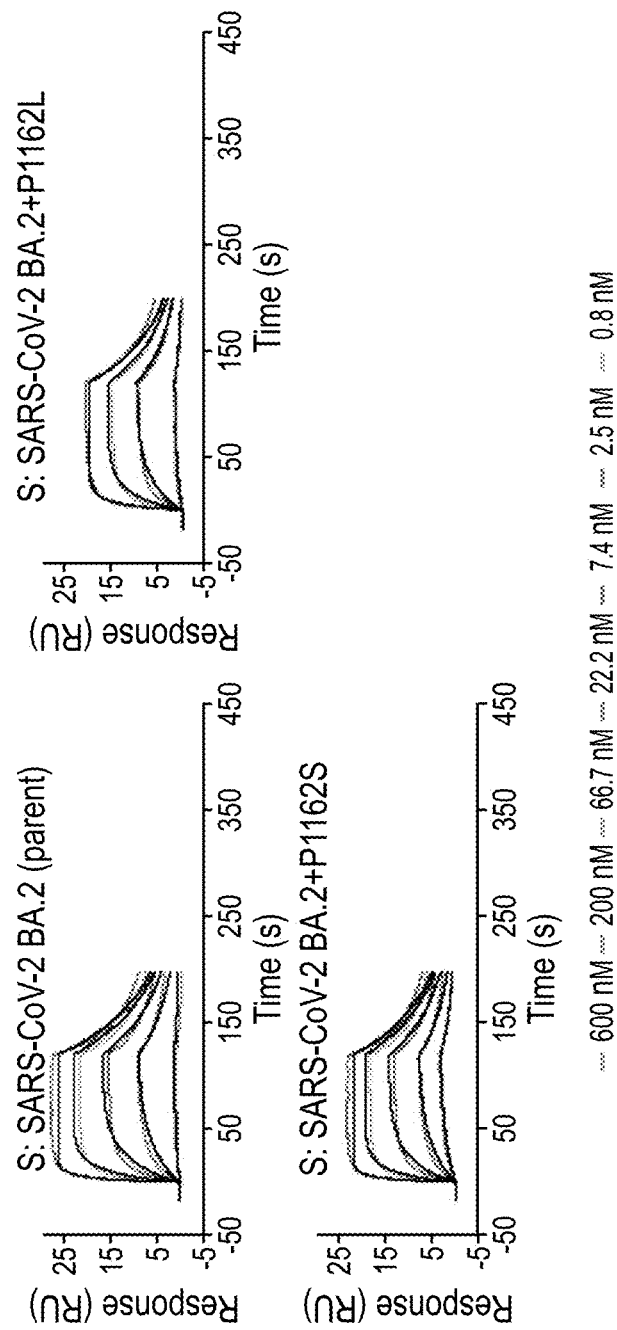
Figure 33D:
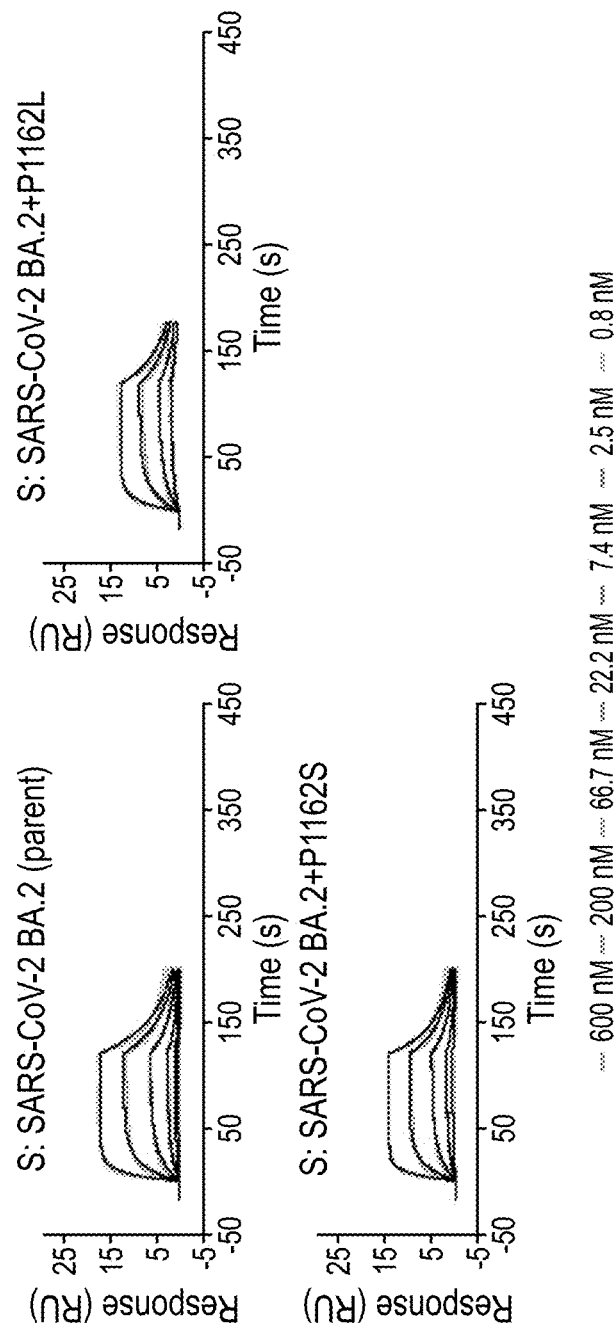

The DELFIA data demonstrates that AB-1 binds to all spike trimers tested in the experiment, showing overall lower EC$_{50}$ values compared to the Reference Antibody (FIGS. 31A-31C, Table 17). The SPR data confirms that AB-1 binds to SARS-CoV-2 D614G, Delta, BA.4, BA.5, BQ.1.1, XBB.1.5 spike trimers with comparable affinities and overall higher affinities than the Reference Antibody (FIGS. 32-33, Tables 18-20). The specificity of these results was confirmed by a lack of binding of the isotype control in the DELFIA experiment, and a lack of binding of AB-1 and the Reference Antibody to the MERS spike trimers used as negative control in the SPR experiment. AB-1 shows similar binding affinities to the spike trimers with polymorphisms in the AB-1 epitope as compared to the spike trimer derived from the parent SARS-CoV-2 BA.2 variant, with overall higher affinities than the Reference Antibody (FIGS. 32-33, Tables 18-20).

AB-1 consistently binds to multiple spike trimers representative of SARS-CoV-2 variants and non-SARS-CoV-2 sarbecoviruses. AB-1 binding affinities to SARS-CoV-2 Delta, BA.4, BA.5, BQ.1.1, XBB.1.5 spike trimers are within 2-fold of SARS-CoV-2 D614G spike trimer. These differences are considered within the range of variability of the methodology. In addition, AB-1 binds to these spike trimers with an approximate 5-fold higher affinity than the Reference Antibody. Similarly, AB-1 binding affinities to SARS-CoV-2 spike trimers of BA.2 variants containing polymorphisms in the AB-1 epitope (BA.2+P1162L and BA.2+P1162S) are within 2-fold of the BA.2 parent, and AB-1 binds to these spike trimers with an approximate 5-fold higher affinity than the Reference Antibody.

Example 9. Neutralization Activity with Pseudotyped Viruses

The goal of Example 9 was to assess neutralization activity of AB-1 as a single agent, or in combination with anti-spike receptor binding domain (RBD) antibodies against pseudoviruses representative of SARS-CoV-2 variants and non-SARS-CoV-2 sarbecoviruses.

SARS-CoV-2 pseudoviruses are non-replicating lentiviruses or deltaG-VSVs expressing a spike protein of interest and a reporter system (e.g., luciferase) to quantify infection in permissive cell lines (e.g., Vero E6 with or without TMPRSS2 expression). This experimental system enables evaluation of therapeutics that affect SARS-CoV-2 cell entry in a BSL-2 environment.

DeltaG-VSVs expressing luciferase and pseudotyped with spike proteins representative of SARS-CoV-2 variants and non-SARS-CoV-2 sarbecoviruses were employed to assess AB-1 neutralization profiles as a single agent, or in combinations with anti-RBD antibodies.

The pseudovirus panel for the single-agent experiments included:
a) SARS-CoV-2 pre-Omicron variants (D614G (ancestral strain with D614G mutation), and Delta (B.1.617.2));
b) major SARS-CoV-2 Omicron variants (BA.1, BA.1.1, BA.2, BA.2.12.1, BA.2.3.20, BA.2.75, BA.2.75.2, BA.4/5, BA.4.6, BF.7, BF.7.14, BN.1, BQ.1, BQ.1.1, XBB.1, XBB.1.5, and CH.1.1); and
c) non-SARS-CoV-2 sarbecoviruses (WIV1, and SARS-CoV-1); and
d) SARS-CoV-2 Omicron variants with polymorphisms in the AB-1 epitope (P1162S, P1162L) identified as part of the mutational analysis studies.

The pseudovirus panel for combination experiments included:
a) SARS-CoV-2 pre-Omicron variants (D614G (ancestral strain with D614G mutation), and Delta (B.1.617.2)); and
b) SARS-CoV-2 Omicron variants (BQ.1.1, and XBB.1.5).

A. AB-1 Neutralization of SARS-CoV-2 and Non-SARS-CoV-2 Pseudoviruses

Pseudoviruses: spike (WIV-1) pseudotyped deltaG-VSV (Luciferase Reporter) (BPS Bioscience, #78696, lot #221201); spike (SARS-CoV-1) pseudotyped deltaG-VSV (Luciferase Reporter) (BPS Bioscience, #78695, lot #221201); spike (SARS-CoV-2, D614G) pseudotyped deltaG-VSV (Luciferase Reporter) (BPS Bioscience, #78642, lot #220512); spike (SARS-CoV-2, B.1.617.2, Delta) pseudotyped deltaG-VSV (Luciferase Reporter) (BPS Bioscience, #78640, lot #220512); spike (SARS-CoV-2, BA.1) pseudotyped deltaG-VSV (Luciferase Reporter) (BPS Bioscience, #78663, lot #220812); spike (SARS-CoV-2, BA.1.1) pseudotyped deltaG-VSV (Luciferase Reporter) (BPS Bioscience, #78641, lot #220512); spike (SARS-CoV-2, BA.2) pseudotyped deltaG VSV (Luc Reporter) (BPS Bioscience, #78635, lot #220407); spike (SARS-CoV-2, BA.2.12.1) pseudotyped deltaG-VSV (Luciferase Reporter) (BPS Bioscience, #78643, lot #220527); spike (SARS-CoV-2, BA.2.3.20) pseudotyped deltaG-VSV (Luciferase Reporter) (BPS Bioscience, #78691, lot #221201); spike (SARS-CoV-2, BA.2.75) pseudotyped deltaG-VSV (Luciferase Reporter) (BPS Bioscience, #78684, lot #221027); spike (SARS-CoV-2, BA.2.75.2) pseudotyped deltaG-VSV (Luciferase Reporter) (BPS Bioscience, #78694, lot #221201); spike (SARS-CoV-2, BA.4/5) pseudotyped deltaG-VSV (Luciferase Reporter) (BPS Bioscience, #78644, lot #220527); spike (SARS-CoV-2, BA.4.6) pseudotyped deltaG-VSV (Luciferase Reporter) (BPS Bioscience, #78685, lot #221027); spike (SARS-CoV-2, BN.1) pseudotyped deltaG-VSV (Luciferase Reporter) (BPS Bioscience, #78731, lot #230112); spike (SARS-CoV-2, BF.7) pseudotyped deltaG-VSV (Luciferase Reporter) (BPS Bioscience, #78690, lot #221118); spike (SARS-CoV-2, BF.7.14) pseudotyped deltaG-VSV (Luciferase Reporter) (BPS Bioscience, #78748, lot #230302); spike (SARS-CoV-2, BQ.1) pseudotyped deltaG-VSV (Luciferase Reporter) (BPS Bioscience, #78688, lot #221118); spike (SARS-CoV-2, BQ.1.1) pseudotyped deltaG-VSV (Luciferase Reporter) (BPS Bioscience, #78689, lot #221118); spike (SARS-CoV-2, XBB.1) pseudotyped deltaG-VSV (Luciferase Reporter) (BPS Bioscience, #78692, lot #221201); spike (SARS-CoV-2, XBB.1.5) pseudotyped deltaG-VSV (Luciferase Reporter) (BPS Bioscience, #78733, lot #230119); spike (SARS-CoV-2, CH.1.1) pseudotyped deltaG-VSV (Luciferase Reporter) (BPS Bioscience, #78732, lot #230112); spike (SARS-CoV-2, BA.5.8 P1162L) pseudotyped AG-VSV (Luciferase Reporter) (BPS Bioscience, #78751, lot #230302); spike (SARS-CoV-2, BA.1.1 P1162S) pseudotyped AG-VSV (Luciferase Reporter) (BPS Bioscience, #78749, lot #230302).

Cell lines: TMPRSS2-Vero E6 Recombinant Cell Line (CL-030, BPS Biosciences, #78081, lot #210522 #20); VERO C1008 (Vero 76, clone E6, Vero E6) (CL-004-001, ATCC, #CRL-1586).

Antibodies: AB-1 (Lonza, lot #1100-130922-01), the Reference Antibody (GenScript USA, Inc., lot #U737NHI220-3, the Reference Antibody variable regions expressed as human IgG1 with LS mutation in the Fc region), isotype control (GenScript USA, Inc., lot #U799WHJ270-3, palivizumab variable regions targeting RSV F protein and expressed as human IgG1 with LS mutation in the Fc region), sotrovimab VH/VL-huIgG1-LS (in-house production, sotrovimab variable regions expressed as human IgG1 with LS mutation in the Fc region), R-AB-2b (R-AB-2b-001, in-house production, variable regions of an internally generated anti-RBD antibody targeting the class 4 epitope and expressed as human IgG1 with LS mutation in the Fc region), bebtelovimab (GenScript USA, Inc., lot #U3767HH180-46).

Stimulation medium: MEM (#5H30024.02, lot #AH29890509) with 2.5% FBS (#A38403-01, lot #262908SRP), 0.1 mM nonessential amino acids (#11140-050, lot #2390759), 1 mM sodium pyruvate (#11360-070, lot #2323639), 1% Penicillin/Streptomycin (#15140-122, lot #2441835).

Luciferase detection buffer: ONE-Step™ Luciferase Assay System, mix components A and B at 100:1 ratio respectively (BPS Bioscience, #60690-3, lot #221221).

Tissue culture plates: white 384-Well plates, with lid, cell culture, sterile, polystyrene (ThermoFisher, #164610).

Dilution plates: 96 well plate round bottom, non-treated, polypropylene (Corning, #3365; Greiner, #650201).

Antibody/pseudovirus incubation plates: Nunc 96-Well polystyrene round bottom microwell plates, with lid, non-tissue culture-treated, sterile (Thermo Fisher Scientific, #268200).

Vero E6 or TMPRSS2-Vero E6 recombinant cells were seeded in 384-well tissue culture plates at a density of 3,500 cells per well in 20 µl of stimulation medium and incubated at 37° C., 5% $CO_2$ for 2-4 hours. In parallel, the antibodies were serially diluted and incubated with the diluted pseudovirus at a desired multiplicity of infection (0.25 for SARS-CoV-2 pre-Omicron variants, and non-SARS-CoV-2 Sarbecoviruses; 0.5 for SARS-CoV-2 Omicron variants). Antibody neutralization was assessed with 12-point titration curves in technical quadruplicate (1:4 serial dilutions prepared in PBS with 0.2% BSA and 1× Pen-Strep solution starting at 18, 9 or 7.5 µg/ml, depending on the reported experimental setting). For single agent experiments, the antibodies were serially diluted starting at 72 µg/ml (4-fold of the final top concentration (18 µg/ml) in the tissue culture plates). For combination experiments, the antibodies were mixed at a 1:1 ratio and serially diluted, each starting at 72 µg/ml (4-fold of the final top concentration (18 µg/ml) in the tissue culture plates). When indicated, AB-1 was combined with R-AB-2b or sotrovimab—VH/VL huIgG1-LS at a 2:1 or 2.4:1 ratio. In these conditions, AB-1, R-AB-2b and sotrovimab VH/VL huIgG1-LS were serially diluted, starting at 72, 36 and 30 µg/ml, respectively (4-fold of the final top concentration (18, 9 and 7.5 µg/ml, respectively) in the tissue culture plates). After 30-60 minutes of incubation at 37° C., 5% $CO_2$, a 20-µl pseudovirus/antibody mixture was added to the tissue culture plates pre-seeded with cells, achieving the final antibody concentrations in a total volume of 40 µl. After 24 hours at 37° C., 5% $CO_2$, an equal volume of luciferase substrate was added directly to culture plates (pseudovirus backbones have luciferase reporters), and luminescence was quantified on a PerkinElmer EnVision plate reader. Percentage neutralization was calculated with the following formula, where "$signal_{positiveControl}$" is defined by the average luminescence signal of wells containing cells without pseudovirus, "$signal_{negativeControl}$" is defined as the average luminescence signal of wells containing cells with pseudovirus, and "$signal_{well}$" is defined as the average luminescence signal of wells containing cells with both antibody and pseudovirus:

$$\text{Percentage neutralization} = \left(1 - \frac{\text{signal}_{well} - \text{signal}_{positiveControl}}{\text{signal}_{negativeControl} - \text{signal}_{positiveControl}}\right) \cdot 100$$

Statistical analysis was performed with Prism 9.5.0 software. The half-maximal effective concentration ($EC_{50}$) values and 95% confidence intervals were derived for each Log-transformed antibody titration curve using log(inhibitor) vs. response-Variable slope (four parameters) equation. The 80% or 90% maximal effective concentration ($EC_{80}$ or $EC_{90}$) values and 95% confidence intervals were derived for each Log-transformed antibody titration curve using log (agonist) vs. response—Find ECanything equation by setting F parameter to 80 or 90. The maximal neutralization ($E_{max}$) values and 95% confidence intervals were defined as percentage neutralization at the top concentration (18 µg/ml).

B. Results

Figure 34:
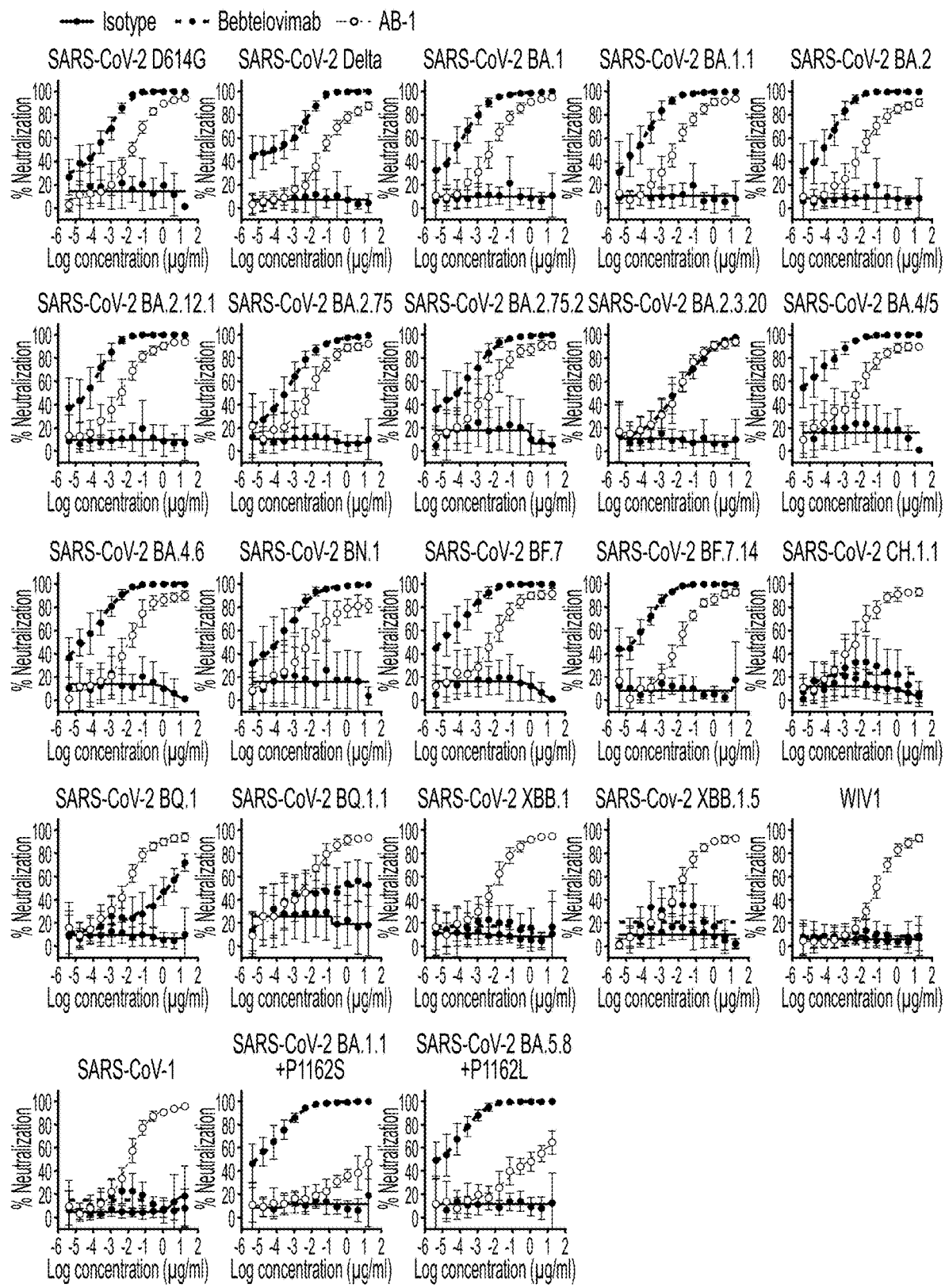
FIG. 34. AB-1 neutralization of SARS-CoV-2 Variants and non-SARS-CoV-2 sarbecoviruses. Neutralization profiles of AB-1, bebtelovimab, and isotype control antibody against pseudoviruses representative of SARS-CoV-2 variants and non-SARS-CoV-2 sarbecoviruses. The results are reported as % neutralization and shown as mean±standard deviation (representative of three to six independent experiments, four technical replicates each).

Experiments with AB-1 as single agent demonstrate consistent neutralization of pseudoviruses representative of SARS-CoV-2 variants and non-SARS-CoV-2 sarbecoviruses as assessed by $EC_{50}$, $EC_{80}$ and $EC_{90}$ values except for pseudoviruses bearing spike proteins with mutations in the AB-1 epitope (BA.1.1+P1162S, BA.5.8+P1162L). These pseudoviruses were neutralized by the clinical-stage antibody bebtelovim8ab but not AB-1 (FIG. 34, Tables 21-23).

AB-1 neutralizes (Table 21): SARS-CoV-2 pre-Omicron variants with mean $EC_{50}$ values <0.040 µg/ml; major SARS-CoV-2 Omicron variants with mean $EC_{50}$ values <0.015 µg/ml; and WIV1 and SARS-CoV-1 with mean $EC_{50}$ values of 0.063 and 0.012 µg/ml. The $EC_{50}$ values and/or complete 95% confidence intervals could not be calculated for BA.1.1+P1162S and BA.5.8+P1162L due to incomplete neutralization. Compared to AB-1 neutralization of SARS-CoV-2 D614G, only AB-1 neutralization of SARS-CoV-2 Delta and WIV1 showed increased mean $EC_{50}$ values and non-overlapping 95% confidence intervals. However, the overall increase in the average $EC_{50}$ values for SARS-CoV-2 Delta and WIV1 over SARS-CoV-2 D614G is <5-fold.

AB-1 neutralizes (Table 22): SARS-CoV-2 pre-Omicron variants with mean $EC_{80}$ values <0.400 µg/ml; major SARS-CoV-2 Omicron variants with mean $EC_{80}$ values <0.150 µg/ml; WIV1 and SARS-CoV-1 with mean $EC_{80}$ values of 0.459 and 0.078 µg/ml, respectively. The $EC_{80}$ values and/or complete 95% confidence intervals could not be calculated for BA.1.1+P1162S and BA.5.8+P1162L. Compared to AB-1 neutralization of SARS-CoV-2 D614G, only AB-1 neutralization of WIV1 showed increased mean $EC_{80}$ values and non-overlapping 95% confidence interval. However, the overall increase in the average $EC_{80}$ value for WIV1 over SARS-CoV-2 D614G is <5-fold.

AB-1 neutralizes (Table 23): SARS-CoV-2 pre-Omicron variants with mean $EC_{90}$ values <1.500 µg/ml; major SARS-CoV-2 Omicron variants with mean $EC_{90}$ values <0.600 µg/ml (except for SARS-CoV-2 BQ.1.1, mean $EC_{90}$ value: 1.027 µg/ml); WIV1 and SARS-CoV-1 with mean $EC_{90}$ values of 1.464 and 0.238 µg/ml, respectively. The $EC_{90}$ values and/or complete 95% confidence intervals could not be calculated for BA.1.1+P1162S and BA.5.8+P1162L.

Figure 35A:
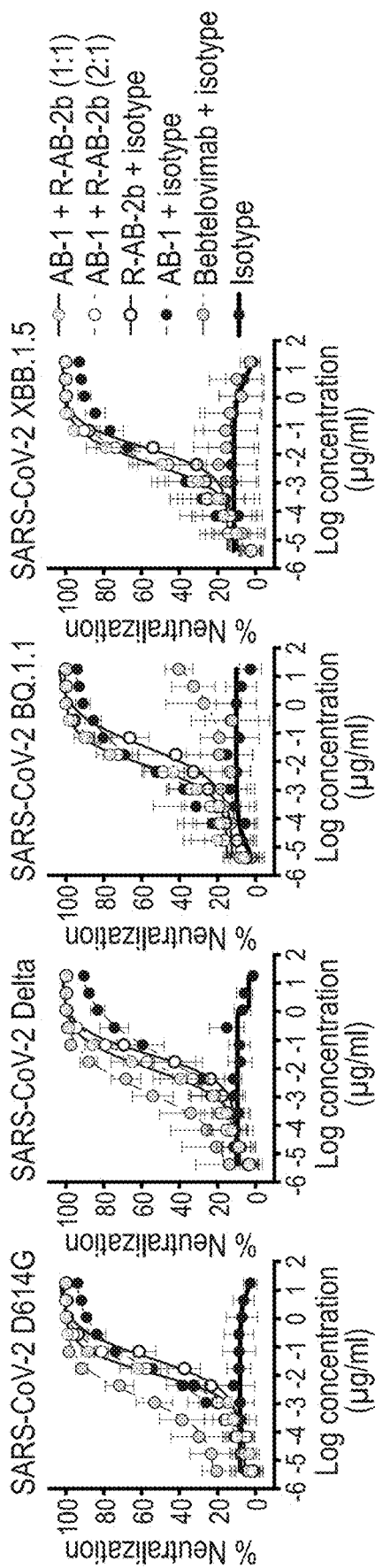
FIGS. 35A-35B. Neutralization of SARS-CoV-2 variants by AB-1 in combination with R-AB-2b. Neutralization profiles of AB-1+R-AB-2b (tested at two different ratios), AB-1, R-AB-2b, and bebtelovimab as single agents, and isotype control antibody against pseudoviruses representative of the indicated SARS-CoV-2 variants using TMPRSS2-Vero E6 (FIG. 35A) or Vero E6 (FIG. 35B) cells. The anti-spike antibodies tested as single agents were combined with isotype at the same concentrations to control for overall mass of anti-spike antibodies tested as combinations. The x-axis indicates the concentration of each individual antibody in the combinations, or of the antibody with the highest concentration if the concentrations differ. The results are reported as % neutralization and shown as mean±standard deviation (representative of three or four independent experiments, four technical replicates each).
Figure 35B:
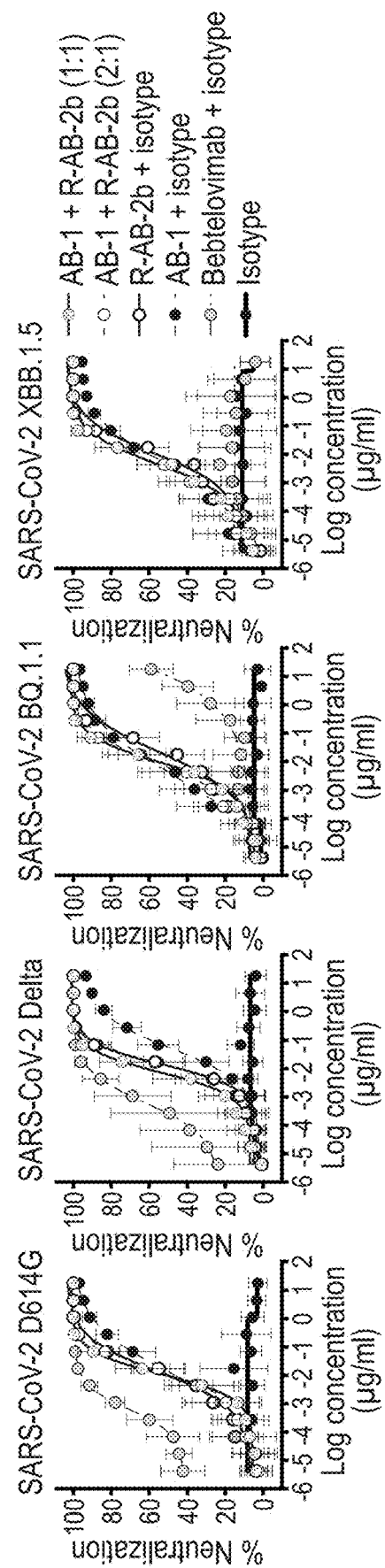

Experiments with the combination of AB-1 and the anti-RBD antibody R-AB-2b (tested at two different ratios) demonstrated improved neutralization profiles against SARS-CoV-2 variants (D614G, Delta, BQ.1.1, XBB.1.5)

compared to the single agents, especially as determined by the EC$_{90}$ values (FIGS. 35A-35B).

For SARS-CoV-2 BQ.1.1, the mean EC$_{90}$ values for TMPRSS2-Vero E6 and Vero E6 cells are, respectively (Table 27): AB-1+R-AB-2b (1:1), 0.085 and 0.109 μg/ml; AB-1+R-AB-2b (2:1), 0.167 and 0.222 μg/ml; R-AB-2b+ isotype, 0.772 and 1.253 μg/ml; AB-1+isotype, 0.518 and 0.629 μg/ml. The AB-1+R-AB-2b (1:1) 95% confidence intervals measured in both TMPRSS2-Vero E6 and Vero E6 cells do not overlap with the R-AB-2b+isotype and AB-1+ isotype 95% confidence intervals.

For SARS-CoV-2 XBB.1.5, the mean EC$_{90}$ values for TMPRSS2-Vero E6 and Vero E6 cells are respectively (Table 27): AB-1+R-AB-2b (1:1), 0.071 and 0.094 μg/ml; AB-1+R-AB-2b (2:1), 0.158 and 0.094 μg/ml; R-AB-2b+ isotype, 0.173 and 0.276 μg/ml; AB-1+isotype, 0.737 and 0.346 μg/ml.

Figure 36:
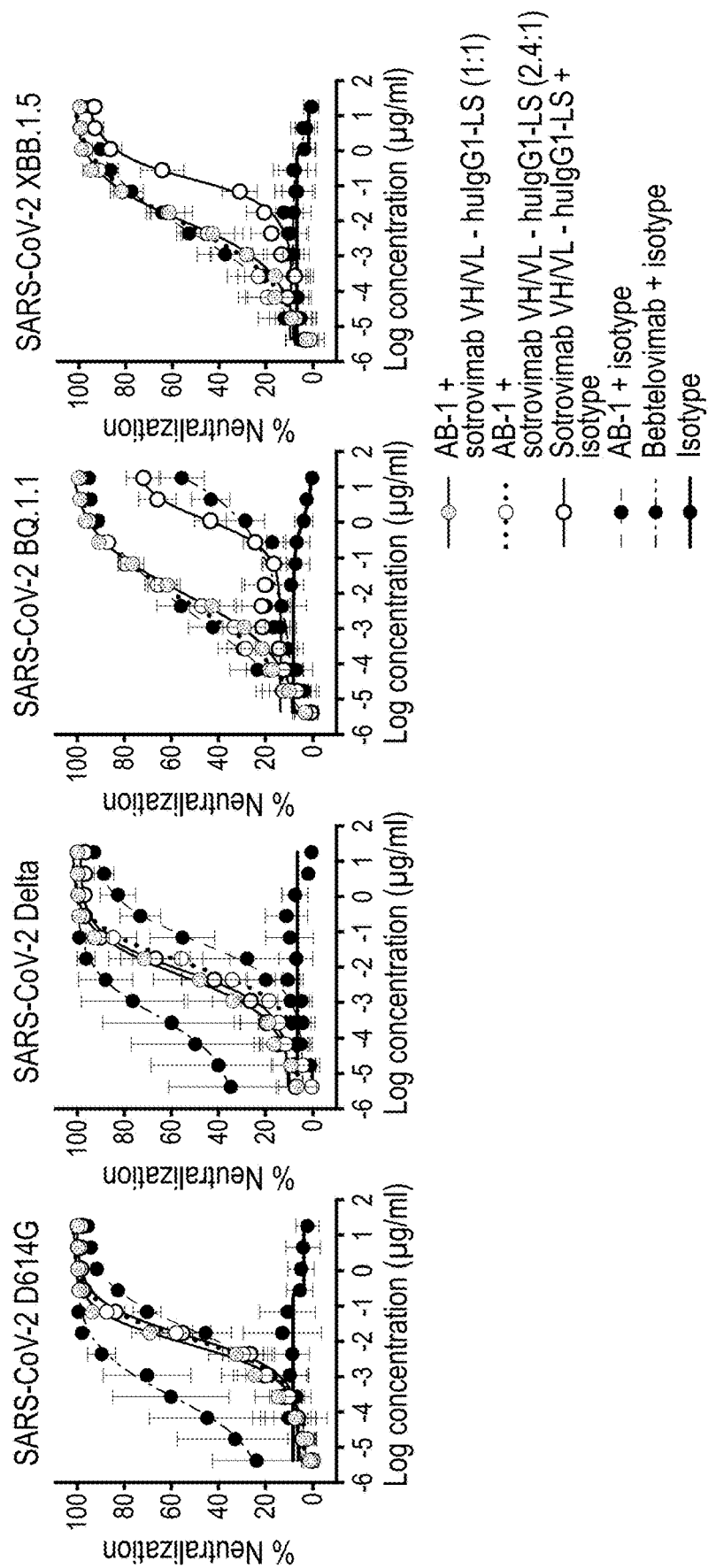
FIG. 36. Neutralization of SARS-CoV-2 variants by AB-1 in combination with Sotrovimab VH/VL-huIgG1-LS. Neutralization profiles of AB-1+sotrovimab VH/VL-huIgG1-LS (tested at two different ratios), AB-1, sotrovimab VH/VL-huIgG1-LS, and bebtelovimab as single agents, and isotype control antibody against pseudoviruses representative of the indicated SARS-CoV-2 variants using Vero E6 cells. The anti-spike antibodies tested as single agents were combined with isotype at the same concentrations to control for overall mass of anti-spike antibodies tested as combinations. The x-axis indicates the concentration of each individual antibody in the combinations, or of the antibody with the highest concentration if the concentrations differ. The results are expressed as % neutralization and shown as mean±standard deviation (representative of three or four independent experiments, four technical replicates each).

The experiments with the combination of AB-1 and sotrovimab VH/VL-huIgG1-LS (tested at two different ratios) demonstrated more subtle but still detectable improvements in neutralization profiles against SARS-CoV-2 variants, compared to the single agents, mainly evidenced by enhanced E$_{max}$ (i.e., exceeding 98% neutralization of SARS-CoV-2 BQ.1.1 and XBB.1.5 pseudoviruses only in the AB-1+sotrovimab VH/VL-huIgG1-LS experimental condition) (FIG. 36).

For SARS-CoV-2 BQ.1.1, the mean E$_{max}$ values (Table 32): AB-1+sotrovimab VH/VL-huIgG1-LS (1:1), 99.55%; AB-1+sotrovimab VH/VL-huIgG1-LS (2:1), 98.84%; sotrovimab VH/VL-huIgG1-LS+isotype, 71.91%; and the AB-1+ isotype, 95.25%. AB-1+sotrovimab VH/VL-huIgG1-LS (1:1) and AB-1+sotrovimab VH/VL-huIgG1-LS (2:1) 95% confidence intervals do not overlap with the sotrovimab VH/VL-huIgG1-LS+isotype and AB-1+isotype 95% confidence intervals.

For SARS-CoV-2 XBB.1.5, mean E$_{max}$ values (Table 32): AB-1+sotrovimab VH/VL-huIgG1-LS (1:1), 99.78%; AB-1+sotrovimab VH/VL-huIgG1-LS (2:1), 99.47%; sotrovimab VH/VL-huIgG1-LS+isotype, 93.43%; AB-1+isotype, 95.49%. AB-1+sotrovimab VH/VL-huIgG1-LS (1:1) and AB-1+sotrovimab VH/VL-huIgG1-LS (2:1) 95% confidence intervals do not overlap with sotrovimab VH/VL-huIgG1-LS+isotype and AB-1+isotype 95% confidence intervals.

For both single agent and combination experiments (FIGS. 34-36), bebtelovimab potently neutralizes several SARS-CoV-2 variants, except for SARS-CoV-2 CH.1.1, BQ.1, BQ.1.1, XBB.1 and XBB.1.5 as well as SARS-CoV-1 and WIV1. These results are consistent with reported literature and escape mutations for bebtelovimab.

In conclusion, AB-1 shows comparable neutralization profiles across multiple pseudoviruses representative of SARS-CoV-2 variants and non-SARS-CoV-2 Sarbecoviruses, with the exception of those bearing mutations in the target epitope (P1162S, P1162L). The latter are neutralized by the clinical-stage antibody bebtelovimab. The combinations of AB-1 and anti-RBD antibodies (in particular, the internally generated R-AB-2b) show improved neutralization profiles against pseudoviruses representative of SARS-CoV-2 variants (ancestral strain with D614G mutation, Delta, BQ.1.1, XBB.1.5), compared to single agent antibodies.

Example 10. Neutralization Activities of AB-1 Surrogate

The goal of Example 10 was to compare neutralization activities of AB-1 and its surrogate antibodies (AB-1 variable regions expressed as human IgG1 without LS mutation in the Fc region or hamster IgG2a) employed in hamster challenge models.

SARS-CoV-2 pseudoviruses are non-replicating lentiviruses or deltaG-VSVs expressing a spike protein of interest. A reporter system (e.g., luciferase) was used to quantify infection in permissive cell lines (e.g., Vero E6, with or without TMPRSS2 expression). This experimental system enables evaluation of therapeutics that affect SARS-CoV-2 cell entry in a BSL-2 environment.

DeltaG-VSVs expressing luciferase and pseudotyped with spike proteins representative of SARS-CoV-2 D614G (ancestral strain with D614G mutation) and BA.2 strain were employed to assess neutralization profiles of monoclonal antibodies in hamster challenge models.

Pseudoviruses: spike (SARS-CoV-2, D614G) pseudotyped deltaG-VSV (Luciferase Reporter) (BPS Bioscience, #78642, lot #220512); spike (SARS-CoV-2, BA.2) pseudotyped deltaG VSV (Luc Reporter) (BPS Bioscience, #78635, lot #220407).

Cell line: VERO C1008 (Vero 76, clone E6, Vero E6) (CL-004-001, ATCC, #CRL-1586).

Antibodies: AB-1 (Lonza, lot #1100-130922-01), AB-1 VH/VL-huIgG1 (GenScript USA, Inc., lot #U507ZHF090-3, AB-1 variable regions expressed as human IgG1 without LS mutation in the Fc region), AB-1 VH/VL-hamIgG2a (GenScript USA, Inc., lot #U9330HG280-3, AB-1 variable regions expressed as hamster IgG2a), sotrovimab VH/VL-huIgG1-LS (in-house production, sotrovimab variable regions expressed as human IgG1 with LS mutation in the Fc region), sotrovimab VH/VL-huIgG1 (GenScript USA, Inc., lot #U069FHA200-14, sotrovimab variable regions expressed as human IgG1 without LS mutation in the Fc region), sotrovimab VH/VL-hamIgG2a (GenScript USA, Inc., lot #U9330HG280-9, sotrovimab variable regions expressed as hamster IgG2a), isotype (GenScript USA, Inc., lot #U799WHJ270-3, palivizumab variable regions targeting RSV F protein and expressed as human IgG1 with LS mutation in the Fc region), isotype-huIgG1 (GenScript USA, Inc., lot #U456BHD290-3, palivizumab variable regions targeting RSV F protein and expressed as human IgG1 without LS mutation in the Fc region), isotype-hamIgG2a (GenScript USA, Inc., lot #U9330HG280-15 palivizumab variable regions targeting RSV F protein and expressed as hamster IgG2a).

Stimulation medium: MEM (#SH30024.02, lot #AH29890509) with 2.5% FBS (#A38403-01, lot #262908SRP), 0.1 mM nonessential amino acids (#11140-050, lot #2390759), 1 mM sodium pyruvate (#11360-070, lot #2323639), 1% Penicillin/Streptomycin (#15140-122, lot #2441835).

Luciferase detection buffer: ONE-Step™ Luciferase Assay System, mix components A and B at 100:1 ratio respectively (BPS Bioscience, #60690-3, lot #221221).

Tissue culture plates: ThermoFisher white 384-well plates, with lid, cell culture, sterile, polystyrene (#164610).

Antibody/pseudovirus incubation plates: ThermoFisher Nunc 96-Well polystyrene round bottom microwell plates, with lid, non-tissue-culture-treated, sterile (#268200).

Vero E6 cells were seeded in 384-well tissue culture plates at a density of 3,500 cells per well in 20 μl of stimulation medium and incubated at 37° C., 5% CO$_2$ for 2-4 hours. In parallel, antibodies were serially diluted and incubated with diluted pseudovirus at a desired multiplicity of infection (0.25 for SARS-CoV-2 D614G, 0.5 for SARS-CoV-2 BA.2). Antibody neutralization was assessed using a 12-point titration curve in technical quadruplicate (1:4 serial dilutions prepared in PBS with 0.2% BSA and 1× Pen-Strep solution starting at 18 µg/ml). After 30-60 minutes of incubation at 37° C., 5% $CO_2$, 20 µl pseudovirus/antibody mixture was added to the tissue culture plates pre-seeded with cells, achieving final antibody concentrations in a total volume of 40 After 24 hours at 37° C., 5% $CO_2$, an equal volume of luciferase substrate was added directly to culture plates (pseudovirus backbones have luciferase reporters), and luminescence was quantified on a PerkinElmer EnVision plate reader. Percentage neutralization was calculated with the following formula, where "$signal_{positiveControl}$" is defined by the average luminescence signal of wells containing cells without pseudovirus, "$signal_{negativeControl}$" is defined as the average luminescence signal of wells containing cells with pseudovirus, "$signal_{well}$" is defined as the average luminescence signal of wells containing cells with both antibody and pseudovirus:

$$\text{Percentage neutralization} = \left(1 - \frac{signal_{well} - signal_{positiveControl}}{signal_{negativeControl} - signal_{positiveControl}}\right) \cdot 100$$

Statistical analysis was performed with Prism 9.5.0 software. Half maximal effective concentration ($EC_{50}$) values and 95% confidence intervals were derived for each Log-transformed antibody titration curve using log(inhibitor) vs. response-Variable slope (four parameters) equation.

Results

Figure 37:
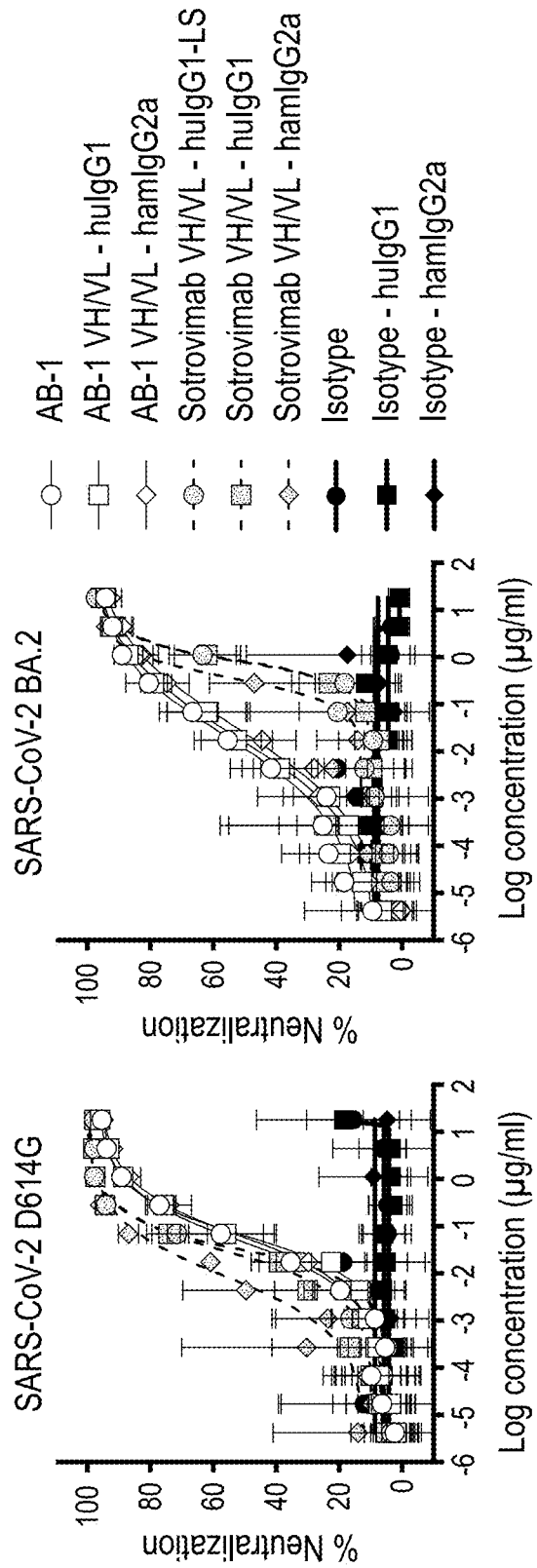
FIG. 37. Evaluation of neutralization profiles of parent and surrogate antibodies. Neutralization profiles of AB-1, sotrovimab VH/VL-huIgG1-LS and isotype control antibody, and their respective surrogate human IgG1 and hamster IgG2a molecules against pseudoviruses representing SARS-CoV-2 ancestral with D614G mutation and BA.2 variant. The results are expressed as % neutralization and shown as mean±standard deviation (representative of three independent experiments, four technical replicates each).
Figure 38:
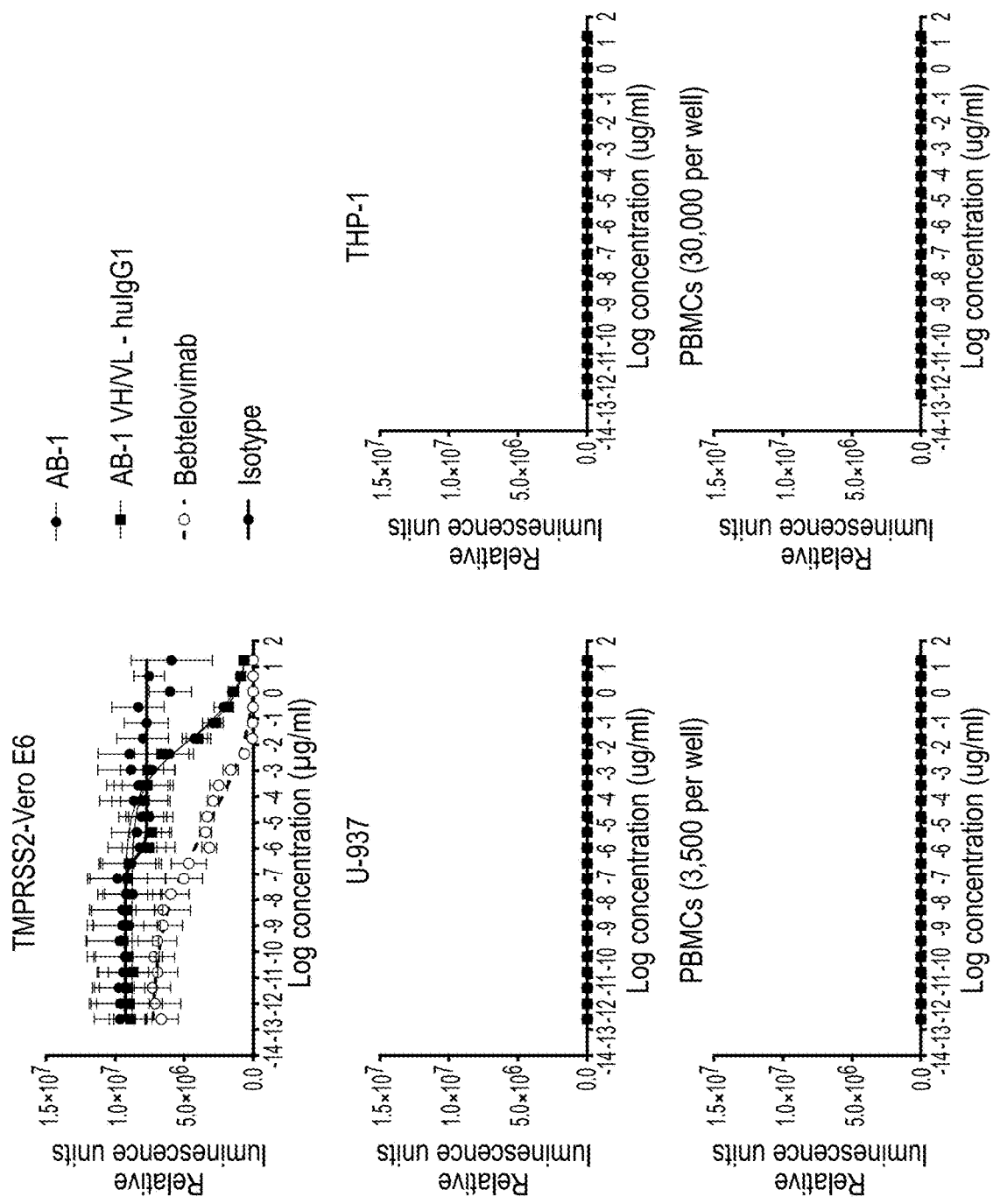
FIG. 38. SARS-CoV-2 Pseudovirus Infectivity of Fc Gamma Receptor-Bearing Cells in the Presence of AB-1. Monocytic cells lines (U-937, THP-1) and human primary PBMCs were infected with SARS-CoV-2 D614G pseudovirus in the presence of AB-1, AB-1 VH/VL-huIgG1, bebtelovimab and isotype control. TMPRSS2-Vero E6 cells were used as a positive control for infection. The results are expressed as relative luminescence units and shown as mean±standard deviation (representative of three independent experiments, three technical replicates each).
Figure 39:
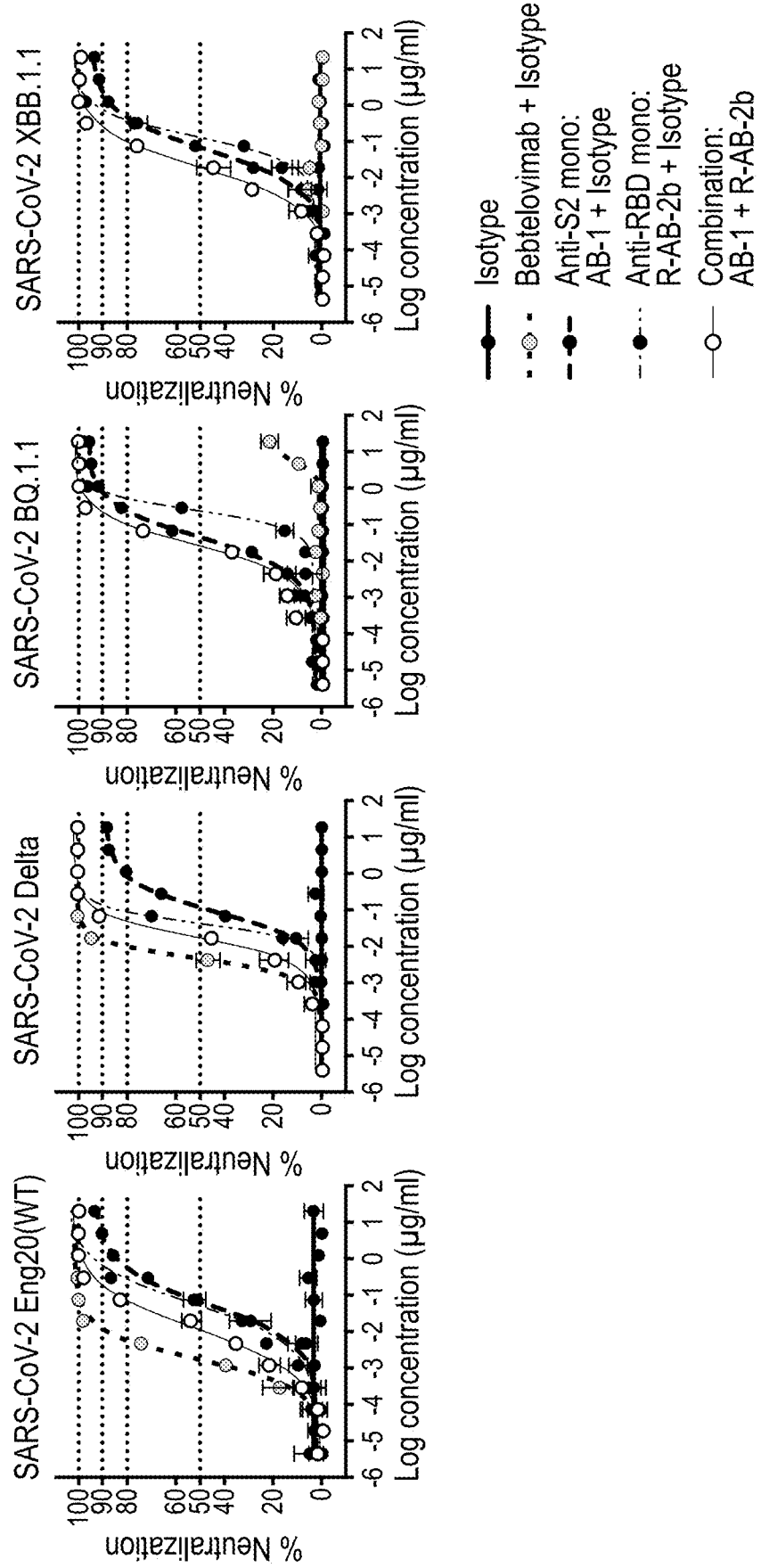
FIG. 39. Neutralization of SARS-CoV-2 live virus variants by AB-1 in combination with R-AB-2b. Neutralization profiles of AB-1+R-AB-2b, AB-1, R-AB-2b, and bebtelovimab as single agents, and isotype control antibody against SARS-CoV-2 ancestral strain (Eng20 (WT)), Delta, BQ.1.1, XBB.1.1 live viruses. The anti-spike antibodies tested as single agents were combined with isotype at the same concentrations to control for overall mass of anti-spike antibodies tested as combinations. The x-axis indicates the concentration of each individual antibody in the combinations, or of the antibody with the highest concentration if the concentrations differ. The results are reported as % neutralization and shown as mean±standard deviation (representative of one experiment, two to three technical replicates).

AB-1 and its surrogate antibodies AB-1 VH/VL-huIgG1 and AB-1 VH/VL-hamIgG2a showed comparable neutralization of SARS-CoV-2 D614G and SARS-CoV-2 BA.2 pseudoviruses as assessed by $EC_{50}$ values (FIG. 37, Table 33). The neutralization profiles of the positive controls used in the hamster challenge models (sotrovimab VH/VL-huIgG1, sotrovimab VH/VL-hamIgG2a) were also comparable with the neutralization profile of sotrovimab VH/VL-huIgG1-LS. No significant neutralization was observed with any of the isotype controls.

In conclusion, AB-1 and its surrogate antibodies used in hamster challenge models showed comparable neutralization profiles against both SARS-CoV-2 D614G and SARS-CoV-2 BA.2 pseudoviruses.

Example 11. Antibody-Dependent Enhancement

The goal of Example 11 was to assess the potential risk of AB-1-dependent enhancement of SARS-CoV-2 infection in Fc gamma receptors-expressing cells (e.g., monocytic cell lines, primary human peripheral blood mononuclear cells (PBMCs)).

The potential risk of antibody dependent enhancement (ADE) was assessed by infecting cells expressing Fc gamma receptors (e.g., monocytic cell lines, PBMCs) with a SARS-CoV-2 pseudovirus in the presence of AB-1 or AB-1 VH/VL-huIgG1 (AB-1 variable regions expressed as human IgG1 without LS mutation). TMPRSS2-Vero E6 cells were used as positive control for SARS-CoV-2 pseudovirus infection.

Pseudovirus: spike (SARS-CoV-2, D614G) pseudotyped deltaG-VSV (Luciferase Reporter) (BPS Bioscience, #78642, lot #220512).

Cell lines: TMPRSS2=Vero E6 Recombinant Cell Line (CL-030, BPS Biosciences, #78081, lot #210522 #20); THP-1 (CL-011-001, ATCC, #TIB-202); U-937 (CL-051-001, ATCC, #CRL-1593.2); PBMCs (Donor D-161-001 AllCells #56012, Donor D-162-001 AllCells #47064, Donor D-164-001 Precision for Medicine #202114106).

Antibodies: AB-1 (Lonza, lot #1100-130922-01), AB-1 VH/VL-huIgG1 (GenScript USA, Inc., lot #U507ZHF090-3, AB-1 variable regions expressed as human IgG1 without LS mutation in the Fc region but identical variable domain), bebtelovimab (GenScript USA, Inc., lot #U819KHL150), isotype (GenScript USA, Inc., lot #U799WHJ270-3, palivizumab variable regions targeting RSV F protein and expressed as human IgG1 with LS mutation in the Fc region).

Cell culture medium (for THP-1, U-937, PBMCs): RPMI-1640 (Thermo Fisher Scientific #61870036, lot #2522773), 20% FBS (#A38403-01, lot #262908SRP), 0.1 mM nonessential amino acids (#11140-050, lot #2390759), 1 mM sodium pyruvate (#11360-070, lot #2323639), 1% Penicillin/Streptomycin (#15140-122, lot #2441835).

Cell culture medium (TMPRSS2-Vero E6): MEM/EBSS (Thermo Fisher Scientific #SH30024.02, lot #AH29890509) 10% FBS (#A38403-01, lot #262908SRP), 0.1 mM nonessential amino acids (#11140-050, lot #2390759), 1 mM sodium pyruvate (#11360-070, lot #2323639), 1% Penicillin/Streptomycin (#15140-122, lot #2441835).

Stimulation medium (for THP-1, U-937, PBMCs): RPMI-1640 (Thermo Fisher Scientific #61870036, lot #2522773).

Stimulation medium (TMPRSS2-Vero E6): MEM (#5H30024.02, lot #AH29890509) with 2.5% FBS (#A38403-01, lot #262908SRP), 0.1 mM nonessential amino acids (#11140-050, lot #2390759), 1 mM sodium pyruvate (#11360-070, lot #2323639), 1% Penicillin/Streptomycin (#15140-122, lot #2441835).

Luciferase Buffer: One-Step Luciferase Assay System (BPS Bioscience #60690-3, lot #221221)

Tissue culture plates: 384-well plate white, tissue culture-treated plates, flat bottom with lid (Thermo Fisher Scientific, #08772129).

Dilution plates: 96 well plate round bottom, non-treated, polypropylene (Corning, #3365; Greiner, #650201).

Antibody/pseudovirus incubation plates: Nunc 96-Well polystyrene round bottom microwell plates, with lid, non-tissue culture-treated, sterile (Thermo Fisher Scientific, #268200).

ADE can be assessed by quantifying viral infection of Fc gamma receptor-bearing cells that lack the canonical virus entry receptor in the presence of antibodies of interest over a range of concentrations. In this study, viral infection of one control cell line (TMPRSS2-Vero E6), two monocytic cell lines (THP-1, U-937) and primary human PBMCs (three independent donors) were assessed in the presence of AB-1 and AB-1 VH/VL-huIgG1 over a range of concentrations (18-0.000000000000256 µg/ml), extending >100-fold below the $EC_{50}$ values measured with TMPRSS2-Vero E6 cells in this experiments for the tested antibodies (AB-1: 0.01303 µg/ml; AB-1 VH/VL-huIgG1: 0.01517 µg/ml). Isotype control and bebtelovimab were used as negative and positive neutralization controls, respectively.

The cells were seeded in 384-well tissue culture plates at a density of 3,500 per well in 20 µl of stimulation medium (PBMCs were also plated at a density of 30,000 cells per well) and incubated at 37° C., 5% $CO_2$ for 2-4 hours. In parallel, the antibodies were serially diluted and incubated with diluted pseudovirus at a desired multiplicity of infection (0.25 for all cell lines plated at 3,500 cells/well, 0.029 for PBMCs plated at 30,000 cells/well). Viral infection in the presence of antibodies was assessed using a 24-point titration curve in technical triplicate (1:4 serial dilutions prepared in PBS with 0.2% BSA and 1× Pen-Strep solution starting at 18 µg/ml). After 30-60 minutes of incubation at 37° C., 5% $CO_2$, the pseudovirus/antibody mixture was added to the tissue culture plates pre-seeded with cells, achieving the final antibody concentrations in a total volume of 40 µl. After 24 hours at 37° C., 5% $CO_2$, an equal volume of luciferase substrate was added directly to the culture plates (pseudovirus backbones have luciferase reporters), and luminescence was quantified on the PerkinElmer EnVision plate reader. Percentage neutralization was calculated with the following formula, where "$signal_{positiveControl}$" is defined by the average luminescence signal of wells containing cells without pseudovirus, "$signal_{negativeControl}$" is defined as the average luminescence signal of wells containing cells with pseudovirus, "$signal_{well}$" is defined as the average luminescence signal of wells containing cells with both antibody and pseudovirus:

Percentage neutralization =

$$\left(1 - \frac{signal_{well} - signal_{positiveControl}}{signal_{negativeControl} - signal_{positiveControl}}\right) \cdot 100$$

Statistical analysis was performed with Prism 9.5.0 software. The half-maximal effective concentration ($EC_{50}$) values were derived for each Log-transformed antibody titration curve using log(inhibitor) vs. response-Variable slope (four parameters) equation.

Results

AB-1 and AB-1 VH/VL-huIgG1 did not enhance SARS-CoV-2 pseudovirus infection in Fc gamma receptor-bearing cells (the monocytic cell lines U-937 and THP-1, human primary PBMCs) as measured by relative luminescence units. The results with the TMPRSS2-Vero E6 cell line confirmed robust infection with the pseudovirus and effective neutralization by AB-1, AB-1 VH/VL-huIgG1 and bebtelovimab, while no neutralization was observed with the isotype control.

In conclusion, AB-1 does not induce ADE in Fc gamma receptor-bearing cells.

REFERENCES

Baden & Rubin, Covid-19 —*The Search for Effective Therapy*, N Engl J Med. 382(19):1851-52 (2020).

Baud et al. *Real estimates of mortality following COVID-19 infection*, Lancet Infect Dis. 20(7):773 (2020).

Chen et al., *CoV-Spectrum: analysis of globally shared SARS-CoV-2 data to identify and characterize new variants*, Bioinformatics 38(6):1735-37 (2022).

Corti et al., *Tackling COVID-19 with neutralizing monoclonal antibodies*, Cell 184(12):3086-3108 (2021).

Hurlburt et al., *Structural definition of a pan-sarbecovirus neutralizing epitope on the spike S2 subunit*, Commun Biol. 5(1):342 (2022).

Ingraham et al., *Generative models for graph-based protein design*, 33rd Conference on Neural Information Processing Systems (NeurIPS 2019), Vancouver, Canada.

Jennewein et al., *Isolation and characterization of cross-neutralizing coronavirus antibodies from COVID-19+ subjects*, Cell Rep. 36(2):109353 (2021).

Li et al., *Structural basis and mode of action for two broadly neutralizing antibodies against SARS-CoV-2 emerging variants of concern*, Cell Rep. 38(2):110210 (2022).

Rambaut et al., *A dynamic nomenclature proposal for SARS-CoV-2 lineages to assist genomic epidemiology*, Nat Microbiol. 5(11):1403-07 (2020).

Saunders, *Conceptual Approaches to Modulating Antibody Effector Functions and Circulation Half-Life*, Front Immunol. 10:1296 (2019).

Song et al., *Cytokine storm induced by SARS-CoV-2*, Clin Chim Acta. 509:280-7 (2020).

Ullah et al., *Live imaging of SARS-CoV-2 infection in mice reveals that neutralizing antibodies require Fc function for optimal efficacy*, Immunity. 54(9):2143-58 (2021).

Zhou et al., *A general-purpose protein design framework based on mining sequence-structure relationships in known protein structures*, Proc Natl Acad Sci USA. 117(2):1059-68 (2020).

TABLE 1

$V_H$ Amino Acid Sequences

| Name | SEQ ID | Amino Acid Sequence |
|---|---|---|
| Consensus (AB-1 to AB-51 or AB-1 to AB-40) | NO: 2 | EVQLVESGAEVKKPGESLKISCKGSGYTFTRYWIGWVRQMPGKGLE WMGIIYPGDX$_1$X$_2$X$_3$RYSPSFQGHVTISADKSISTAYLQWNSLKASD TAMYYCARX$_4$PQYCX$_5$X$_6$X$_7$X$_8$CX$_9$RWFDPWGQGTLVTVSS |
| Reference Antibody, AB-51 | NO: 3 | EVQLVESGAEVKKPGESLKISCKGSGYTFTRYWIGWVRQMPGKGLE WMGIIYPGDSDTRYSPSFQGHVTISADKSISTAYLQWNSLKASDTA MYYCARLPQYCSNGVCQRWFDPWGQGTLVTVSS |
| AB-1, 19, 23 | NO: 4 | EVQLVESGAEVKKPGESLKISCKGSGYTFTRYWIGWVRQMPGKGLE WMGIIYPGDSDVRYSPSFQGHVTISADKSISTAYLQWNSLKASDTA MYYCARLPQYCSKGVCYRWFDPWGQGTLVTVSS |
| AB-2 | NO: 5 | EVQLVESGAEVKKPGESLKISCKGSGYTFTRYWIGWVRQMPGKGLE WMGIIYPGDSDTRYSPSFQGHVTISADKSISTAYLQWNSLKASDTA MYYCARLPQYCQNGICKRWFDPWGQGTLVTVSS |
| AB-3, 17 | NO: 6 | EVQLVESGAEVKKPGESLKISCKGSGYTFTRYWIGWVRQMPGKGLE WMGIIYPGDNDVRYSPSFQGHVTISADKSISTAYLQWNSLKASDTA MYYCARLPQYCRKGICKRWFDPWGQGTLVTVSS |

TABLE 1-continued

V_H Amino Acid Sequences

| Name | SEQ ID | Amino Acid Sequence |
|---|---|---|
| AB-4 | NO: 7 | EVQLVESGAEVKKPGESLKISCKGSGYTFTRYWIGWVRQMPGKGLE<br>WMGIIYPGDSDTRYSPSFQGHVTISADKSISTAYLQWNSLKASDTA<br>MYYCARLPQYCRNGVCYRWFDPWGQGTLVTVSS |
| AB-5 | NO: 8 | EVQLVESGAEVKKPGESLKISCKGSGYTFTRYWIGWVRQMPGKGLE<br>WMGIIYPGDSDTRYSPSFQGHVTISADKSISTAYLQWNSLKASDTA<br>MYYCARLPQYCRANVCFRWFDPWGQGTLVTVSS |
| AB-6 | NO: 9 | EVQLVESGAEVKKPGESLKISCKGSGYTFTRYWIGWVRQMPGKGLE<br>WMGIIYPGDSDVRYSPSFQGHVTISADKSISTAYLQWNSLKASDTA<br>MYYCARLPQYCKKLICKRWFDPWGQGTLVTVSS |
| AB-7, 14 | NO: 10 | EVQLVESGAEVKKPGESLKISCKGSGYTFTRYWIGWVRQMPGKGLE<br>WMGIIYPGDSDTRYSPSFQGHVTISADKSISTAYLQWNSLKASDTA<br>MYYCARLPQYCRNGVCQRWFDPWGQGTLVTVSS |
| AB-8 | NO: 11 | EVQLVESGAEVKKPGESLKISCKGSGYTFTRYWIGWVRQMPGKGLE<br>WMGIIYPGDNDVRYSPSFQGHVTISADKSISTAYLQWNSLKASDTA<br>MYYCARLPQYCSAGSCFRWFDPWGQGTLVTVSS |
| AB-9 | NO: 12 | EVQLVESGAEVKKPGESLKISCKGSGYTFTRYWIGWVRQMPGKGLE<br>WMGIIYPGDNDVRYSPSFQGHVTISADKSISTAYLQWNSLKASDTA<br>MYYCARLPQYCRSGICKRWFDPWGQGTLVTVSS |
| AB-10 | NO: 13 | EVQLVESGAEVKKPGESLKISCKGSGYTFTRYWIGWVRQMPGKGLEWMGI<br>TYPGDSDVRYSPSFQGHVTISADKSISTAYLQWNSLKASDTAMYYCARLP<br>QYCSAGVCFRWFDPWGQGTLVTVSS |
| AB-11 | NO: 14 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCRNGVCHRWFDPWGQGTLVTVSS |
| AB-12 | NO: 15 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCSRGVCKRWFDPWGQGTLVTVSS |
| AB-13 | NO: 16 | EVQLVESGAEVKKPGESLKISCKGSGYTFTRYWIGWVRQMPGKGLEWMGI<br>TYPGDSDVRYSPSFQGHVTISADKSISTAYLQWNSLKASDTAMYYCARLP<br>QYCRKGVCHRWFDPWGQGTLVTVSS |
| AB-15 | NO: 17 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCYAGVCHRWFDPWGQGTLVTVSS |
| AB-16 | NO: 18 | EVQLVESGAEVKKPGESLKISCKGSGYTFTRYWIGWVRQMPGKGLEWMGI<br>IYPGDSDVRYSPSFQGHVTISADKSISTAYLQWNSLKASDTAMYYCARLP<br>QYCRSGSCHRWFDPWGQGTLVTVSS |
| AB-18 | NO: 19 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCRNGSCKRWFDPWGQGTLVTVSS |
| AB-20 | NO: 20 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCRAGVCHRWFDPWGQGTLVTVSS |
| AB-21 | NO: 21 | EVQLVESGAEVKKPGESLKISCKGSGYTFTRYWIGWVRQMPGKGLEWMGI<br>TYPGDADVRYSPSFQGHVTISADKSISTAYLQWNSLKASDTAMYYCARLP<br>QYCRKGVCYRWFDPWGQGTLVTVSS |
| AB-22 | NO: 22 | EVQLVESGAEVKKPGESLKISCKGSGYTFTRYWIGWVRQMPGKGLEWMGI<br>TYPGDSDTRYSPSFQGHVTISADKSISTAYLQWNSLKASDTAMYYCARLP<br>QYCRSGVCQRWFDPWGQGTLVTVSS |
| AB-24 | NO: 23 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCRSGSCYRWFDPWGQGTLVTVSS |
| AB-25 | NO: 24 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCYAGVCKRWFDPWGQGTLVTVSS |
| AB-26 | NO: 25 | EVQLVESGAEVKKPGESLKISCKGSGYTFTRYWIGWVRQMPGKGLEWMGI<br>TYPGDSDTRYSPSFQGHVTISADKSISTAYLQWNSLKASDTAMYYCARVP<br>QYCRSGVCFRWFDPWGQGTLVTVSS |

TABLE 1-continued

V_H Amino Acid Sequences

| Name | SEQ ID | Amino Acid Sequence |
|---|---|---|
| AB-27 | NO: 26 | EVQLVESGAEVKKPGESLKISCKGSGYTFTRYWIGWVRQMPGKGLEWMGI<br>TYPGDSETRYSPSFQGHVTISADKSISTAYLQWNSLKASDTAMYYCARVP<br>QYCSRGVCYRWFDPWGQGTLVTVSS |
| AB-28 | NO: 27 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCYRGVCKRWFDPWGQGTLVTVSS |
| AB-29, 30 | NO: 28 | EVQLVESGAEVKKPGESLKISCKGSGYTFTRYWIGWVRQMPGKGLEWMGI<br>TYPGDRDTRYSPSFQGHVTISADKSISTAYLQWNSLKASDTAMYYCARLP<br>QYCSRGVCFRWFDPWGQGTLVTVSS |
| AB-31 | NO: 29 | EVQLVESGAEVKKPGESLKISCKGSGYTFTRYWIGWVRQMPGKGLEWMGI<br>IYPGDLDTRYSPSFQGHVTISADKSISTAYLQWNSLKASDTAMYYCARLP<br>QYCYKGVCKRWFDPWGQGTLVTVSS |
| AB-32 | NO: 30 | EVQLVESGAEVKKPGESLKISCKGSGYTFTRYWIGWVRQMPGKGLEWMGI<br>TYPGDSETRYSPSFQGHVTISADKSISTAYLOWNSLKASDTAMYYCARLP<br>QYCRRGVCKRWFDPWGQGTLVTVSS |
| AB-33 | NO: 31 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCRAGKCKRWFDPWGQGTLVTVSS |
| AB-34 | NO: 32 | EVQLVESGAEVKKPGESLKISCKGSGYTFTRYWIGWVRQMPGKGLEWMGI<br>TYPGDADVRYSPSFQGHVTISADKSISTAYLQWNSLKASDTAMYYCARLP<br>QYCRKGVCKRWFDPWGQGTLVTVSS |
| AB-35 | NO: 33 | EVQLVESGAEVKKPGESLKISCKGSGYTFTRYWIGWVRQMPGKGLEWMGI<br>TYPGDADTRYSPSFQGHVTISADKSISTAYLQWNSLKASDTAMYYCARLP<br>QYCSRGVCQRWFDPWGQGTLVTVSS |
| AB-36 | NO: 34 | EVQLVESGAEVKKPGESLKISCKGSGYTFTRYWIGWVRQMPGKGLEWMGI<br>IYPGDADTRYSPSFQGHVTISADKSISTAYLQWNSLKASDTAMYYCARLP<br>QYCSKGVCYRWFDPWGQGTLVTVSS |
| AB-37 | NO: 35 | EVQLVESGAEVKKPGESLKISCKGSGYTFTRYWIGWVROMPGKGLEWMGI<br>IYPGDFDTRYSPSFQGHVTISADKSISTAYLQWNSLKASDTAMYYCARLP<br>QYCRRGICFRWFDPWGQGTLVTVSS |
| AB-38 | NO: 36 | EVQLVESGAEVKKPGESLKISCKGSGYTFTRYWIGWVRQMPGKGLEWMGI<br>TYPGDSDTRYSPSFQGHVTISADKSISTAYLQWNSLKASDTAMYYCARLP<br>QYCQRGVCQRWFDPWGQGTLVTVSS |
| AB-39 | NO: 37 | EVQLVESGAEVKKPGESLKISCKGSGYTFTRYWIGWVRQMPGKGLEWMGI<br>IYPGDADVRYSPSFQGHVTISADKSISTAYLQWNSLKASDTAMYYCARLP<br>QYCRKGKCKRWFDPWGQGTLVTVSS |
| AB-40 | NO: 38 | EVQLVESGAEVKKPGESLKISCKGSGYTFTRYWIGWVRQMPGKGLEWMGI<br>TYPGDSETRYSPSFQGHVTISADKSISTAYLQWNSLKASDTAMYYCARLP<br>QYCRSGVCQRWFDPWGQGTLVTVSS |
| AB-41 | NO: 39 | EVQLVESGAEVKKPGESLKISCKGSGYTFTRYWIGWVRQMPGKGLEWMGI<br>IYPGDNDVRYSPSFQGHVTISADKSISTAYLQWNSLKASDTAMYYCARLP<br>QYCSAGVCFRWFDPWGQGTLVTVSS |
| AB-42 | NO: 40 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCQSGVCKRWFDPWGQGTLVTVSS |
| AB-43 | NO: 41 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCSAGVCFRWFDPWGQGTLVTVSS |
| AB-44 | NO: 42 | EVQLVESGAEVKKPGESLKISCKGSGYTFTRYWIGWVRQMPGKGLEWMGI<br>TYPGDLDVRYSPSFQGHVTISADKSISTAYLQWNSLKASDTAMYYCARLP<br>QYCREGKCHRWFDPWGQGTLVTVSS |
| AB-45 | NO: 43 | EVQLVESGAEVKKPGESLKISCKGSGYTFTRYWIGWVRQMPGKGLEWMGI<br>IYPGDSDTRYSPSFQGHVTISADKSISTAYLOWNSLKASDTAMYYCARLP<br>QYCSSGVCQRWFDPWGQGTLVTVSS |
| AB-46 | NO: 44 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCSSGVCHRWFDPWGQGTLVTVSS |

TABLE 1-continued

V<sub>H</sub> Amino Acid Sequences

| Name | SEQ ID | Amino Acid Sequence |
|---|---|---|
| AB-47 | NO: 45 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCQNGVCHRWFDPWGQGTLVTVSS |
| AB-48 | NO: 46 | EVQLVESGAEVKKPGESLKISCKGSGYTFTRYWIGWVRQMPGKGLEWMGI<br>IYPGDNDVRYSPSFQGHVTISADKSISTAYLQWNSLKASDTAMYYCARLP<br>QYCDKGICKRWFDPWGQGTLVTVSS |
| AB-49 | NO: 47 | EVQLVESGAEVKKPGESLKISCKGSGYTFTRYWIGWVRQMPGKGLEWMGI<br>IYPGDSDTRYSPSFQGHVTISADKSISTAYLQWNSLKASDTAMYYCARLP<br>QYCENGICKRWFDPWGQGTLVTVSS |
| AB-50 | NO: 48 | EVQLVESGAEVKKPGESLKISCKGSGYTFTRYWIGWVRQMPGKGLEWMGI<br>TYPGDADVRYSPSFQGHVTISADKSISTAYLQWNSLKASDTAMYYCARLP<br>QYCSSGSCFRWFDPWGQGTLVTVSS |
| Consensus<br>(AB-1 to<br>AB-20) | NO: 163 | EVQLVESGAEVKKPGESLKISCKGSGYTFTRYWIGWVRQMPGKGLEWMGI<br>IYPGDX$_1$DX$_2$RYSPSFQGHVTISADKSISTAYLQWNSLKASDTAMYYCARL<br>PQYCX$_3$X$_4$X$_5$X$_6$CX$_7$RWFDPWGQGTLVTVSS |
| Consensus<br>(AB-1 and<br>AB-41<br>to AB-51) | NO: 164 | EVQLVESGAEVKKPGESLKISCKGSGYTFTRYWIGWVRQMPGKGLEWMGI<br>IYPGDX$_1$DX$_2$RYSPSFQGHVTISADKSISTAYLQWNSLKASDTAMYYCARL<br>PQYCX$_3$X$_4$GX$_5$CX$_6$RWFDPWGQGTLVTVSS |

TABLE 2

V<sub>L</sub> Amino Acid Sequences

| Name | SEQ ID | Amino Acid Sequence |
|---|---|---|
| Consensus<br>(AB-1 to<br>AB-51 or<br>AB-1 to<br>AB-40) | NO: 49 | EIVLTQSPSSVSASVGDRVTITCRASX$_{10}$X$_{11}$IX$_{12}$X$_{13}$WLAWYQQKPG<br>KAPKLLIYAASSLQSGVPSRFSGSGSGTDFTLTISSLQPEDFATYY<br>CQQGX$_{14}$X$_{15}$X$_{16}$PX$_{17}$TFGQGTNLEIK |
| Reference<br>Antibody,<br>AB-14 | NO: 50 | EIVLTQSPSSVSASVGDRVTITCRASQGISSWLAWYQQKPGKAPKL<br>LIYAASSLQSGVPSRFSGSGSGTDFTLTISSLQPEDFATYYCQQGN<br>SFPYTFGQGTNLEIK |
| AB-1, 5,<br>13, 26, 37,<br>43, 46 | NO: 51 | EIVLTQSPSSVSASVGDRVTITCRASQGISSWLAWYQQKPGKAPKL<br>LIYAASSLQSGVPSRFSGSGSGTDFTLTISSLQPEDFATYYCQQGH<br>SFPYTFGQGTNLEIK |
| AB-2, 42,<br>49 | NO: 52 | EIVLTQSPSSVSASVGDRVTITCRASQGIRSWLAWYQQKPGKAPKL<br>LIYAASSLQSGVPSRFSGSGSGTDFTLTISSLQPEDFATYYCQQGD<br>QYPLTFGQGTNLEIK |
| AB-3, 48 | NO: 53 | EIVLTQSPSSVSASVGDRVTITCRASQGISSWLAWYQQKPGKAPKL<br>LIYAASSLQSGVPSRFSGSGSGTDFTLTISSLQPEDFATYYCQQGD<br>QLPYTFGQGTNLEIK |
| AB-4 | NO: 54 | EIVLTQSPSSVSASVGDRVTITCRASKGISSWLAWYQQKPGKAPKLLIYAA<br>SSLQSGVPSRFSGSGSGTDFTLTISSLQPEDFATYYCQQGNQVPYTFGQGT<br>NLEIK |
| AB-6 | NO: 55 | EIVLTQSPSSVSASVGDRVTITCRASQGIRSWLAWYQQKPGKAPKLLIYAA<br>SSLQSGVPSRFSGSGSGTDFTLTISSLQPEDFATYYCQQGDQLPYTFGQGT<br>NLEIK |
| AB-7, 12, 24,<br>27, 29, 35,<br>38, 45, 51 | NO: 56 | EIVLTQSPSSVSASVGDRVTITCRASQGISSWLAWYQQKPGKAPKLLIYAA<br>SSLQSGVPSRFSGSGSGTDFTLTISSLQPEDFATYYCQQGNQFPYTFGQGT<br>NLEIK |
| AB-8 | NO: 57 | EIVLTQSPSSVSASVGDRVTITCRASIGIRNWLAWYQQKPGKAPKLLIYAA<br>SSLQSGVPSRFSGSGSGTDFTLTISSLQPEDFATYYCQQGYSYPYTFGQGT<br>NLEIK |
| AB-9 | NO: 58 | EIVLTQSPSSVSASVGDRVTITCRASQGISSWLAWYQQKPGKAPKLLIYAA<br>SSLQSGVPSRFSGSGSGTDFTLTISSLQPEDFATYYCQQGDQFPYTFGQGT<br>NLEIK |

TABLE 2-continued

V_L Amino Acid Sequences

| Name | SEQ ID | Amino Acid Sequence |
|---|---|---|
| AB-10 | NO: 59 | EIVLTQSPSSVSASVGDRVTITCRASQGISSWLAWYQQKPGKAPKLLIYAASSLQSGVPSRFSGSGSGTDFTLTISSLQPEDFATYYCQQGNSYPYTFGQGTNLEIK |
| AB-11 | NO: 60 | EIVLTQSPSSVSASVGDRVTITCRASQGIRSWLAWYQQKPGKAPKLLIYAASSLQSGVPSRFSGSGSGTDFTLTISSLQPEDFATYYCQQGNFPYTFGQGTNLEIK |
| AB-15, 19, 20, 28 | NO: 61 | EIVLTQSPSSVSASVGDRVTITCRASQGIRSWLAWYQQKPGKAPKLLIYAASSLQSGVPSRFSGSGSGTDFTLTISSLQPEDFATYYCQQGHSFPYTFGQGTNLEIK |
| AB-16 | NO: 62 | EIVLTQSPSSVSASVGDRVTITCRASQGIRSWLAWYQQKPGKAPKLLIYAASSLQSGVPSRFSGSGSGTDFTLTISSLQPEDFATYYCQQGYSFPYTFGQGTNLEIK |
| AB-17, 39 | NO: 63 | EIVLTQSPSSVSASVGDRVTITCRASQGISSWLAWYQQKPGKAPKLLIYAASSLQSGVPSRFSGSGSGTDFTLTISSLQPEDFATYYCQQGHQFPYTFGQGTNLEIK |
| AB-18 | NO: 64 | EIVLTQSPSSVSASVGDRVTITCRASQGIRSWLAWYQQKPGKAPKLLIYAASSLQSGVPSRFSGSGSGTDFTLTISSLQPEDFATYYCQQGDQFPLTFGQGTNLEIK |
| AB-21 | NO: 65 | EIVLTQSPSSVSASVGDRVTITCRASQGIVSWLAWYQQKPGKAPKLLIYAASSLQSGVPSRFSGSGSGTDFTLTISSLQPEDFATYYCQQGHSFPYTFGQGTNLEIK |
| AB-22 | NO: 66 | EIVLTQSPSSVSASVGDRVTITCRASQSISSWLAWYQQKPGKAPKLLIYAASSLQSGVPSRFSGSGSGTDFTLTISSLQPEDFATYYCQQGSQTPYTFGQGTNLEIK |
| AB-23, 34 | NO: 67 | EIVLTQSPSSVSASVGDRVTITCRASQGIRSWLAWYQQKPGKAPKLLIYAASSLQSGVPSRFSGSGSGTDFTLTISSLQPEDFATYYCQQGHSTPYTFGQGTNLEIK |
| AB-25 | NO: 68 | EIVLTQSPSSVSASVGDRVTITCRASQGIRSWLAWYQQKPGKAPKLLIYAASSLQSGVPSRFSGSGSGTDFTLTISSLQPEDFATYYCQQGYSVPYTFGQGTNLEIK |
| AB-30, 40 | NO: 69 | EIVLTQSPSSVSASVGDRVTITCRASQGISSWLAWYQQKPGKAPKLLIYAASSLQSGVPSRFSGSGSGTDFTLTISSLQPEDFATYYCQQGNQVPYTFGQGTNLEIK |
| AB-31 | NO: 70 | EIVLTQSPSSVSASVGDRVTITCRASQGIRSWLAWYQQKPGKAPKLLIYAASSLQSGVPSRFSGSGSGTDFTLTISSLQPEDFATYYCQQGHSVPYTFGQGTNLEIK |
| AB-32 | NO: 71 | EIVLTQSPSSVSASVGDRVTITCRASQGISSWLAWYQQKPGKAPKLLIYAASSLQSGVPSRFSGSGSGTDFTLTISSLQPEDFATYYCQQGNQLPYTFGQGTNLEIK |
| AB-33 | NO: 72 | EIVLTQSPSSVSASVGDRVTITCRASQGISSWLAWYQQKPGKAPKLLIYAASSLQSGVPSRFSGSGSGTDFTLTISSLQPEDFATYYCQQGNQYPYTFGQGTNLEIK |
| AB-36 | NO: 73 | EIVLTQSPSSVSASVGDRVTITCRASQGISSWLAWYQQKPGKAPKLLIYAASSLQSGVPSRFSGSGSGTDFTLTISSLQPEDFATYYCQQGHSTPYTFGQGTNLEIK |
| AB-41 | NO: 74 | EIVLTQSPSSVSASVGDRVTITCRASQGISNWLAWYQQKPGKAPKLLIYAASSLQSGVPSRFSGSGSGTDFTLTISSLQPEDFATYYCQQGYSYPYTFGQGTNLEIK |
| AB-44, 47 | NO: 75 | EIVLTQSPSSVSASVGDRVTITCRASQGIRNWLAWYQQKPGKAPKLLIYAASSLQSGVPSRFSGSGSGTDFTLTISSLQPEDFATYYCQQGDQDPLTFGQGTNLEIK |
| AB-50 | NO: 76 | EIVLTQSPSSVSASVGDRVTITCRASQGISSWLAWYQQKPGKAPKLLIYAASSLQSGVPSRFSGSGSGTDFTLTISSLQPEDFATYYCQQGYSTPYTFGQGTNLEIK |
| Consensus (AB-1 to AB-20) | NO: 165 | EIVLTQSPSSVSASVGDRVTITCRASX$_8$GIX$_9$X$_{10}$WLAWYQQKPGKAPKLLIYAASSLQSGVPSRFSGSGSGTDFTLTISSLQPEDFATYYCQQGX$_{11}$X$_{12}$X$_{13}$PX$_{14}$TFGQGTNLEIK |

TABLE 2-continued $V_L$ Amino Acid Sequences

| Name | SEQ ID | Amino Acid Sequence |
|---|---|---|
| Consensus (AB-1 and AB-41 to AB-51) | NO: 166 | EIVLTQSPSSVSASVGDRVTITCRASQGIX$_7$X$_8$WLAWYQQKPGKAPKLLIYA ASSLQSGVPSRFSGSGSGTDFTLTISSLQPEDFATYYCQQGX$_9$X$_{10}$X$_{11}$PX$_{12}$ TFGQGTNLEIK |

TABLE 3

CDR Amino Acid Sequences

| Name | SEQ ID | Amino Acid Sequence |
|---|---|---|
| HCDR1 | | |
| Consensus, Reference Antibody, AB-1-51 | NO: 77 | GYTFTRYW |
| HCDR2 | | |
| Consensus (AB-1 to AB-51 or AB-1 to AB-40) | NO: 78 | IYPGDX$_1$X$_2$X$_3$ |
| Reference Antibody, AB-2, 4, 5, 7, 11, 12, 14, 15, 18, 20, 22, 24-26, 28, 33, 38, 42, 43, 45-47, 49, 51 | NO: 79 | IYPGDSDT |
| AB-1, 6, 10, 13, 16, 19, 23 | NO: 80 | IYPGDSDV |
| AB-3, 8, 9, 17, 41, 48 | NO: 81 | IYPGDNDV |
| AB-21, 34, 39, 50 | NO: 82 | IYPGDADV |
| AB-27, 32, 40 | NO: 83 | IYPGDSET |
| AB-29, 30 | NO: 84 | IYPGDRDT |
| AB-31 | NO: 85 | IYPGDLDT |
| AB-35, 36 | NO: 86 | IYPGDADT |
| AB-37 | NO: 87 | IYPGDFDT |
| AB-44 | NO: 88 | IYPGDLDV |
| Consensus (AB-1 to AB-20 or AB-1 and AB-41 to AB-51) | NO: 167 | IYPGDX$_1$DX$_2$ |
| HCDR3 | | |
| Consensus (AB-1 to AB-51 or AB-1 to AB-40) | NO: 89 | ARX$_4$PQYCX$_5$X$_6$X$_7$X$_8$CX$_9$RWFDP |
| Reference Antibody, AB-51 | NO: 90 | ARLPQYCSNGVCQRWFDP |
| AB-1, 19, 23, 36 | NO: 91 | ARLPQYCSKGVCYRWFDP |
| AB-2 | NO: 92 | ARLPQYCQNGICKRWFDP |
| AB-3, 17 | NO: 93 | ARLPQYCRKGICKRWFDP |
| AB-4 | NO: 94 | ARLPQYCNGVCYRWFDP |
| AB-5 | NO: 95 | ARLPQYCRANVCFRWFDP |
| AB-6 | NO: 96 | ARLPQYCKKLICKRWFDP |
| AB-7, 14 | NO: 97 | ARLPQYCRNGVCQRWFDP |
| AB-8 | NO: 98 | ARLPQYCSAGSCFRWFDP |
| AB-9 | NO: 99 | ARLPQYCRSGICKRWFDP |
| AB-10, 41, 43 | NO: 100 | ARLPQYCSAGVCFRWFDP |
| AB-11 | NO: 101 | ARLPQYCRNGVCHRWFDP |
| AB-12 | NO: 102 | ARLPQYCSRGVCKRWFDP |
| AB-13 | NO: 103 | ARLPQYCRKGVCHRWFDP |
| AB-15 | NO: 104 | ARLPQYCYAGVCHRWFDP |
| AB-16 | NO: 105 | ARLPQYCRSGSCHRWFDP |
| AB-18 | NO: 106 | ARLPQYCRNGSCKRWFDP |
| AB-20 | NO: 107 | ARLPQYCRAGVCHRWFDP |
| AB-21 | NO: 108 | ARLPQYCRKGVCYRWFDP |
| AB-22, 40 | NO: 109 | ARLPQYCRSGVCQRWFDP |
| AB-24 | NO: 110 | ARLPQYCRSGSCYRWFDP |
| AB-25 | NO: 111 | ARLPQYCYAGVCKRWFDP |
| AB-26 | NO: 112 | ARVPQYCRSGVCFRWFDP |
| AB-27 | NO: 113 | ARVPQYCSRGVCYRWFDP |
| AB-28 | NO: 114 | ARLPQYCYRGVCKRWFDP |
| AB-29, 30 | NO: 115 | ARLPQYCSRGVCFRWFDP |
| AB-31 | NO: 116 | ARLPQYCYKGVCKRWFDP |
| AB-32 | NO: 117 | ARLPQYCRRGVCKRWFDP |
| AB-33 | NO: 118 | ARLPQYCRAGKCKRWFDP |
| AB-34 | NO: 119 | ARLPQYCRKGVCKRWFDP |
| AB-35 | NO: 120 | ARLPQYCSRGVCQRWFDP |
| AB-37 | NO: 121 | ARLPQYCRRGICFRWFDP |

TABLE 3-continued

CDR Amino Acid Sequences

| Name | SEQ ID | Amino Acid Sequence |
|---|---|---|
| AB-38 | NO: 122 | ARLPQYCQRGVCQRWFDP |
| AB-39 | NO: 123 | ARLPQYCRKGKCKRWFDP |
| AB-42 | NO: 124 | ARLPQYCQSGVCKRWFDP |
| AB-44 | NO: 125 | ARLPQYCREGKCHRWFDP |
| AB-45 | NO: 126 | ARLPQYCSSGVCQRWFDP |
| AB-46 | NO: 127 | ARLPQYCSSGVCHRWFDP |
| AB-47 | NO: 128 | ARLPQYCQNGVCHRWFDP |
| AB-48 | NO: 129 | ARLPQYCDKGICKRWFDP |
| AB-49 | NO: 130 | ARLPQYCENGICKRWFDP |
| AB-50 | NO: 131 | ARLPQYCSSGSCFRWFDP |
| Consensus (AB-1 to AB-20) | NO: 168 | ARLPQYC$X_3X_4X_5X_6$C$X_7$RWFDP |
| Consensus (AB-1 and AB-41 to AB-51) | NO: 169 | ARLPQYC$X_3X_4$G$X_5$C$X_6$RWFDP |

LCDR1

| Consensus (AB-1 to AB-51 or AB-1 to AB-40) | NO: 132 | $X_{10}X_{11}IX_{12}X_{13}$W |
|---|---|---|
| Reference Antibody, AB-1, 3, 5, 7, 9, 10, 12-14, 17, 24, 26, 27, 29, 30, 32, 33, 35-40, 43, 45, 46, 48, 50, 51 | NO: 133 | QGISSW |
| AB-2, 6, 11, 15, 16, 18-20, 23, 25, 28, 31, 34, 42, 49 | NO: 134 | QGIRSW |
| AB-4 | NO: 135 | KGISSW |
| AB-8 | NO: 136 | IGIRNW |
| AB-21 | NO: 137 | QGIVSW |
| AB-22 | NO: 138 | QSISSW |
| AB-41 | NO: 139 | QGISNW |
| AB-44, 47 | NO: 140 | QGIRNW |
| Consensus (AB-1 to AB-20) | NO: 170 | $X_8$GI$X_9X_{10}$W |
| Consensus (AB-1 and AB-41 to AB-51) | NO: 171 | QGI$X_7X_8$W |

LCDR2

| Consensus, Reference Antibody, AB-1-51 | NO: 141 | AAS |
|---|---|---|

LCDR3

| Consensus (AB-1 to AB-51 or AB-1 to AB-40) | NO: 142 | QQG$X_{14}X_{15}X_{16}$P$X_{17}$T |
|---|---|---|
| Reference Antibody, AB-14 | NO: 143 | QQGNSFPYT |
| AB-1, 5, 13, 15, 19, 20, 21, 26, 28, 37, 43, 46 | NO: 144 | QQGHSFPYT |
| AB-2, 42, 49 | NO: 145 | QQGDQYPLT |
| AB-3, 6, 48 | NO: 146 | QQGDQLPYT |
| AB-4, 30, 40 | NO: 147 | QQGNQVPYT |
| AB-7, 11, 12, 24, 27, 29, 35, 38, 45, 51 | NO: 148 | QQGNQFPYT |
| AB-8, 41 | NO: 149 | QQGYSYPYT |
| AB-9 | NO: 150 | QQGDQFPYT |
| AB-10 | NO: 151 | QQGNSYPYT |
| AB-16 | NO: 152 | QQGYSFPYT |
| AB-17, 39 | NO: 153 | QQGHQFPYT |
| AB-18 | NO: 154 | QQGDQFPLT |
| AB-22 | NO: 155 | QQGSQTPYT |
| AB-23, 34, 36 | NO: 156 | QQGHSTPYT |
| AB-25 | NO: 157 | QQGYSVPYT |
| AB-31 | NO: 158 | QQGHSVPYT |
| AB-32 | NO: 159 | QQGNQLPYT |
| AB-33 | NO: 160 | QQGNQYPYT |
| AB-44, 47 | NO: 161 | QQGDQDPLT |
| AB-50 | NO: 162 | QQGYSTPYT |
| Consensus (AB-1 to AB-20) | NO: 172 | QQG$X_{11}X_{12}X_{13}$P$X_{14}$T |
| Consensus (AB-1 and AB-41 to AB-51) | NO: 173 | QQG$X_9X_{10}X_{11}$P$X_{12}$T |

TABLE 4

Characterization of Polypeptides

| [ng/ml] | IC$_{50}$ | | | | | |
|---|---|---|---|---|---|---|
| | BA.2 | BA.2.12.1 | BA.4/5 | Delta | SARS-CoV-1 | WIV1 |
| Sotrovimab | 704 | 1203 | >4500 | 65 | 14 | 32 |
| Reference Antibody | 1251 | 337 | 634 | 256 | 244 | 473 |
| AB-17 | 29 | 24 | 24 | 24 | 18 | 25 |
| AB-15 | 52 | 45 | 70 | 28 | 20 | 57 |
| AB-1 | 31 | 53 | 75 | 34 | 40 | 69 |

TABLE 5

| [ng/ml] | IC$_{50}$ | | | | | | |
|---|---|---|---|---|---|---|---|
| | BA.1 | BA.2 | BA.2.12.1 | BA.4/5 | Delta | SARS-CoV-1 | WIV1 |
| Sotrovimab V$_H$/V$_L$ | 63.3 | 392.5 | 714.3 | 666.4 | 12.3 | 8.9 | 27.4 |
| AZD1061 | 1217 | 5.8 | 5.1 | 41.2 | 5.9 | NA | NA |
| AZD8895 | 1161 | 607.7 | 415 | NA | 0.5 | NA | NA |
| Reference Antibody | 26.1 | 94.1 | 30.7 | 31.4 | 68.1 | 35.2 | 19.6 |
| AB-17 (8 mutations) | 10.7 | 24.5 | 11.7 | 25.5 | 17.8 | 7.1 | 12.6 |
| AB-15 (5 mutations) | 5.6 | 21.5 | 9.3 | 24.8 | 8.2 | 8.7 | 15.3 |
| AB-1 (4 mutations) | 8.8 | 21.9 | 13.3 | 27.8 | 13.9 | 9.0 | 13.9 |

IC$_{50}$ values expressed as ng/ml of the results reported in FIGS. 10A-10B. Log(inhibitor) vs normalized response - variable slope (four parameters). Delta/WIV1/Omicron BA.1 and Omicron BA.2/BA.2.12.1/BA.4/5 neutralization experiments respectively use lentivirus and VSV-dG vectors.
Results are representative of at least 8 technical replicates across at least 2 biological replicates.

TABLE 6

Efficacy at 4.5 µg/ml

| % neutralization | BA.1 | BA.2 | BA.2.12.1 | BA.4/5 | Delta | SARS-CoV-1 | WIV1 |
|---|---|---|---|---|---|---|---|
| Sotrovimab VH/VL | 99.4 | 73.1 | 76.9 | 60.5 | 101.3 | 101.3 | 99.4 |
| AZD1061 | 83.9 | 99.7 | 99.8 | 96.7 | 100.1 | 1.2 | 0.8 |
| AZD8895 | 96.5 | 93.9 | 94.2 | 25.8 | 101.7 | 1.7 | 0.6 |
| Reference Antibody | 91.9 | 74.5 | 79.0 | 74.4 | 93.9 | 94.3 | 97.6 |
| AB-17 (8 mutations) | 99.9 | 93.4 | 93.8 | 91.9 | 101.8 | 101.4 | 101.4 |
| AB-15 (5 mutations) | 98.2 | 84.6 | 92.9 | 87.1 | 101.4 | 99.0 | 98.7 |
| AB-1 (4 mutations) | 96.5 | 89.9 | 89.2 | 90.4 | 99.5 | 99.0 | 100.7 |

Maximum percentage neutralization at 4.5 µg/ml of the results reported in FIGS. 10A-10B

TABLE 7

| [ng/ml] | IC$_{50}$ | |
|---|---|---|
| | BA.1 | Delta |
| Sotrovimab V$_H$/V$_L$ | 410.5 | 57.9 |
| Reference Antibody | 527.8 | 7446 |
| AB-17 (8 mutations) | 82.3 | 153.9 |
| AB-15 (5 mutations) | 113.8 | 261.6 |
| AB-1 (4 mutations) | 119.2 | 236.4 |

IC$_{50}$ values expressed as ng/ml of the results reported in FIG. 11

TABLE 8

| Fold over Sotrovimab neutralization of Delta | IC$_{50}$ | | | | | |
|---|---|---|---|---|---|---|
| | Pseudovirus | | | Live virus | | |
| | AB-1 | AB-17 | AB-15 | AB-1 | AB-17 | AB-15 |
| Delta | 1.3 | 1.7 | 0.8 | 4.1 | 2.7 | 4.5 |
| Omicron/BA.1 | 0.7 | 0.8 | 0.4 | 2.1 | 1.4 | 2.0 |
| Omicron/BA.2 | 1.7 | 1.9 | 1.7 | na | na | na |
| Omicron/BA.2.12.1 | 1.0 | 0.9 | 0.7 | na | na | na |
| Omicron/BA.4/5 | 2.2 | 2.0 | 1.9 | na | na | na |
| WIV1 | 0.9 | 0.8 | 0.8 | na | na | na |

IC$_{50}$ values expressed as ratios over Sotrovimab neutralization of SARS-CoV-2 Delta

TABLE 9

Characterization of Polypeptides

| | Neutralization - IC$_{50}$ (ng/ml) | |
|---|---|---|
| | BA.4/5 | BA.4/5 + K444T |
| Sotrovimab | 424.5 | 304.4 |
| Bebtelovimab | 0.3 | 1223 |
| AB-1 | 10.1 | 9.4 |

IC$_{50}$ values expressed as ng/ml. Log(inhibitor) vs normalized response - variable slope (four parameters). BA.4/5 and BA.4/5 + K444T neutralization experiments use VSV-dG vectors. Results are representative of 1 or 2 biological replicates, 8 technical replicates each.

TABLE 10

V$_H$ Amino Acid Sequences of Anti-RBD Class 4 Polypeptides

| Name | SEQ ID | Amino Acid Sequence |
|---|---|---|
| RBD Class 4 mAb-1a, 1b, 1c, 1d | NO: 174 | QVQLVQSGAEVKKPGSSVKVSCKASGGY DNTYTISWVRQAPGQGLEWMGRIILLFG AANYAQKIQGRVTITADKSTSTAYMELT SLRSDDTAVYYCARGFHPDYYGWGDDDA FDFWGQGTLVTVYS |
| RBD Class 4 mAb-2a, 2b, 2c, 2d | NO: 175 | QVQLVQSGAEVKKPGSSVKVSCKASGDT SDTYTISWVRQAPGQGLEWMGRIILLSG YANYAQKIQGRVTITADKSTSTAYMELT SLRSDDTAVYYCARGFNGDYYGWGDDDA FDFWGQGTLVTVYS |
| RBD Class 4 mAb-3a, 3b, 3c, 3d | NO: 176 | QVQLVQSGAEVKKPGSSVKVSCKASGDT SDTYTISWVRQAPGQGLEWMGRIILMSG YANYAQKIQGRVTITADKSTSTAYMELT SLRSDDTAVYYCARGFNGDYYGWGDDDA FDFWGQGTLVTVYS |
| RBD Class 4 mAb-4a | NO: 177 | QVQLVQSGAEVKKPGSSVKVSCKASGGY DNTYTISWVRQAPGQGLEWMGRIILLFG AANYAQKIQGRVTITADKSTSTAYMELT SLRSDDTAVYYCARGFNGDYYGWGDDDA FDFWGQGTLVTVYS |

Predicted CDR residues are in bold.

TABLE 11

V$_L$ Amino Acid Sequences of Anti-RBD Class 4 Polypeptides

| Name | SEQ ID | Amino Acid Sequence |
|---|---|---|
| RBD Class 4 mAb-1a | NO: 178 | QTVLTQPPSVSGAPGQRVTISCTGSSSNIGAGYDVHWYQQLPGTAPKLLICGRDNRPSGVPDRFSGSKSGTSASLAITGLQAEDEADYYCQSYDSSSSGP HWVFGGGTKLTVL |
| RBD Class 4 mAb-1b | NO: 179 | QTVLTQPPSVSGAPGQRVTISCTGSSSNIGAGYDVHWYQQLPGTAPKLLIAGRDNRPSGVPDRFSGSKSGTSASLAITGLQAEDEADYYCQSYDSSSSGP HWVFGGGTKLTVL |
| RBD Class 4 mAb-1c | NO: 180 | QTVLTQPPSVSGAPGQRVTISCTGSSSNIGAGYDVHWYQQLPGTAPKLLISGRDNRPSGVPDRFSGSKSGTSASLAITGLQAEDEADYYCQSYDSSSSGP HWVFGGGTKLTVL |
| RBD Class 4 mAb-1d | NO: 181 | QTVLTQPPSVSGAPGQRVTISCTGSSSNIGAGYDVHWYQQLPGTAPKLLIYGRDN RPSGVPDRFSGSKSGTSASLAITGLQAEDEADYYCQSYDSSSSGPHWV**FGGGTKL TVL |
| RBD Class 4 mAb-2a | NO: 182 | QTVLTQPPSVSGAPGQRVTISCTGSSSNIGAGYRVHWYQQLPGTAPKLLICGRSNRPSGVPDRFSGSKSGTSASLAITGLQAEDEADYYCQSYDSSLFDPHWVFGGGTKL TVL |
| RBD Class 4 mAb-2b | NO: 183 | QTVLTQPPSVSGAPGQRVTISCTGSSSNIGAGYRVHWYQQLPGTAPKLLIAGRSNRPSGVPDRFSGSKSGTSASLAITGLQAEDEADYYCQSYDSSLFDPHWVFGGGTKL TVL |
| RBD Class 4 mAb-2c | NO: 184 | QTVLTQPPSVSGAPGQRVTISCTGSSSNIGAGYRVHWYQQLPGTAPKLLISGRSNRPSGVPDRFSGSKSGTSASLAITGLQAEDEADYYCQSYDSSLFDPHWVFGGGTKL TVL |
| RBD Class 4 mAb-2d | NO: 185 | QTVLTQPPSVSGAPGQRVTISCTGSSSNIGAGYRVHWYQQLPGTAPKLLIYGRSNRPSGVPDRFSGSKSGTSASLAITGLQAEDEADYYCQSYDSSLFDPHWVFGGGTKL TVL |
| RBD Class 4 mAb-3a | NO: 186 | QTVLTQPPSVSGAPGQRVTISCTGSSSNIGAGYDVHWYQQLPGTAPKLLICGRSNRPSGVPDRFSGSKSGTSASLAITGLQAEDEADYYCQSYDSSLSDPHWVFGGGTKL TVL |
| RBD Class 4 mAb-3b | NO: 187 | QTVLTQPPSVSGAPGQRVTISCTGSSSNIGAGYDVHWYQQLPGTAPKLLIAGRSNRPSGVPDRFSGSKSGTSASLAITGLQAEDEADYYCQSYDSSLSDPHWVFGGGTKL TVL |
| RBD Class 4 mAb-3c | NO: 188 | QTVLTQPPSVSGAPGQRVTISCTGSSSNIGAGYDVHWYQQLPGTAPKLLISGRSNRPSGVPDRFSGSKSGTSASLAITGLQAEDEADYYCQSYDSSLSDPHWVFGGGTKL TVL |

TABLE 11-continued

V_L Amino Acid Sequences of Anti-RBD Class 4 Polypeptides

```
Name         SEQ ID   Amino Acid Sequence

RBD Class    NO: 189  QTVLTQPPSVSGAPGQRVTISCTGSSSNIGAGYDVHWYQQLPGTAPKLLIYGRSN
4 mAb-3d              RPSGVPDRFSGSKSGTSASLAITGLQAEDEADYYCQSYDSSLSDPHWVFGGGTKL
                      TVL RBD Class    NO: 190  QTVLTQPPSVSGAPGQRVTISCTGSSSNIGAGYDVHWYQQLPGTAPKLLICGNDN
4 mAb-4a              RPSGVPDRFSGSKSGTSASLAITGLQAEDEADYYCQSYDSSSSGPHWVFGGGTKL
                      TVL
```

Predicted CDR residues are in bold.

TABLE 12

Binding of AB-1 and the Reference Antibody to S2 peptides

| Ligand | Analyte | Ligand Capture Level (RU) | ka (1/Ms) | kd (1/s) | KD (nM) | Rmax (RU) | Chi$^2$/Rmax (%) |
|---|---|---|---|---|---|---|---|
| 1133-1147 | AB-1 Fab | 11 ± 0 | no binding | no binding | no binding | no binding | no binding |
| | Ref. Ab Fab | | no binding | no binding | no binding | no binding | no binding |
| 1137-1151 | AB-1 Fab | 14 ± 0 | no binding | no binding | no binding | no binding | no binding |
| | Ref. Ab Fab | | no binding | no binding | no binding | no binding | no binding |
| 1141-1155 | AB-1 Fab | 19 ± 0 | no binding | no binding | no binding | no binding | no binding |
| | Ref. Ab Fab | | no binding | no binding | no binding | no binding | no binding |
| 1145-1159 | AB-1 Fab | 10 ± 0 | inconclusive | inconclusive | inconclusive | inconclusive | inconclusive |
| | Ref. Ab Fab | | inconclusive | inconclusive | inconclusive | inconclusive | inconclusive |
| 1149-1163 | AB-1 Fab | 9 ± 0 | 1.76E+06 | 1.46E−01 | 83.1* | 173 | 6.3% |
| | Ref. Ab Fab | | 2.72E+05 | 6.63E−02 | 243.6* | 137 | 9.3% |
| 1153-1167 | AB-1 Fab | 10 ± 0 | 6.97E+05 | 7.74E−02 | 111.0* | 139 | 10.8%** |
| | Ref. Ab Fab | | 1.72E+05 | 5.35E−02 | 311.1* | 94 | 6.6% |
| 1157-1171 | AB-1 Fab | 9 ± 0 | no binding | no binding | no binding | no binding | no binding |
| | Ref. Ab Fab | | no binding | no binding | no binding | no binding | no binding |
| 1149-1167 | AB-1 Fab | 13 ± 0 | 2.61E+06 | 2.41E−03 | 0.9 | 52 | 9.3% |
| | Ref. Ab Fab | | 9.29E+05 | 4.98E−03 | 5.4 | 49 | 8.1% |
| 1143-1162 stem helix region | AB-1 Fab | 15 ± 0 | 3.00E+06 | 3.70E−02 | 12.3 | 79 | 15.0%** |
| | Ref. Ab Fab | | 4.77E+05 | 3.06E−02 | 64.2* | 70 | 13.1%** |
| HIV-1 Env | AB-1 Fab | 17 ± 0 | no binding | no binding | no binding | no binding | no binding |
| | Ref. Ab Fab | | no binding | no binding | no binding | no binding | no binding |

*Highest concentration within analyte dilution series should be 10X above KD for accurate kinetic measurements
**Favorable for chi2 to be <10% of Rmax for robust data fitting (>10% may be due to heterogenous binding behavior and/or highest analyte concentration <10X of KD)

TABLE 13

Binding of AB-1 and the Reference Antibody to SARS-CoV-2 spike S2 peptides by DELFIA.

| | S: 1133-1147 | S: 1137-1151 | S: 1141-55 | S: 1145-1159 | S: 1149-1163 | S: 1153-1167 | S: 1157-1171 | S: 1149-1167 | S: 1143-1162 | HIV-1 Env |
|---|---|---|---|---|---|---|---|---|---|---|
| AB-1 | 27146 (0.000 to 64116) | 21546 (0.000 to 43785) | 17984 (3114 to 32853) | 1702718 (1631060 to 1774377) | 3516897 (3430770 to 3603023) | 3323695 (3249316 to 3398073) | 30042 (23523 to 36561) | 3271444 (3210513 to 3332375) | 3521580 (3441895 to 3601266) | 9864 (0.000 to 26358) |
| Reference Antibody | 3265 (0.000 to 12018) | 5048 (0.000 to 10383) | 2268 (0.000 to 5339) | 1319064 (1236997 to 1401132) | 3256673 (3221731 to 3291615) | 3118316 (3082677 to 3153955) | 6011 (4995 to 7027) | 3045993 (3014085 to 3077902) | 3245236 (3200303 to 3290170) | 16115 (0.000 to 35133) |
| Isotype | 4061 (0.000 to 10913) | 19256 (0.000 to 41130) | 13301 (0.000 to 33834) | 1517 (0.000 to 8125) | 20545 (0.000 to 59471) | 8117 (0.000 to 31167) | 3112 (0.000 to 6252) | 2605 (0.000 to 10188) | 3106 (0.000 to 12937) | 41468 (2214 to 80722) |

Bindings of AB-1, the Reference Antibody and isotype control to SARS-CoV-2 spike S2 peptides (indicated as "S:" followed by amino acid positions) and HIV-1 Env negative control peptide were assessed by DELFIA. The results are reported as AUC values (95% confidence interval), and representative of two independent experiments, three technical replicates each.

TABLE 14

Kinetics of Fabs of AB-1 and the Reference Antibody s binding
to SARS-CoV-2 spike S2 [aa 1149-1167] peptide by SPR.

| Ligand | Analyte | $k_a$ (M$^{-1}$s$^{-1}$) | $k_d$ (s$^{-1}$) | $K_D$ (M) | $R_{max}$ (RU) | Chi$^2$ (RU$^2$) |
|---|---|---|---|---|---|---|
| S: 1149-1167 | AB-1 | 2.61E+06 | 2.41E-03 | 9.25E-10 | 51.7 | 4.82 |
| S: 1149-1167 | Reference Antibody | 9.29E+05 | 4.98E-03 | 5.36E-09 | 49.1 | 3.99 |
| HIV-1 Env | AB-1 | no binding | no binding | no binding | no binding | no binding |
| HIV-1 Env | Reference Antibody | no binding | no binding | no binding | no binding | no binding |

Kinetics of Fabs of AB-1 and the Reference Antibody binding to SARS-CoV-2 spike S2 (aa 1149-1167) peptide (indicated as "S:" followed by amino acid positions) and HIV-1 Env negative control peptide were obtained by SPR at 25° C. The parameters displayed in the table represent the following: $k_a$ refers to the association rate constant, $k_d$ refers to the dissociation rate constant, $K_D$ refers to the equilibrium dissociation constant, $R_{max}$ is the maximum analyte binding capacity of the surface, and Chi$^2$ is a measure of the closeness of fit calculated as the average squared residual. The results are representative of one experiment without technical replicates.

TABLE 15

Regions of interest in the SARS-CoV-2 spike protein.

| Region Description | Original residue coordinates | Non-intersecting residue coordinates for analysis |
|---|---|---|
| Epitope | 1152-1178 | 1152-1178 |
| Epitope Adjacent | 1147-1151, 1179-1183 | 1147-1151 |
| Heptad Repeat 1 (HR1) | 918-983 | 918-983 |
| Heptad Repeat 2 (HR2) | 1162-1203 | 1179-1203 |

Regions of interest in the SARS-COV-2 spike protein. Two sets of coordinates are reported: the full original region, and the pairwise non-overlapping regions that were analyzed for categorization purposes.

TABLE 16

Summary of Mutations of Interest

| | | Relative frequency | | | |
|---|---|---|---|---|---|
| Mutation | Region | 1 month | 3 months | earliest | Most prevalent lineages (earliest) |
| D950N | HR1 | 0.0000 | 0.0000 | 0.3472 | AY.4, AY.103, AY.44, AY.3 |
| L981F | HR1 | 0.0000 | 0.0002 | 0.1833 | BA.1.1, BA.1, BA.1.17.2, BA.1.15 |
| N969K | HR1 | 0.8454 | 0.9463 | 0.4725 | BA.2, BA.1.1, BA.1, BA.2.12.1 |
| Q954H | HR1 | 0.8381 | 0.9425 | 0.4707 | BA.2, BA.1.1, BA.1, BA.2.12.1 |
| Q957R | HR1 | 0.0000 | 0.0000 | 0.0013 | B.1.526, B.1, B.1.1.7, B.1.533 |
| S939F | HR1 | 0.0013 | 0.0016 | 0.0019 | B.1.1.7, AY.4, AY.44, BA.2.10 |
| S982A | HR1 | 0.0000 | 0.0000 | 0.0759 | B.1.1.7, Q.7, Q.3, Q.4 |
| K1191N | HR2 | 0.0000 | 0.0001 | 0.0051 | B.1.1.7, AY.64, AY.4, AY.103 |
| G1167V | Epitope | 0.0000 | 0.0000 | 0.0011 | B.1.617.2, AY.41, B.1.177, AY.4 |
| P1162L | Epitope | 0.002 | 0.0035 | 0.0017 | BA.5.8, BA.2, AY.4, B.1.1.7 |
| P1162S | Epitope | 0.0025 | 0.002 | 0.0019 | AY.4, BA.2, B.1.1.7, BA.1.1 |
| V1176F | Epitope | 0.0001 | 0.0002 | 0.0047 | P.1, P.1.17, P.1.10, P.2 |

All mutations satisfying the indicated criteria are listed. relative frequencies are for the period ending Mar. 1$^{st}$, 2023. The four most prevalent lineages amongst sequences harboring each mutation were identified by querying GenBank for all sequences with a given mutation and then tallying the most common Gango lineages (Rambaut 2020) amongst these sequences.

TABLE 17

AB-1 Binding to SARS-CoV-2 and Non-SARS-CoV-2 Spike Trimers by DELFIA

| | | S: SARS-CoV-2 | | | | | | | | |
|---|---|---|---|---|---|---|---|---|---|---|
| | D614G | Delta | BA.1 | BA.1.1 | BA.2 | BA.2.12.1 | BA.2.3.20 | BA.2.75 | BA.2.75.2 | BA.4 |
| AB-1 | 0.057 (0.055 to 0.058) | 0.058 (0.057 to 0.059) | 0.054 (0.053 to 0.055) | 0.055 (0.054 to 0.057) | 0.049 (0.048 to 0.050) | 0.058 (0.057 to 0.060) | 0.058 (0.057 to 0.060) | 0.052 (0.051 to 0.054) | 0.062 (0.060 to 0.064) | 0.056 (0.054 to 0.058) |

TABLE 17-continued

AB-1 Binding to SARS-CoV-2 and Non-SARS-CoV-2 Spike Trimers by DELFIA

| Ref. | 0.068 (0.066 to 0.071) | 0.073 (0.070 to 0.075) | 0.068 (0.066 to 0.069) | 0.069 (0.067 to 0.071) | 0.061 (0.060 to 0.062) | 0.072 (0.070 to 0.074) | 0.070 (0.068 to 0.073) | 0.064 (0.062 to 0.066) | 0.078 (0.076 to 0.081) | 0.070 (0.068 to 0.072) |
|---|---|---|---|---|---|---|---|---|---|---|
| Isotype | 12 (NA) | 6.1 (NA) | 5.9 (NA) | 9.2 (NA) | 5.8 (NA) | 13 (NA) | 23 (NA) | 7.5 (NA) | 5.9 (NA) | 6.1 (NA) |

| | S: SARS-CoV-2 | | | | | | | | S: | |
|---|---|---|---|---|---|---|---|---|---|---|
| | BA.4.6 | BF.7 | BN.1 | BQ.1 | BQ.1.1 | XBB | XBB.1 | XBB.1.5 | WIV1 | SARS-CoV-1 |
| AB-1 | 0.058 (0.057 to 0.059) | 0.053 (0.051 to 0.054) | 0.056 (0.052 to 0.060) | 0.055 (0.053 to 0.057) | 0.053 (0.051 to 0.056) | 0.059 (0.058 to 0.061) | 0.057 (0.056 to 0.059) | 0.057 (0.055 to 0.060) | 0.061 (0.058 to 0.064) | 0.065 (0.063 to 0.068) |
| Ref. | 0.072 (0.070 to 0.073) | 0.065 (0.063 to 0.067) | 0.069 (0.064 to 0.075) | 0.068 (0.064 to 0.071) | 0.066 (0.063 to 0.069) | 0.073 (0.071 to 0.075) | 0.069 (0.066 to 0.071) | 0.072 (0.068 to 0.076) | 0.076 (0.072 to 0.081) | 0.079 (0.076 to 0.082) |
| Isotype | 7.4 (NA) | 60 (NA) | 5.3 (NA) | 28 (NA) | 15 (NA) | 11 (NA) | 6.9 (NA) | 6.7 (NA) | 0.0055 (NA) | NA (NA) |

| | S: SARS-CoV-2 | | |
|---|---|---|---|
| | BA.2 (parent) | BA.2 + P1162L | BA.2 + P1162S |
| AB-1 | 0.048 (0.046 to 0.050) | 0.054 (0.051 to 0.058) | 0.052 (0.050 to 0.055) |
| Ref. | 0.062 (0.059 to 0.065) | 0.067 (0.063 to 0.070) | 0.059 (0.056 to 0.062) |
| Isotype | 4.8e−006 (NA) | 2.0e−005 (NA) | 1.6e−005 (NA) |

Binding of AB-1, the Reference Antibody (Ref.) and isotype control to spike trimers (indicated as "S:" followed by the respective virus name) as reported in FIGs. 31A-31C. Results are expressed as $EC_{50}$ values (µg/ml), shown as mean (95% confidence interval) and representative of two independent experiments, four technical replicates each.
"NA" indicates inability to determine accurate values due to lack of binding.

TABLE 18

Kinetics of Fabs of AB-1 and the Reference Antibody Binding to a Panel of SARS-CoV-2 Spike Trimers by SPR at 25° C.

| Ligand | Analyte | $k_a$ ($10^5$ $M^{-1}s^{-1}$) | $k_d$ ($10^{-4}$ $s^{-1}$) | $K_D$ ($10^{-9}$ M) | $R_{max}$ (RU) | Chi$^2$ (RU$^2$) |
|---|---|---|---|---|---|---|
| S: SARS-CoV-2 D614G | AB-1 | 1.43 ± 0.02 | 5.19 ± 0.32 | 3.64 ± 0.19 | 21.28 ± 0.69 | 0.08 ± 0.01 |
| | Reference Antibody | 0.51 ± 0.01 | 10.99 ± 0.42 | 21.71 ± 0.47 | 20.65 ± 0.06 | 0.07 ± 0.01 |
| S: SARS-CoV-2 Delta | AB-1 | 1.42 ± 0.05 | 5.36 ± 0.21 | 3.79 ± 0.02 | 30.29 ± 0.26 | 0.15 ± 0.01 |
| | Reference Antibody | 0.50 ± 0.00 | 10.84 ± 0.40 | 21.84 ± 0.62 | 30.01 ± 0.05 | 0.15 ± 0.03 |
| S: SARS-CoV-2 BA.4 | AB-1 | 1.33 ± 0.11 | 5.13 ± 0.04 | 3.86 ± 0.35 | 30.71 ± 0.39 | 0.25 ± 0.18 |
| | Reference Antibody | 0.52 ± 0.00 | 9.97 ± 0.52 | 19.02 ± 1.06 | 30.42 ± 0.05 | 0.29 ± 0.07 |
| S: SARS-CoV-2 BA.5 | AB-1 | 0.87 ± 0.07 | 5.57 ± 0.08 | 6.40 ± 0.45 | 36.88 ± 0.56 | 1.01 ± 0.03 |
| | Reference Antibody | 0.85 ± 0.45 | 12.38 ± 3.47 | 15.62 ± 4.11 | 30.42 ± 0.38 | 0.36 ± 0.24 |
| S: SARS-CoV-2 BQ.1.1 | AB-1 | 1.29 ± 0.06 | 5.30 ± 0.01 | 4.10 ± 0.19 | 30.95 ± 0.13 | 0.27 ± 0.21 |
| | Reference Antibody | 0.48 ± 0.00 | 10.59 ± 0.61 | 21.99 ± 1.46 | 30.65 ± 0.01 | 0.31 ± 0.12 |
| S: SARS-CoV-2 XBB.1.5 | AB-1 | 1.32 ± 0.09 | 4.89 ± 0.07 | 3.71 ± 0.30 | 28.24 ± 0.49 | 0.16 ± 0.09 |
| | Reference Antibody | 0.53 ± 0.01 | 9.89 ± 0.21 | 18.81 ± 0.13 | 26.83 ± 0.25 | 0.19 ± 0.06 |
| S: MERS | AB-1 | no binding | no binding | no binding | no binding | no binding |
| | Reference Antibody | no binding | no binding | no binding | no binding | no binding |
| S: SARS-CoV-2 BA.2 (parent) | AB-1 | 2.35 ± 0.07 | 37.43 ± 0.89 | 15.92 ± 0.06 | 34.59 ± 0.22 | 0.53 ± 0.03 |
| | Reference Antibody | 0.85 ± 0.04 | 72.98 ± 2.83 | 85.84 ± 7.38 | 33.26 ± 0.45 | 0.34 ± 0.14 |
| S: SARS-CoV-2 BA.2 + P1162L | AB-1 | 1.01 ± 0.05 | 36.92 ± 1.09 | 36.61 ± 0.68 | 33.56 ± 0.40 | 0.78 ± 0.16 |
| | Reference Antibody | 0.58 ± 0.04 | 66.25 ± 3.25 | 113.47 ± 1.77 | 23.82 ± 0.02 | 0.20 ± 0.05 |
| S: SARS-CoV-2 BA.2 + P1162S | AB-1 | 2.53 ± 0.11 | 36.75 ± 1.69 | 14.54 ± 0.04 | 29.58 ± 0.43 | 0.37 ± 0.04 |
| | Reference Antibody | 0.93 ± 0.06 | 72.52 ± 1.87 | 78.00 ± 2.63 | 27.78 ± 0.70 | 0.25 ± 0.05 |

Kinetics of Fabs of AB-1 and the Reference Antibody binding to a panel of SARS-CoV-2 spike trimers and MERS spike trimer as (negative control) were obtained by SPR at 25° C. The parameters displayed in the table represent the following: $k_a$ refers to the association rate constant, $k_d$ refers to the dissociation rate constant, $K_D$ refers to the equilibrium dissociation constant, $R_{max}$ is the maximum analyte binding capacity of the surface and Chi$^2$ is a measure of the closeness of fit calculated as the average squared residual. The results are expressed as average ± standard deviation of one independent experiment with technical replicates.

TABLE 19

Kinetics of Fabs of AB-1 and the Reference Antibody Binding to a Panel of SARS-CoV-2 Spike Trimers by SPR at 37° C.

| Ligand | Analyte | $k_a$ ($10^5$ M$^{-1}$s$^{-1}$) | $k_d$ ($10^{-3}$ s$^{-1}$) | $K_D$ ($10^{-9}$ M) | $R_{max}$ (RU) | Chi$^2$ (RU$^2$) |
|---|---|---|---|---|---|---|
| S: SARS-CoV-2 D614G | AB-1 | 4.87 ± 0.06 | 2.20 ± 0.06 | 4.52 ± 0.18 | 17.02 ± 0.41 | 0.06 ± 0.02 |
|  | Reference Antibody | 1.38 ± 0.18 | 5.56 ± 0.82 | 40.37 ± 0.67 | 18.32 ± 0.38 | 0.17 ± 0.01 |
| S: SARS-CoV-2 Delta | AB-1 | 4.84 ± 0.12 | 2.22 ± 0.05 | 4.58 ± 0.21 | 18.41 ± 0.26 | 0.11 ± 0.02 |
|  | Reference Antibody | 1.29 ± 0.04 | 5.16 ± 0.06 | 39.91 ± 1.71 | 20.58 ± 0.34 | 0.23 ± 0.02 |
| S: SARS-CoV-2 BA.4 | AB-1 | 4.67 ± 0.04 | 2.22 ± 0.01 | 4.75 ± 0.06 | 24.18 ± 0.07 | 0.08 ± 0.00 |
|  | Reference Antibody | 1.27 ± 0.06 | 4.77 ± 0.13 | 37.40 ± 0.61 | 27.24 ± 0.02 | 0.43 ± 0.06 |
| S: SARS-CoV-2 BA.5 | AB-1 | 3.96 ± 0.17 | 2.60 ± 0.07 | 6.59 ± 0.46 | 21.21 ± 0.29 | 0.06 ± 0.02 |
|  | Reference Antibody | 1.20 ± 0.00 | 5.49 ± 0.13 | 45.86 ± 0.96 | 23.75 ± 0.34 | 0.32 ± 0.05 |
| S: SARS-CoV-2 BQ.1.1 | AB-1 | 4.26 ± 0.08 | 2.48 ± 0.07 | 5.83 ± 0.26 | 23.51 ± 0.08 | 0.11 ± 0.04 |
|  | Reference Antibody | 1.19 ± 0.00 | 5.18 ± 0.21 | 43.72 ± 1.68 | 25.92 ± 0.13 | 0.39 ± 0.06 |
| S: SARS-CoV-2 XBB.1.5 | AB-1 | 4.48 ± 0.25 | 2.40 ± 0.10 | 5.37 ± 0.53 | 14.73 ± 0.09 | 0.04 ± 0.02 |
|  | Reference Antibody | 1.23 ± 0.06 | 4.90 ± 0.01 | 39.77 ± 1.81 | 16.29 ± 0.14 | 0.12 ± 0.03 |
| S: MERS | AB-1 | no binding | no binding | no binding | no binding | no binding |
|  | Reference Antibody | no binding | no binding | no binding | no binding | no binding |
| S: SARS-CoV-2 BA.2 (parent) | AB-1 | 4.26 ± 0.32 | 17.99 ± 0.50 | 42.37 ± 4.34 | 28.42 ± 0.68 | 1.11 ± 0.01 |
|  | Reference Antibody | 2.03 ± 0.14 | 29.50 ± 1.55 | 146.22 ± 17.76 | 21.29 ± 1.03 | 0.24 ± 0.05 |
| S: SARS-CoV-2 BA.2 + P1162L | AB-1 | 2.51 ± 0.22 | 20.48 ± 0.51 | 81.70 ± 5.07 | 27.13 ± 0.16 | 0.58 ± 0.00 |
|  | Reference Antibody | 1.65 ± 0.28 | 32.74 ± 0.57 | 200.94 ± 30.40 | 17.10 ± 0.59 | 0.22 ± 0.04 |
| S: SARS-CoV-2 BA.2 + P1162S | AB-1 | 4.73 ± 0.48 | 18.37 ± 0.38 | 39.07 ± 4.73 | 23.60 ± 1.02 | 0.72 ± 0.06 |
|  | Reference Antibody | 3.38 ± 0.82 | 49.92 ± 5.07 | 150.07 ± 21.32 | 17.92 ± 1.25 | 0.15 ± 0.02 |

Kinetics of Fabs of AB-1 and the Reference Antibody binding to a panel of SARS-CoV-2 spike trimers and MERS spike trimer (negative control) were obtained by SPR at 37° C.
The parameters displayed in the table represent the following: $k_a$ refers to the association rate constant, $k_d$ refers to the dissociation rate constant, $K_D$ refers to the equilibrium dissociation constant, $R_{max}$ is the maximum analyte binding capacity of the surface and Chi$^2$ is a measure of the closeness of fit calculated as the average squared residual. The results are expressed as average ± standard deviation of one independent experiment with technical replicates.

TABLE 20

Affinity Comparison of Fabs of AB-1 and the Reference Antibody Binding to a Panel of SARS-CoV-2 Spike Trimers by SPR at 25° C. and 37° C.

| SARS-CoV-2 spike trimer | $K_D$ ($10^{-9}$ M), 25° C. | | $K_D$ ($10^{-9}$ M), 37° C. | |
|---|---|---|---|---|
|  | AB-1 | Reference Antibody | AB-1 | Reference Antibody |
| S: SARS-CoV-2 D614G | 3.64 ± 0.19 | 21.71 ± 0.47 | 4.52 ± 0.18 | 40.37 ± 0.67 |
| S: SARS-CoV-2 Delta | 3.79 ± 0.02 | 21.84 ± 0.62 | 4.58 ± 0.21 | 39.91 ± 1.71 |
| S: SARS-CoV-2 BA.4 | 3.86 ± 0.35 | 19.02 ± 1.06 | 4.75 ± 0.06 | 37.40 ± 0.61 |
| S: SARS-CoV-2 BA.5 | 6.40 ± 0.45 | 15.62 ± 4.11 | 6.59 ± 0.46 | 45.86 ± 0.96 |
| S: SARS-CoV-2 BQ.1.1 | 4.10 ± 0.19 | 21.99 ± 1.46 | 5.83 ± 0.26 | 43.72 ± 1.68 |
| S: SARS-CoV-2 XBB.1.5 | 3.71 ± 0.30 | 18.81 ± 0.13 | 5.37 ± 0.53 | 39.77 ± 1.81 |
| S: MERS | no binding | no binding | no binding | no binding |
| S: SARS-CoV-2 BA.2 (parent) | 15.92 ± 0.06 | 85.84 ± 7.38 | 42.37 ± 4.34 | 146.22 ± 17.76 |
| S: SARS-CoV-2 BA.2 + P1162L | 36.61 ± 0.68 | 113.47 ± 1.77 | 81.70 ± 5.07 | 200.94 ± 30.40 |
| S: SARS-CoV-2 BA.2 + P1162S | 14.54 ± 0.04 | 78.00 ± 2.63 | 39.07 ± 4.73 | 150.07 ± 21.32 |

Affinity comparison of Fabs of AB-1 and the Reference Antibody binding to a panel of SARS-CoV-2 spike trimers and MERS spike trimer (negative control) were obtained by globally fitting the kinetic parameters to a 1:1 binding model at 25° C. and 37° C. The parameters displayed in the table represent the equilibrium dissociation constant $K_D$. The results are expressed as average ± standard deviation of one independent experiment with technical replicates.

TABLE 21

AB-1 Neutralization of SARS-CoV-2 Variants and Non-SARS-CoV-2 Sarbecoviruses (EC$_{50}$ Values).

| | SARS-CoV-2 | | | | | | | |
|---|---|---|---|---|---|---|---|---|
| | D614G | Delta | BA.1 | BA.1.1 | BA.2 | BA.2.12.1 | BA.2.75 | BA.2.75.2 |
| AB-1 | 0.019 (0.016 to 0.0235) | 0.039 (0.030 to 0.052) | 0.0064 (0.0049 to 0.0085) | 0.0065 (0.0049 to 0.0087) | 0.0096 (0.0069 to 0.013) | 0.0046 (0.0033 to 0.0062) | 0.0097 (0.007 to 0.014) | 0.0049 (0.0027 to 0.0082) |
| Reference Antibody | 0.18 (0.11 to 0.38) | 0.80 (0.36 to 4.6) | 0.064 (0.038 to 0.14) | 0.078 (0.046 to 0.15) | 0.16 (0.073 to 0.74) | 0.053 (0.037 to 0.082) | 0.069 (0.037 to 0.17) | NA |
| Bebtelovimab | 0.00057 (0.00038 to 0.0008) | 0.0038 (0.0027 to 0.0052) | 0.00017 (0.000078 to 0.00028) | 0.00012 (0.000037 to 0.00022) | 0.0002 (0.00012 to 0.00029) | 0.00020 (0.00012 to 0.0003) | 0.00065 (0.00037 to 0.0010) | 0.00046 (0.00017 to 0.00088) |

| | SARS-CoV-2 | | | | | | | | |
|---|---|---|---|---|---|---|---|---|---|
| | BA.2.3.20 | BA.4/5 | BA.4.6 | BN.1 | BF.7 | BF.7.14 | CH.1.1 | BQ.1 | BQ.1.1 |
| AB-1 | 0.012 (0.0088 to 0.017) | 0.0048 (0.0024 to 0.0084) | 0.0094 (0.0065 to 0.014) | 0.0042 (0.0013 to 0.0098) | 0.0089 (0.0063 to 0.013) | 0.011 (0.0079 to 0.015) | 0.0038 (0.0024 to 0.0057) | 0.0085 (0.0064 to 0.011) | 0.0051 (0.0019 to 0.010) |
| Reference Antibody | 0.10 (0.065 to 0.19) | NA | NA | NA | 0.078 (0.026 to 27) | 0.12 (0.061 to 0.32) | 0.028 (0.013 to 0.083) | 0.094 (0.052 to 0.23) | NA |
| Bebtelovimab | 0.012 (0.0073 to 0.02) | 0.000073 (0.0000062 to 0.00020) | 0.0002 (0.000066 to 0.00038) | 0.0004674 (0.00018 to 0.00086) | 0.00011 (0.000017 to 0.00026) | 0.00022 (0.00014 to 0.00033) | NA | NA | NA |

| | SARS-CoV-2 | | | | SARS-CoV-2 | |
|---|---|---|---|---|---|---|
| | XBB.1 | XBB.1.5 | WIV1 | SARS-CoV-1 | BA.1.1 + P1162S | BA.5.8 + P1162L |
| AB-1 | 0.0097 (0.0072 to 0.013) | 0.0088 (0.0065 to 0.012) | 0.063 (0.053 to 0.075) | 0.012 (0.0094 to 0.015) | NA | NA |
| Reference Antibody | 0.098 (0.060 to 0.19) | 0.093 (0.033 to 3.0) | 1.1 (0.64 to 2.7) | 0.22 (0.13 to 0.54) | NA | NA |
| Bebtelovimab | NA | NA | NA | NA | 0.00012 (0.000024 to 0.00026) | 0.00013 (0.00004 to 0.00024) |

Neutralization profiles of AB-1 and bebtelovimab against pseudoviruses representative of SARS-CoV-2 variants and non-SARS-CoV-2 sarbecoviruses as reported in FIG. 34. The results are reported as EC$_{50}$ values (μg/ml), shown as mean (95% confidence interval) and representative of three to six independent experiments, four technical replicates each. The values in bold indicate AB-1 EC$_{50}$ values that are increased compared to SARS-CoV-2 D614G and with no overlapping 95% confidence intervals. AB-1 EC$_{50}$ values and 95% confidence intervals that cannot be correctly quantified due to incomplete neutralization are reported as NA.

TABLE 22

AB-1 Neutralization of SARS-CoV-2 Variants and Non-SARS-CoV-2 Sarbecoviruses (EC$_{80}$ values)

| | SARS-CoV-2 | | | | | | | | | |
|---|---|---|---|---|---|---|---|---|---|---|
| | D614G | Delta | BA.1 | BA.1.1 | BA.2 | BA.2.12.1 | BA.2.75 | BA.2.75.2 | BA.2.3.20 | BA.4/5 |
| AB-1 | 0.17 (0.12 to 0.24) | 0.37 (0.23 to 0.66) | 0.073 (0.047 to 0.12) | 0.065 (0.042 to 0.11) | 0.11 (0.066 to 0.21) | 0.047 (0.030 to 0.081) | 0.080 (0.048 to 0.15) | 0.078 (0.038 to 0.20) | 0.10 (0.061 to 0.18) | 0.099 (0.046 to 0.29) |
| Bebtelovimab | 0.0049 (0.0035 to 0.0072) | 0.023 (0.015 to 0.037) | 0.0018 (0.0012 to 0.0029) | 0.0013 (0.00081 to 0.0022) | 0.0014 (0.00096 to 0.0021) | 0.0012 (0.00083 to 0.0019) | 0.0082 (0.0050 to 0.015) | 0.0063 (0.0034 to 0.013) | 0.36 (0.15 to 1.1) | 0.0012 (0.00036 to 0.0025) |

| | SARS-CoV-2 | | | | | | | | | |
|---|---|---|---|---|---|---|---|---|---|---|
| | BA.4.6 | BN.1 | BF.7 | BF.7.14 | CH.1.1 | BQ.1 | BQ.1.1 | XBB.1 | XBB.1.5 | WIV1 |
| AB-1 | 0.075 (0.043 to 0.15) | 0.095 (0.031 to 0.65) | 0.080 (0.046 to 0.15) | 0.074 (0.045 to 0.13) | 0.056 (0.031 to 0.11) | 0.077 (0.050 to 0.12) | 0.15 (0.055 to 0.73) | 0.085 (0.054 to 0.15) | 0.12 (0.075 to 0.20) | 0.46 (0.34 to 0.64) |

TABLE 22-continued

AB-1 Neutralization of SARS-CoV-2 Variants and Non-SARS-CoV-2 Sarbecoviruses (EC$_{80}$ values)

| Bebtelovimab | 0.0025 (0.0015 to 0.0043) | 0.0053 (0.0028 to 0.011) | 0.0017 (0.00073 to 0.0033) | 0.0014 (0.00093 to 0.0022) | NA | NA | NA | NA | NA | NA |
|---|---|---|---|---|---|---|---|---|---|---|

|  | | SARS-CoV-2 | |
|---|---|---|---|
|  | SARS-CoV-1 | BA.1.1 + P1162S | BA.5.8 + P1162L |
| AB-1 | 0.078 (0.055 to 0.12) | NA | NA |
| Bebtelovimab | NA | 0.0014 (0.00072 to 0.0027) | 0.0011 (0.00059 to 0.0020) |

Neutralization profiles of AB-1 and bebtelovimab against pseudoviruses representative of SARS-CoV-2 variants and non-SARS-CoV-2 Sarbecoviruses as reported in FIG. 34. The results are reported as EC$_{80}$ values (μg/mL), shown as mean (95% confidence interval) and representative of three to six independent experiments, four technical replicates each. The values in bold indicate: AB-1 EC$_{80}$ values and 95% confidence intervals that cannot be correctly quantified due to incomplete neutralization (reported as NA); AB-1 EC$_{80}$ values that are increased compared to SARS-CoV-2 D614G and with no overlapping 95% confidence intervals.

TABLE 23

AB-1 Neutralization of SARS-CoV-2 Variants and Non-SARS-CoV-2 Sarbecoviruses (EC$_{90}$ values)

|  | SARS-CoV-2 | | | | | | | | | |
|---|---|---|---|---|---|---|---|---|---|---|
|  | D614G | Delta | BA.1 | BA.1.1 | BA.2 | BA.2.12.1 | BA.2.75 | BA.2.75.2 | BA.2.3.20 | BA.4/5 |
| AB-1 | 0.60 (0.39 to 1.0) | 1.4 (0.73 to 3.1) | 0.30 (0.16 to 0.62) | 0.25 (0.134 to 0.51) | 0.46 (0.22 to 1.1) | 0.19 (0.098 to 0.40) | 0.28 (0.14 to 0.65) | 0.39 (0.14 to 1.7) | 0.35 (0.17 to 0.80) | 0.58 (0.19 to 3.2) |
| Reference Antibody | 8.9 (2.4 to 73) | 131 (20 to 4980) | 19 (4.4 to 190) | 3.2 (0.94 to 21) | 82 (11 to 4382) | 3.6 (1.4 to 13) | 5.6 (1.2 to 74) | NA | 5.5 (1.8 to 28) | NA |
| Bebtelovimab | 0.018 (0.010 to 0.031) | 0.066 (0.036 to 0.13) | 0.0072 (0.0038 to 0.015) | 0.0056 (0.0030 to 0.011) | 0.0044 (0.0026 to 0.0079) | 0.0036 (0.0020 to 0.0068) | 0.036 (0.017 to 0.089) | 0.029 (0.012 to 0.090) | 2.6 (0.81 to 14) | 0.0064 (0.0029 to 0.016) |

|  | SARS-CoV-2 | | | | | | | | | |
|---|---|---|---|---|---|---|---|---|---|---|
|  | BA.4.6 | BN.1 | BF.7 | BF.7.14 | CH.1.1 | BQ.1 | BQ.1.1 | XBB.1 | XBB.1.5 | WIV1 |
| AB-1 | 0.25 (0.11 to 0.68) | 0.59 (0.12 to 12) | 0.29 (0.13 to 0.74) | 0.23 (0.11 to 0.50) | 0.27 (0.12 to 0.79) | 0.28 (0.16 to 0.55) | 1.0 (0.24 to 14) | 0.31 (0.16 to 0.65) | 0.54 (0.28 to 1.2) | 1.5 (0.97 to 2.3) |
| Reference Antibody | NA | NA | NA | 14 (2.8 to 232) | 8.2 (1.2 to 414) | 9.2 (2.0 to 128) | NA | 6.0 (1.8 to 37) | NA | 89 (26 to 546) |
| Bebtelovimab | 0.011 (0.0055 to 0.024) | 0.022 (0.0089 to 0.068) | 0.0085 (0.0040 to 0.021) | 0.0041 (0.0023 to 0.0086) | NA | NA | NA | NA | NA | NA |

|  | | SARS-CoV-2 | |
|---|---|---|---|
|  | SARS-CoV-1 | BA.1.1 + P1162S | BA.5.8 + P1162L |
| AB-1 | 0.24 (0.15 to 0.41) | NA | NA |
| Reference Antibody | 31 (7.8 to 273) | NA | NA |
| Bebtelovimab | NA | 0.0060 (0.0027 to 0.015) | 0.0037 (0.0017 to 0.0095) |

Neutralization profiles of AB-1 and bebtelovimab against pseudoviruses representative of SARS-CoV-2 variants and non-SARS-CoV-2 Sarbecoviruses as reported in FIG. 34. The results are reported as EC$_{90}$ values (μg/mL), shown as mean (95% confidence interval) and representative of three to six independent experiments, four technical replicates each. The values in bold indicate: AB-1 EC$_{90}$ values and 95% confidence intervals that cannot be correctly quantified due to incomplete neutralization (reported as NA); AB-1 EC$_{90}$ values that are increased compared to SARS-CoV-2 D614G and with no overlapping 95% confidence intervals.

TABLE 24

AB-1 Neutralization of SARS-CoV-2 Variants and Non-SARS-CoV-2 Sarbecoviruses ($E_{max}$ values).

| | SARS-CoV-2 | | | | | | | | | |
|---|---|---|---|---|---|---|---|---|---|---|
| | D614G | Delta | BA.1 | BA.1.1 | BA.2 | BA.2.12.1 | BA.2.75 | BA.2.75.2 | BA.2.3.20 | BA.4/5 |
| AB-1 | 94.36 (93.79 to 94.92) | 87.73 (86.31 to 89.15) | 95.13 (94.14 to 96.12) | 93.94 (93.28 to 94.60) | 90.52 (89.16 to 91.89) | 93.71 (92.88 to 94.54) | 92.11 (90.89 to 93.33) | 91.07 (89.66 to 92.49) | 94.23 (92.66 to 95.81) | 89.75 (88.37 to 91.12) |
| Reference Antibody | 84.69 (83.42 to 85.96) | 73.52 (71.73 to 75.30) | 91.17 (90.06 to 92.27) | 89.60 (88.00 to 91.19) | 84.71 (82.60 to 86.83) | 89.23 (87.12 to 89.23) | 85.05 (83.17 to 86.92) | 85.28 (82.80 to 87.75) | 87.89 (86.49 to 89.29) | 84.66 (82.50 to 86.83) |
| Bebtelovimab | 99.89 (99.82 to 99.97) | 99.90 (99.86 to 99.95) | 99.85 (99.76 to 99.94) | 99.93 (99.89 to 99.97) | 99.89 (99.84 to 99.94) | 99.88 (99.83 to 99.94) | 99.47 (99.26 to 99.68) | 99.51 (99.23 to 99.78) | 97.94 (97.32 to 98.55) | 99.85 (99.74 to 99.96) |

| | SARS-CoV-2 | | | | | | | | | |
|---|---|---|---|---|---|---|---|---|---|---|
| | BA.4.6 | BN.1 | BF.7 | BF.7.14 | CH.1.1 | BQ.1 | BQ.1.1 | XBB.1 | XBB.1.5 | WIV1 |
| AB-1 | 90.11 (87.96 to 92.26) | 81.51 (78.71 to 84.32) | 91.54 (89.49 to 93.58) | 92.71 (90.74 to 94.68) | 93.17 (91.52 to 94.82) | 93.76 (92.15 to 95.36) | 93.54 (92.15 to 94.93) | 94.58 (93.45 to 95.71) | 92.88 (91.87 to 93.89) | 92.90 (91.59 to 94.20) |
| Reference Antibody | 80.89 (76.18 to 85.60) | 70.27 (65.97 to 74.56) | 82.44 (79.97 to 84.91) | 86.56 (83.15 to 89.98) | 86.70 (83.94 to 89.45) | 89.21 (87.36 to 91.05) | 87.48 (85.19 to 89.78) | 89.92 (88.52 to 91.32) | 88.11 (86.67 to 89.54) | 81.97 (79.69 to 84.24) |
| Bebtelovimab | 99.63 (99.33 to 99.94) | 99.36 (98.99 to 99.72) | 99.84 (99.75 to 99.94) | 99.81 (99.67 to 99.95) | 5.32 (0.31 to 10.34) | 72.15 (68.98 to 75.33) | 52.99 (44.19 to 61.79) | 10.83 (−0.96 to 22.61) | 2.01 (−0.08 to 4.10) | 6.99 (2.38 to 11.60) |

| | | SARS-CoV-2 | |
|---|---|---|---|
| | SARS-CoV-1 | BA.1.1 + P1162S | BA.5.8 + P1162L |
| AB-1 | 95.81 (94.85 to 96.77) | 47.06 (38.20 to 55.92) | 64.54 (58.07 to 71.01) |
| Reference Antibody | 86.11 (84.05 to 88.17) | 54.58 (42.75 to 66.41) | 58.97 (45.62 to 72.33) |
| Bebtelovimab | 8.00 (0.28 to 15.72) | 99.98 (99.91 to 99.98 ) | 99.92 (99.85 to 99.99) |

Neutralization profiles of AB-1, the Reference Antibody and bebtelovimab against pseudoviruses representative of SARS-CoV-2 variants and non-SARS-CoV-2 Sarbecoviruses as reported in FIG. 34. The results are reported as $E_{Max}$ values (μg/mL), shown as mean (95% confidence interval) and representative of 3-6 independent experiments, four technical replicates each. The values in bold indicate: AB-1 Emax values that are increased compared to the Reference Antibody and with no overlapping 95% confidence interval.

TABLE 25

Neutralization of SARS-CoV-2 Variants by AB-1 in Combination with R-AB-2b ($EC_{50}$ Values)

| | SARS-CoV-2 | | | | | | | |
|---|---|---|---|---|---|---|---|---|
| | D614G | Delta | BQ.1.1 | XBB.1.5 | D614G | Delta | BQ.1.1 | XBB.1.5 |
| | (TMPRSS2-Vero E6) | | | | (Vero E6) | | | |
| AB-1 + R-AB-2b (1:1) | 0.011 (0.010 to 0.013) | 0.0097 (0.0079 to 0.012) | 0.0074 (0.0057 to 0.0096) | 0.0049 (0.0038 to 0.0063) | 0.011 (0.0090 to 0.013) | 0.0074 (0.0062 to 0.0087) | 0.0094 (0.0074 to 0.012) | 0.0047 (0.0033 to 0.0065) |
| AB-1 + R-AB-2b (2:1) | 0.013 (0.011 to 0.016) | 0.016 (0.012 to 0.020) | 0.0064 (0.0049 to 0.0081) | 0.0056 (0.0041 to 0.0076) | 0.014 (0.011 to 0.018) | 0.014 (0.012 to 0.016) | 0.0077 (0.0055 to 0.011) | 0.0042 (0.0032 to 0.0055) |
| R-AB-2b + isotype | 0.041 (0.034 to 0.050) | 0.033 (0.028 to 0.039) | 0.034 (0.024 to 0.049) | 0.018 (0.013 to 0.023) | 0.014 (0.010 to 0.018) | 0.015 (0.012 to 0.018) | 0.022 (0.015 to 0.032) | 0.011 (0.0076 to 0.016) |
| AB-1 + isotype | 0.010 (0.0079 to 0.013) | 0.034 (0.023 to 0.052) | 0.0032 (0.0016 to 0.0056) | 0.0028 (0.0012 to 0.0051) | 0.017 (0.011 to 0.027) | 0.051 (0.042 to 0.063) | 0.0036 (0.0021 to 0.0059) | 0.0063 (0.0041 to 0.0095) |

TABLE 25-continued

Neutralization of SARS-CoV-2 Variants by AB-1 in Combination with R-AB-2b (EC$_{50}$ Values)

| | SARS-CoV-2 | | | | | | | |
|---|---|---|---|---|---|---|---|---|
| | D614G | Delta | BQ.1.1 | XBB.1.5 | D614G | Delta | BQ.1.1 | XBB.1.5 |
| | | (TMPRSS2-Vero E6) | | | | (Vero E6) | | |
| Bebtelovimab + isotype | 0.0017 (0.0013 to 0.0023) | 0.0016 (0.0011 to 0.0023) | NA | NA | 0.00064 (0.00049 to 0.00084) | 0.00063 (0.00030 to 0.0011) | NA | NA |

Neutralization profiles of AB-1 + R-AB-2b (tested at two different ratios), AB-1, R-AB-2b and bebtelovimab as single agents against pseudoviruses representative of the indicated SARS-CoV-2 variants using TMPRSS2-Vero E6 or Vero E6 cells as reported in FIG. 35. Results are reported as EC$_{50}$ values (µg/mL), shown as mean (95% confidence interval) and representative of three or four independent experiments, four technical replicates each. For each experimental condition (defined by a SARS-CoV-2 pseudovirus and a cell line), values in bold indicate: AB-1 + R-AB-2b EC$_{50}$ values that are lower compared to R-AB-2b + isotype and AB-1 + isotype, and with no overlapping 95% confidence intervals.

TABLE 26

Neutralization of SARS-CoV-2 Variants by AB-1 in Combination with R-AB-2b (EC$_{80}$ Values)

| | SARS-CoV-2 | | | | | | | |
|---|---|---|---|---|---|---|---|---|
| | D614G | Delta | BQ.1.1 | XBB.1.5 | D614G | Delta | BQ.1.1 | XBB.1.5 |
| | | (TMPRSS2-Vero E6) | | | | (Vero E6) | | |
| AB-1 + R-AB-2b (1:1) | 0.048 (0.039 to 0.058) | 0.056 (0.041 to 0.077) | 0.035 (0.024 to 0.054) | 0.027 (0.019 to 0.039) | 0.042 (0.031 to 0.058) | 0.028 (0.022 to 0.037) | 0.044 (0.031 to 0.065) | 0.031 (0.020 to 0.051) |
| AB-1 + R-AB-2b (2:1) | 0.084 (0.065 to 0.11) | 0.10 (0.072 to 0.16) | 0.050 (0.035 to 0.075) | 0.04609 (0.030 to 0.075) | 0.081 (0.055 to 0.12) | 0.050 (0.040 to 0.065) | 0.064 (0.041 to 0.11) | 0.030 (0.021 to 0.045) |
| R-AB-2b + isotype | 0.23 (0.17 to 0.33) | 0.15 (0.11 to 0.20) | 0.24 (0.14 to 0.50) | 0.075 (0.050 to 0.12) | 0.10 (0.068 to 0.17) | 0.058 (0.045 to 0.078) | 0.28 (0.16 to 0.60) | 0.084 (0.052 to 0.16) |
| AB-1 + isotype | 0.13 (0.087 to 0.22) | 0.4896 (0.25 to 1.2) | 0.080 (0.038 to 0.22) | 0.094 (0.042 to 0.29) | 0.26 (0.12 to 0.72) | 0.37 (0.26 to 0.57) | 0.094 (0.048 to 0.22) | 0.079 (0.043 to 0.17) |
| Bebtelovimab + isotype | 0.011 (0.0077 to 0.016) | 0.013 (0.0083 to 0.021) | NA | NA | 0.0027 (0.0019 to 0.0039) | 0.0042 (0.0022 to 0.0091) | NA | NA |

Neutralization profiles of AB-1 + R-AB-2b (tested at two different ratios), AB-1, R-AB-2b and bebtelovimab as single agents against pseudoviruses representative of the indicated SARS-CoV-2 variants using TMPRSS2-Vero E6 or Vero E6 cells as reported in FIG. 35. Results are reported as EC$_{80}$ values (µg/mL), shown as mean (95% confidence interval) and representative of three or four independent experiments, four technical replicates each. For each experimental condition (defined by a SARS-CoV-2 pseudovirus and a cell line), values in bold indicate: AB-1 + R-AB-26 EC$_{80}$ values that are lower compared to R-AB-2b + isotype and AB-1 + isotype, and with no overlapping 95% confidence intervals.

TABLE 27

Neutralization of SARS-CoV-2 Variants by AB-1 in Combination with R-AB-2b (EC$_{90}$ Values).

| | SARS-COV-2 | | | | | | | |
|---|---|---|---|---|---|---|---|---|
| | D614G | Delta | BQ.1.1 | XBB.1.5 | D614G | Delta | BQ.1.1 | XBB.1.5 |
| | | (TMPRSS2-Vero E6) | | | | (Vero E6) | | |
| AB-1+R-AB-2b (1:1) | 0.11 (0.084 to 0.14) | 0.15 (0.10 to 0.25) | 0.085 (0.049 to 0.16) | 0.071 (0.044 to 0.12) | 0.092 (0.062 to 0.14) | 0.061 (0.043 to 0.089) | 0.11 (0.068 to 0.19) | 0.094 (0.052 to 0.19) |
| AB-1+ R-AB-2b (2:1) | 0.24 (0.17 to 0.37) | 0.31 (0.19 to 0.57) | 0.17 (0.10 to 0.30) | 0.16 (0.087 to 0.32) | 0.22 (0.13 to 0.42) | 0.11 (0.077 to 0.15) | 0.22 (0.12 to 0.48) | 0.094 (0.056 to 0.17) |
| R-AB-2b + isotype | 0.62 (0.40 to 1.0) | 0.35 (0.25 to 0.53) | 0.77 (0.35 to 2.2) | 0.17 (0.096 to 0.36) | 0.34 (0.19 to 0.71) | 0.13 (0.090 to 0.20) | 1.3 (0.55 to 3.7) | 0.28 (0.13 to 0.70) |
| AB-1 + isotype | 0.60 (0.33 to 1.2) | 2.3 (0.89 to 8.6) | 0.52 (0.17 to 2.5) | 0.74 (0.22 to 4.5) | 1.3 (0.44 to 5.6) | 1.2 (0.73 to 2.1) | 0.63 (0.24 to 2.3) | 0.35 (0.15 to 1.1) |

TABLE 27-continued

Neutralization of SARS-CoV-2 Variants by AB-1 in Combination with R-AB-2b (EC$_{90}$ Values).

| | SARS-COV-2 | | | | | | | |
|---|---|---|---|---|---|---|---|---|
| | D614G | Delta | BQ.1.1 | XBB.1.5 | D614G | Delta | BQ.1.1 | XBB.1.5 |
| | | (TMPRSS2-Vero E6) | | | | (Vero E6) | | |
| Bebtelovimab + isotype | 0.032 (0.020 to 0.054) | 0.043 (0.024 to 0.088) | NA | NA | 0.0061 (0.0038 to 0.011) | 0.013 (0.0051 to 0.040) | NA | NA |

Neutralization profiles of AB-1 + R-AB-2b (tested at two different ratios), AB-1, R-AB-2b and bebtelovimab as single agents against pseudoviruses representative of the indicated SARS-CoV-2 variants using TMPRSS2-Vero E6 or Vero E6 cells as reported in FIG. 35. Results are reported as EC$_{90}$ values (μg/mL), shown as mean (95% confidence interval) and representative of three or four independent experiments, four technical replicates each. For each experimental condition (defined by a SARS-CoV-2 pseudovirus and a cell line), values in bold indicate: AB-1 + R-AB-26 EC$_{90}$ values that are lower compared to R-AB-2b + isotype and AB-1 + isotype, and with no overlapping 95% confidence intervals.

TABLE 28

Neutralization of SARS-CoV-2 variants by AB-1 in Combination with R-AB-2b (E$_{max}$ Values)

| | SARS-CoV-2 | | | | | | | |
|---|---|---|---|---|---|---|---|---|
| | D614G | Delta | BQ.1.1 | XBB.1.5 | D614G | Delta | BQ.1.1 | XBB.1.5 |
| | | (TMPRSS2-Vero E6) | | | | (Vero E6) | | |
| AB-1 + R-AB-2b (1:1) | 100.1 (99.99 to 100.24) | 99.95 (99.88 to 100.02) | 100.12 (100.04 to 100.21) | 100.08 (99.99 to 100.18) | 100.16 (100.05 to 100.26) | 100.03 (100.03 to 100.04) | 100.13 (100.04 to 100.21) | 100.11 (100.03 to 100.18) |
| AB-1 + R-AB-2b (2:1) | 100.12 (100.00 to 100.23) | 99.98 (99.94 to 100.02) | 100.10 (100.02 to 100.19) | 100.10 (100.03 to 100.16) | 100.15 (100.05 to 100.25) | 100.03 (100.02 to 100.03) | 100.12 (100.04 to 100.20) | 100.10 (100.03 to 100.17) |
| R-AB-2b + isotype | 100.05 (99.93 to 100.18) | 99.97 (99.92 to 100.01) | 100.06 (100.00 to 100.12) | 100.04 (100.00 to 100.09) | 100.12 (100.03 to 100.22) | 100.01 (100.00 to 100.02) | 100.08 (100.02 to 100.14) | 100.04 (100.00 to 100.09) |
| AB-1 + isotype | 93.82 (92.15 to 95.49) | 90.51 (89.78 to 91.25) | 94.20 (92.91 to 95.50) | 92.90 (91.42 to 94.38) | 97.11 (96.02 to 98.19) | 93.44 (92.15 to 94.73) | 96.66 (95.85 to 97.47) | 95.54 (94.58 to 96.50) |
| Bebtelovimab + isotype | 99.40 (98.94 to 99.86) | 99.66 (99.54 to 99.79) | 40.47 (36.66 to 44.28) | 2.93 (0.15 to 5.71) | 99.37 (98.77 to 99.97) | 99.69 (99.56 to 99.82) | 59.12 (53.09 to 65.16) | 4.21 (−0.08 to 8.49) |

Neutralization profiles of AB-1 + R-AB-2b (tested at two different ratios), AB-1, R-AB-2b and bebtelovimab as single agents pseudoviruses representative of the indicated SARS-CoV-2 variants using TMPRSS2-Vero E6 or Vero E6 cells as reported in FIG. 35. Results are reported as E$_{max}$ values (% neutralization), shown as mean (95% confidence interval) and representative of three or four independent experiments, four technical replicates each.

TABLE 29

Neutralization of SARS-CoV-2 Variants by AB-1 in Combination with Sotrovimab VH/VL - huIgG1-LS (EC$_{50}$ Values).

| | SARS-CoV-2 | | | |
|---|---|---|---|---|
| | D614G | Delta | BQ.1.1 | XBB.1.5 |
| | | (Vero E6) | | |
| AB-1 + sotrovimab VH/VL - huIgG1-LS (1:1) | 0.0089 (0.0075 to 0.010) | 0.0057 (0.0041 to 0.0078) | 0.0098 (0.0077 to 0.012) | 0.0094 (0.0072 to 0.012) |
| AB-1 + sotrovimab VH/VL - huIgG1-LS (2.4:1) | 0.012 (0.011 to 0.014) | 0.013 (0.010 to 0.018) | 0.0056 (0.0040 to 0.0076) | 0.0080 (0.0058 to 0.011) |
| Sotrovimab VH/VL - huIgG1-LS + isotype | 0.014 (0.012 to 0.018) | 0.0079 (0.0060 to 0.010) | 1.2 (0.84 to 2.7) | 0.17 (0.14 to 0.20) |
| AB-1 + isotype | 0.020 (0.015 to 0.026) | 0.053 (0.039 to 0.075) | 0.0015 (0.00067 to 0.0026) | 0.0041 (0.0029 to 0.0056) |
| Bebtelovimab + isotype | 0.00029 (0.000077 to 0.00063) | 0.00044 (0.000086 to 0.0010) | NA | NA |

Neutralization profiles of AB-1 + sotrovimab VH/VL - huIgG1-LS (tested at two different ratios), AB-1, sotrovimab VH/VL - huIgG1-LS and bebtelovimab as single agents pseudoviruses representative of the indicated SARS-CoV-2 variants using Vero E6 cells as reported in FIG. 36. Results are reported as EC$_{50}$ values (μg/mL), shown as mean (95% confidence interval) and representative of three or four independent experiments, four technical replicates each.

TABLE 30

Neutralization of SARS-CoV-2 variants by AB-1 in combination with sotrovimab VH/VL - huIgG1-LS (EC$_{80}$ values).

| | SARS-CoV-2 | | | |
|---|---|---|---|---|
| | D614G | Delta | BQ.1.1 | XBB.1.5 |
| | | (Vero E6) | | |
| AB-1 + sotrovimab VH/VL - huIgG1-LS (1:1) | 0.038 (0.030 to 0.049) | 0.039 (0.025 to 0.065) | 0.15 (0.10 to 0.23) | 0.091 (0.061 to 0.14) |
| AB-1 + sotrovimab VH/VL - huIgG1-LS (2.4:1) | 0.060 (0.050 to 0.074) | 0.075 (0.050 to 0.12) | 0.16 (0.096 to 0.28) | 0.12 (0.075 to 0.22) |
| Sotrovimab VH/VL - huIgG1-LS + isotype | 0.069 (0.052 to 0.095) | 0.042 (0.029 to 0.064) | 4.4 (2.3 to 27) | 0.68 (0.50 to 0.96) |
| AB-1 + isotype | 0.18 (0.11 to 0.30) | 0.38 (0.22 to 0.78) | 0.12 (0.062 to 0.27) | 0.082 (0.051 to 0.14) |
| Bebtelovimab + isotype | 0.0029 (0.0014 to 0.0066) | 0.0035 (0.0014 to 0.011) | NA | NA |

Neutralization profiles of AB-1 + sotrovimab VH/VL - huIgG1-LS (tested at two different ratios), AB-1, sotrovimab VH/VL - huIgG1-LS and bebtelovimab as single agents against pseudoviruses representative of the indicated SARS-CoV-2 variants using Vero E6 cells as reported in FIG. 36. Results are reported as EC$_{80}$ values (μg/mL), shown as mean (95% confidence interval) and representative of three or four independent experiments, four technical replicates each.

TABLE 31

Neutralization of SARS-CoV-2 Variants by AB-1 in Combination with Sotrovimab VH/VL - huIgG1-LS (EC$_{90}$ Values)

| | SARS-CoV-2 | | | |
|---|---|---|---|---|
| | D614G | Delta | BQ.1.1 | XBB.1.5 |
| | | (Vero E6) | | |
| AB-1 + sotrovimab VH/VL - huIgG1-LS (1:1) | 0.090 (0.064 to 0.13) | 0.12 (0.066 to 0.25) | 0.75 (0.44 to 1.4) | 0.34 (0.19 to 0.66) |
| AB-1 + sotrovimab VH/VL - huIgG1-LS (2.4:1) | 0.15 (0.12 to 0.20) | 0.20 (0.12 to 0.41) | 1.1 (0.54 to 2.7) | 0.59 (0.30 to 1.4) |
| Sotrovimab VH/VL - huIgG1-LS + isotype | 0.17 (0.11 to 0.27) | 0.11 (0.066 to 0.20) | 9.6 (4.0 to 107) | 1.5 (1.0 to 2.5) |
| AB-1 + isotype | 0.63 (0.34 to 1.3) | 1.2 (0.56 to 3.2) | 1.5 (0.55 to 6.1) | 0.48 (0.24 to 1.1) |
| Bebtelovimab + isotype | 0.011 (0.0043 to 0.038) | 0.012 (0.0033 to 0.074) | NA | NA |

Neutralization profiles of AB-1 + sotrovimab VH/VL - huIgG1-LS (tested at two different ratios), AB-1, sotrovimab VH/VL - huIgG1-LS and bebtelovimab as single agents against pseudoviruses representative of the indicated SARS-CoV-2 variants using Vero E6 cells as reported in FIG. 36. Results are reported as EC$_{90}$ values (μg/mL), shown as mean (95% confidence interval) and representative of three or four independent experiments, four technical replicates each.

TABLE 32

Neutralization of SARS-CoV-2 Variants by AB-1 in Combination with Sotrovimab VH/VL - huIgG1-LS ($E_{max}$ Values).

| | SARS-CoV-2 | | | |
|---|---|---|---|---|
| | D614G | Delta | BQ.1.1 | XBB.1.5 |
| | | (Vero E6) | | |
| AB-1 + sotrovimab VH/VL - huIgG1-LS (1:1) | 99.99 (99.93 to 100.06) | 99.98 (99.91 to 100.05) | 99.55 (99.31 to 99.79) | 99.78 (99.64 to 99.93) |
| AB-1 + sotrovimab VH/VL - huIgG1-LS (2.4:1) | 100.00 (99.97 to 100.04) | 100.00 (99.97 to 100.03) | 98.84 (98.11 to 99.56) | 99.47 (99.02 to 99.92) |
| Sotrovimab VH/VL - huIgG1-LS + isotype | 98.27 (97.63 to 98.91) | 96.86 (95.31 to 98.40) | 71.91 (67.97 to 75.85) | 93.43 (91.87 to 94.98) |
| AB-1 + isotype | 95.60 (94.60 to 96.59) | 92.99 (91.56 to 94.41) | 95.25 (94.16 to 96.34) | 95.49 (94.62 to 96.36) |

TABLE 32-continued

Neutralization of SARS-CoV-2 Variants by AB-1 in Combination with Sotrovimab VH/VL - huIgG1-LS ($E_{max}$ Values).

| | SARS-CoV-2 | | | |
|---|---|---|---|---|
| | D614G | Delta | BQ.1.1 | XBB.1.5 |
| | | (Vero E6) | | |
| Bebtelovimab + isotype | 99.70 (99.52 to 99.88) | 99.72 (99.55 to 99.88) | 55.64 (50.51 to 60.77) | 0.55 (0.00-1.37) |

Neutralization profiles of AB-1 + sotrovimab VH/VL - huIgG1-LS (tested at two different ratios), AB-1, sotrovimab VH/VL - huIgG1-LS and bebtelovimab as single agents against pseudoviruses representative of the indicated SARS-CoV-2 variants using Vero E6 cells as reported in FIG. 36. Results are reported as Emax values (% neutralization), shown as mean (95% confidence interval) and representative of three or four independent experiments, four technical replicates each. For each experimental condition (defined by a SARS-CoV-2 pseudovirus), values in bold indicate: AB-1 + sotrovimab VH/VL - huIgG1-LS Emax values that are higher compared to sotrovimab VH/VL - huIgG1-LS + isotype and AB-1 + isotype, and with no overlapping 95% confidence intervals.

TABLE 33

Evaluation of Neutralization Profiles of Parent and Surrogate Antibodies ($EC_{50}$ Values).

| | AB-1 | AB-1 VH/VL - huIgG1 | AB-1 VH/VL - hamIgG2a | Sotrovimab VH/VL - huIgG1-LS | Sotrovimab VH/VL - huIgG1 | Sotrovimab VH/VL - hamIgG2a |
|---|---|---|---|---|---|---|
| SARS-CoV-2 D614G | 0.04687 (0.03701 to 0.05991) | 0.06372 (0.05247 to 0.07805) | 0.05984 (0.04545 to 0.08013) | 0.03517 (0.02867 to 0.04297) | 0.02789 (0.02137 to 0.03607) | 0.008514 (0.004801 to 0.01465) |
| SARS-CoV-2 BA.2 | 0.02058 (0.01234 to 0.03584) | 0.02329 (0.01381 to 0.04188) | 0.02991 (0.01611 to 0.06489) | 0.8510 (0.6640 to 1.151) | 0.8616 (0.6628 to 1.137) | 0.3613 (0.2639 to 0.5145) |

Neutralization profiles of AB-1, sotrovimab VH/VL - huIgG1-LS, and their respective surrogate human IgG1 and hamster IgG2a molecules against pseudoviruses representative SARS-CoV-2 ancestral with D614G mutation and BA.2 variant as reported in FIG. 37. The results are expressed as $EC_{50}$ values (µg/mL), shown as mean (95% confidence interval) and representative of three independent experiments, four technical replicates each.

TABLE 34

| | $EC_{50}$ (95% CI) | | | | $EC_{90}$ (95% CI) | | | |
|---|---|---|---|---|---|---|---|---|
| [ng/ml] | Bebtelovimab | AB-1 | R-AB-2b | AB-1 + R-AB-2b | Bebtelovimab | AB-1 | PRO-37587 | AB-1 + R-AB-2b |
| SARS-CoV-2 Eng20 (WT) | 1.6 | 53.8 (42.2, 69.5) | 57.5 (43.6, 75.7) | 11.5 (9.3, 14.1) | 12.3 (9.9, 15.5) | 838.1 (493.0, 1554) | 1023 (563.2, 2145) | 266.4 (176.3, 425.0) |
| SARS-CoV-2 Delta | 4.6 (4.4, 4.9) | 93.3 (83.0, 105.3) | 44.4 (42.3, 46.6) | 18.6 (16.1, 21.2) | 15.9 (13.7, 18.3) | 769.3 (585.8, 1032) | 146.9 (134.8, 161.0) | 100.0 (75.4, 135.8) |
| SARS-CoV-2 BQ.1.1 | N/A | 42.8 (37.5, 48.9) | 241.3 (216.3, 268.3) | 28.4 (23.6, 35.0) | N/A | 475.9 (348.6, 669.8) | 866.2 (682.1, 1130) | 270.1 (176.5, 442.4) |
| SARS-CoV-2 XBB.1.1 | N/A | 52.6 (48.3, 57.4) | 123 (106.2, 142.3) | 18.5 (15.4, 22.0) | N/A | 742.4 (610.1, 913.8) | 760.2 (544.5, 1113) | 267.9 (188.6, 395.4) |

TABLE 35

| | $EC_{90}$ (95% CI) | | | |
|---|---|---|---|---|
| [ng/ml] | Bebtelovimab | AB-1 | R-AB-2b | AB-1 + R-AB-2b |
| SARS-CoV-2 D614G | 16.1 (9.8, 28.1) | 1861 (879.4, 4827) | 338.0 (238.5, 501.1) | 133.6 (72.6, 277.0) |
| SARS-CoV-1 | NA | 149.6 (33.5, 1570) | 10.0 (6.8, 15.4) | 9.8 (5.0, 21.1) |
| WIV1 | NA | 859.2 (337.0, 2972) | 7.9 (4.5, 14.6) | 6.7 (3.6, 13.2) |

TABLE 36

SARS-CoV-2 S2 Peptide Reconstitution

| Sample | AA Sequence | Net Charge pH 7 | MW (Da) | Conc. mg/mL | Buffer |
|---|---|---|---|---|---|
| SARS-CoV-2 S2 peptide | | | | | |
| 1133-1147 | Biotin-VNNTVYDPLQPELDS-OH | −4.00 | 2043.3 | 1.0 | 50% DMSO/water |
| 1137-1151 | Biotin-VYDPLQPELDSFKEE-OH | −4.99 | 2148.4 | 1.0 | |
| 1141-1155 | Biotin-LQPELDSFKEELDKY-OH | −3.99 | 2193.5 | 1.0 | |
| 1145-1159 | Biotin-LDSFKEELDKYFKNH-OH | −1.91 | 2252.6 | 1.0 | 5% DMSO/water |
| 1149-1163 | Biotin-KEELDKYFKNHTSPD-OH | −1.91 | 2574.9 | 1.0 | |
| 1153-1167 | Biotin-DKYFKNHTSPDVDLG-OH | −1.91 | 2075.3 | 1.0 | |
| 1157-1171 | Biotin-KNHTSPDVDLGDISG-OH | −2.91 | 1894.1 | 1.0 | |
| 1149-1167 | Biotin-KEELDKYFKNHTSPDVDLG-OH | −2.91 | 2190.5 | 1.0 | |
| 1149-1167 | H2N-KEELDKYFKNHTSPDVDLG-OH | −1.91 | 2235.4 | | lyophilized |
| 1143-1162 | Biotin-PELDSFKEELDKYFKNHTSP-OH | −2.90 | 2764.1 | 1.0 | 5% DMSO/water |
| 1143-1162 | H2N-PELDSFKEELDKYFKNHTSP-OH | −1.91 | 2424.6 | | lyophilized |
| HIV-1 Env peptide | | | | | |
| | Biotin-NMWKNDMVDQMHEDI-OH | −3.91 | 2245.6 | 1.0 | 50% acetonitrile/water |

TABLE 37

Epitope/paratope analysis of AB-1 and the Reference Antibody in complex with the S2 stem helix peptide

| | Epitope | | | | | | | | | | | | |
|---|---|---|---|---|---|---|---|---|---|---|---|---|---|
| | E1150 | L1152 | D1153 | F1156 | K1157 | N1158 | H1159 | T1160 | S1161 | P1162 | D1163 | V1164 | D1165 |
| AB-1 | ✓ | x | ✓ | ✓ | ✓ | ✓ | ✓ | ✓ | ✓ | ✓ | x | x | x |
| the Reference Antibody | x | ✓ | ✓ | ✓ | ✓ | ✓ | ✓ | ✓ | ✓ | ✓ | ✓ | ✓ | ✓ |

| | Paratope (heavy chain) | | | | | | | | | | |
|---|---|---|---|---|---|---|---|---|---|---|---|
| | CDR1 | | | | CDR2 | | | CDR3 | | | |
| | T35 | R36 | Y37 | W38 | Y57 | D62 | D64 | R106 | P108 | Q109 | Y110 | C111 |
| AB-1 | ✓ | ✓ | ✓ | ✓ | ✓ | ✓ | ✓ | x | ✓ | ✓ | ✓ | ✓ |
| the Reference Antibody | ✓ | ✓ | ✓ | ✓ | ✓ | ✓ | ✓ | ✓ | ✓ | ✓ | ✓ | ✓ |

List of amino acid contacts between the epitope (S2 stem helix peptide, upper table) and the paratope (heavy chain, lower table) of AB-1 and the Reference Antibody.
"✓" indicates contact,
"x" indicates lack of contact.

What is claimed is:

1. A polypeptide that specifically binds a severe acute respiratory syndrome coronavirus 2 Spike glycoprotein (SARS-CoV-2-Spike) comprising:
   a) a heavy chain variable domain ($V_H$) that comprises a heavy chain complementarity-determining region (HCDR) 1 comprising the amino acid sequence of SEQ ID NO:77, a HCDR2 comprising the amino acid sequence of SEQ ID NO:80, and a HCDR3 comprising the amino acid sequence of SEQ ID NO:91; and
   b) a light chain variable domain ($V_L$) that comprises a light chain complementarity-determining region (LCDR) 1 comprising the amino acid sequence of SEQ ID NO:133, a LCDR2 comprising the amino acid sequence of SEQ ID NO:141, and a LCDR3 comprising the amino acid sequence of SEQ ID NO:144, wherein the polypeptide is an antibody or an antigen-binding fragment thereof.

2. A polypeptide that specifically binds a severe acute respiratory syndrome coronavirus 2 Spike glycoprotein (SARS-CoV-2-Spike) comprising:
   a) a heavy chain variable domain ($V_H$) that comprises a heavy chain complementarity-determining region (HCDR) 1 consisting of the amino acid sequence of SEQ ID NO:77, a HCDR2 consisting of the amino acid sequence of SEQ ID NO:80, and a HCDR3 consisting of the amino acid sequence of SEQ ID NO:91; and
   b) a light chain variable domain ($V_L$) that comprises a light chain complementarity-determining region (LCDR) 1 consisting of the amino acid sequence of SEQ ID NO:133, a LCDR2 consisting of the amino acid sequence of SEQ ID NO:141, and a LCDR3 consisting of the amino acid sequence of SEQ ID NO:144, wherein the polypeptide is an antibody or an antigen-binding fragment thereof.

3. The polypeptide of claim 1, comprising:
   a) a heavy chain variable domain ($V_H$) that is humanized, contains human framework regions, or a combination thereof,
   b) a light chain variable domain ($V_L$) that is humanized, contains human framework regions, or a combination thereof, or both a) and b).

4. The polypeptide of claim 1, comprising a $V_H$ comprising the amino acid sequence of SEQ ID NO:4.

5. The polypeptide of claim 1, comprising a $V_L$ comprising the amino acid sequence of SEQ ID NO:51.

6. The polypeptide of claim 1, comprising a $V_H$ comprising the amino acid sequence of SEQ ID NO:4 and a $V_L$ comprising the amino acid sequence of SEQ ID NO:51.

7. The polypeptide of claim 1, wherein the polypeptide is an antigen-binding fragment of an antibody, and wherein the antigen-binding fragment comprises a single-chain fragment variable (scFv), a fragment antigen-binding (Fab), a Fab' or a F(ab')$_2$.

8. The polypeptide of claim 1, comprising an antibody heavy chain constant domain, an antibody light chain constant domain, or both an antibody heavy chain constant domain and an antibody light chain constant domain.

9. The polypeptide of claim 8, wherein the antibody heavy chain constant domain is an IgG1, IgG2, IgG3 or IgG4 constant domain.

10. The polypeptide of claim 8, wherein the antibody heavy chain constant domain is an IgG1 constant domain.

11. The polypeptide of claim 10, wherein the antibody heavy chain constant domain comprises one or more mutations which increase serum half-life of the antibody or antigen-binding fragment thereof in humans.

12. The polypeptide of claim 1, comprising an antibody heavy chain (HC) constant domain comprising the amino acid sequence of SEQ ID NO:194.

13. The polypeptide of claim 1, comprising an antibody light chain (LC) constant domain comprising the amino acid sequence of SEQ ID NO:195.

14. The polypeptide of claim 1, comprising an antibody light chain (LC) constant domain comprising the amino acid sequence of SEQ ID NO:196.

15. A composition comprising the polypeptide of claim 1 and one or more pharmaceutical excipients, diluents, or carriers.

16. A method of treating a subject in need thereof, comprising administering an effective amount of the composition of claim 15 to the subject.

17. The method of claim 16, further comprising administering a therapeutically effective amount of an additional therapeutic or prophylactic agent to the subject.

18. The method of claim 17, wherein the additional therapeutic agent is selected from the group consisting of an antiviral agent, an ACE2 inhibitors, an additional SARS-CoV-2-Spike-binding antibody, an antibiotic, an antimalarial agent, a vaccine, and combinations thereof.

19. The method of claim 18, wherein:
   a) the additional SARS-CoV-2-Spike-binding antibody is selected from the group consisting of bamlanivimab, etesevimab, bebtelovimab, casirivimab, imdevimab, Cilgavimab, Tixagevimab, AZD7442, Regdanvimab, Sotrovimab and combinations thereof;
   b) the antiviral agent is selected from the group consisting of Molnupiravir, PF-07817883, STI-1558, PBI-0451, EDP-235, oseltamivir, favipiravir, amantadine, remdesivir, rimantadine, pleconaril, an anti-sense RNA to SARS-CoV-2, a siRNA to SARS-CoV-2, and combinations thereof;
   c) the ACE2 inhibitor is selected from the group consisting of an RNAi to ACE2, a siRNA to ACE2, CRISPR-based inhibitor of ACE2, a soluble ACE2, a soluble ACE2 variant, an anti-ACE2 antibody, and combinations thereof;
   d) the antibiotic comprises azithromycin;
   e) the antimalarial agent comprises a chloroquine;
   f) the vaccine is a nucleic acid vaccine or an inactivated virus vaccine; or
   g) a combination thereof.

20. The method of claim 16, wherein the subject has COVID-19, is suspected of having COVID-19, or is at risk of developing COVID-19.

21. The method of claim 16, wherein the subject has a heart disease, diabetes, a lung disease, is immune comprised, is on immunosuppressive therapy, or any combination thereof.

22. A method of reducing infectivity of a betacoronavirus in a subject in need thereof, comprising administering an effective amount of the composition of claim 15 to the subject.

23. The method of claim 22, further comprising administering a therapeutically effective amount of an additional therapeutic or prophylactic agent to the subject.

24. The method of claim 23, wherein the additional therapeutic agent is selected from the group consisting of an antiviral agent, an ACE2 inhibitors, an additional SARS-CoV-2-Spike-binding antibody, an antibiotic, an antimalarial agent, a vaccine, and combinations thereof.

25. The method of claim 24, wherein:
   a) the additional SARS-CoV-2-Spike-binding antibody is selected from the group consisting of bamlanivimab, etesevimab, bebtelovimab, casirivimab, imdevimab, Cilgavimab, Tixagevimab, AZD7442, Regdanvimab, Sotrovimab and combinations thereof;
b) the antiviral agent is selected from the group consisting of Molnupiravir, PF-07817883, STI-1558, PBI-0451, EDP-235, oseltamivir, favipiravir, amantadine, remdesivir, rimantadine, pleconaril, an anti-sense RNA to SARS-CoV-2, a siRNA to SARS-CoV-2, and combinations thereof;
c) the ACE2 inhibitor is selected from the group consisting of an RNAi to ACE2, a siRNA to ACE2, CRISPR-based inhibitor of ACE2, a soluble ACE2, a soluble ACE2 variant, an anti-ACE2 antibody, and combinations thereof;
d) the antibiotic comprises azithromycin;
e) the antimalarial agent comprises a chloroquine;
f) the vaccine is a nucleic acid vaccine or an inactivated virus vaccine; or
g) a combination thereof.

26. The method of claim 22, wherein the subject has COVID-19, is suspected of having COVID-19, or is at risk of developing COVID-19.

27. The method of claim 22, wherein the subject has a heart disease, diabetes, a lung disease, is immune comprised, is on immunosuppressive therapy, or any combination thereof.

28. A polynucleotide comprising a nucleotide sequence encoding the polypeptide of claim 1.

29. A host cell comprising the polynucleotide of claim 28.

30. A method of making the polypeptide of claim 1, comprising culturing a host cell comprising a nucleotide sequence encoding the polypeptide under conditions where the polypeptide is expressed in the host cell.

* * * * *

UNITED STATES PATENT AND TRADEMARK OFFICE
CERTIFICATE OF CORRECTION

| | | |
|---|---|---|
| PATENT NO. | : 11,993,644 B2 | Page 1 of 1 |
| APPLICATION NO. | : 18/313306 | |
| DATED | : May 28, 2024 | |
| INVENTOR(S) | : Francesco Borriello and Alexis Hiram Ramos | |

It is certified that error appears in the above-identified patent and that said Letters Patent is hereby corrected as shown below:

On the Title Page

The following persons are being added as Item (72) inventors:
Vincent Frappier, Victoriaville, Quebec (CA); Hongru Li, Arlington, MA (US)

Signed and Sealed this
Third Day of September, 2024

Katherine Kelly Vidal
*Director of the United States Patent and Trademark Office*